(12) United States Patent
Ebetino et al.

(10) Patent No.: US 8,822,435 B2
(45) Date of Patent: Sep. 2, 2014

(54) BISPHOSPHONATE COMPOUNDS

(71) Applicant: Warner Chilcott Company, LLC, Fajardo, PR (US)

(72) Inventors: Frank Hallock Ebetino, Cincinnati, OH (US); Adam Wieslaw Mazur, Mason, OH (US); Roy Lee Martin Dobson, Hamilton, OH (US)

(73) Assignee: Warner Chilcott Company, LLC, Fajardo, PR (US)

( * ) Notice: Subject to any disclaimer, the term of this patent is extended or adjusted under 35 U.S.C. 154(b) by 0 days.

(21) Appl. No.: 14/205,937

(22) Filed: Mar. 12, 2014

(65) Prior Publication Data

US 2014/0194389 A1 Jul. 10, 2014

Related U.S. Application Data

(62) Division of application No. 13/650,785, filed on Oct. 12, 2012, now Pat. No. 8,710,215, which is a division of application No. 12/912,514, filed on Oct. 26, 2010, now Pat. No. 8,314,081.

(60) Provisional application No. 61/254,886, filed on Oct. 26, 2009.

(51) Int. Cl.
 *A61K 31/675* (2006.01)
 *A61P 19/00* (2006.01)
 *A61P 29/00* (2006.01)

(52) U.S. Cl.
 USPC .............................................. 514/89; 514/90

(58) Field of Classification Search
 None
 See application file for complete search history.

(56) References Cited

U.S. PATENT DOCUMENTS

| | | | |
|---|---|---|---|
| 4,309,364 A | 1/1982 | Bentzen et al. | |
| 4,371,527 A | 2/1983 | Bentzen et al. | |
| 4,971,958 A | 11/1990 | Bosies et al. | |
| 4,990,503 A | 2/1991 | Isomura et al. | |
| 5,039,669 A | 8/1991 | Isomura et al. | |
| 5,157,027 A | 10/1992 | Biller et al. | |
| 5,227,506 A | 7/1993 | Saari et al. | |
| 5,347,029 A | 9/1994 | Johnson | |
| 5,366,965 A | 11/1994 | Strein | |
| 5,393,748 A | 2/1995 | Pohjala et al. | |
| 5,453,524 A | 9/1995 | Tagami et al. | |
| 5,510,517 A | 4/1996 | Dauer et al. | |
| 5,719,303 A | 2/1998 | Yoshida et al. | |
| 7,645,459 B2 | 1/2010 | Dansereau et al. | |
| 7,645,460 B2 | 1/2010 | Dansereau et al. | |
| 7,745,422 B2 | 6/2010 | Sanders et al. | |
| 8,314,081 B2 | 11/2012 | Ebetino et al. | |
| 2006/0079487 A1 | 4/2006 | Sanders et al. | |
| 2013/0035482 A1 | 2/2013 | Ebetino et al. | |

FOREIGN PATENT DOCUMENTS

| | | |
|---|---|---|
| CA | 2154624 A1 | 1/1996 |
| CN | 1040590 A | 3/1990 |
| EP | 0015370 A1 | 9/1980 |
| EP | 0273190 A1 | 7/1988 |
| EP | 0354806 A2 | 2/1990 |
| EP | 0513761 A2 | 11/1992 |
| EP | 0541037 A2 | 5/1993 |
| EP | 0609440 A1 | 8/1994 |
| EP | 0705834 A1 | 4/1996 |
| WO | 92/11269 A1 | 7/1992 |
| WO | 92/22559 A1 | 12/1992 |
| WO | 94/20508 A1 | 9/1994 |
| WO | 95/06052 A1 | 3/1995 |
| WO | 2008/076417 A1 | 6/2008 |
| WO | 2010/033978 A2 | 3/2010 |
| WO | 2010/033980 A2 | 3/2010 |
| WO | 2010/033981 A2 | 3/2010 |

OTHER PUBLICATIONS

Vippagunta et al., Crystalline Solids, 48 Adv. Drug Delivery Rev., pp. 3-26 (2001).
Xie et al., Synthesis & Biological Evaluation of Novel Bisphosphonates with Dual Activities on Bone In Vitro, 15 Bioorg. Med. Chem. Lett., pp. 3267-3270 (2005).
Dunford, J., et al., "Structure-Activity Relationships Among the Nitrogen Containing Bisphosphonates in Clinical Use and Other Analogues: Time-Dependent Inhibition of Human Farnesyl Pyrophosphate Synthase", J. Med. Chem., vol. 51, No. 7, pp. 2187-2195 (2008).
International Search Report and Written Opinion of the International Searching Authority dated Feb. 16, 2011, in International Application No. PCT/US2010/054124.
Office Action issued in Chinese Application No. 201080054060.1, dated Jan. 6, 2014 (6 pages).

*Primary Examiner* — Janet L Andres
*Assistant Examiner* — Timothy R. Rozof
(74) *Attorney, Agent, or Firm* — Fitzpatrick, Cella, Harper & Scinto

(57) ABSTRACT

Novel bisphosphonate cyclic acetal compounds are disclosed, as well as methods of preparing the compounds, pharmaceutical compositions including the compounds, and administration of the compounds in methods of treating bone metabolism disorders, such as abnormal calcium and phosphate metabolism.

16 Claims, 1 Drawing Sheet

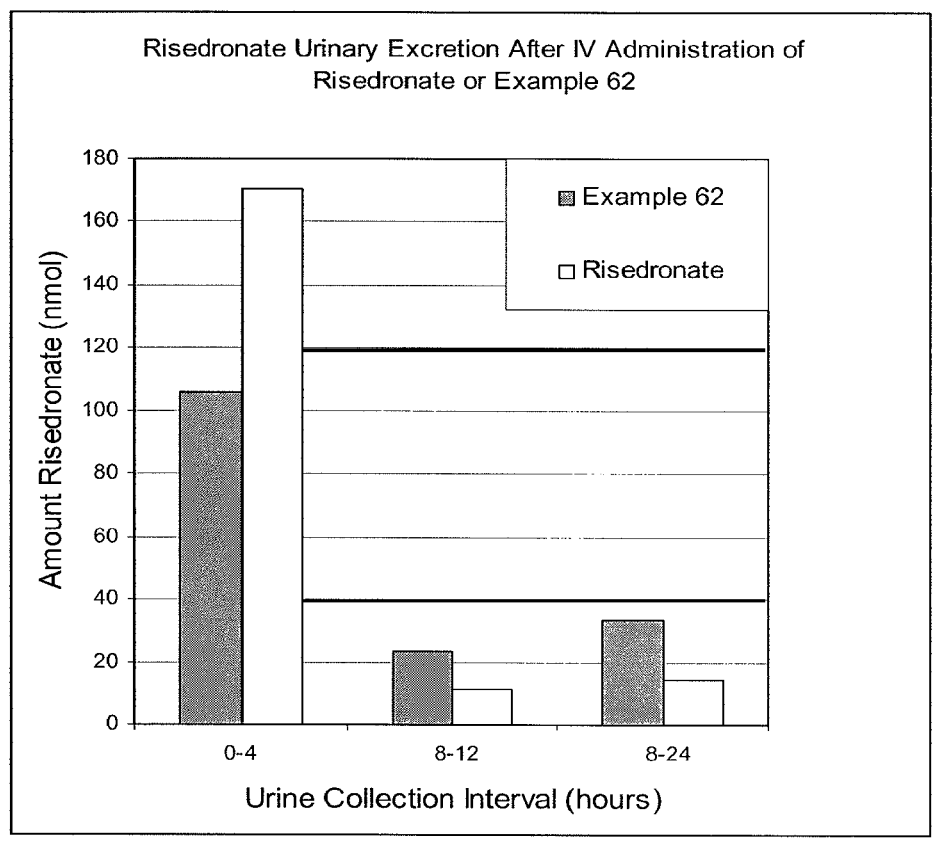

BISPHOSPHONATE COMPOUNDS

This application is a divisional application of U.S. patent application Ser. No. 13/650,785, filed Oct. 12, 2012, which is a divisional application of U.S. patent application Ser. No. 12/912,514, filed Oct. 26, 2010, which issued as U.S. Pat. No. 8,314,081 on Nov. 20, 2012, which claims the benefit of priority of U.S. Provisional Patent Application No. 61/254,886, filed Oct. 26, 2009, the contents of which are all incorporated by reference herein in their entirety.

FIELD OF THE INVENTION

Novel bisphosphonate cyclic acetal compounds are disclosed, as well as their uses as antiresorptive agents and for the treatment and prevention of disorders associated with bone metabolism, such as abnormal calcium and phosphate metabolism. Processes for preparing the novel bisphosphonate cyclic acetal compounds, as well as methods of using them and pharmaceutical compositions containing them are also disclosed.

BACKGROUND

Bisphosphonates were first developed to complex calcium in hard water to improve detergent performance. Bisphosphonates have since been found to be useful in the treatment and prevention of diseases or conditions characterized by abnormal calcium and phosphate metabolism. Such conditions may be divided into two broad categories:

1. Conditions which are characterized by anomalous mobilization of calcium and phosphate leading to general or specific bone loss or excessively high calcium and phosphate levels in the fluids of the body. Such conditions are sometimes referred to as pathological hard tissue demineralization.

2. Conditions which cause or result from deposition of calcium and phosphate anomalously in the body. These conditions are sometimes referred to as pathological calcifications.

The first category includes osteoporosis, a condition in which bone hard tissue is lost disproportionately to the development of new hard tissue ultimately resulting in fractures. Essential quantities of cancellous bone are lost, and marrow and bone spaces become larger, resulting in reduced cancellous bone strength. Bone also becomes less dense and fragile. Osteoporosis can be sub-classified as genetic, senile, drug induced (e.g., adrenocorticoid, as can occur in steroid therapy), disease induced (e.g., arthritic and tumor), etc., however the manifestations are similar. Another condition in the first category is Paget's disease (osteitis deformans). In this disease, dissolution of normal bone occurs, which is then haphazardly replaced by soft, poorly mineralized tissue such that the bone becomes deformed from pressures of weight bearing, particularly in the tibia and femur. Hyperparathyroidism, hypercalcemia of malignancy, arthritis, and osteolytic bone metastasis are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis, and other inflammatory conditions which predispose involved tissue to deposition of calcium phosphates.

A variety of polyphosphonic acid derivatives have been proposed for use in the treatment and prophylaxis of conditions involving abnormal calcium and phosphate metabolism. For example, diphosphonates, like ethane-1-hydroxy-1,1-diphosphonic acid (EHDP), propane-3-amino-1-hydroxy-1,1-diphosphonic acid (APD), and dichloromethane diphosphonic acid ($Cl_2MDP$), have been the subject of considerable research efforts in this area. Paget's disease and heterotopic ossification have been treated with EHDP. Similarly, risedronate and alendronate have been used for treatment of bone disorders, U.S. Pat. No. 4,990,503 discloses heterocyclic bisphosphonic acid derivatives and their use as bone resorption inhibitors, and U.S. Pat. No. 7,745,422 teaches bisphosphonate derivatives for use in bone resorption and bone pain. However, these patents fail to teach bisphosphonate cyclic acetal compounds. U.S. Pat. No. 5,719,303 discloses bisphosphonic acid derivatives, and one bisphosphonic cyclic acetal, Example No. 471. This example, however, has a chemical structure unlike the bisphosphonate cyclic acetals disclosed herein and, in vivo, would not likely release an effective amount of the bisphosphonate.

However, bisphosphonates suffer from side effects and pharmacological disadvantages as orally administered agents. Some of the currently available bisphosphonates, e.g., alendronate, tiludronate, and risedronate, may cause esophageal irritation and ulceration. Therefore, it is recommended that the patients remain upright for 30 minutes after taking the medication. In addition, bisphosphonates usually have very low oral bioavailability: generally only 0.2% to 5% of an orally administered bisphosphonate is absorbed from the gastrointestinal tract. Bisphosphonates are usually very polar and can easily become negative charged, thus preventing absorption through paracellular transportation. They also have very low affinity to lipids, which makes it difficult for bisphosphonates to move across the cell membrane. Oral absorption is further reduced when taken with food, especially food rich in calcium. This "food effect" phenomenon can be explained by the formation of insoluble calcium salts of bisphosphonic acids which remain in the digestive tract without any detectable absorption. Bisphosphonic acids are known strong chelators of metal ions, including calcium, due to the presence of four acidic groups and a alpha-hydroxy substituent, when present. For example, with the calcium salts of alpha-hydroxybisphosphonic acids, the crystal structures show that the calcium ion is bound to two acidic hydroxyl groups from the different phosphate moieties and to the alpha-hydroxyl group. Therefore, there remains a need to develop bisphosphonates that maintain or enhance the pharmacological activity with fewer side effects and better absorption profiles.

Farnesyl pyrophosphate synthase (FPPS) is a key regulatory enzyme in the mevalonate pathway. This pathway, ubiquitous in mammalian cells, provides essential lipid molecules, such as cholesterol and isoprenoids, with isoprenoids being necessary for posttranslational prenylation of small GTPases. The blockage of this pathway is a concept that has found widespread clinical use, with statins as drugs that inhibit hydroxymethylglutaryl CoA reductase and reduce cholesterol biosynthesis, and nitrogen-containing bisphosphonates (N-BPs) as drugs for osteoporosis therapy that target FPPS and inhibit protein prenylation. In the case of N-BPs, the unique bone-targeting pharmacokinetic properties of these compounds cause selected inhibition of FPPS and loss of prenylated proteins in osteoclasts, thereby inhibiting the bone-destroying function of these cells.

SUMMARY OF THE INVENTION

The bisphosphonate cyclic acetal compounds described herein are useful in the treatment and/or prevention of disorders associated with bone metabolism, such as abnormal calcium and phosphate metabolism, including bone and joint diseases such as osteoporosis, rheumatoid arthritis, osteoarthritis, Paget's disease, bone related and other cancer therapy, orthopedic disorders, and alveolar bone loss often associated with periodontal disease. The nitrogen-containing bisphosphonates (N-BPs) have the ability to inhibit the resorption of bone tissue and are inhibitors of farnesyl pyrophosphate synthase (FPPS). Furthermore, such compounds correspondingly have orthopedic uses (including, but not restricted to, fracture repair and implant fixation; and prevention of prosthesis loosening, and osteonecrosis of various bones). Other uses include immunomodulation and anti-inflammatory effects, and use in various parasitic disorders (e.g., malaria, leishmaniasis, trypanasomal diseases, entamoeba, giardia, and cryptosporidial infections). The cyclic acetal functionality of the bisphosphonate cyclic acetal compounds described herein is cleaved in vivo to release the tetra acid bisphosphonates often at a different rate than direct introduction of the tetra acid bisphosphonate into the bloodstream.

In one aspect, compounds of Formula I are described herein:

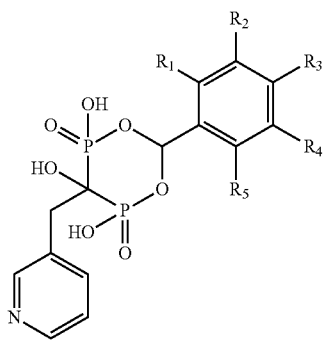

(I)

where $R_1$, $R_2$, $R_3$, $R_4$, and $R_5$ are as described herein.

In some embodiments, compositions including a compound of Formula I and one or more pharmaceutically acceptable carriers are described herein.

In other embodiments, the method includes the step of administering to the patient a therapeutically effective amount of a compound of Formula I.

In another aspect, compounds of Formula II are described herein:

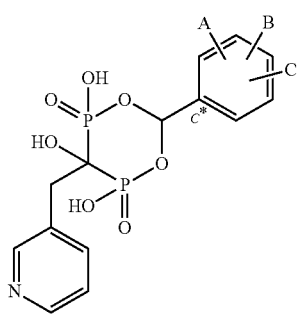

(II)

where A, B, and C are as described herein.

In some embodiments, compositions including a compound of Formula II and one or more pharmaceutically acceptable carriers are described herein.

In other embodiments, methods of treating and/or preventing a disorder associated with abnormal calcium and phosphate metabolism are described herein, including the step of administering to the patient a therapeutically effective amount of a compound of Formula II.

In yet another aspect, compounds of Formula III are described herein:

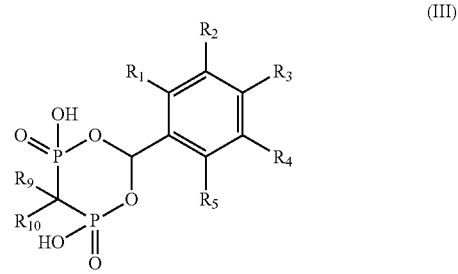

(III)

where $R_1$, $R_2$, $R_3$, $R_4$, $R_5$, $R_9$, and $R_{10}$ are as described herein.

In some embodiments, compositions including a compound of Formula III and one or more pharmaceutically acceptable carriers are described herein.

In other embodiments, methods of treating and/or preventing a disorder associated with abnormal calcium and phosphate metabolism are described herein, including the step of administering to the patient a therapeutically effective amount of a compound of Formula III.

In another aspect, compounds of Formula IV are described herein:

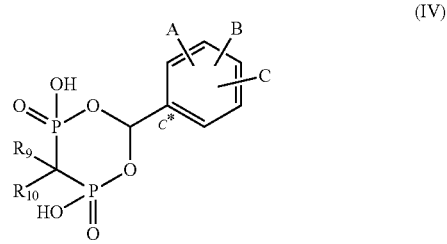

(IV)

where A, B, and C are as described herein.

In some embodiments, compositions including a compound of Formula IV and one or more pharmaceutically acceptable carriers are described herein.

In other embodiments, methods of treating and/or preventing a disorder associated with abnormal calcium and phosphate metabolism are described herein, including the step of administering to the patient a therapeutically effective amount of a compound of Formula IV.

As used herein, the exposure of risedronate after intravenous (IV) or oral (PO) administration of risedronate or a risedronate cyclic acetal compound is defined by the percentage of the risedronate recovered from a urine sample based on the amount of risedronate or risedronate cyclic acetal dosed.

As used herein, the compound(s) of the invention include compound(s) of Formula I, II, IIa, IIb, IIc, IId, IIe, III, IV, IVa, IVb, IVc, IVd, IVe or IVf.

As used herein, the gastrointestinal stability of the bisphosphonate refers to the stability of the bisphosphonate cyclic acetal in the presence of acidic gastric fluid in the stomach. As used herein, the systemic stability of the bisphosphonate cyclic acetal refers to the stability of the bisphosphonate cyclic acetal towards metabolic or chemical conversions to risedronate after entering into systemic circulation via absorption or injection.

BRIEF DESCRIPTION OF THE FIGURES

FIG. 1 shows the amount of urinary excretion of risedronate after intravenous (IV) administration of risedronate and of the trans isomer of Example 62 in rats over time.

DETAILED DESCRIPTION

Novel bisphosphonate cyclic acetal compounds are disclosed. The compound(s) of the invention include compound(s) of Formula I, II, IIa, IIb, IIc, IId, IIe, III, IV, IVa, IVb, IVc, IVd, IVe, or IVf. In the bisphosphonate cyclic acetal, the bisphosphonic acid functionality is "masked" as a cyclic acetal moiety which results in an increase of the lipophilicity of the molecule, thus improving the absorption profile of the bisphosphonates. The cyclic acetal moiety in bisphosphonate cyclic acetal molecules also prevents the chelation of the bisphosphonates with metal ions such as calcium in milk and other calcium-containing food by blocking two hydroxy groups from the bisphosphonate (one from each phosphonate moiety). Therefore, the bisphosphonate compounds described herein are likely to have a decreased "food effect" derived absorption loss. Also, the bisphosphonate compounds described herein are less likely to interact with the GI surface similarly to unmasked bisphosphonates and therefore are less likely to be associated with GI irritation. Since the acetal linkage is hydrolytically labile, the cyclic acetal moiety in bisphosphonate cyclic acetal compounds described herein can be cleaved under in vivo conditions, thereby releasing the tetra acid bisphosphonates after absorption.

The term "halogen" as used herein refers to F, Cl, Br, or I.

The term "alkyl" as used herein refers to a linear, branched, or cyclic saturated hydrocarbon having from 1 to 20 carbon atoms. The term "$C_1$-$C_8$ alkyl" as used herein refers to a linear, branched, or cyclic saturated hydrocarbon having from 1 to 8 carbon atoms. Representative $C_1$-$C_8$ alkyl groups include, but are not limited to, methyl, ethyl, propyl, isopropyl, cyclopropyl, butyl, sec-butyl, iso-butyl, tert-butyl, cyclobutyl, pentyl, iso-pentyl, neo-pentyl, tert-pentyl, cyclopentyl, hexyl, cyclohexyl, heptyl, cycloheptyl, octyl, sec-octyl (1-methylheptyl), and cyclooctyl.

The term "$C_1$-$C_8$ haloalkyl" as used herein refers to a $C_1$-$C_8$ alkyl as defined above, with one or more hydrogens substituted by halogen atoms.

The term "alkenyl" as used herein refers to a linear, branched, or cyclic unsaturated hydrocarbon having from 2 to 20 carbon atoms and at least one carbon-carbon double bond. The term "$C_2$-$C_8$ alkenyl" as used herein refers to a linear, branched, or cyclic unsaturated hydrocarbon having from 2 to 8 carbon atoms and at least one carbon-carbon double bond.

The term "$C_2$-$C_8$ haloalkenyl" as used herein refers to a $C_2$-$C_8$ alkenyl as defined above, with one or more hydrogens substituted by halogen atoms.

The term "alkynyl" as used herein refers to a linear, branched, or cyclic unsaturated hydrocarbon having from 2 to 20 carbon atoms and at least one carbon-carbon triple bond. The term "$C_2$-$C_8$ alkynyl" as used herein refers to a linear, branched, or cyclic unsaturated hydrocarbon having from 2 to 8 carbon atoms and at least one carbon-carbon triple bond.

The term "$C_2$-$C_8$ haloalkynyl" as used herein refers to a $C_2$-$C_8$ alkynyl as defined above, with one or more hydrogens substituted by halogen atoms.

Similarly, the term "$C_1$-$C_4$ alkyl" as used herein refers to a linear, branched, or cyclic saturated hydrocarbon having from 1 to 4 carbon atoms. Representative $C_1$-$C_4$ alkyl groups include, but are not limited to, methyl, ethyl, propyl, isopropyl, cyclopropyl, butyl, sec-butyl, iso-butyl, tert-butyl, and cyclobutyl.

Similarly, the term "$C_1$-$C_3$ alkyl" as used herein refers to a linear, branched, or cyclic saturated hydrocarbon having from 1 to 3 carbon atoms. Representative $C_1$-$C_3$ alkyl groups include, but are not limited to, methyl, ethyl, propyl, isopropyl, and cyclopropyl.

The term "alkoxyl" as used herein refers to an alkyl group linked to an oxygen. Similarly, the term "$C_1$-$C_8$ alkoxyl" as used herein refers to a $C_1$-$C_8$ alkyl group linked to an oxygen.

The term "acyl" as used herein refers to a group containing the acyl radical ($CH_3CO$—) or a carbonyl group, compounds and moities which contain a carbon connected with a double bond to an oxygen.

Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted.

Unless otherwise specifically defined, the term "heteroaryl" refers to aryls as defined above where one or more carbons are substituted by heteroatoms. Exemplary heteroatoms include, but not limited to, nitrogen, sulfur, and oxygen.

The term "carbocyclic ring" refers to cyclic compounds containing only carbon atoms. The carbocyclic ring may be optionally substituted by one or more substituents, and may be saturated, unsaturated or aromatic.

The term "heterocyclic ring" refers to cyclic compounds where one or more carbons are substituted by heteroatoms. Exemplary heteroatoms include, but not limited to, nitrogen, sulfur, and oxygen. The heterocyclic ring may be optionally substituted, and may be saturated, unsaturated or aromatic.

The term "saturated" as used herein means that the compound does not contain double or triple bonds. The term "unsaturated" as used herein means that the compound contains at least one double or triple bond. The term "aromatic" as used herein means that the compound contains alternating double and single bonds.

The term "optionally substituted" as used herein means that the compounds may contain one or more substituents, including, but not limited to, optionally substituted alkyl, alkenyl, $C_1$-$C_8$ haloalkyl, alkynyl, alkoxyl, acyl, halogen, aryl, carbocyclic or heterocyclic ring, —$NH_2$, —NH-alkyl, —N-(alkyl)$_2$, —C(=NH)—$NH_2$, —C(=N—OH)—$NH_2$, —C(=NH)—NH—OH, —C(=NH)—NH—C(=O)—O-alkyl, —COOH, —C(=O)—O-optionally substituted alkyl, —C(=O)—O-optionally substituted aryl, —C(=O)—O-optionally substituted heteroaryl, —CN, —$NO_2$, —OH, —O—CO-optionally substituted alkyl, —O—CO—$NH_2$, —O—CO—NH-alkyl, —O—CO—N-(alkyl)$_2$, —SH, —C(=O)—$NH_2$, —C(=O)—NH-(lower alkyl) and —C(=O)—N-(lower alkyl)$_2$.

The carbon number, as used herein, refers to the carbon backbone and carbon branching, but does not include carbon atoms of the substituents, such as alkoxy substitutions and the like.

The term "administer", "administering", or "administration", as used herein refers to administering a compound or pharmaceutically acceptable salt or hydrate of the compound or a composition to an animal.

The term "animal" as used herein includes, without limitation, a human, mouse, rat, guinea pig, dog, cat, horse, cow, pig, monkey, chimpanzee, baboon, or rhesus monkey. In one embodiment, the animal is a mammal. In another embodiment, the animal is a human.

The term "conditions effective to" as used herein refers to synthetic reaction conditions that will be apparent to those skilled in the art of synthetic organic chemistry.

The term "effective amount" as used herein refers to an amount of a compound or pharmaceutically acceptable salt or hydrate of a compound that, when administered to an animal, is effective to prevent, to at least partially ameliorate, or to cure, a condition from which the animal suffers or is suspected to suffer.

The term "pharmaceutically acceptable salt", as used herein, refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes hydrates of a salt of a compound described herein.

The term "hydrate", as used herein, refers to a compound formed by the addition of water. The hydrates may be obtained by any known method in the art by dissolving the compounds in water and recrystallizing them to incorporate water into the crystalline structure.

The term "carrier", as used herein, shall encompass carriers, excipients, and diluents.

When ranges are used herein for physical properties, such as molecular weight, or chemical properties, such as chemical formulae, all combinations and subcombinations of ranges of specific embodiments therein are intended to be included.

The disclosure of each patent, patent application, and publication cited or described in this document is hereby incorporated by reference, in their entirety.

Compounds

In one aspect, compounds of Formula I or a pharmaceutically-acceptable salt or hydrate thereof are provided:

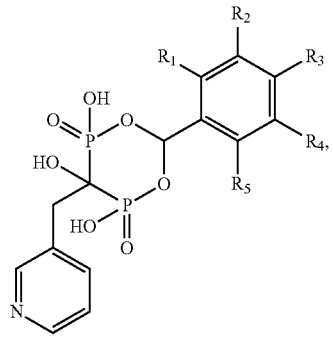

(I)

where $R_1$, $R_2$, $R_3$, $R_4$ and $R_5$ are each independently:
a) hydrogen;
b) halogen, —CN, —$CF_3$, or —$NO_2$;
c) $C_1$-$C_8$ alkyl or $C_1$-$C_8$ haloalkyl;
d) $C_2$-$C_8$ alkenyl or $C_2$-$C_8$ haloalkenyl;
e) $C_2$-$C_8$ alkynyl or $C_2$-$C_8$ haloalkynyl;
f) optionally substituted aryl or optionally substituted heteroaryl;
g) —C(O)$R_6$;
h) —C(O)O$R_6$, or —$CO_2R_6$;
i) —O$R_6$, —O-L-OC(O)$R_6$, or —O-L—OC(O)O$R_6$;
j) —OC(O)$R_6$, or —OC(O)-L-OC(O)$R_6$;
k) —OC(O)O$R_6$, —OC(O)O-L-C(O)$R_7$, —OC(O)O-L-C(O)O$R_7$, or -L—OC(O)$R_6$;
l) —C(O)N$R_6R_7$, or —CN$R_6R_7$;
m) —OC(O)N$R_6R_7$, —OC(O)N($R_6$)-L-OC(O)$R_7$, —OC(O)O-L-($R_6$)-L-C(O)$R_7$, —OC(O)—C($R_6$)($R_7$)-L-OC(O)$R_8$, —OC(O)N(-L—OC(O)$R_7$)(-L-OC(O)$R_8$);
n) —S$R_6$, or —N$R_6R_7$;
o) —N$R_6$C(O)$R_7$;
p) —N$R_6$C(O)O$R_7$;
q) —N$R_6$C(O)N$R_7$;
r) —OS$O_2R_6$;
s) —S$O_2$O$R_6$;
t) —S$O_2R_6$;
u) —N$R_6$S$O_2R_7$;
v) —$O_2$N$R_6R_7$;

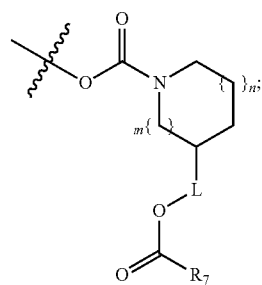

w)

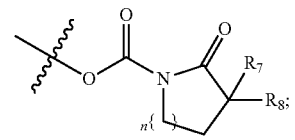

x)

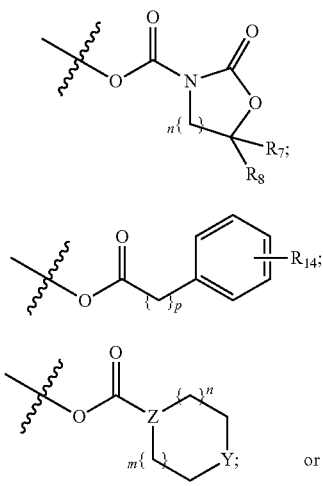

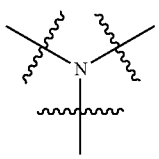

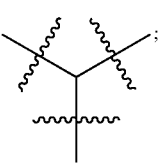 [SMILES: *C(*)*]

or bb) $R_1$ and $R_2$, $R_2$ and $R_3$, $R_3$ and $R_4$, or $R_4$ and $R_5$ taken together form an optionally substituted 4- to 8-membered carbocyclic or heterocyclic ring, wherein the ring is saturated, unsaturated or aromatic;

wherein m and n are each independently an integer from 0 to 2;

Y is —$CH_2$—, —O—, —$NR_7$—, or —S—;

p is an integer from 1 to 3;

$R_{14}$ is hydrogen, halogen, $C_1$-$C_8$ alkyl, or $C_1$-$C_8$ alkoxyl;

Z is each $R_6$ is independently hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

$R_7$ and $R_8$ are each independently hydrogen or $C_1$-$C_8$ alkyl; and L is $C_1$-$C_8$ alkyl; or $R_6$ and $R_7$ taken together form an optionally substituted 4- to 8-membered carbocyclic or heterocyclic ring, wherein the ring is saturated, unsaturated or aromatic.

In some embodiments, $R_1$, $R_2$, $R_3$, $R_4$, and $R_5$ are each independently hydrogen, halogen, —$CF_3$, $C_1$-$C_8$ alkyl, optionally substituted phenyl, —$OR_6$, —O-L-OC(O)$R_6$, —O-L-OC(O)O$R_6$, —OC(O)$R_6$, —OC(O)-L-OC(O)$R_6$, —C(O)O$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

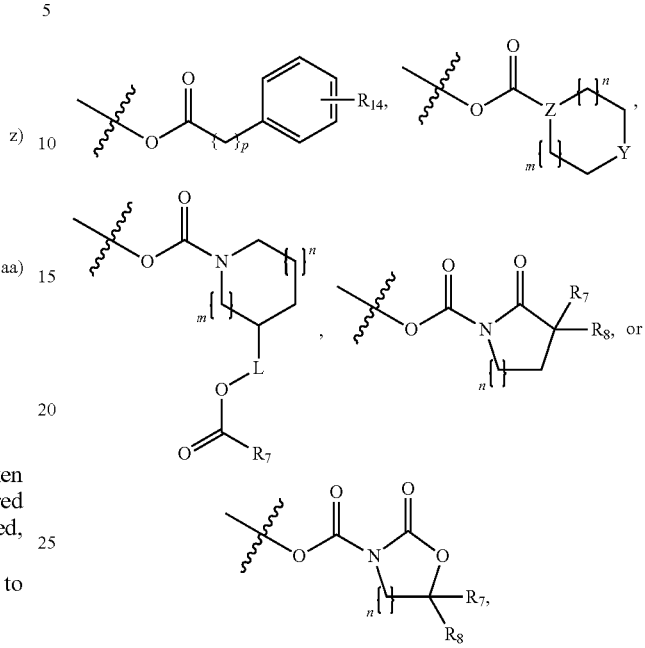

wherein Y is —$CH_2$—, —O—, —$NR_7$—, or —S—; p is an integer from 1 to 3; $R_{14}$ is hydrogen, halogen, $C_1$-$C_8$ alkyl, or $C_1$-$C_8$ alkoxyl; Z is N or CH; and $R_6$, $R_7$, $R_8$, L, m and n are as defined above.

In some embodiments, $R_1$, $R_2$, $R_3$, $R_4$, and $R_5$ are each independently —$OR_6$, —O—$(CH_2)_p$—OC(O)$R_6$, —O—$(CH_2)_p$—OC(O)O$R_6$, —OC(O)$R_6$, —OC(O)—C($R_6$)($R_7$)—$(CH_2)_p$—OC(O)$R_8$, —C(O)O$R_6$, —OC(O)O$R_6$, —OC(O)O—CH($R_6$)($CH_2)_p$C(O)$R_7$, —OC(O)N$R_6R_7$, —OC(O)N($R_6$)($CH_2)_p$—OC(O)$R_7$, —OC(O)N(—($CH_2)_p$—OC(O)$R_7$)(—($CH_2)_p$—OC(O)$R_8$),

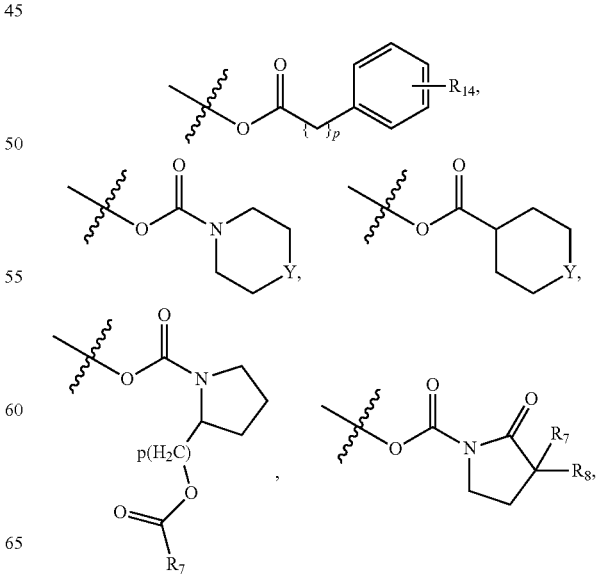

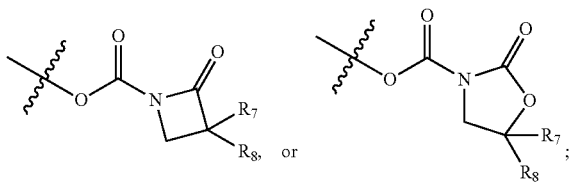

and $R_6$, $R_7$, $R_8$, L, Y, m, n, and p are as defined above.

In some embodiments, $R_6$ is $C_1$-$C_8$ alkyl, $C_2$-$C_8$ alkenyl, $C_3$-$C_6$ cycloalkyl, benzyl; $R_7$ and $R_8$ are each independently hydrogen, methyl, or ethyl; Y is —O—; and L is $C_1$-$C_3$ alkyl. In a specific embodiment, m is 0 and n is 0 or 1.

In some embodiments, $R_1$ and $R_2$, $R_2$ and $R_3$, $R_3$ and $R_4$, or $R_4$ and $R_5$ taken together form an optionally substituted 5- to 7-membered carbocyclic or heterocyclic ring, wherein the ring is saturated, unsaturated or aromatic. In certain specific embodiments, the 5- to 7-membered carbocyclic or heterocyclic ring is unsubstituted. In other specific embodiments, the 5- to 7-membered carbocyclic or heterocyclic ring is saturated or aromatic. In yet other specific embodiments, the 5- to 7-membered heterocyclic ring includes 1 or 2 heteroatoms. In yet other specific embodiments, $R_1$ and $R_2$, $R_2$ and $R_3$, $R_3$ and $R_4$, or $R_4$ and $R_5$ taken together form

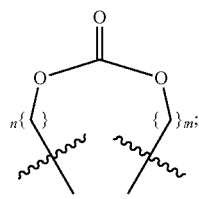 [SMILES: *COC(=O)OC*]

and n and m are as defined above. In yet other specific embodiments, $R_1$ and $R_2$, $R_2$ and $R_3$, $R_3$ and $R_4$, or $R_4$ and $R_5$ taken together are

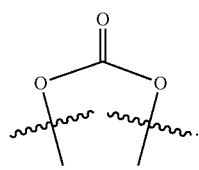 [SMILES: *OC(=O)O*]

In yet other specific embodiments, $R_1$ and $R_2$, $R_2$ and $R_3$, $R_3$ and $R_4$, or $R_4$ and $R_5$ taken together are

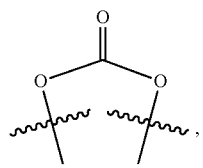

and the remaining R-groups of $R_1$, $R_2$, $R_3$, $R_4$, and $R_5$ are each hydrogen. In yet other specific embodiments, $R_1$ and $R_2$, $R_2$ and $R_3$, $R_3$ and $R_4$, or $R_4$ and $R_5$ taken together are

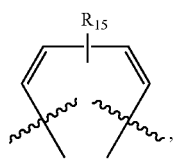

wherein $R_{15}$ is hydrogen, halogen, or —$OR_6$. In yet other specific embodiments, $R_1$ and $R_2$, $R_2$ and $R_3$, $R_3$ and $R_4$, or $R_4$ and $R_5$ taken together are

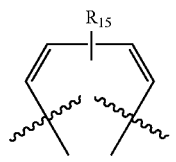

and the remaining R-groups of $R_1$, $R_2$, $R_3$, $R_4$, and $R_5$ are each independently —H or —OC(O)$OR_6$.

In some embodiments, one of $R_1$, $R_2$, $R_3$, $R_4$, and $R_5$ is —$OR_6$, —O-L-OC(O)$R_6$, —O-L—OC(O)$OR_6$, —OC(O)$R_6$, —OC(O)-L-OC(O)$R_6$, —OC(O)$OR_6$, —OC(O)O-L-C(O)$R_7$, —OC(O)$NR_6R_7$, —OC(O)N($R_6$)-L-OC(O)$R_7$, —OC(O)N(-L-OC(O)$R_7$)(-L-OC(O)$R_8$),

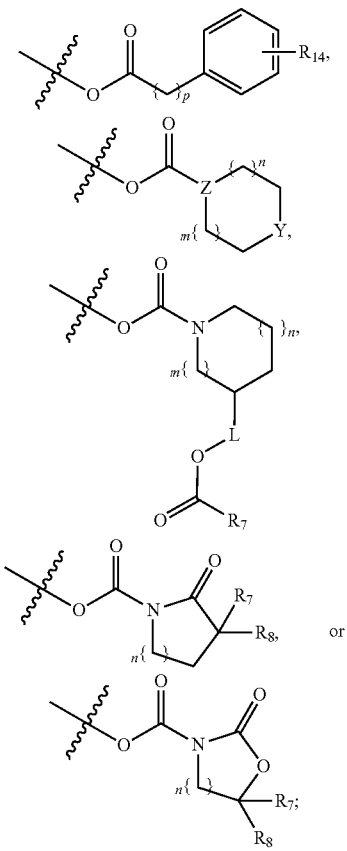

any two of the remaining groups of $R_1$, $R_2$, $R_3$, $R_4$, and $R_5$ are halogen; each of the remaining R-groups of $R_1$, $R_2$, $R_3$, $R_4$, and $R_5$ are hydrogen; and $R_6$, $R_7$, $R_8$, L, Z, Y, m, n, and p are as defined above.

In some embodiments, one of $R_1$, $R_2$, $R_3$, $R_4$, and $R_5$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

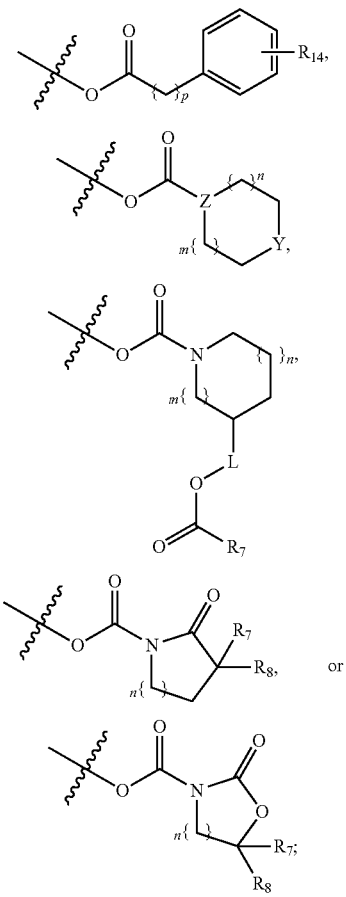

one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; and each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, one of $R_1$, $R_2$, $R_3$, $R_4$, and $R_5$ is —$OR_6$, —O-L-OC(O)$R_6$, —O-L-OC(O)O$R_6$, —OC(O)$R_6$, —OC(O)-L—OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

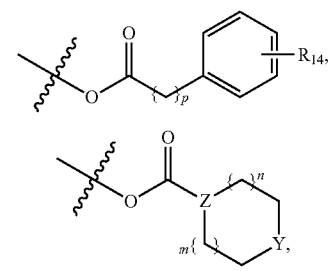

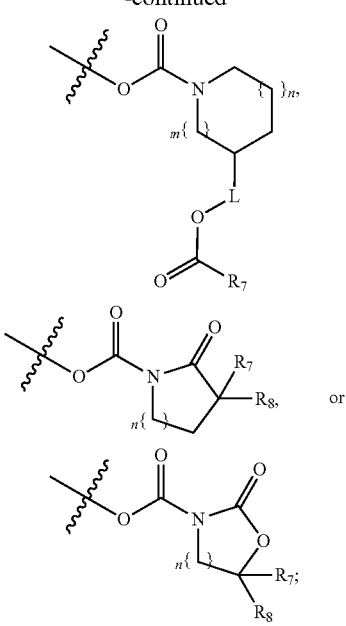

the remaining R-groups of $R_1$, $R_2$, $R_3$, $R_4$, and $R_5$ are each hydrogen; and $R_6$, $R_7$, $R_8$, L, Z, Y, m, n, and p are as defined above.

In some embodiments, $R_1$ and $R_5$ are each independently halogen; and $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

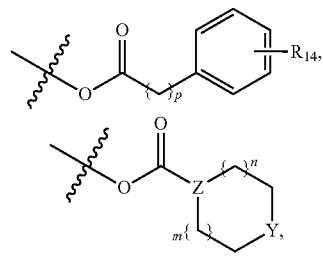

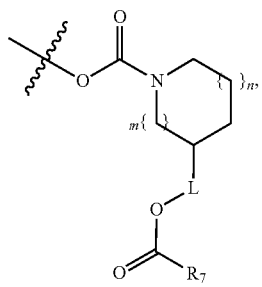

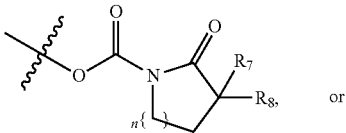

-continued

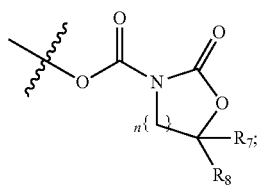

the remaining R-groups of $R_1$, $R_2$, $R_3$, $R_4$, and $R_5$ are each hydrogen; and $R_6$, $R_7$, $R_8$, L, Z, Y, m, n, and p are as defined above. In certain specific embodiments, $R_1$ and $R_5$ are each independently —F or —Cl.

In some embodiments, $R_1$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

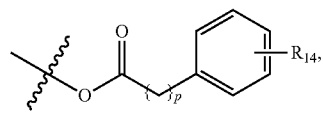

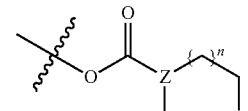

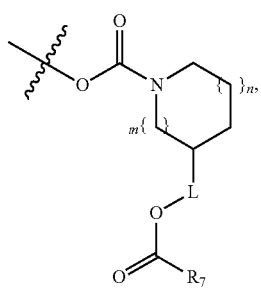

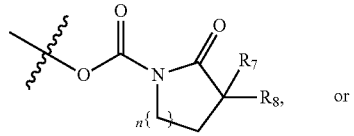

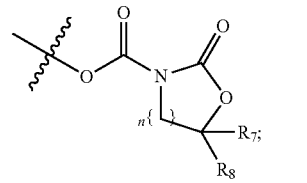

one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, $R_5$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

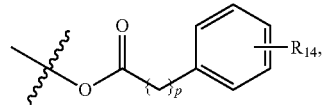

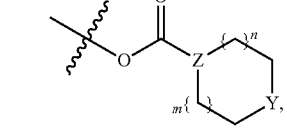

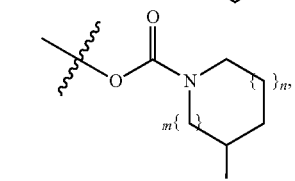

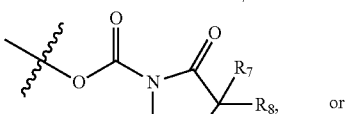

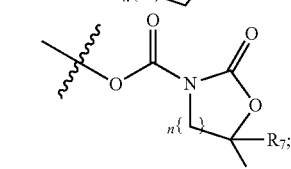

one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

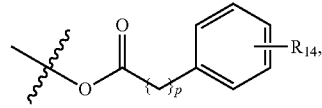

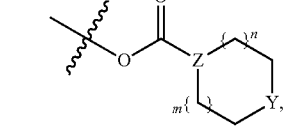

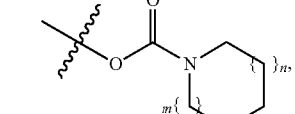

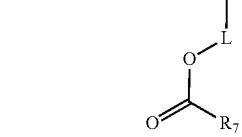

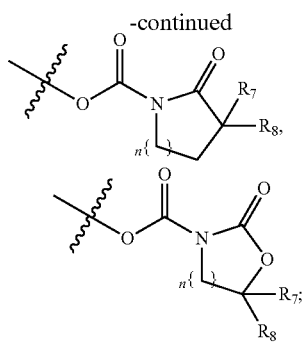

one of the remaining R-groups of $R_1$, $R_2$, $R_3$, $R_4$, and $R_5$ is halogen, —$CF_3$, $C_1$-$C_8$ alkyl, phenyl, —$OR_6$, or —$C(O)OR_6$; each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, $R_1$ is —$OR_6$, —O-L-OC(O)$R_6$, —O-L—OC(O)$OR_6$, —OC(O)$R_6$, —OC(O)-L-OC(O)$R_6$, —OC(O)$OR_6$, —OC(O)O-L-C(O)$R_7$, —OC(O)$NR_6R_7$, —OC(O)N($R_6$)-L-OC(O)$R_7$, —OC(O)N(-L-OC(O)$R_7$)(-L-OC(O)$R_8$),

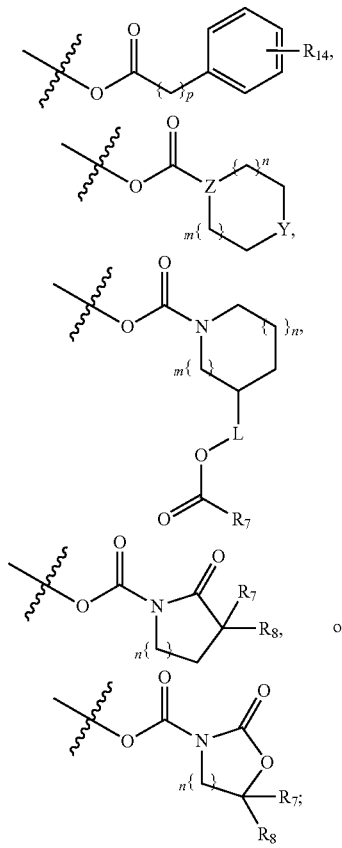

$R_2$, $R_3$, $R_4$, and $R_5$ are each hydrogen; and $R_6$, $R_7$, $R_8$, L, m and n are as defined above. In certain specific embodiments, $R_1$ is —OC(O)$OR_{16}$, —OC(O)$R_{16}$ or —OC(O)$NR_{16}R_{17}$ and $R_{16}$ and $R_{17}$ are each independently $C_1$-$C_4$ alkyl.

In some embodiments, $R_3$ is —$OR_6$, —O-L-OC(O)$R_6$, —O-L—OC(O)$OR_6$, —OC(O)$R_6$, —OC(O)-L-OC(O)$R_6$, —OC(O)$OR_6$, —OC(O)O-L-C(O)$R_7$, —OC(O)$NR_6R_7$, —OC(O)N($R_6$)-L-OC(O)$R_7$, —OC(O)N(-L-OC(O)$R_7$)(-L-OC(O)$R_8$),

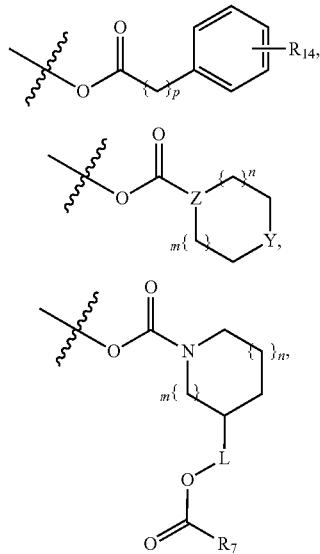

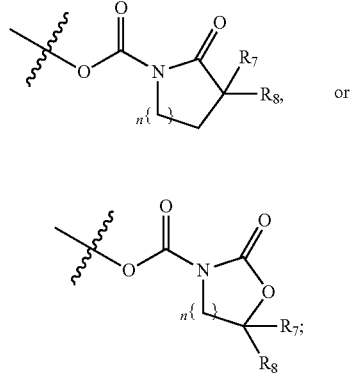

$R_1$, $R_2$, $R_4$, and $R_5$ are each hydrogen; and $R_6$, $R_7$, $R_8$, L, Z, Y, m, n, and p are as defined above. In certain specific embodiments, $R_3$ is —OC(O)$OR_{16}$, —OC(O)$R_{16}$ or —OC(O)$NR_{16}R_{17}$ and $R_{16}$ and $R_{17}$ are each independently $C_1$-$C_4$ alkyl.

In certain embodiments, $R_1$ is —OC(O)$R_6$ or —OC(O)$OR_6$ and $R_2$, $R_3$, $R_4$ and $R_5$ are each independently hydrogen, halogen, —$CF_3$, $C_1$-$C_8$ alkyl, optionally substituted phenyl, —$OR_6$, or —C(O)$OR_6$. Preferably, $R_2$, $R_3$, $R_4$ and $R_5$ are each hydrogen. In some preferred embodiments, $R_2$, $R_3$, $R_4$ and $R_5$ are each hydrogen, $R_1$ is —OC(O)$OR_6$ and $R_6$ is $C_1$-$C_8$ alkyl, and more preferred, $R_6$ is $C_1$-$C_3$ alkyl.

In certain embodiments, $R_1$ is —OC(O)$OR_6$ or —OC(O)$OR_6$ and $R_2$, $R_3$, $R_4$ and $R_5$ are each hydrogen. More preferably, $R_1$ is —OC(O)$OR_6$, $R_2$, $R_3$, $R_4$ and $R_5$ are each hydrogen, and $R_6$ is $C_1$-$C_8$ alkyl. In other certain embodiments, $R_1$ is —OC(O)$OCH_3$, —OC(O)$OCH_2CH_3$ or —OC(O)OCH($CH_3$)$_2$; and $R_2$, $R_3$, $R_4$ and $R_5$ are each independently hydrogen, halogen, —$CF_3$, $C_1$-$C_8$ alkyl, optionally substituted phenyl, —$OR_6$, or —C(O)$OR_6$. In a preferred embodiment $R_1$ is —OC(O)$OCH_3$ or —OC(O)OCH($CH_3$)$_2$; and $R_2$, $R_3$, $R_4$ and $R_5$ are each independently hydrogen, halogen, or —$CF_3$.

In some embodiments, specific examples of compounds or pharmaceutically acceptable salts or hydrates of the compounds of Formula I include, without limitation:

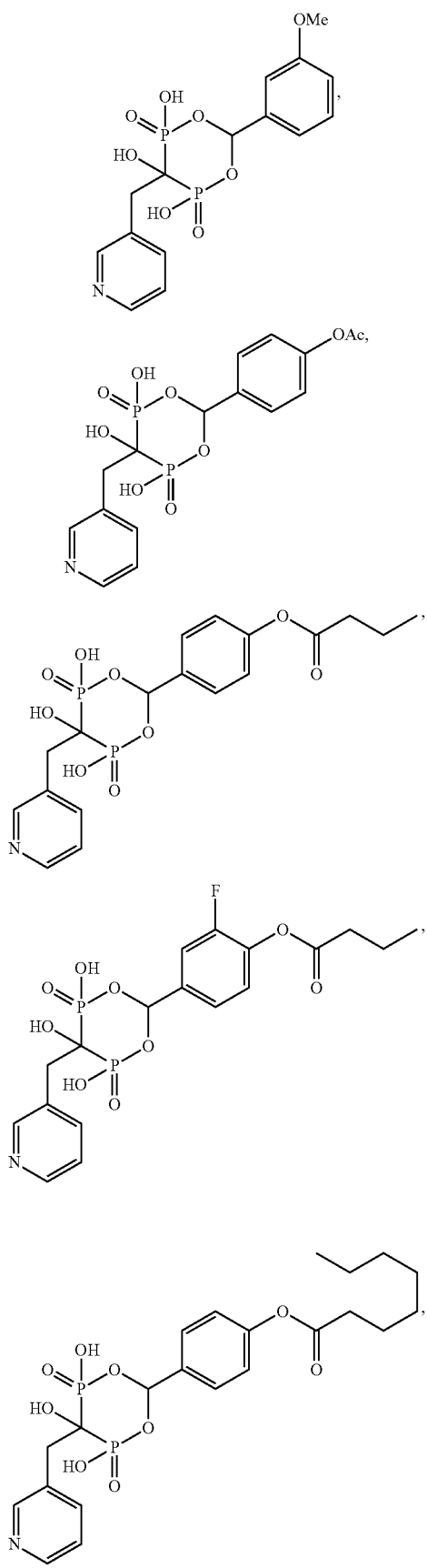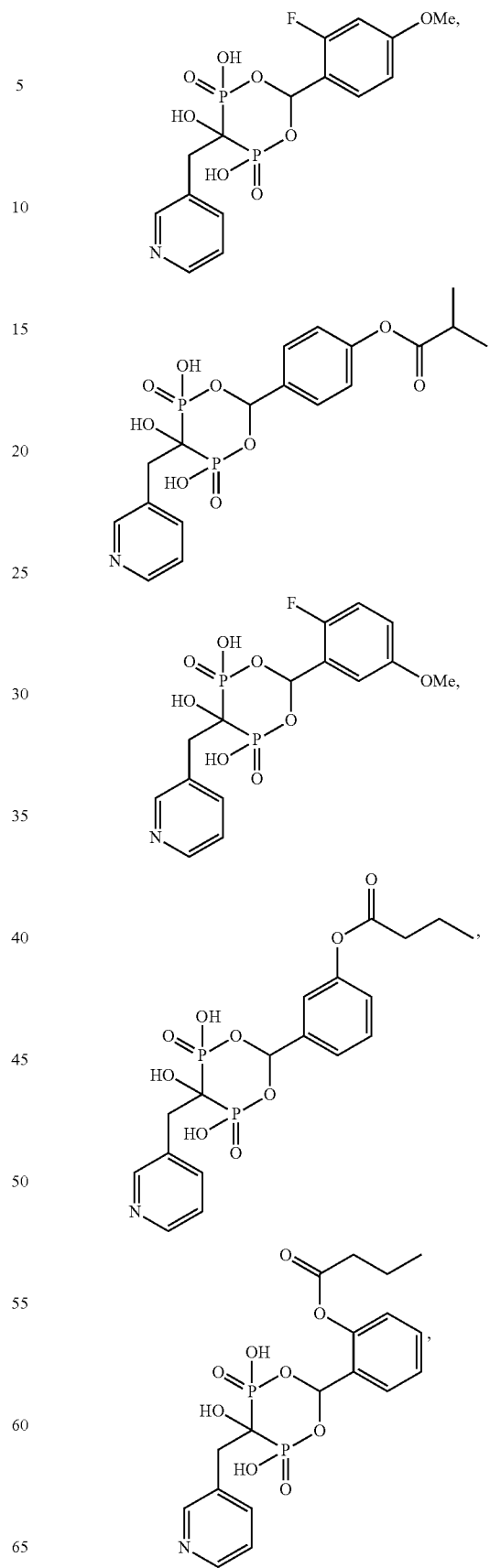

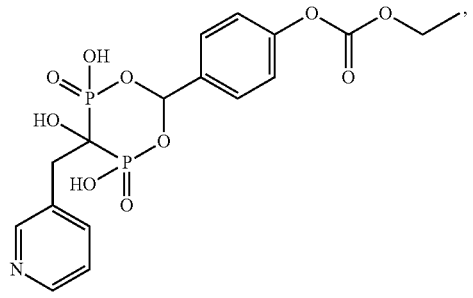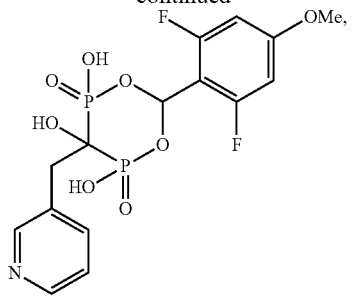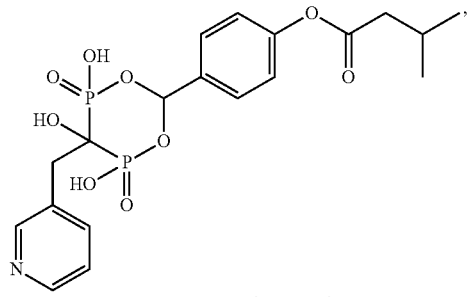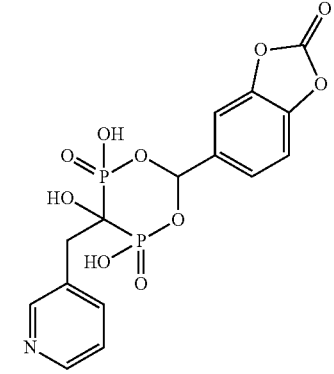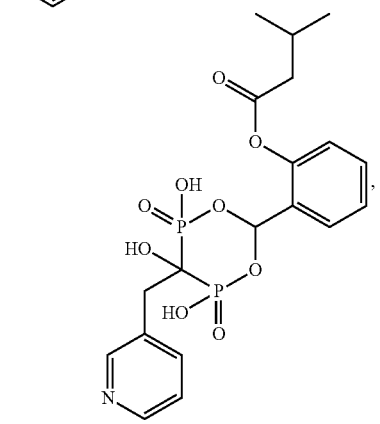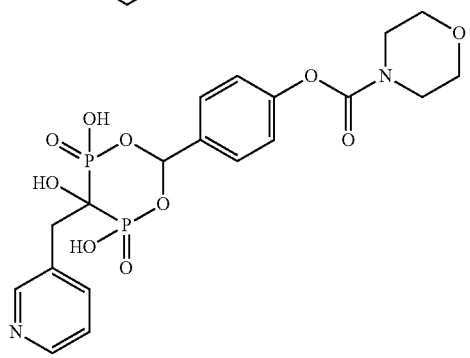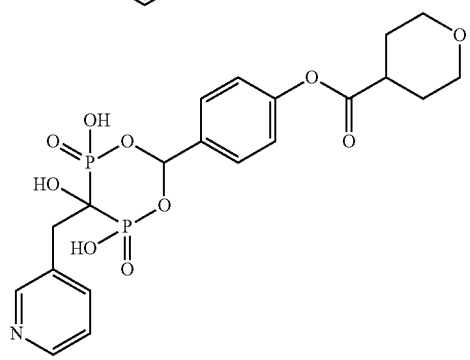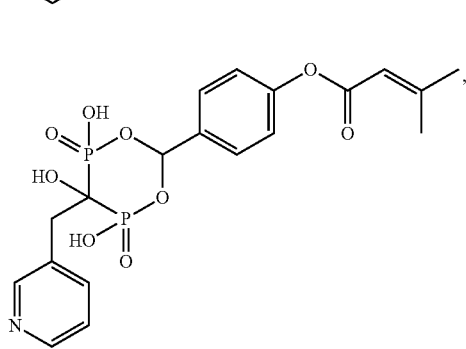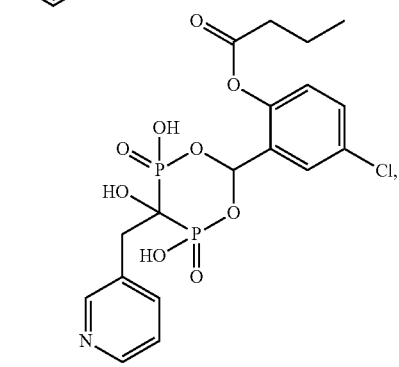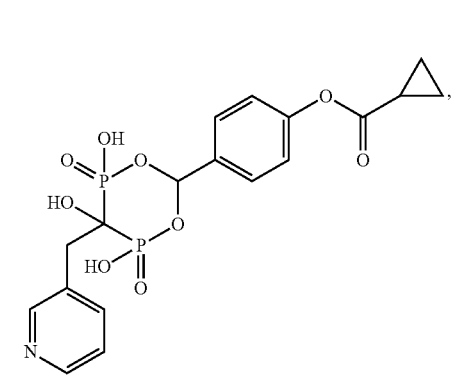

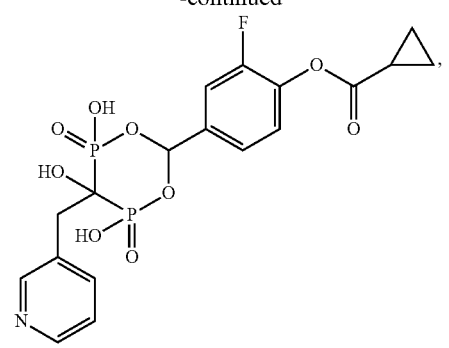
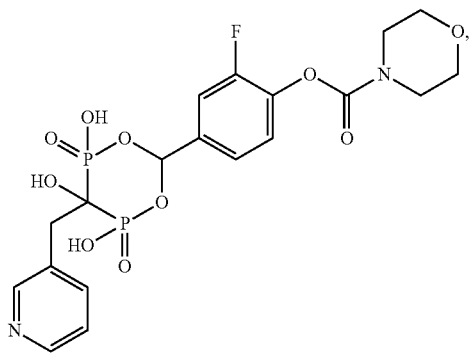
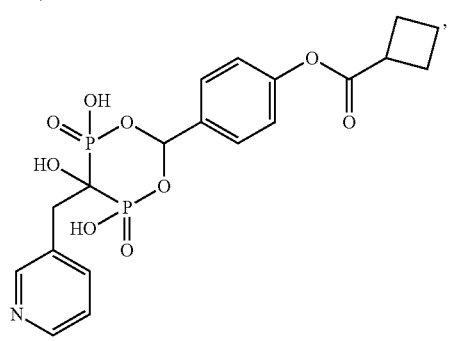
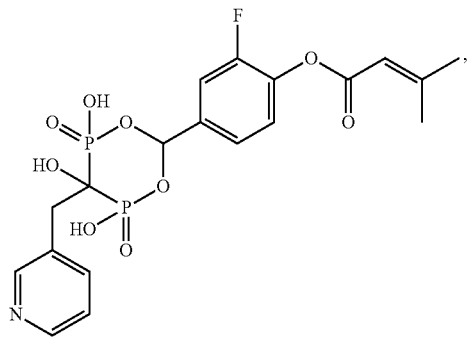
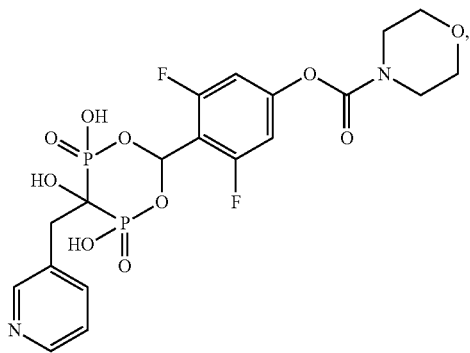
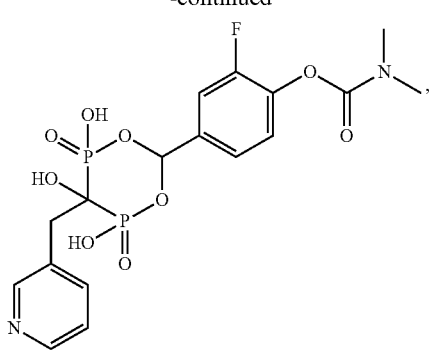
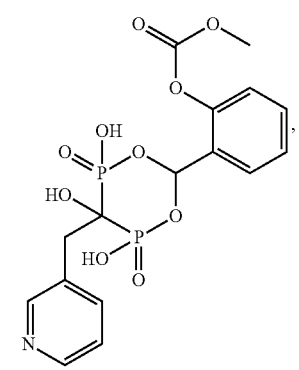
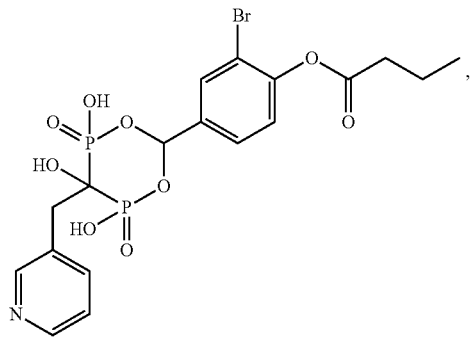
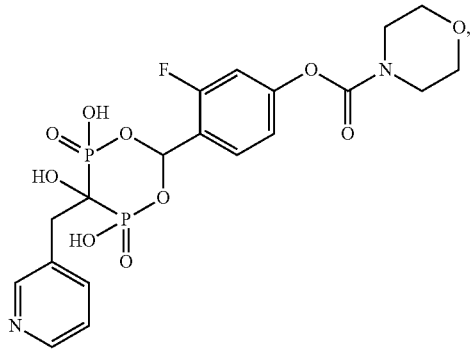

25
-continued
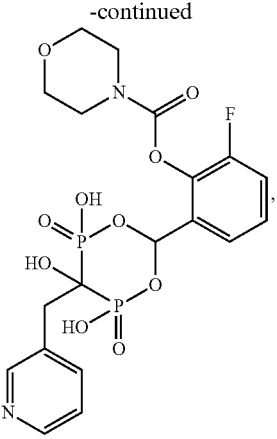
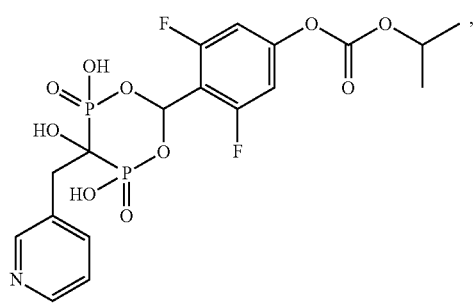
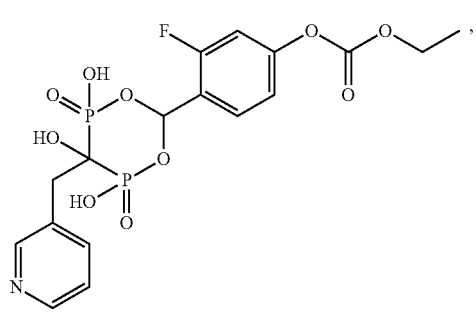
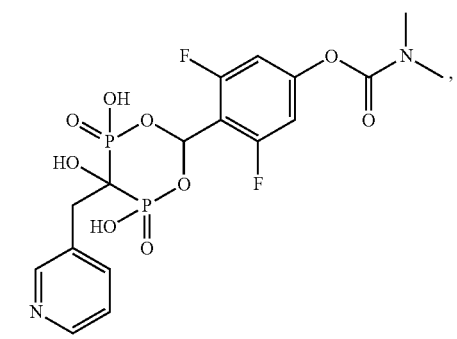
26
-continued
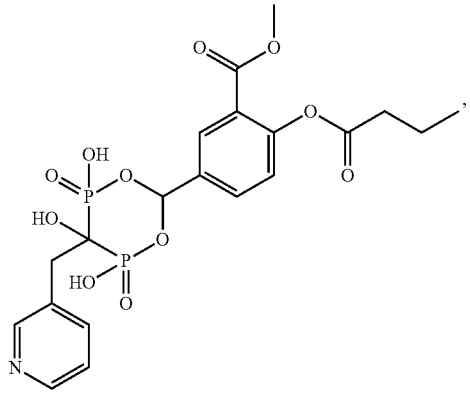
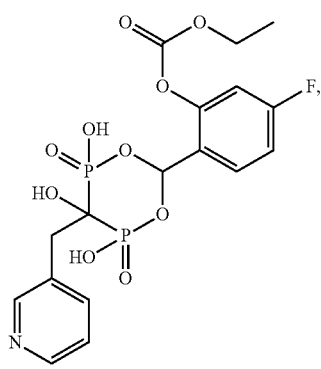
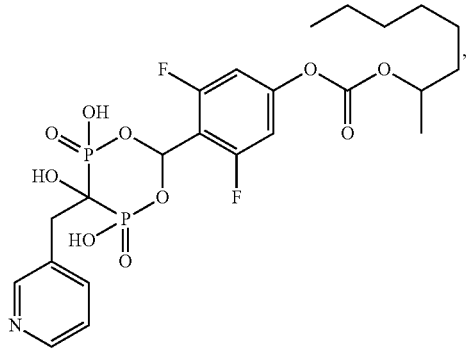
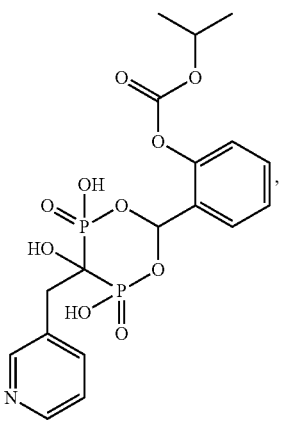

27
-continued
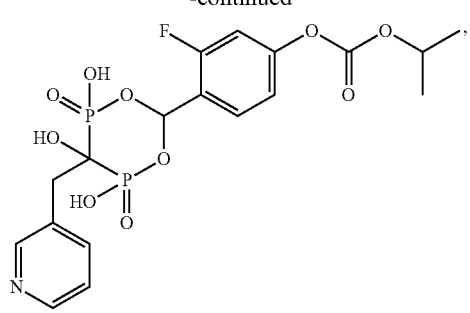
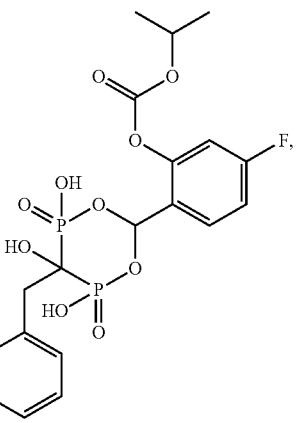
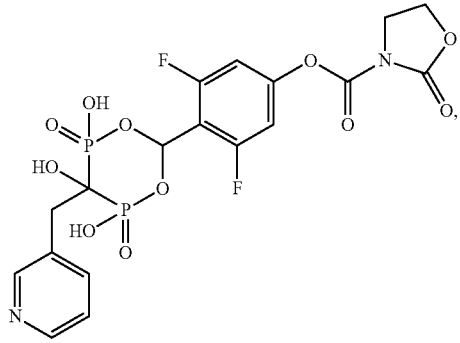
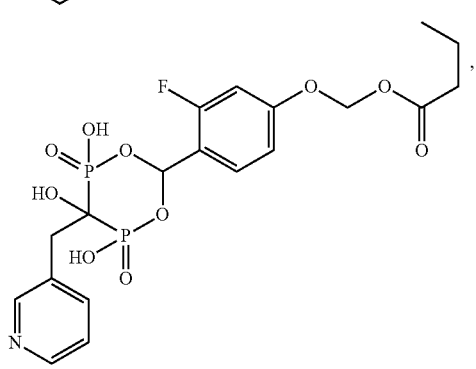
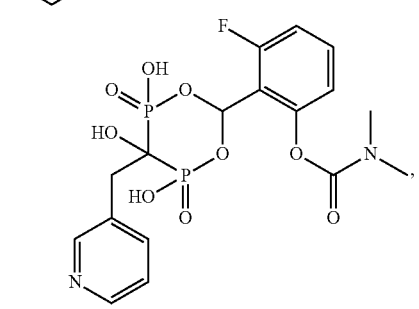
28
-continued
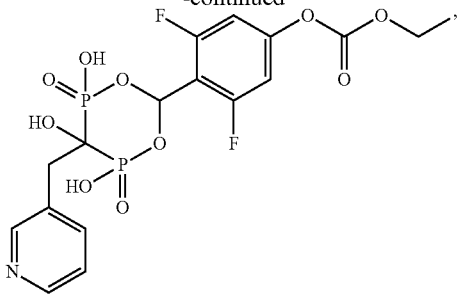
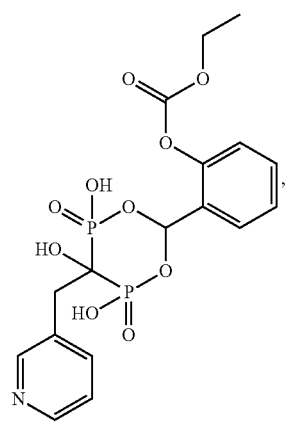
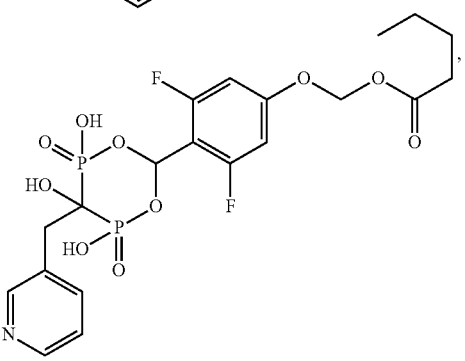
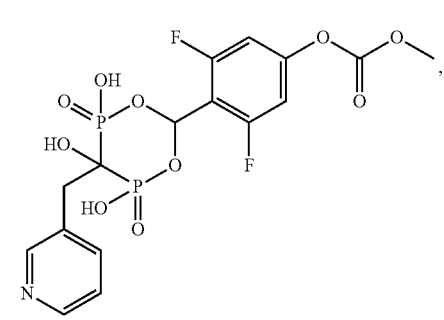
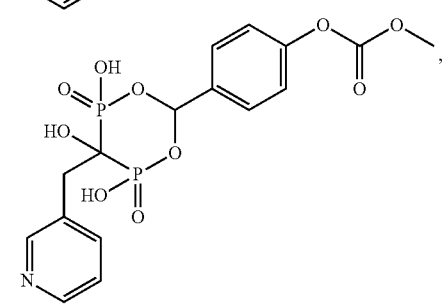

-continued
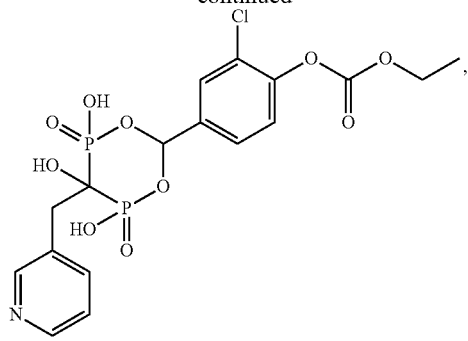
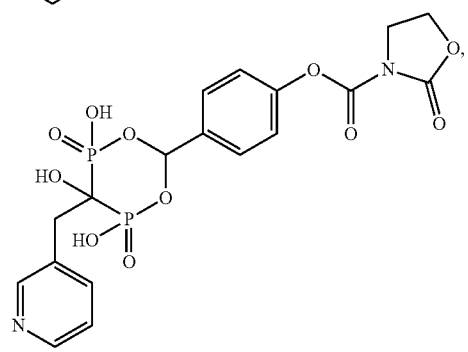
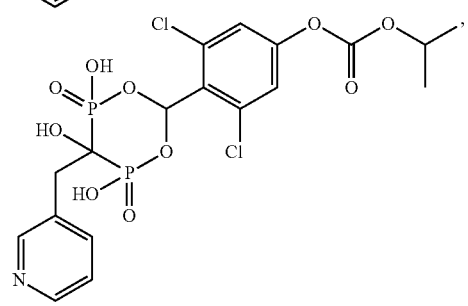
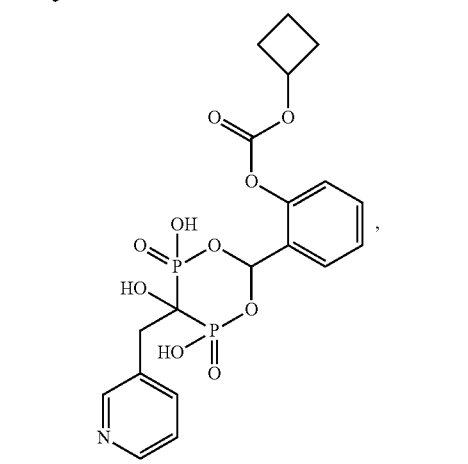
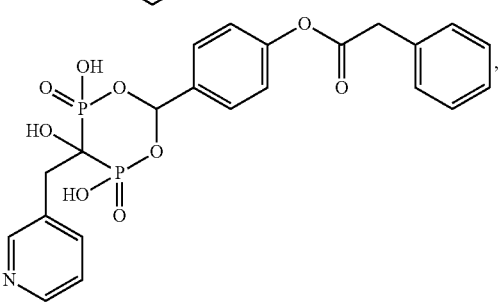
-continued
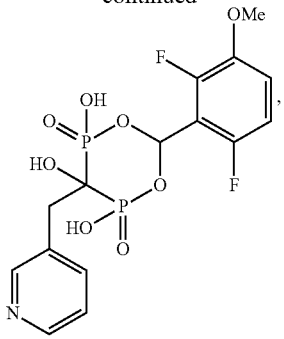
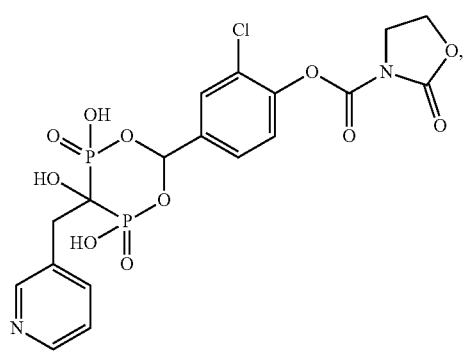
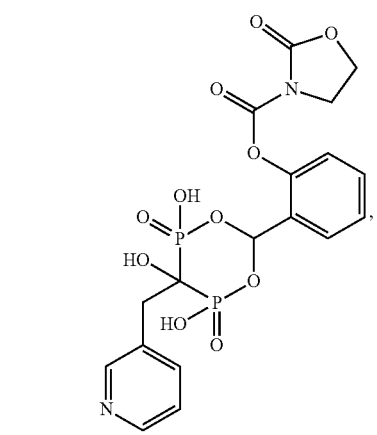
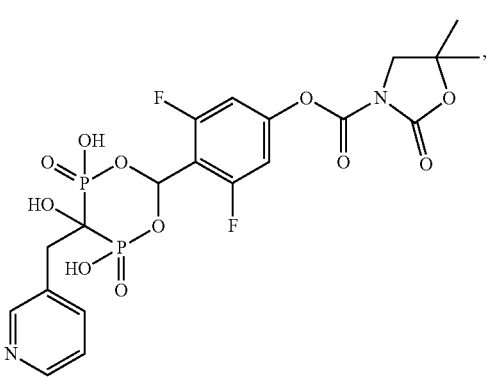

-continued
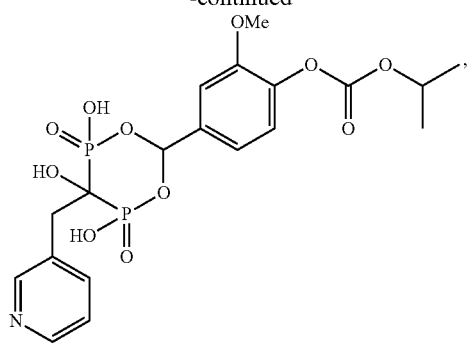
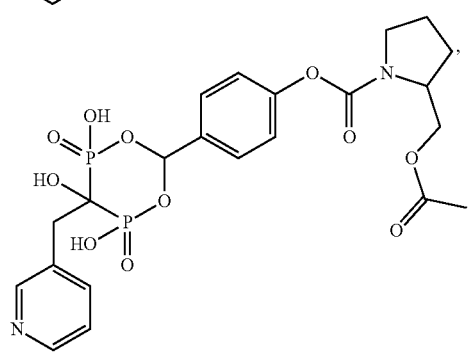
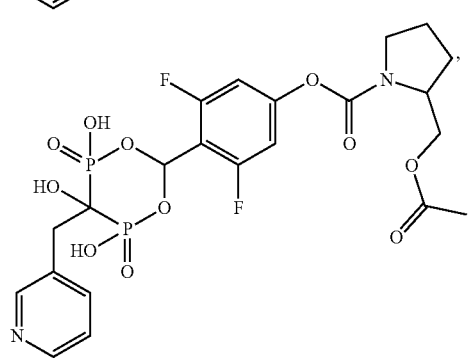
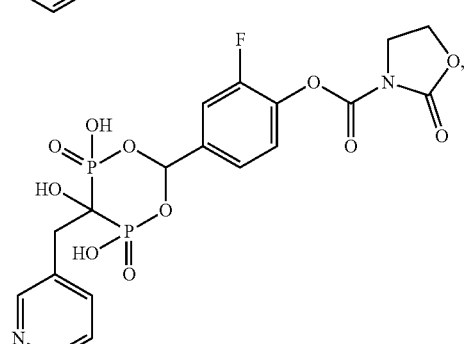
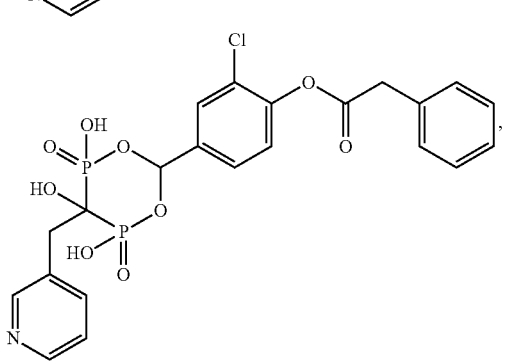
-continued
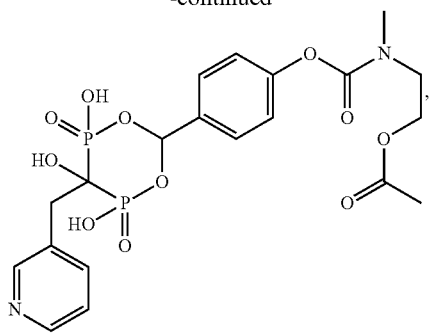
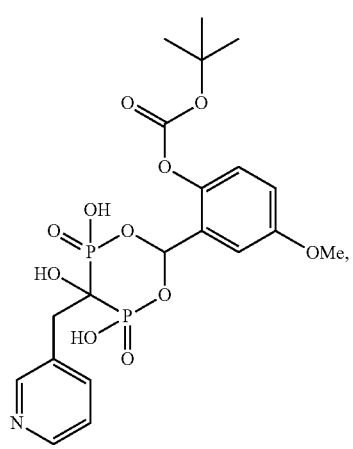
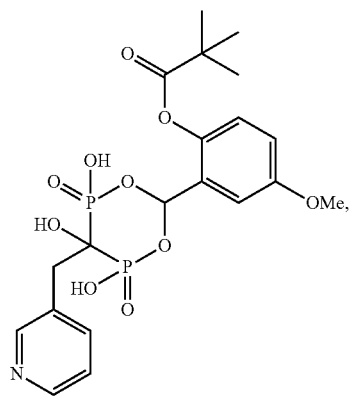
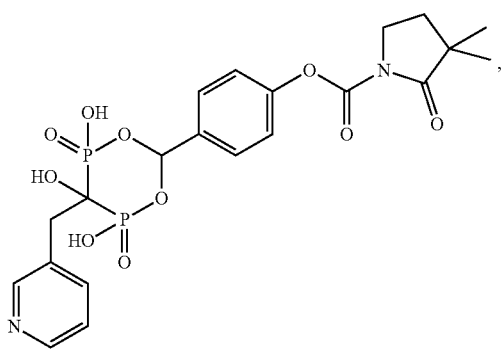

33
-continued
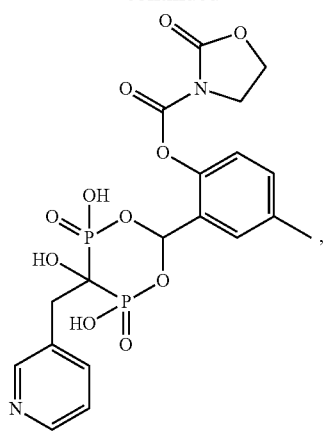
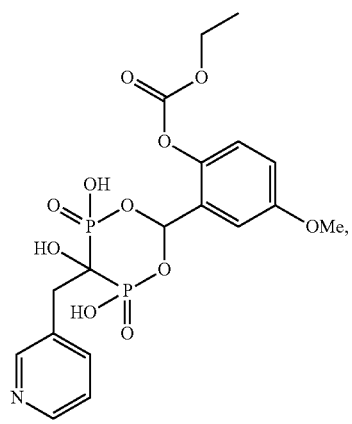
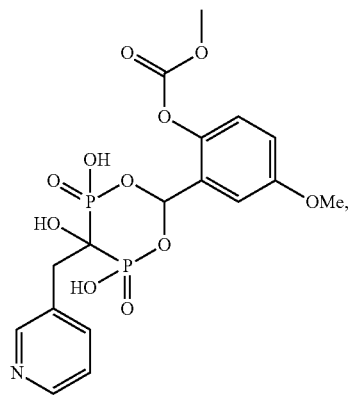
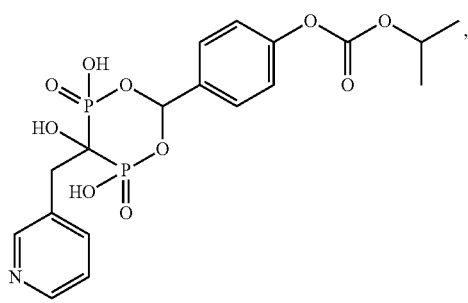
34
-continued
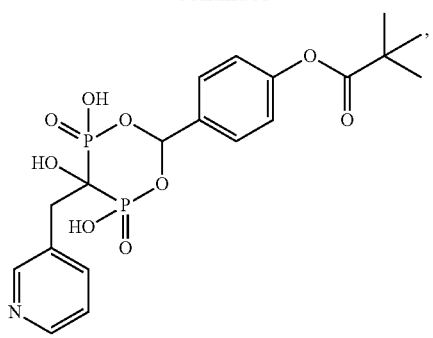
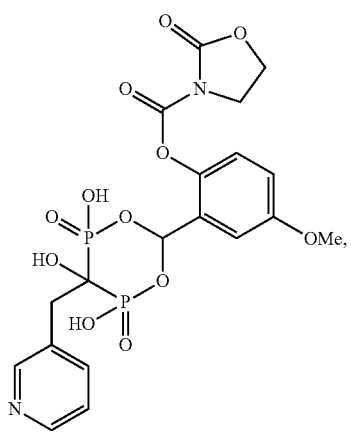
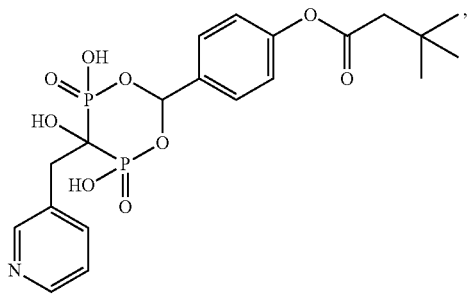
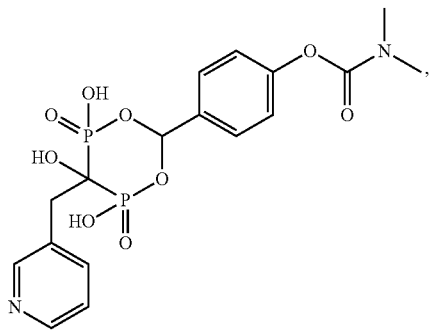

35
-continued
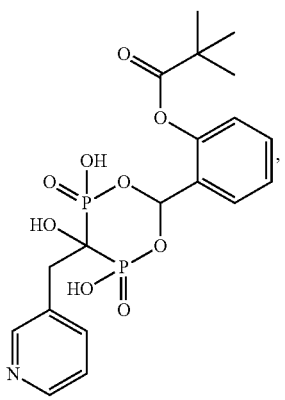
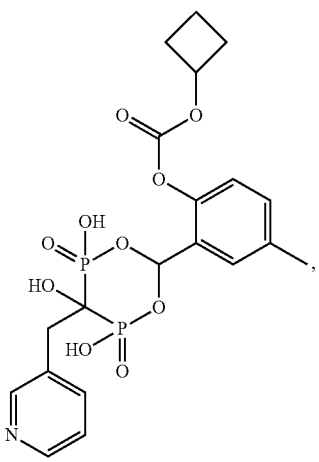

36
-continued
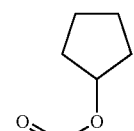
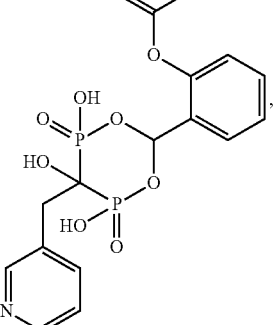
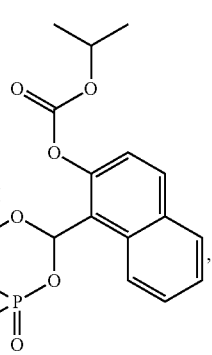
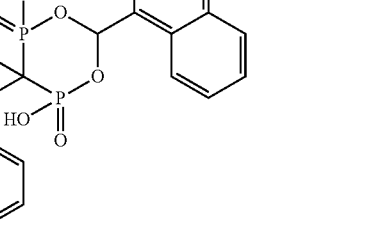
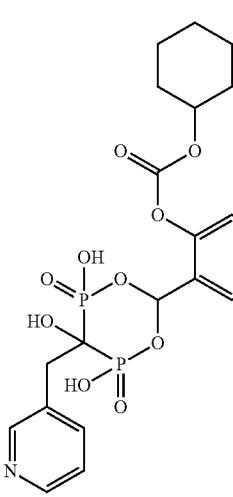

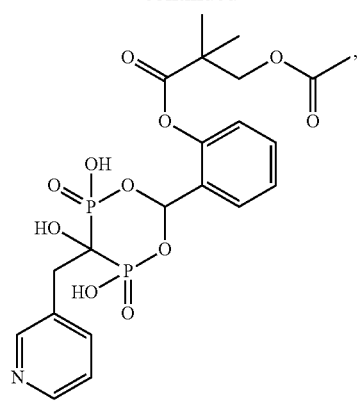
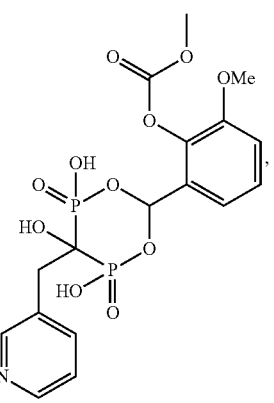
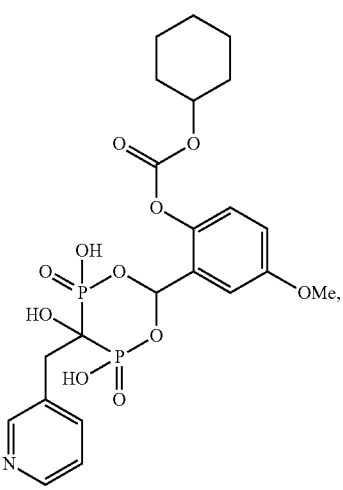
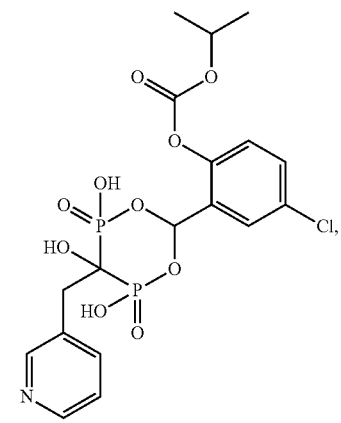
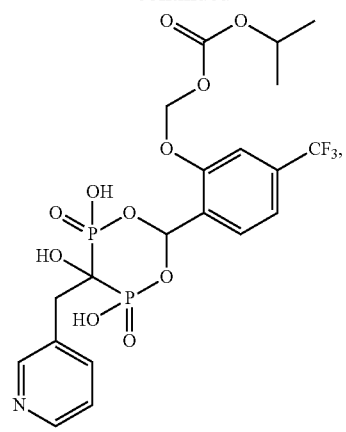
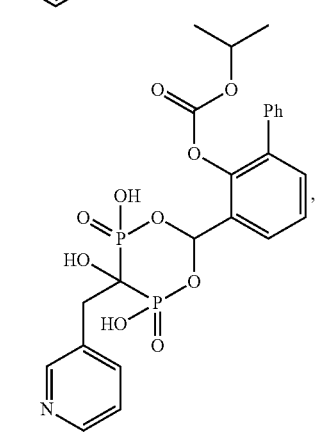
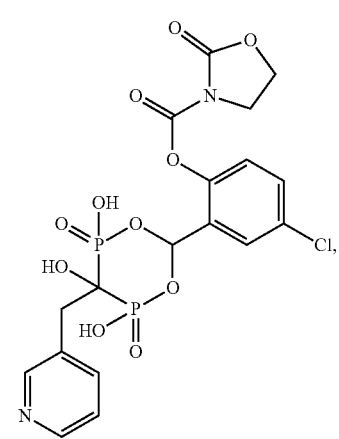
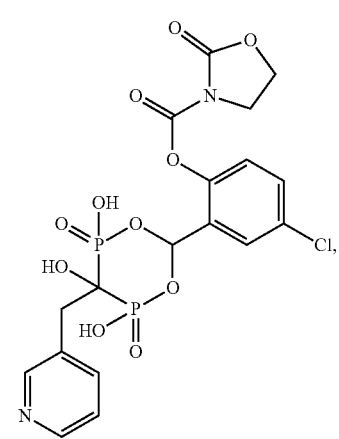

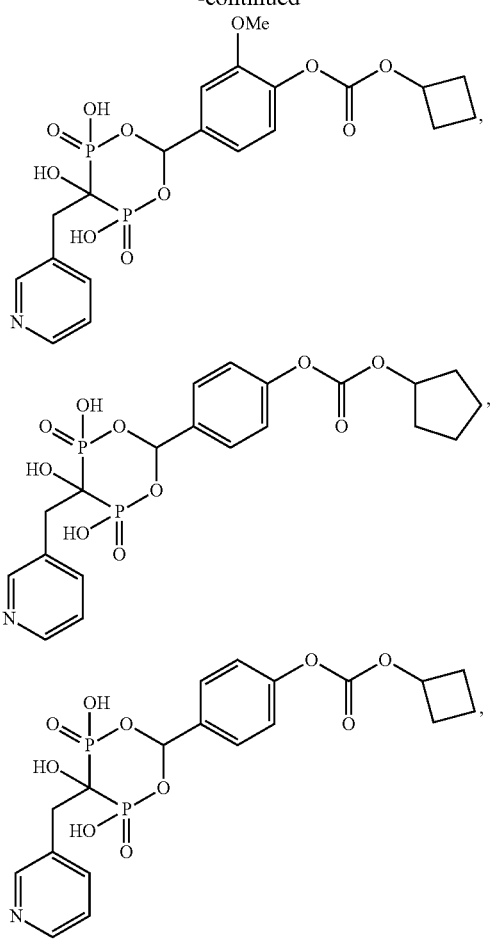
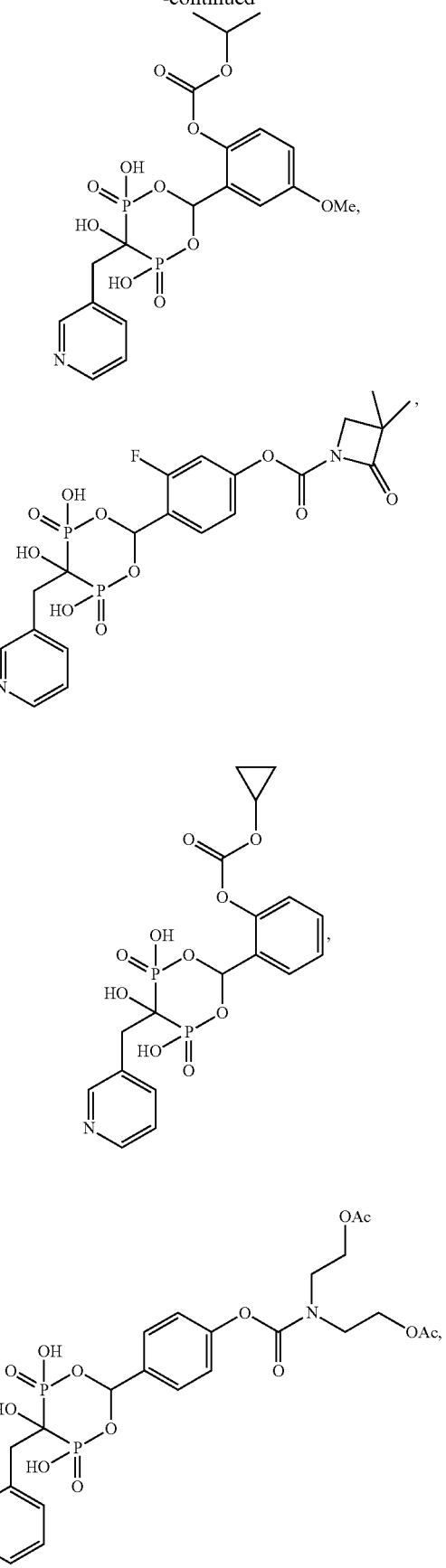

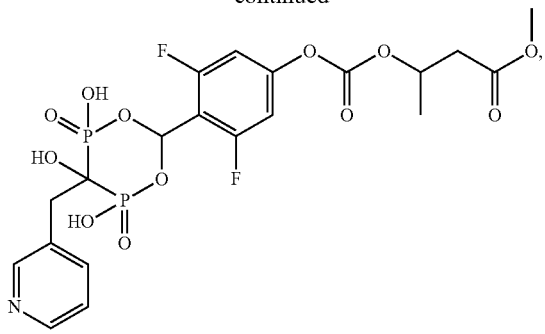
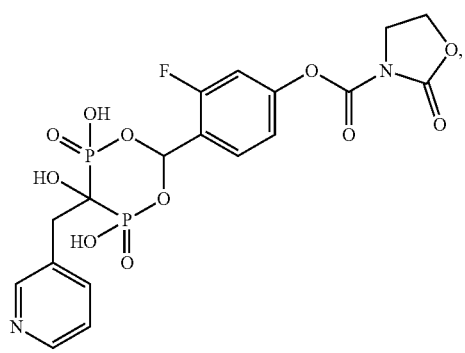
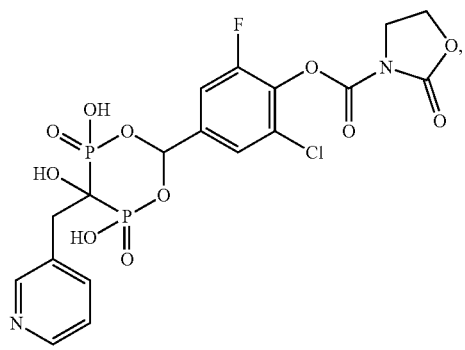
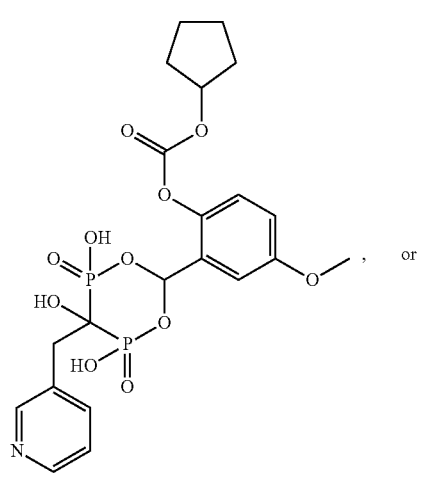
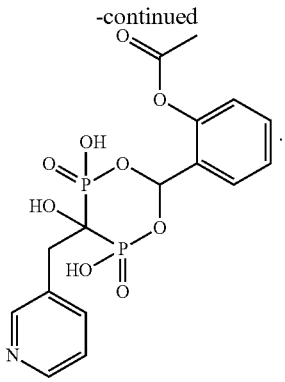
In another aspect, compounds of Formula II or a pharmaceutically-acceptable salt or hydrate thereof are provided:
(II)
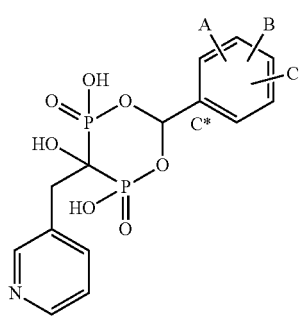
where A is —OR$_6$, —CO$_2$R$_6$, -L-OC(O)R$_6$, —O-L-OC(O)R$_6$, —O-L-OC(O)OR$_6$, —OC(O)R$_6$, —OC(O)-L-OC(O)R$_6$, —OC(O)OR$_6$, —OC(O)O-L-C(O)R$_7$, —OC(O)O-L-C(O)OR$_7$, —C(O)NR$_6$R$_7$, —CNR$_6$R$_7$, —OC(O)NR$_6$R$_7$, —OC(O)N(R$_6$)-L-OC(O)R$_7$, —OC(O)N(-L-OC(O)R$_7$)(-L-OC(O)R$_8$),
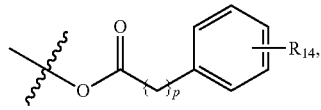
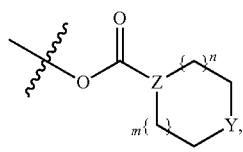
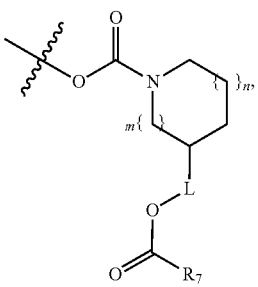

-continued

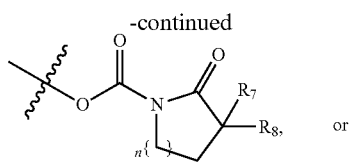

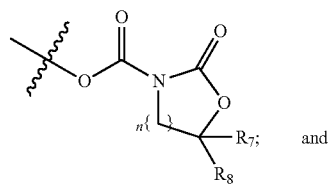

B and C are each independently hydrogen, halogen, —$CF_3$, —CN, $C_1$-$C_8$ alkyl, phenyl, —$OR_6$, or —$C(O)OR_6$, or B and C when taken together form an optionally substituted 4- to 8-membered carbocyclic or heterocyclic ring, wherein the ring is saturated, unsaturated or aromatic;

wherein m and n are each independently an integer from 0 to 2; Y is —$CH_2$—, —O—, —$NR_7$—, or —S—; p is an integer from 1 to 3;

Z is

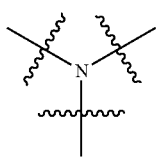

or

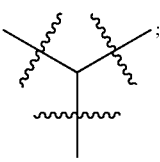

each $R_6$ is independently hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl; L is $C_1$-$C_8$ alkyl; $R_{14}$ is hydrogen, halogen, $C_1$-$C_8$ alkyl, or $C_1$-$C_8$ alkoxyl; $R_7$ and $R_8$ are each independently hydrogen or $C_1$-$C_8$ alkyl;

or $R_6$ and $R_7$ taken together form an optionally substituted 4- to 8-membered carbocyclic or heterocyclic ring, wherein the ring is saturated, unsaturated or aromatic.

In some embodiments, A is in the ortho or para position relative to C. In other embodiments, A is in the meta position relative to C*.

In some embodiments, the compound provided is a compound or a pharmaceutically acceptable salt or hydrate of a compound of Formula IIa, IIb, IIc, IId, or IIe:

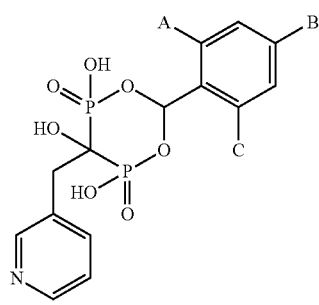 (IIa)

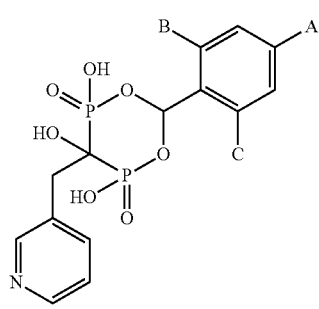 (IIb)

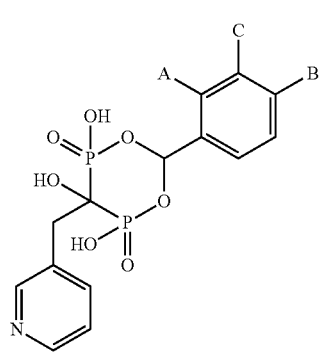 (IIc)

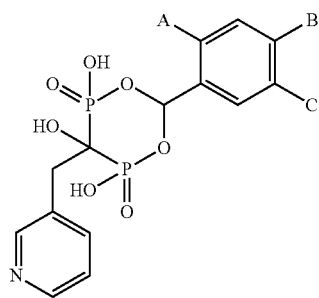 (IId)

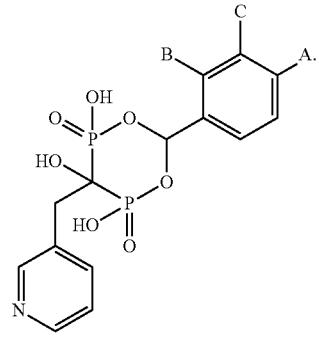 (IIe)

In some embodiments, A is —$OC(O)NR_6R_7$, —$OC(O)R_6$, or —$OC(O)OR_6$.

In some embodiments, $R_6$ and $R_7$ are each independently hydrogen or $C_1$-$C_8$ alkyl.

In some embodiments, B and C are each independently hydrogen, cyano, halogen, or —OC(O)$R_6$.

In some embodiments, B and C are each independently halogen.

In some embodiments, B and C are each fluoro.

In some embodiments, $R_6$ is hydrogen, methyl, ethyl, propyl, isopropyl, tert-butyl, —CH$_2$CH(CH$_3$)$_2$, pentyl, —CH$_2$C(CH$_3$)$_3$, heptyl, —CH(CH$_3$)(CH$_2$)$_5$CH$_3$, —CH═C(CH$_3$)$_2$, cyclopropyl, cyclobutyl, cyclopentyl, cyclohexyl, benzyl, or tetrahydro-2H-pyranyl.

In some embodiments, $R_6$ is hydrogen, methyl, ethyl, propyl, isopropyl, tert-butyl, —CH$_2$CH(CH$_3$)$_2$, pentyl, —CH$_2$C(CH$_3$)$_3$, heptyl, —CH(CH$_3$)(CH$_2$)$_5$CH$_3$, —CH═C(CH$_3$)$_2$, cyclopropyl, cyclobutyl, cyclopentyl, cyclohexyl, benzyl, or tetrahydro-2H-pyranyl; and $R_7$ and $R_8$ are each independently hydrogen, methyl, ethyl, propyl, isopropyl, tert-butyl.

In some embodiments, L is $C_1$-$C_3$ alkyl.

In some embodiments, a pharmaceutical composition including a compound or a pharmaceutically acceptable salt or hydrate of a compound of Formula I or II and a pharmaceutically acceptable carrier is provided. Preferably, the compound of Formula I or Formula II is selected from one of the specific embodiments disclosed above, and, more preferably, the compound is selected from the examples of compounds listed above.

In some embodiments, the pharmaceutical composition further comprises at least one pharmaceutically active ingredient selected from the group consisting of: an anti-inflammatory, an immunomodulator, a chelator, a musculoskeletal anabolic agent, and a combination thereof.

In yet another aspect, a method of treating or preventing disorders associated with abnormal calcium and phosphate metabolism is disclosed, including administering an effective amount of a compound of Formula I or Formula II, or a pharmaceutically acceptable salt or hydrate thereof to a patient in need of such treatment. Preferably, the compound of Formula I or Formula II is selected from one of the specific embodiments disclosed above, and, more preferably, the compound is selected from the examples of compounds listed above.

In certain specific embodiments of the method of treating or preventing disorders associated with abnormal calcium and phosphate metabolism, the disorder associated with abnormal calcium and phosphate metabolism is osteoporosis, rheumatoid arthritis, osteoarthritis, Paget's disease, alveolar bone loss, bone related cancer, or an orthopedic disorder. In other embodiments, the disorder is a non-skeletal disorder selected from the group consisting of; a non-bone cancer, an inflammatory disorder, an immunomodulatory disorder, and a parasitic disorder.

In further embodiments, the parasitic disorder is selected from the group consisting of malaria, leishmaniasis, a trypanasomal disease, an entamoebal infection, a giardia infection, and a cryptosporidial infection.

In other embodiments of the method of treating or preventing disorders associated with abnormal calcium and phosphate metabolism, the compound of Formula I or Formula II is administered to the subject animal or human, wherein it modifies the activity of farnesyl pyrophosphate synthase in the subject animal or human.

In some embodiments, the method includes administering an effective amount of a compound of Formula II or a pharmaceutically acceptable salt or hydrate thereof to a patient in need of such treatment. In some embodiments, the method includes administering an effective amount of a compound of Formula IIa, IIb, IIc, IId, or IIe or a pharmaceutically acceptable salt or hydrate thereof to a patient in need of such treatment. In some embodiments, the method includes administering an effective amount of a compound or a pharmaceutically acceptable salt or hydrate of a compound selected from:

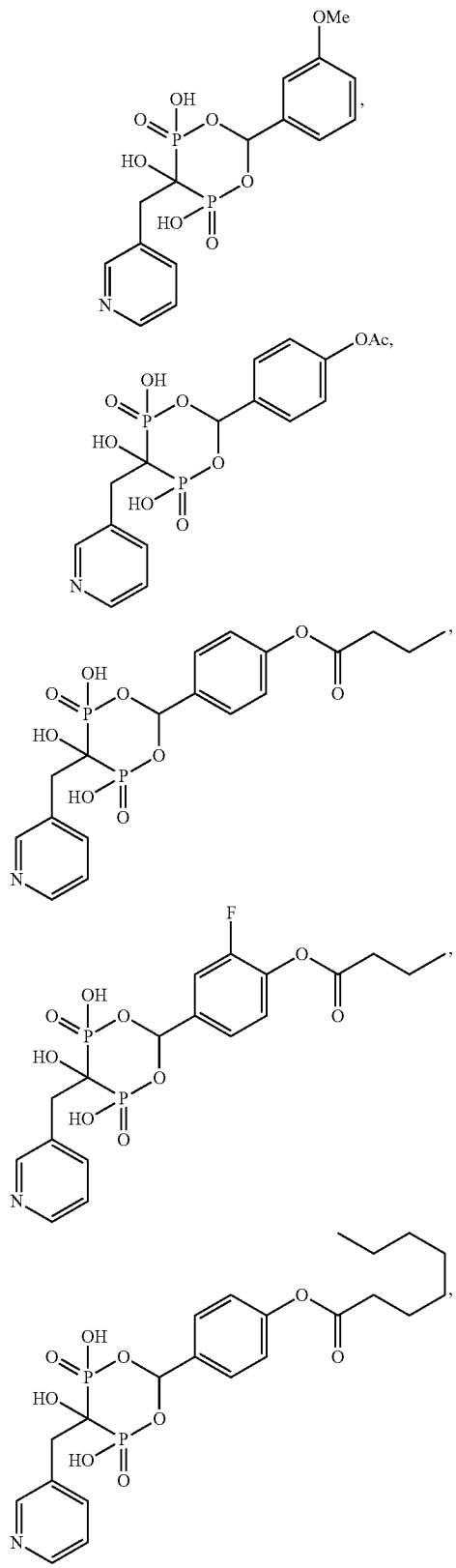

47
-continued
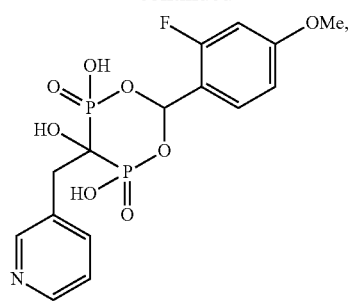
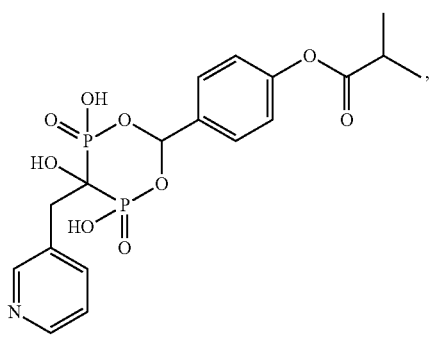
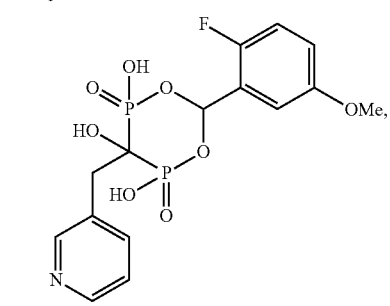
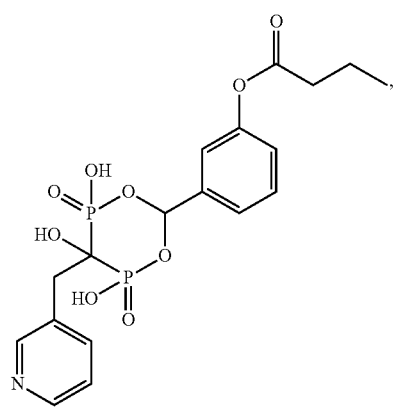
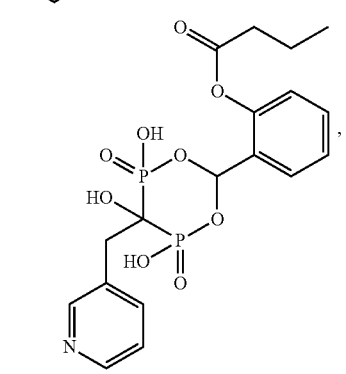
48
-continued
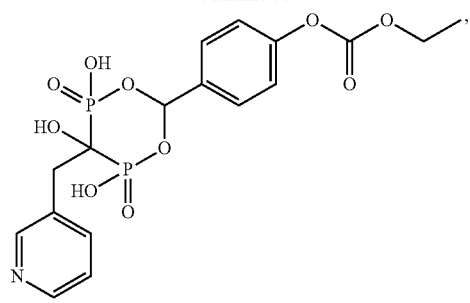
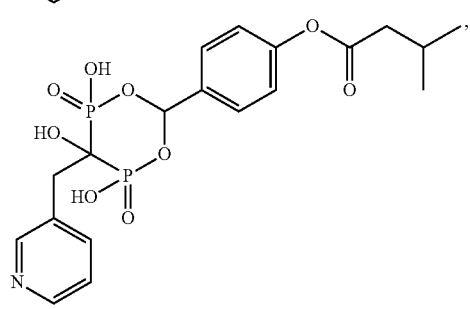
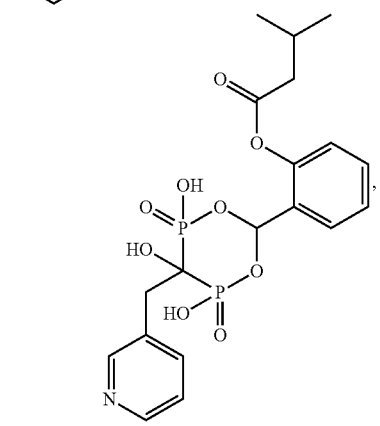
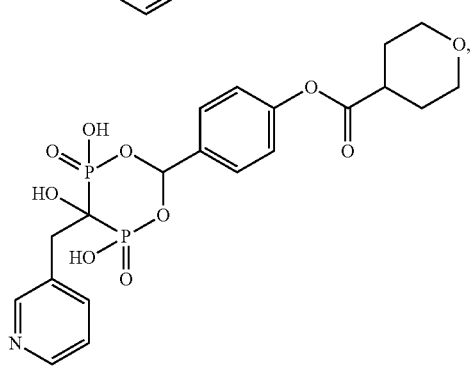
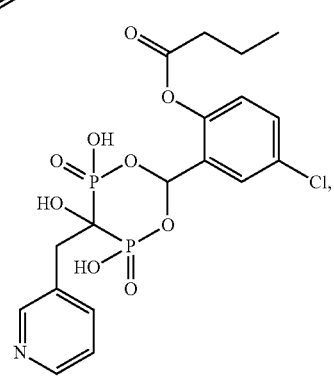

49
-continued
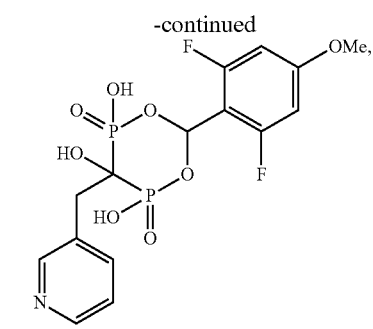
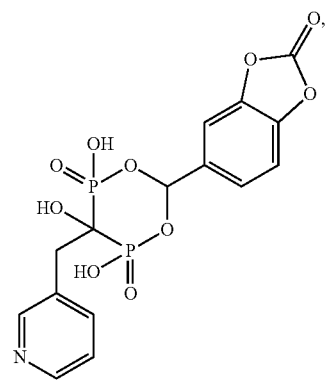
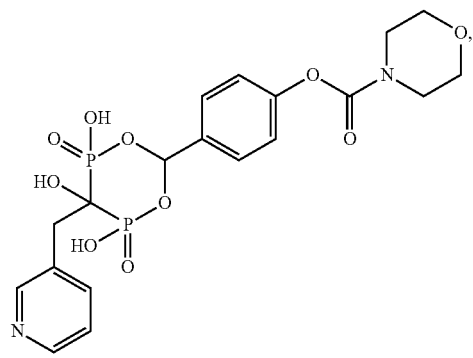
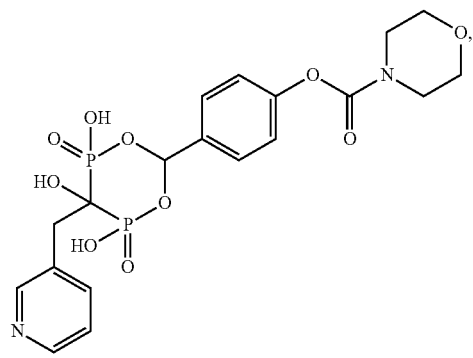
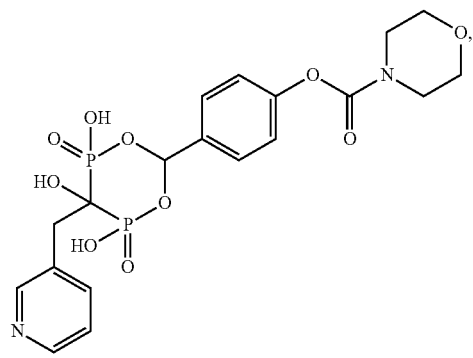
50
-continued
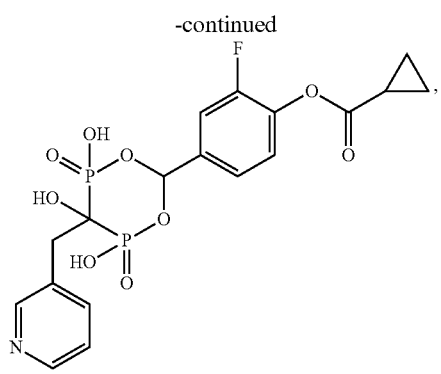
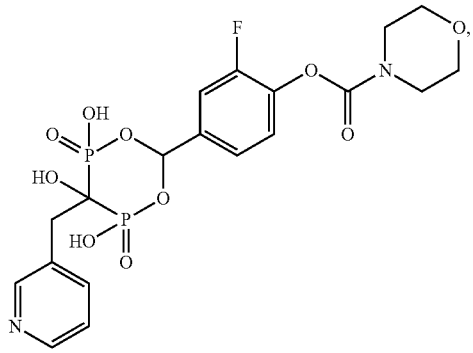
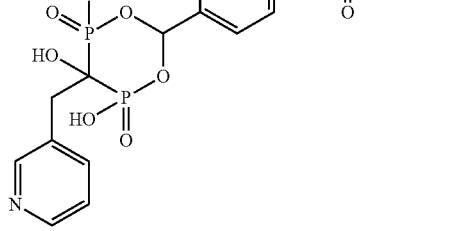
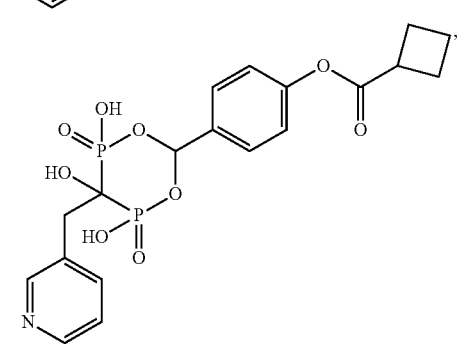
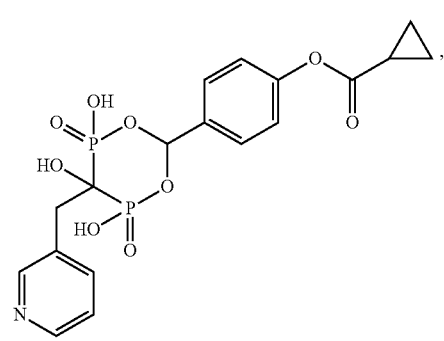

51
-continued
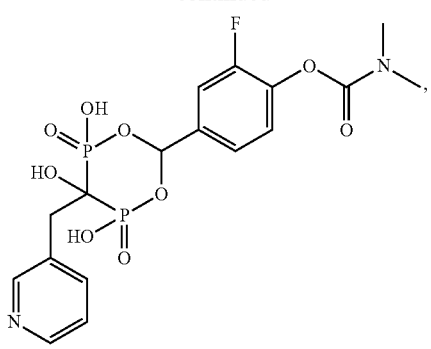
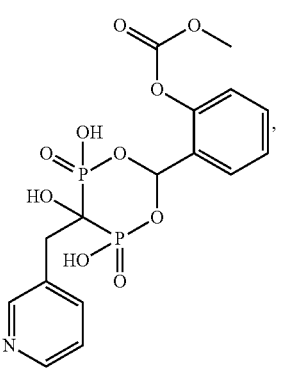
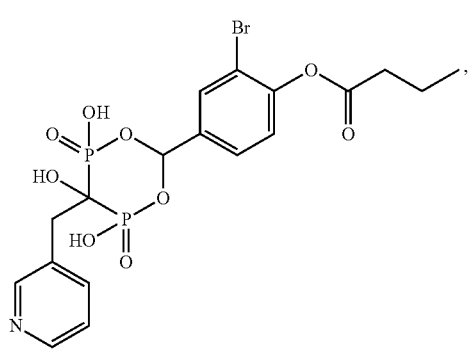
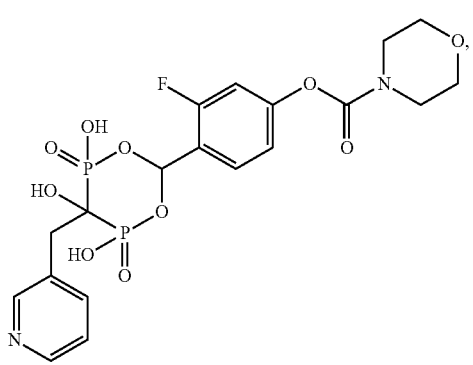
52
-continued
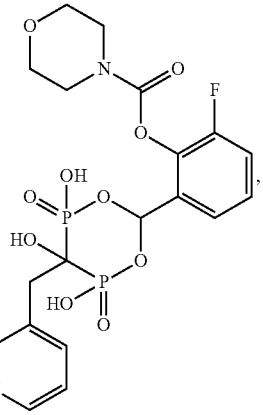
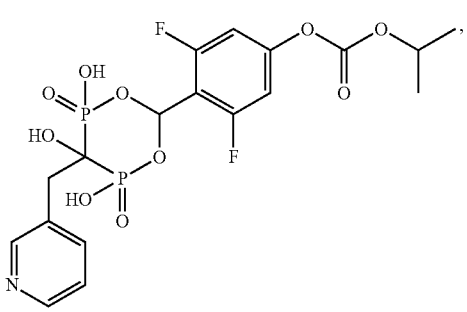
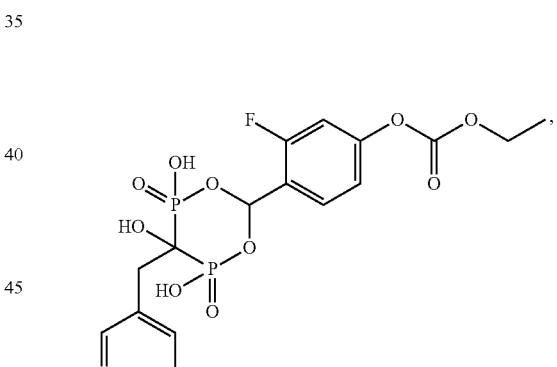
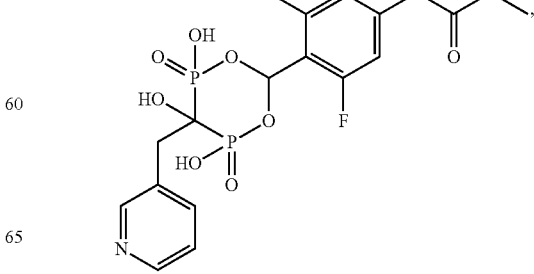

53
-continued
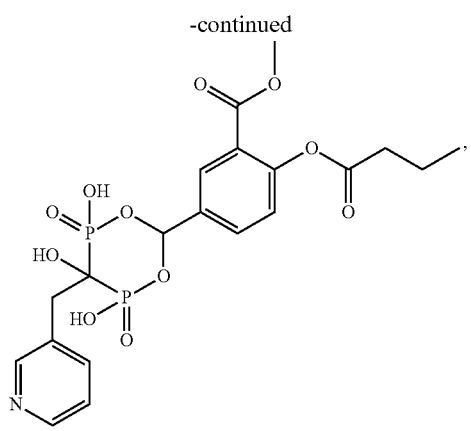
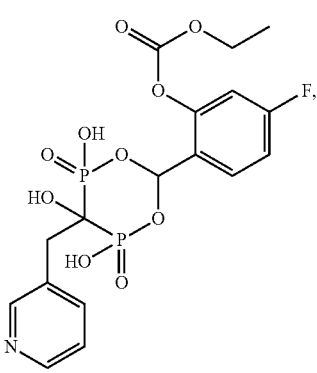
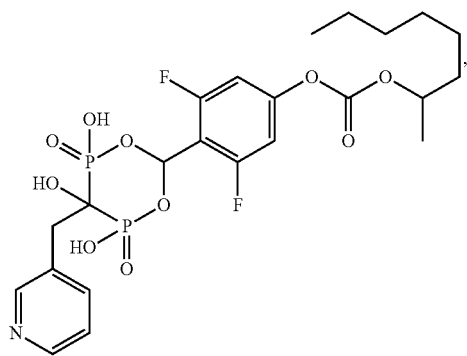
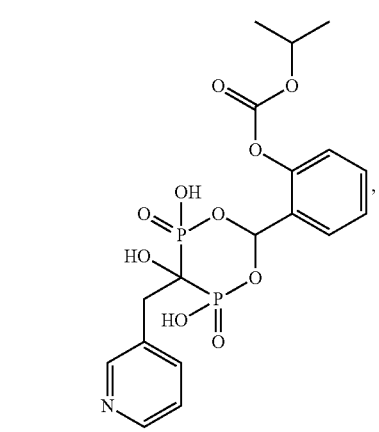
54
-continued
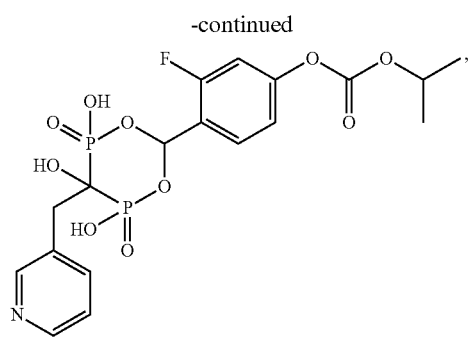
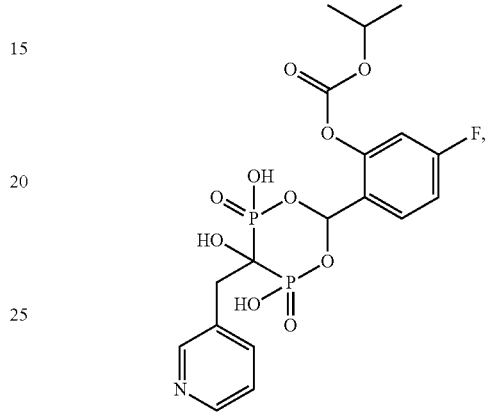
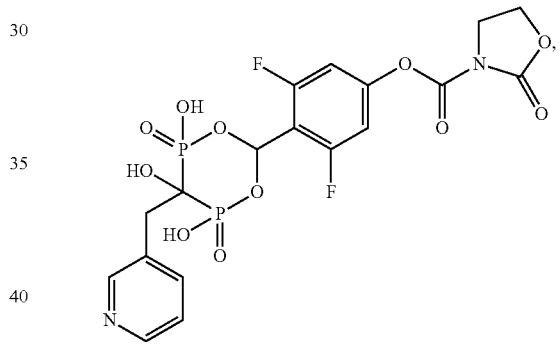
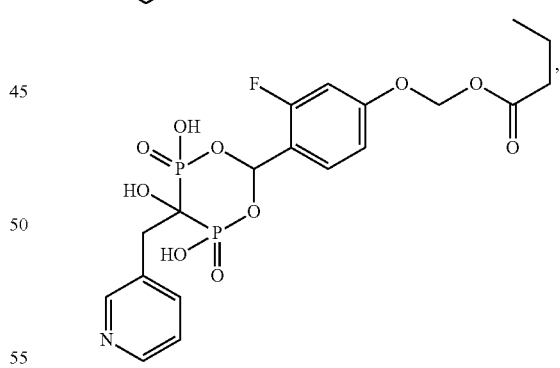
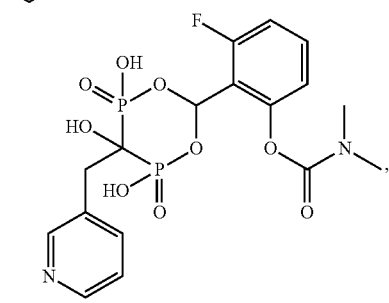

55
-continued
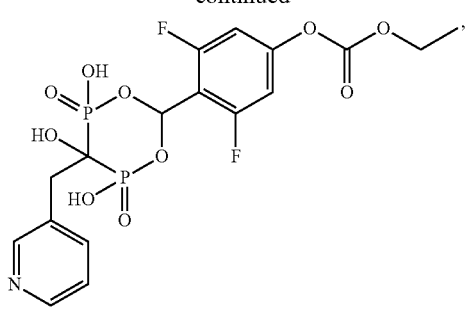
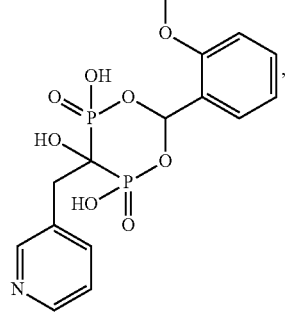
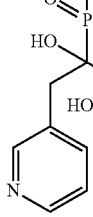
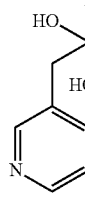
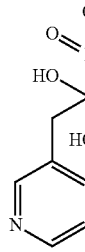
56
-continued
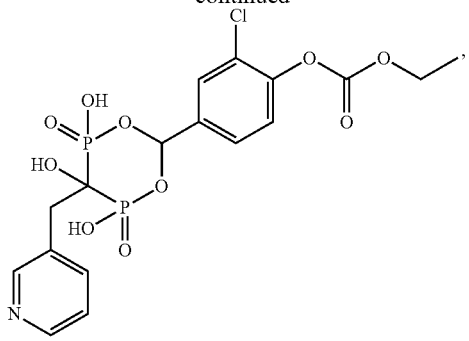
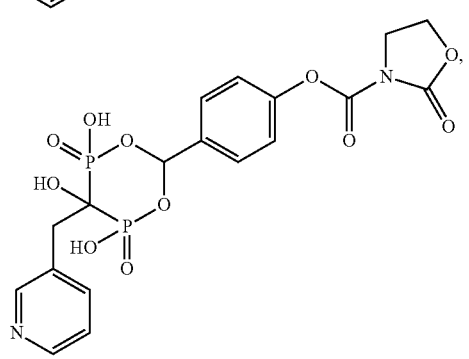
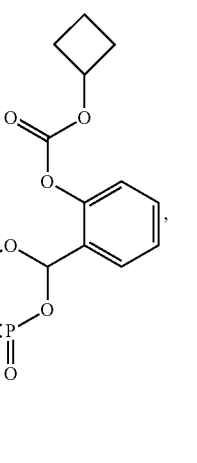
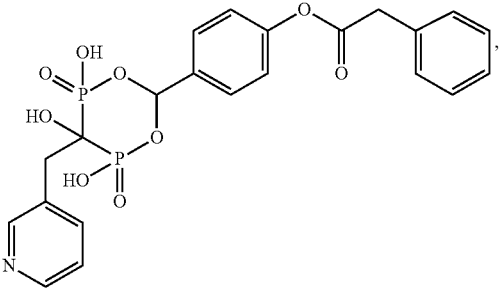

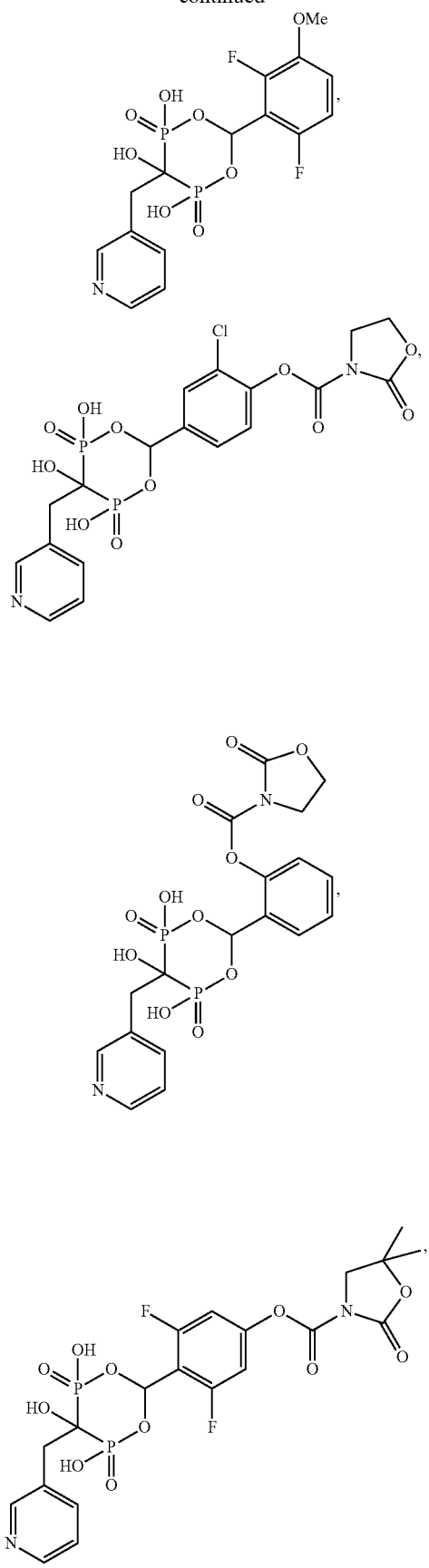
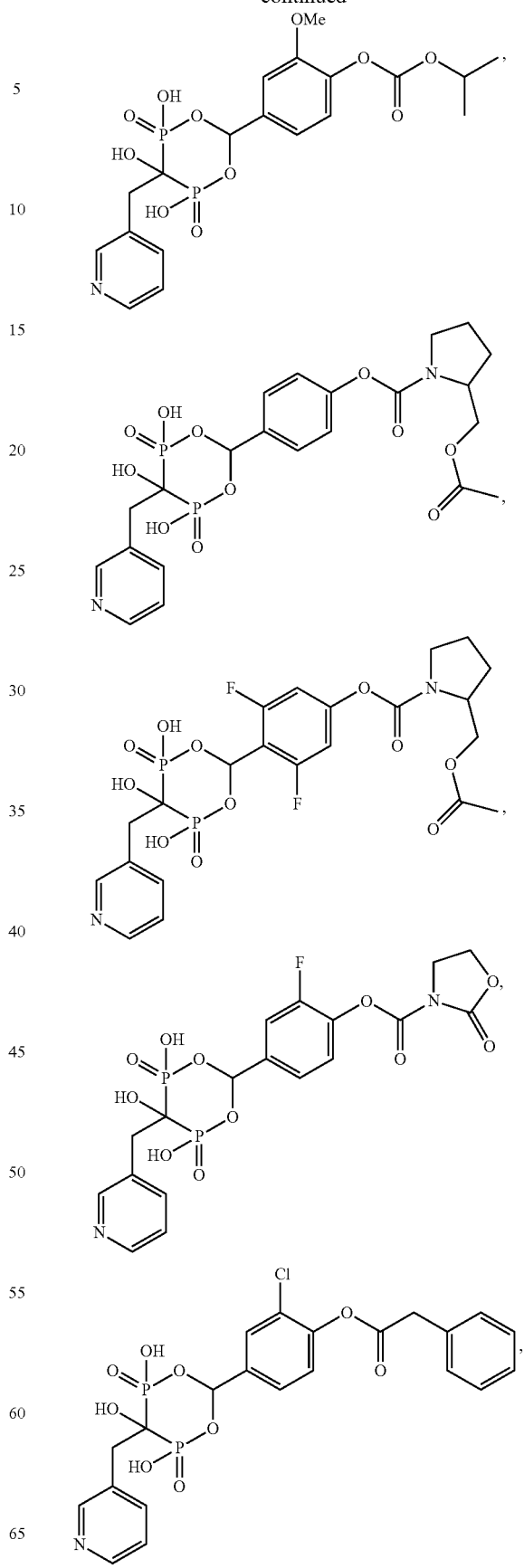

59
-continued
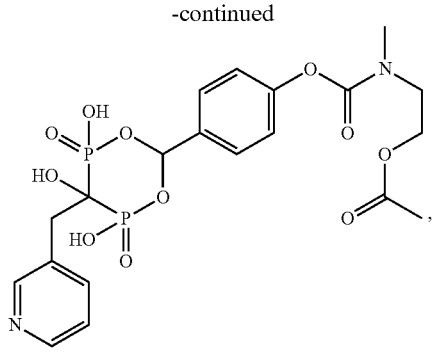
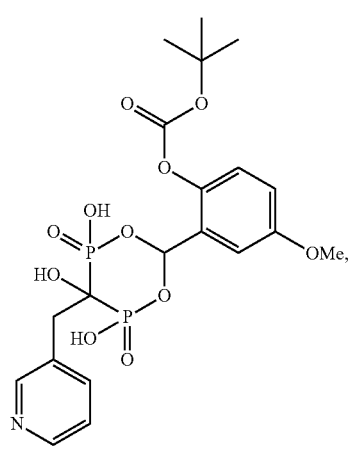
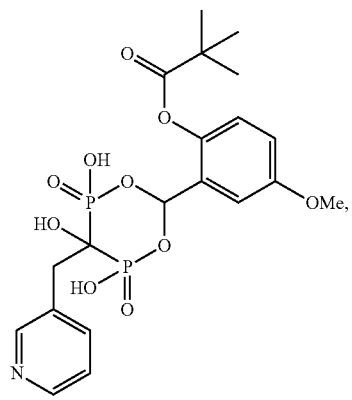
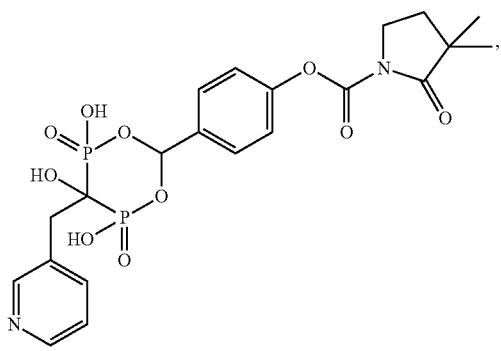
60
-continued
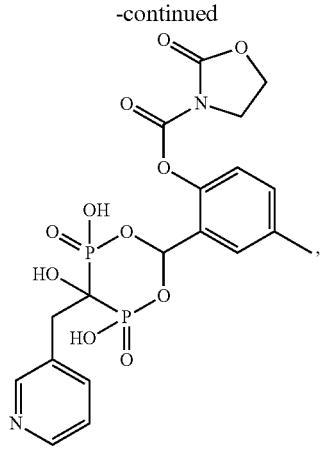
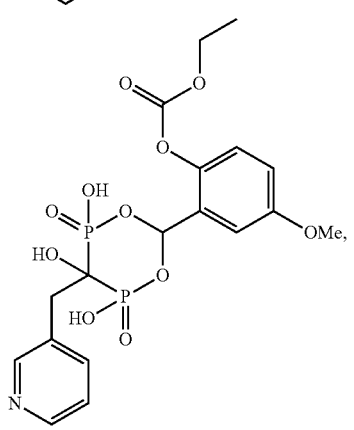
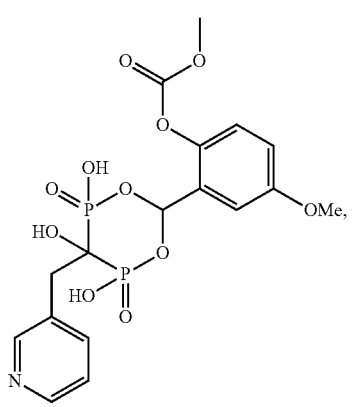
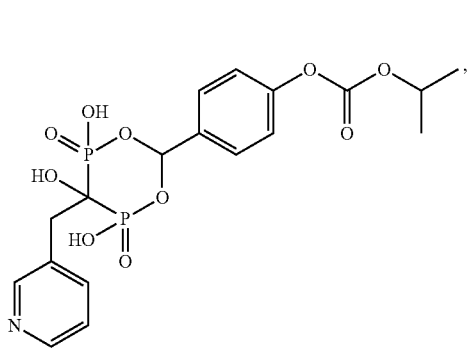

61
-continued
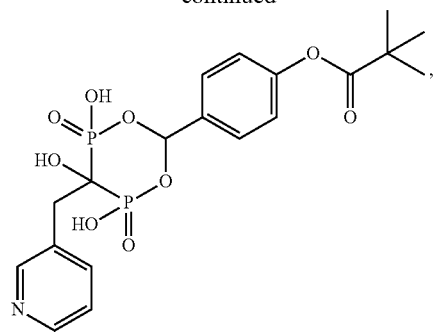
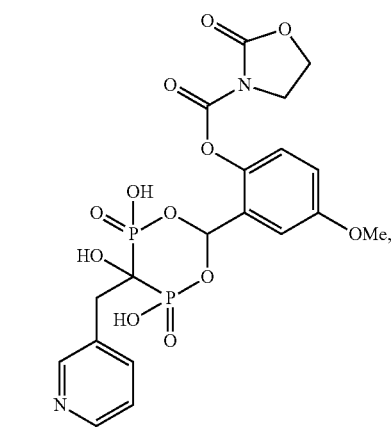
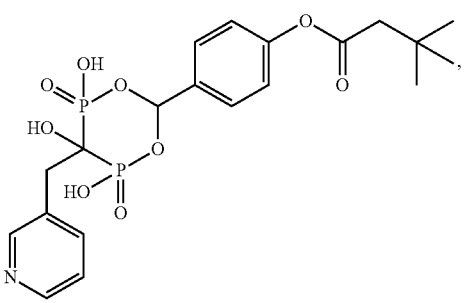
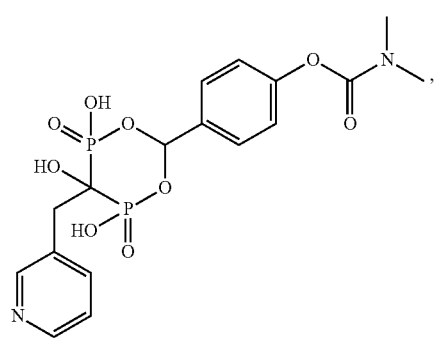
62
-continued
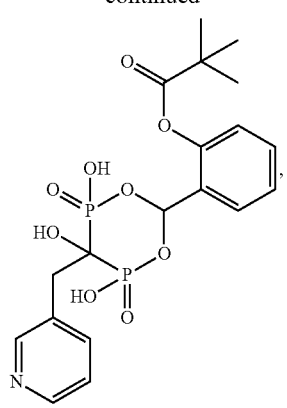
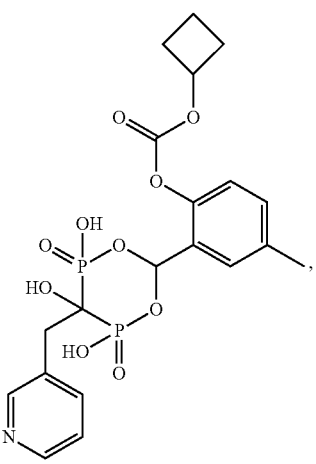
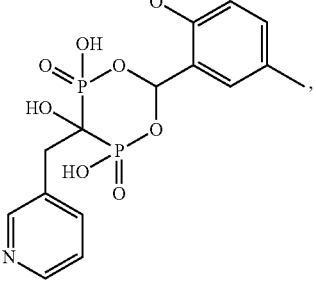

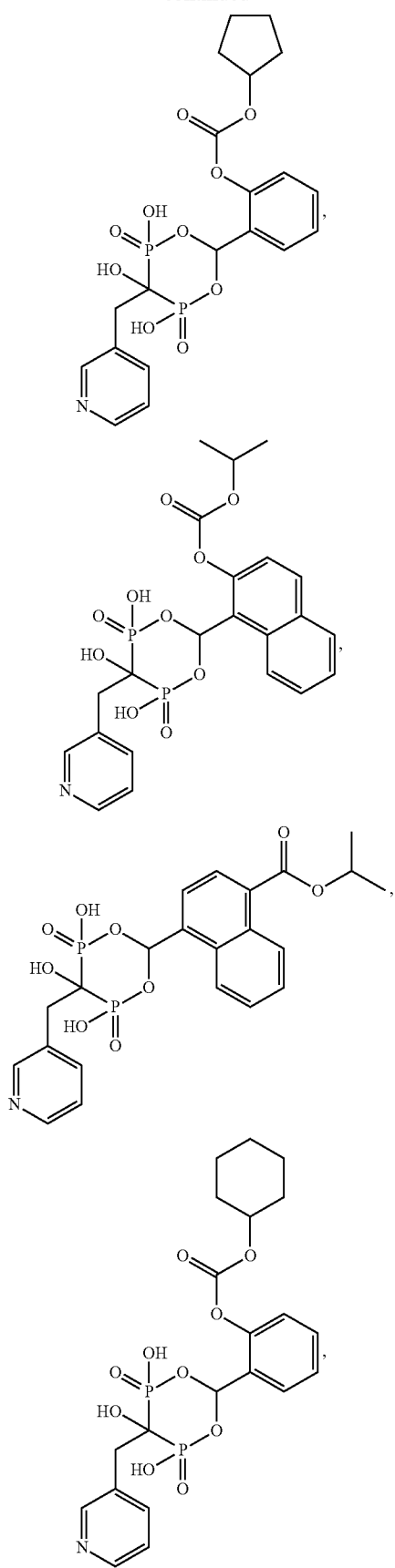
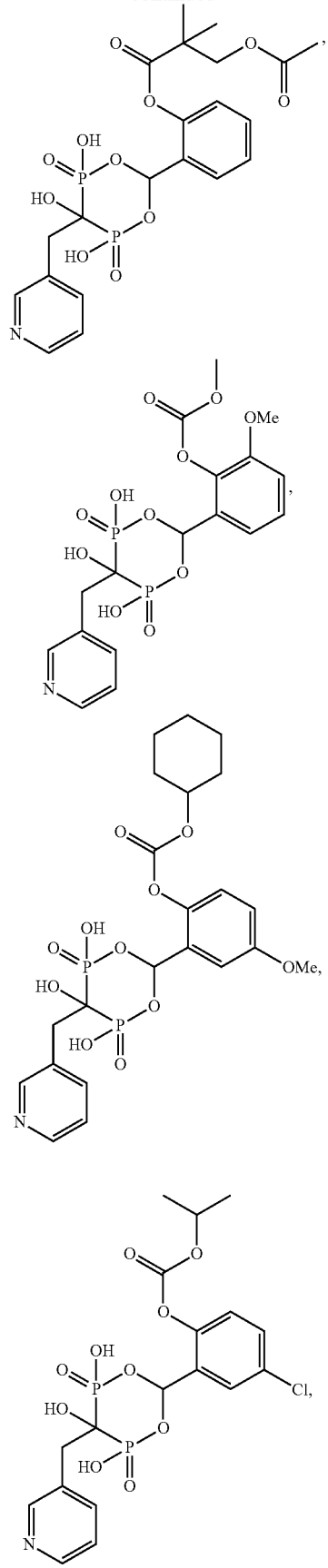

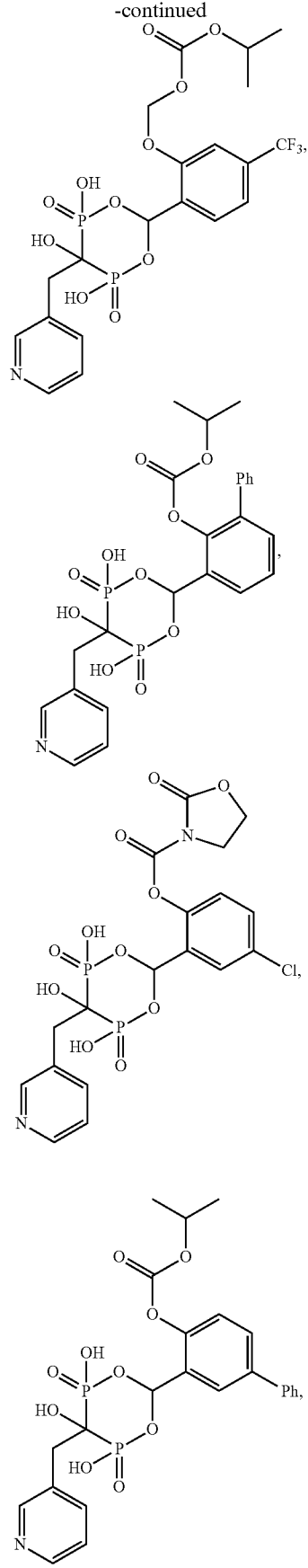
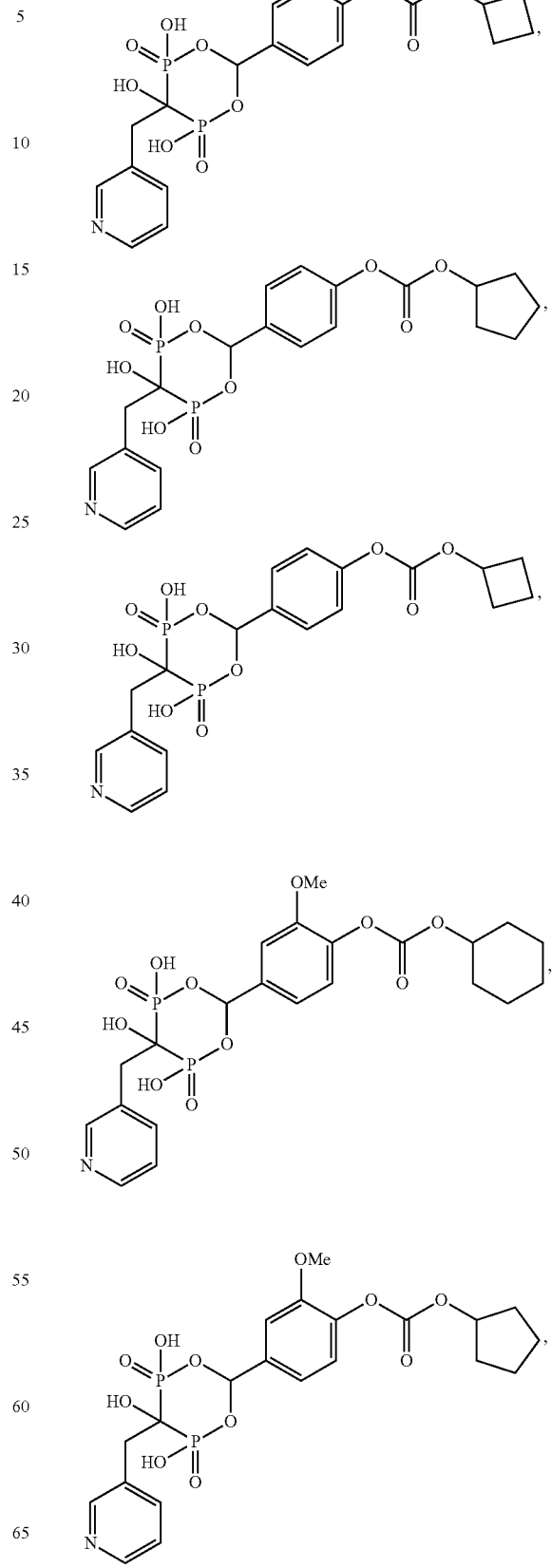

67
-continued
68
-continued
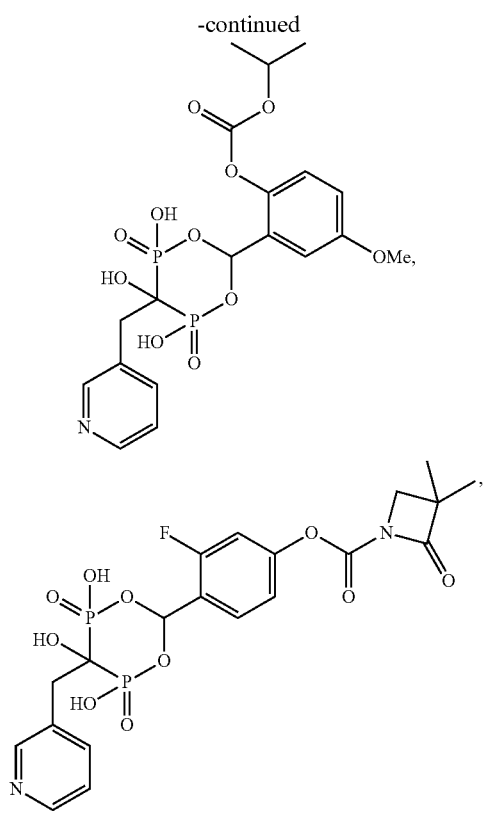
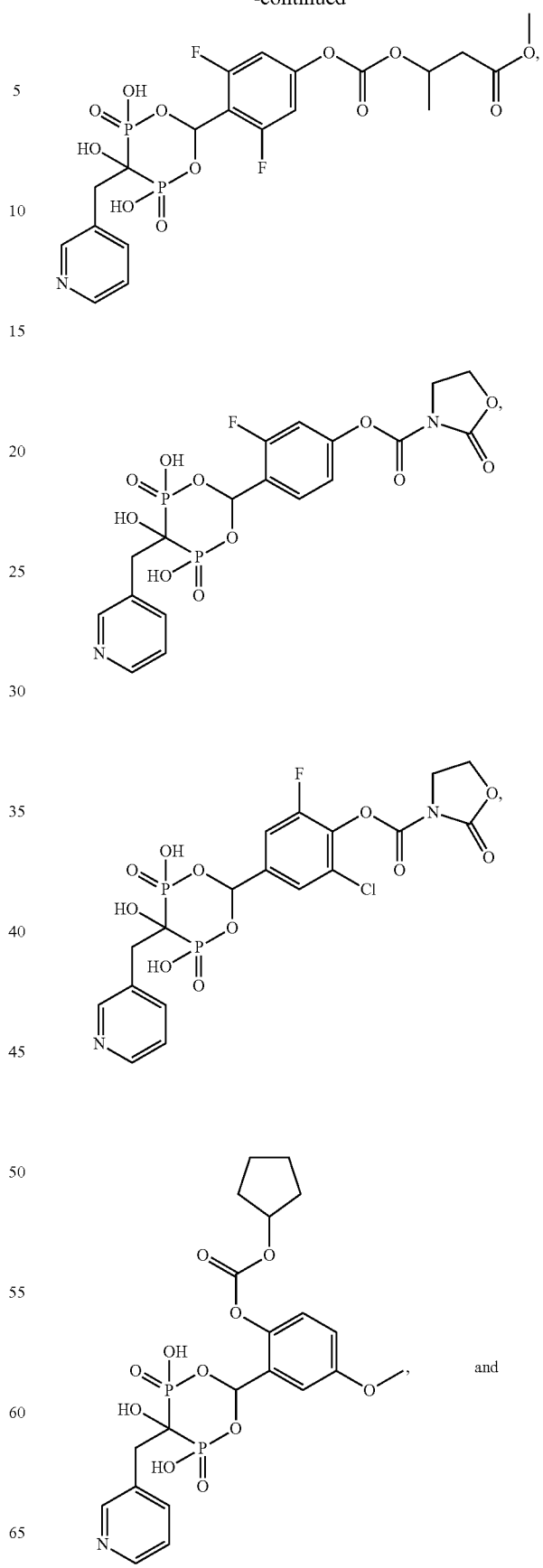

-continued

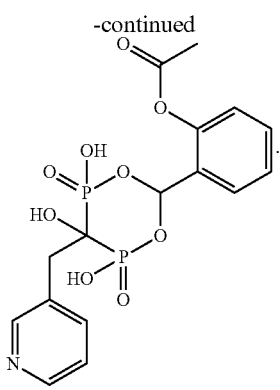

In yet another aspect, a pharmaceutically acceptable salt or hydrate of a compound of Formula III is provided, (III)

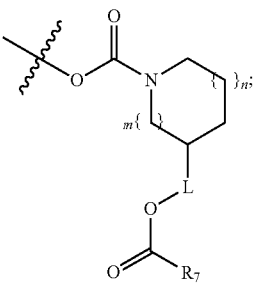

where $R_1$, $R_2$, $R_3$, $R_4$ and $R_5$ are each independently:

a) hydrogen;
b) halogen, —CN, —CF$_3$, or —NO$_2$;
c) $C_1$-$C_8$ alkyl or $C_1$-$C_8$ haloalkyl;
d) $C_2$-$C_8$ alkenyl or $C_2$-$C_8$ haloalkenyl;
e) $C_2$-$C_8$ alkynyl or $C_2$-$C_8$ haloalkynyl;
f) optionally substituted aryl or optionally substituted heteroaryl;
g) —C(O)R$_6$;
h) —C(O)OR$_6$, or —CO$_2$R$_6$;
i) —OR$_6$, —O-L-OC(O)R$_6$, or —O-L—OC(O)OR$_6$;
j) —OC(O)R$_6$, or —OC(O)-L-OC(O)R$_6$;
k) —OC(O)OR$_6$, —OC(O)O-L-C(O)R$_7$, —OC(O)O-L-C(O)OR$_7$, or -L—OC(O)R$_6$;
l) —C(O)NR$_6$R$_7$, or —CNR$_6$R$_7$;
m) —OC(O)NR$_6$R$_7$, —OC(O)N(R$_6$)-L-OC(O)R$_7$, —OC(O)O-L-(R$_6$)-L-C(O)R$_7$, —OC(O)—C(R$_6$)(R$_7$)-L-OC(O)R$_8$, —OC(O)N(-L-OC(O)R$_7$)(-L-OC(O)R$_8$);
n) —SR$_6$, or —NR$_6$R$_7$;
o) —NR$_6$C(O)R$_7$;
p) —NR$_6$C(O)OR$_7$;
q) —NR$_6$C(O)NR$_7$;
r) —OSO$_2$R$_6$;
s) —SO$_2$OR$_6$;
t) —SO$_2$R$_6$;
u) —NR$_6$SO$_2$R$_7$;
v) —SO$_2$NR$_6$R$_7$;

w)
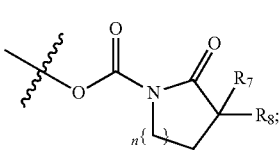

x)
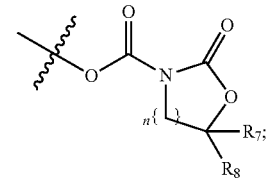

y)
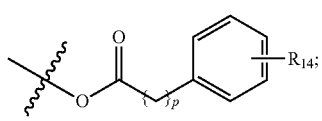

z)
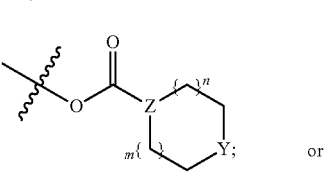

aa)

or bb) $R_1$ and $R_2$, $R_2$ and $R_3$, $R_3$ and $R_4$, or $R_4$ and $R_5$ taken together form an optionally substituted 4- to 8-membered carbocyclic or heterocyclic ring, wherein the ring is saturated, unsaturated or aromatic;

wherein m and n are each independently an integer from 0 to 2;

Y is —CH$_2$—, —O—, —NR$_7$—, or —S—;

p is an integer from 1 to 3;

$R_{14}$ is hydrogen, halogen, $C_1$-$C_8$ alkyl, or $C_1$-$C_8$ alkoxyl;

Z is

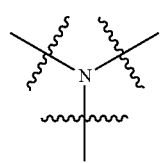 [SMILES: *N(*)*]

or

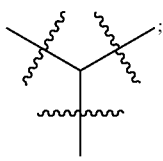 [SMILES: *C(*)*]

$R_6$ is independently hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

$R_7$ and $R_8$ are each independently hydrogen or $C_1$-$C_8$ alkyl; and L is $C_1$-$C_8$ alkyl; or $R_6$ and $R_7$ taken together form an optionally substituted 4- to 8-membered carbocyclic or heterocyclic ring, wherein the ring is saturated, unsaturated or aromatic; and $R_9$ and $R_{10}$ are each independently hydrogen, halogen, oxygen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, optionally substituted aryl, optionally substituted heteroaryl, —$OR_6$, —$SR_6$, —$NR_6R_7$, —($C_1$-$C_8$ alkyl)-$NR_6R_7$, —($C_1$-$C_8$ haloalkyl)-$NR_6R_7$, —($C_2$-$C_8$ alkenyl)-$NR_6R_7$, —($C_2$-$C_8$ haloalkenyl)-$NR_6R_7$, —($C_2$-$C_8$ alkynyl)-$NR_6R_7$, —($C_2$-$C_8$ haloalkyl)-$NR_6R_7$, -L-$R_{11}$; or $R_9$ and $R_{10}$ taken together form a monocyclic or bicyclic optionally substituted carbocyclic or heterocyclic ring, wherein the ring is saturated, unsaturated or aromatic; and $R_{11}$ is optionally substituted aryl or optionally substituted heteroaryl.

In some embodiments, $R_9$ is hydrogen, oxygen, —F, —Cl, —$CH_3$, —OH, —SH, —$NH_2$, —$CH_2$—$R_{11}$, or —N—($C_1$-$C_8$ alkyl); $R_{10}$ is —Cl, —$CH_3$, —S-phenyl, —S(p-chlorophenyl), —$(CH_2)_qNH_2$, —$(CH_2)_qNR_6R_7$,

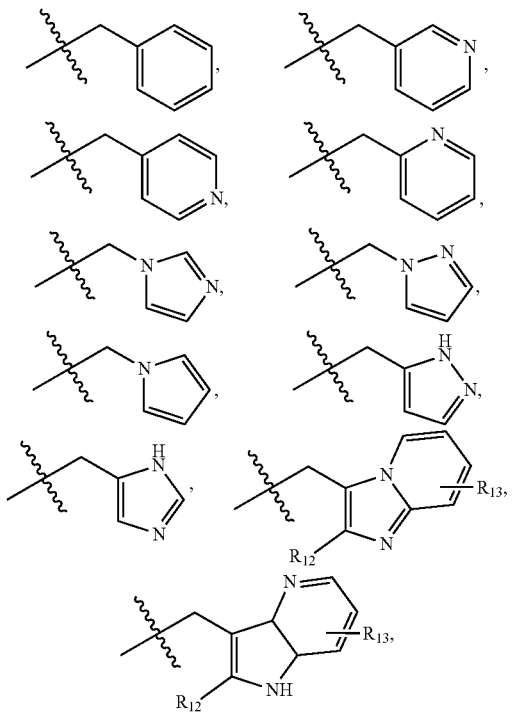

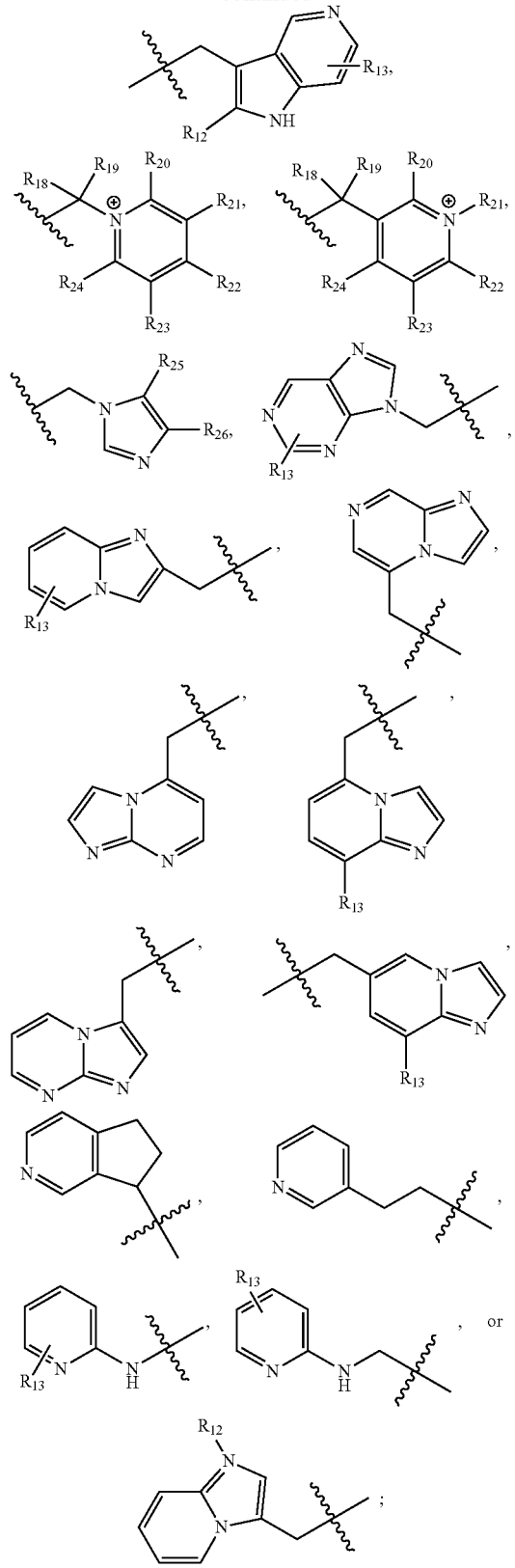

q is an integer from 0 to 8; $R_{11}$ is an optionally substituted aryl group, wherein the substituent is chosen from a group consisting of —$CF_3$, —CN, and —F; $R_{12}$ is hydrogen, —OH, $C_1$-$C_8$ alkyl, —$CH_3$, or —F; $R_{13}$ is hydrogen, —OH, $C_1$-$C_8$ alkyl, —$OCH_3$, —$OCH_2$-phenyl, —$CF_3$, —$NH_2$, —F, or —Br;

$R_{18}$ and $R_{19}$ are each independently hydrogen, halogen, —$N(R_y)_2$, —$SR_y$, an optionally substituted alkyl group, an optionally substituted alkenyl group, an optionally substituted alkoxyl group, and an optionally substituted aryl group, where $R_y$ is selected from hydrogen, an optionally substituted alkyl group and an optionally substituted aryl group; or $R_{18}$ and $R_{19}$ taken together form an optionally substituted carbocyclic or heterocyclic ring, wherein the ring is saturated, unsaturated or aromatic; and $R_{20}$-$R_{24}$ are each independently hydrogen, halogen, —CN, —$COOR_z$, —$OCOOR_z$, —$COR_z$, —$CON(R_z)_2$, —$OCON(R_z)_2$, —$N(R_z)_2$, —$NO_2$, —$SR_z$, —$SO_2R$, —$SO_2N(R_z)_2$ or —$SOR_z$ group, an optionally substituted alkyl group, an optionally substituted alkenyl group, and an optionally substituted aryl group, where $R_1$ is selected from hydrogen, an optionally substituted alkyl group, an optionally substituted aryl group, and an optionally substituted acyl group; or $R_{20}$ and $R_{21}$, $R_{21}$ and $R_{22}$, $R_{22}$ and $R_{23}$, or $R_{23}$ and $R_{24}$ when taken together form one or more optionally substituted carbocyclic or heterocyclic rings, wherein the ring is saturated, unsaturated or aromatic; and either $R_{25}$ or $R_{26}$ is hydrogen and the other is an alkyl group substituted with a substituted or unsubstituted aryl group.

In certain specific embodiments, $R_{10}$ is —$CH_2CH_2NH_2$, —$(CH_2)_3NH_2$, —$(CH_2)_2N(CH_3)((CH_2)_4CH_3)$,

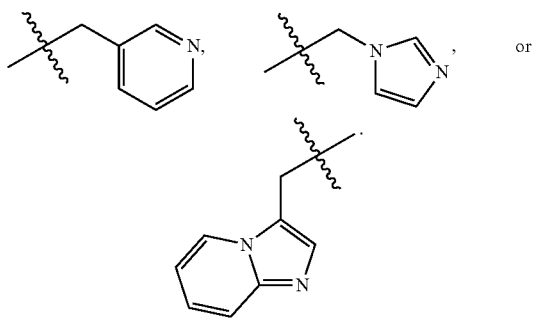

In certain other embodiments, $R_9$ is —OH.

In some embodiments, $R_9$ is hydrogen, —F, or —Cl; $R_{10}$ is

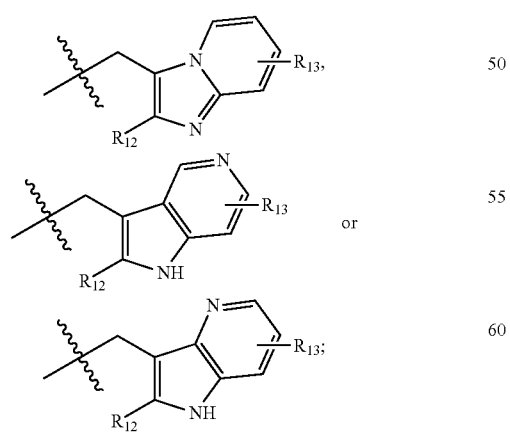

$R_{12}$ is hydrogen, —OH, $C_1$-$C_8$ alkyl, —$OCH_3$, or —F; and $R_{13}$ is hydrogen, —OH, $C_1$-$C_8$ alkyl, or —F. In certain specific embodiments, $R_9$ is hydrogen or —F; and $R_{12}$ and $R_{13}$ are each independently hydrogen, —OH, —$CH_3$, —$CH_2CH_3$, —$C(CH_3)_3$, or —F. In certain other embodiments, $R_9$ is hydrogen or —F; and $R_{12}$ and $R_{13}$ are each hydrogen.

In some embodiments, $R_9$ and $R_{10}$ are taken together to form one of the following bicyclic rings:

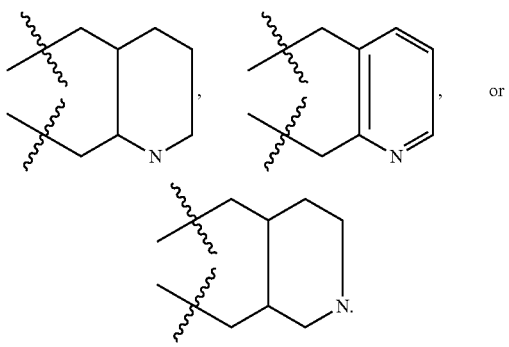

In some embodiments, $R_1$ and $R_5$ are each independently halogen; and $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

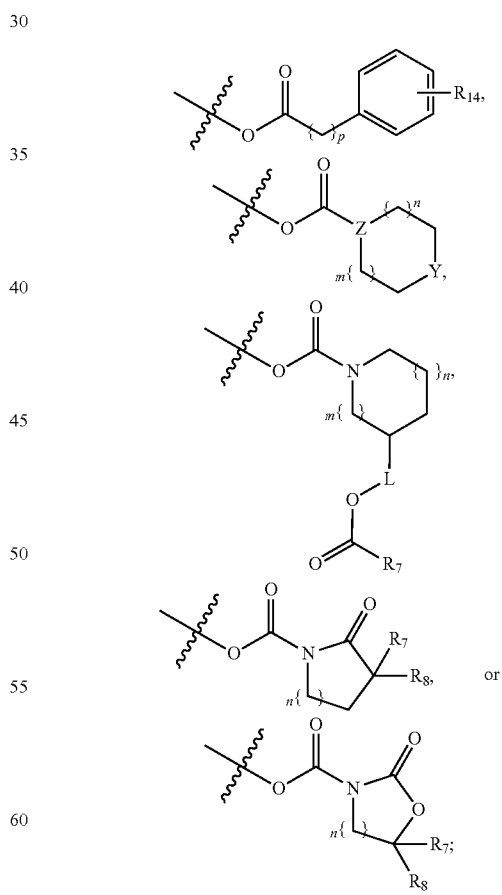

the remaining R-groups of $R_1$, $R_2$, $R_3$, $R_4$, and $R_5$ are each hydrogen; and $R_6$, $R_7$, $R_8$, L, Z, Y, m, n, and p are as defined above.

In some embodiments, $R_1$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

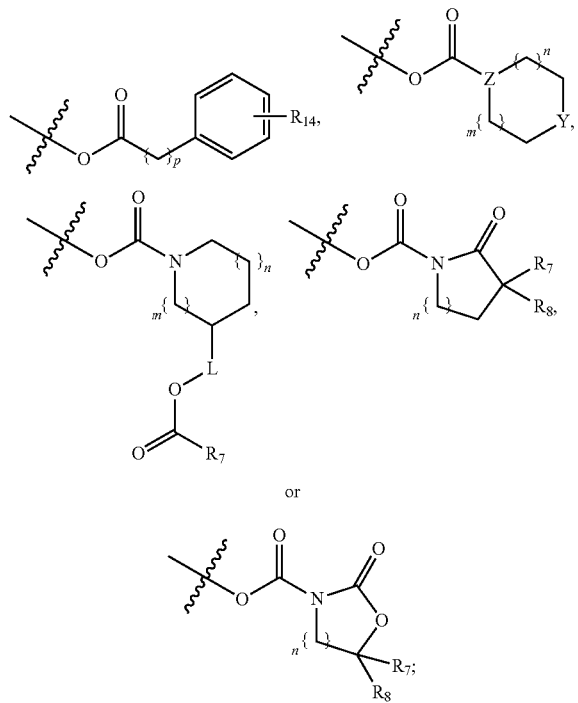

or one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

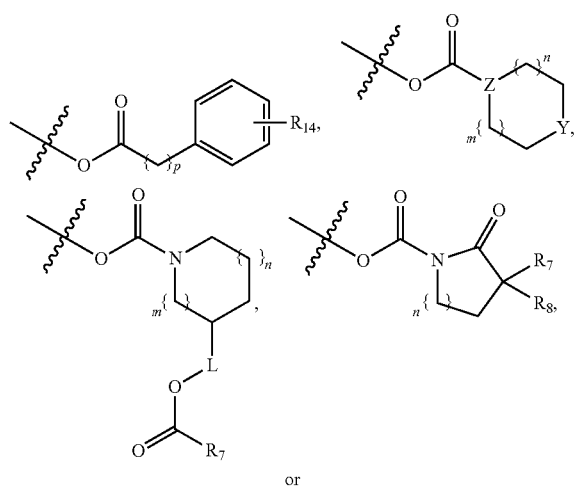

or

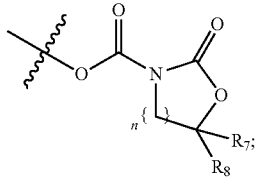

one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; each remaining R-group of $R_1$, $R_2$, $R_3$, $R_4$, and $R_5$ is hydrogen; and $R_6$, $R_7$, $R_8$, L, Z, Y, m, n, and p are as defined above.

In some embodiments, $R_1$ is —$OR_6$, —O-L-OC(O)$R_6$, —O-L-OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

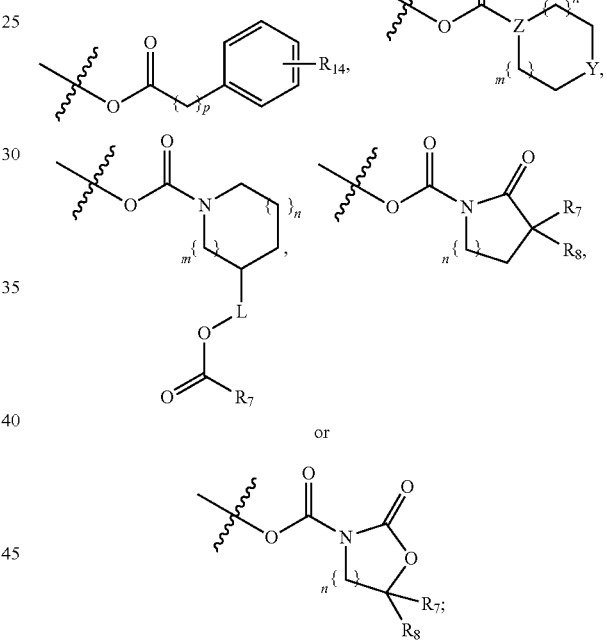

or $R_2$, $R_3$, $R_4$, and $R_5$ are each hydrogen; and $R_6$, $R_7$, $R_8$, L, Z, Y, m, n, and p are as defined above.

In some embodiments, $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

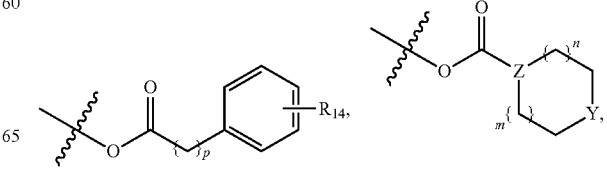

-continued

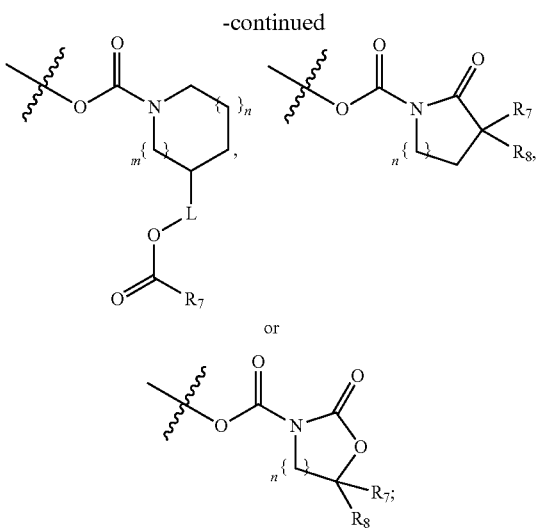

$R_1$, $R_2$, $R_4$, and $R_5$ are each hydrogen; and $R_6$, $R_7$, $R_8$, L, Z, Y, m, n, and p are as defined above.

In some embodiments, $R_{10}$ is —$CH_2CH_2NH_2$, —$(CH_2)_3NH_2$, —$(CH_2)_2N(CH_3)((CH_2)_4CH_3)$,

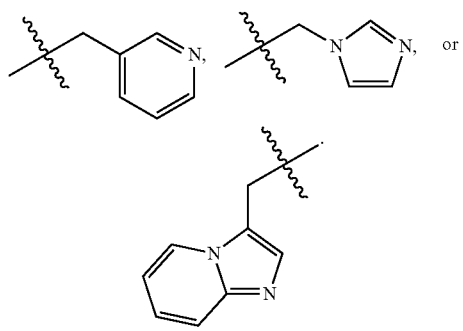

In some embodiments, $R_1$ is —OC(O)OCH$_3$, —OC(O)OCH$_2$CH$_3$ or —OC(O)OCH(CH$_3$)$_2$; $R_2$, $R_3$, $R_4$ and $R_5$ are each independently hydrogen, halogen, —CF$_3$, $C_1$-$C_8$ alkyl, optionally substituted phenyl, —OR$_6$, or —C(O)OR$_6$; $R_9$ is hydrogen, —F, —OH, or —Cl; $R_{10}$ is —CH$_3$, —Cl, —(CH$_2$)$_q$NH$_2$, —(CH$_2$)$_2$NR$_6$R$_7$, —S(p-chlorophenyl),

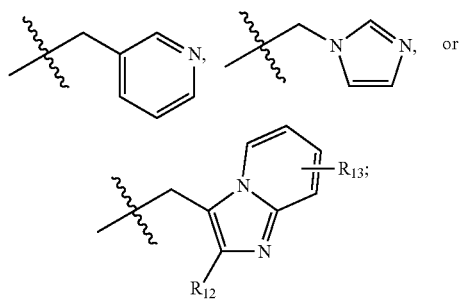

wherein $R_{12}$ is hydrogen, —OH, $C_1$-$C_8$ alkyl, —OCH$_3$, or —F; and $R_{13}$ is hydrogen, —OH, $C_1$-$C_8$ alkyl, or —F. In certain specific embodiments, $R_9$ is hydrogen, —OH, or —F; and $R_{12}$ and $R_{13}$ are each independently hydrogen, —OH, —CH$_3$, —CH$_2$CH$_3$, —C(CH$_3$)$_3$, or —F. In certain other embodiments, $R_9$ is hydrogen or —F; and $R_{12}$ and $R_{13}$ are each hydrogen. In preferred embodiments, $R_2$, $R_3$, $R_4$ and $R_5$ are each independently hydrogen, halogen, or —CF$_3$, and in more preferred embodiments, $R_2$, $R_3$, $R_4$ and $R_5$ are each hydrogen. In preferred embodiments, $R_2$, $R_3$, $R_4$, $R_5$, $R_{12}$ and $R_{13}$ are each hydrogen.

In yet another aspect, a compound or a pharmaceutically acceptable salt or hydrate of a compound of Formula IV is provided,

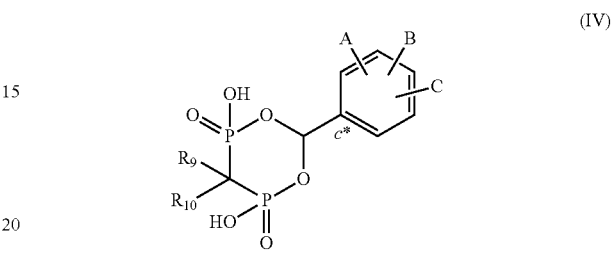

wherein A is —OR$_6$, —CO$_2$R$_6$, -L—OC(O)R$_6$, —O-L-OC(O)R$_6$, —O-L—OC(O)OR$_6$, —OC(O)R$_6$, —OC(O)-L-OC(O)R$_6$, —OC(O)OR$_6$, —OC(O)O-L-C(O)R$_7$, —OC(O)O-L-C(O)OR$_7$, —C(O)NR$_6$R$_7$, —CNR$_6$R$_7$, —OC(O)NR$_6$R$_7$, —OC(O)N(R$_6$)-L-OC(O)R$_7$, —OC(O)N(-L-OC(O)R$_7$)(-L-OC(O)R$_8$),

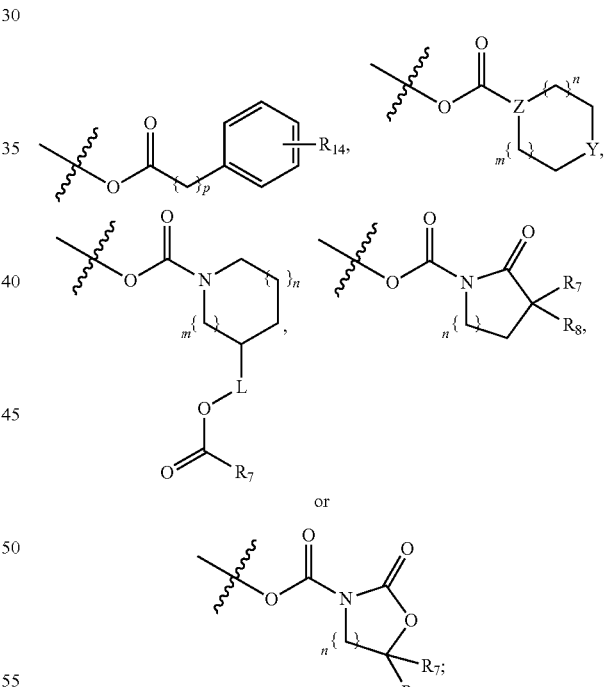

and B and C are each independently hydrogen, halogen, —CF$_3$, —CN, $C_1$-$C_8$ alkyl, phenyl, —OR$_6$, or —C(O)OR$_6$, or B and C when taken together form an optionally substituted 4- to 8-membered carbocyclic or heterocyclic ring, wherein the ring is saturated, unsaturated or aromatic; and $R_9$ and $R_{10}$ are each independently hydrogen, halogen, oxygen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, optionally substituted aryl, optionally substituted heteroaryl, —OR$_6$, —SR$_6$, —NR$_6$R$_7$, —(C$_1$-C$_8$ alkyl)-NR$_6$R$_7$, —(C$_1$-C$_8$ haloalkyl)-

$NR_6R_7$, —($C_2$-$C_8$ alkenyl)-$NR_6R_7$, —($C_2$-$C_8$ haloalkenyl)-$NR_6R_7$, —($C_2$-$C_8$ alkynyl)-$NR_6R_7$, —($C_2$-$C_8$ haloalkyl)-$NR_6R_7$, -L-$R_{11}$; or $R_9$ and $R_{10}$ taken together form a monocyclic or bicyclic optionally substituted carbocyclic or heterocyclic ring, wherein the ring is saturated, unsaturated or aromatic; and $R_{11}$ is optionally substituted aryl or optionally substituted heteroaryl; m and n are each independently an integer from 0 to 2; Y is —$CH_2$—, —O—, —$NR_7$—, or —S—; p is an integer from 1 to 3; Z is N or CH;

each $R_6$ is independently hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

L is $C_1$-$C_8$ alkyl; $R_{14}$ is hydrogen, halogen, $C_1$-$C_8$ alkyl, or $C_1$-$C_8$ alkoxyl;

$R_7$ and $R_8$ are each independently hydrogen or $C_1$-$C_8$ alkyl;

or $R_6$ and $R_7$ taken together form an optionally substituted 4- to 8-membered carbocyclic or heterocyclic ring, wherein the ring is saturated, unsaturated or aromatic.

In some embodiments, $R_9$ is hydrogen, oxygen, —F, —Cl, —$CH_3$, —OH, —SH, —$NH_2$, —$CH_2$—$R_{11}$, or —N—($C_1$-$C_8$ alkyl); $R_{10}$ is —Cl, —$CH_3$, —S-phenyl, —S(p-chlorophenyl), —$(CH_2)_qNH_2$, —$(CH_2)_qNR_6R_7$,

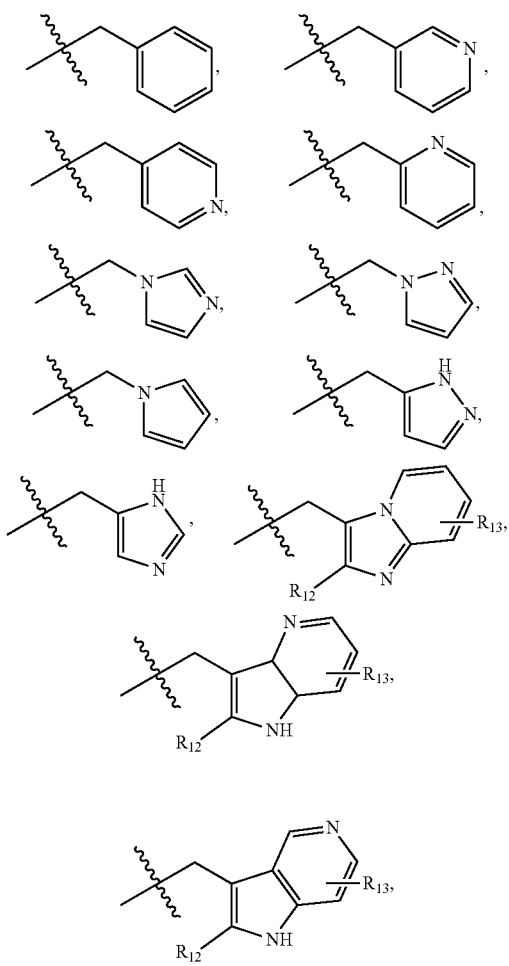

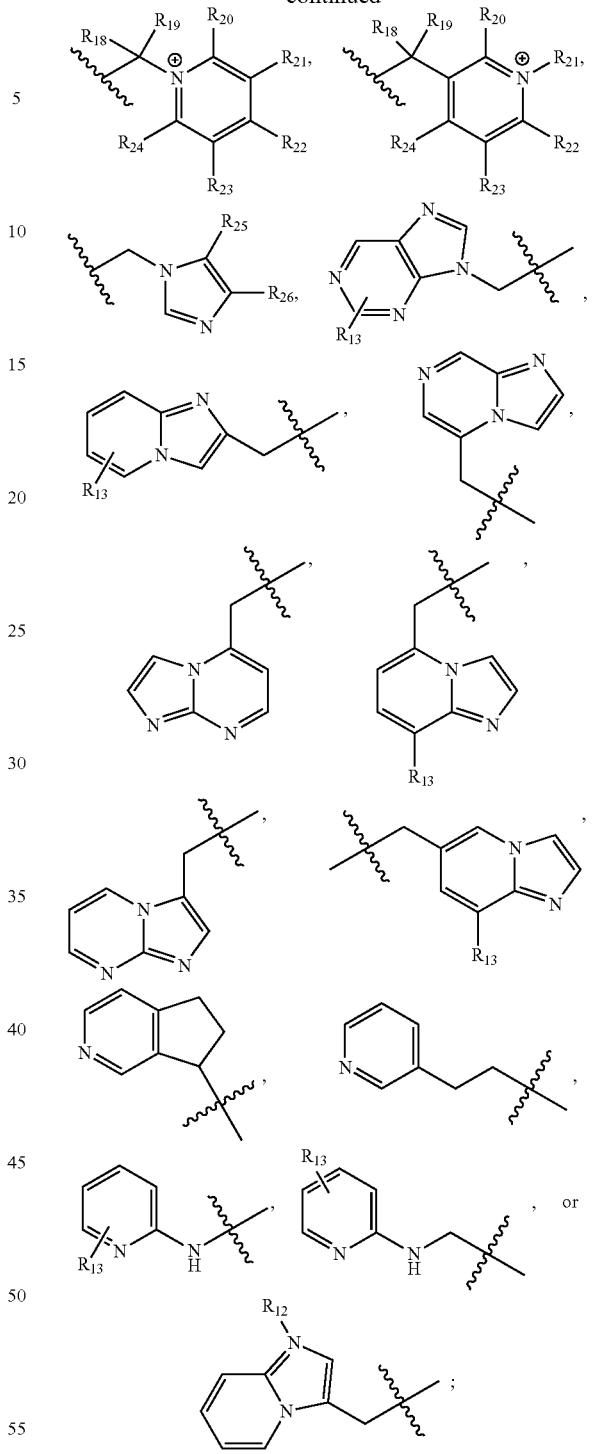

q is an integer from 0 to 8; $R_{11}$ is an optionally substituted aryl group, wherein the substituent is chosen from a group consisting of —$CF_3$, —CN, and —F; $R_{12}$ is hydrogen, —OH, $C_1$-$C_8$ alkyl, —$CH_3$, or —F; $R_{13}$ is hydrogen, —OH, $C_1$-$C_8$ alkyl, —$OCH_3$, —$OCH_2$-phenyl, —$CF_3$, —$NH_2$, —F, or —Br;

$R_{18}$ and $R_{19}$ are each independently hydrogen, halogen, —$N(R_y)_2$, —$SR_y$, an optionally substituted alkyl group, an optionally substituted alkenyl group, an optionally substituted alkoxyl group, and an optionally substituted aryl group, where $R_y$ is selected from hydrogen, an optionally substituted alkyl group and an optionally substituted aryl group; or $R_{18}$ and $R_{19}$ taken together form an optionally substituted carbocyclic or heterocyclic ring, wherein the ring is saturated, unsaturated or aromatic; and $R_{20}$-$R_{24}$ are each independently hydrogen, halogen, —CN, —$OR_z$, —$COOR_z$, —$OCOOR_z$, —$COR_z$, —$CON(R_z)_2$, —$OCON(R_z)_2$, —$N(R_z)_2$, —$NO_2$, —$SR_z$, —$SO_2R$, —$SO_2N(R_z)_2$ or —$SOR_z$ group, an optionally substituted alkyl group, an optionally substituted alkenyl group, and an optionally substituted aryl group, where $R_z$ is selected from hydrogen, an optionally substituted alkyl group, an optionally substituted aryl group, and an optionally substituted acyl group; or $R_{20}$ and $R_{21}$, $R_{21}$ and $R_{22}$, $R_{22}$ and $R_{23}$, or $R_{23}$ and $R_{24}$ when taken together form one or more optionally substituted carbocyclic or heterocyclic rings, wherein the ring is saturated, unsaturated or aromatic; and either $R_{25}$ or $R_{26}$ is hydrogen and the other is an alkyl group substituted with a substituted or unsubstituted aryl group.

In certain specific embodiments, $R_{10}$ is —$CH_2CH_2NH_2$, —$(CH_2)_3NH_2$, —$(CH_2)_2N(CH_3)((CH_2)_4CH_3)$,

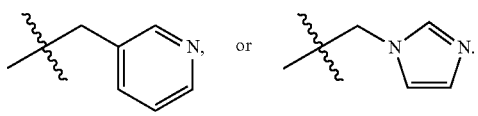 [SMILES: *Cc1cccnc1 ; *Cn1ccnc1]

In certain other embodiments, $R_9$ is —OH.

In some embodiments, A is in the ortho or para position relative to C*. In other embodiments, A is in the meta position relative to C.

In some embodiments, the compound is a compound or a pharmaceutically acceptable salt or hydrate of a compound of Formula IVa, IVb, IVc, IVd, or IVe:

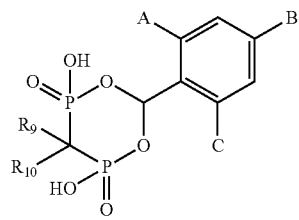
(IVa)

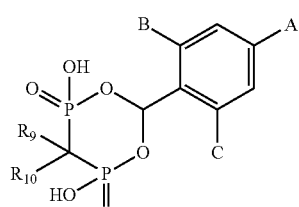
(IVb)

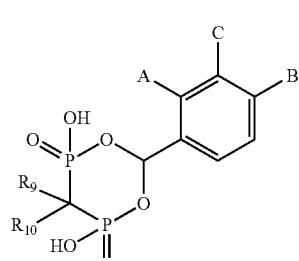
(IVc)

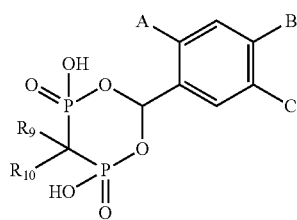
(IVd)

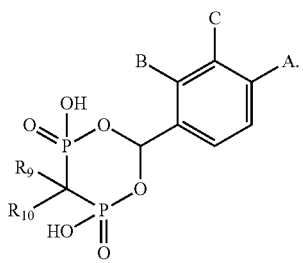
(IVe)

In some embodiments, the compound is a compound or a pharmaceutically acceptable salt or hydrate of a compound of Formula IVf, wherein $R_9$ is H, OH or F; $R_{10}$ is

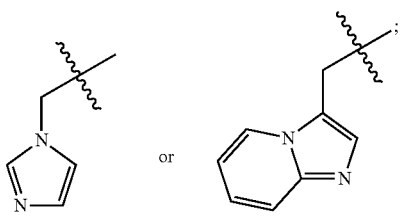

$R_x$ is $C_1$-$C_8$ alkyl, $C_1$-$C_8$ alkoxyl, or

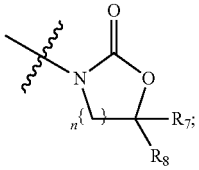

and $R_7$, $R_8$, and n are as defined above.

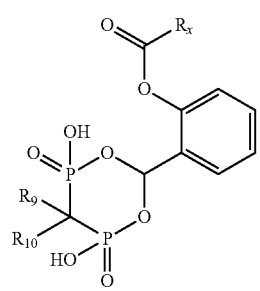
(IVf)

In some embodiments, specific examples of compounds or pharmaceutically acceptable salts or hydrates of the compounds of Formula III and Formula IV, and, specifically of Formula IVf, include, without limitation:

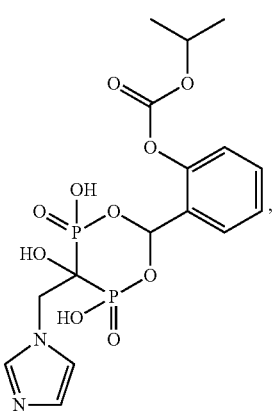
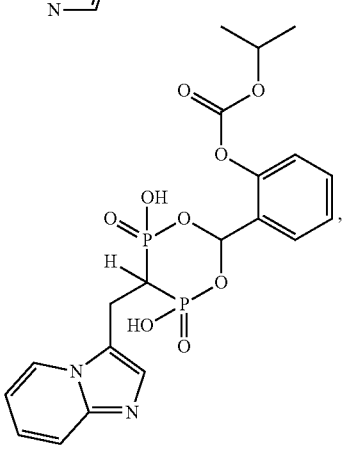
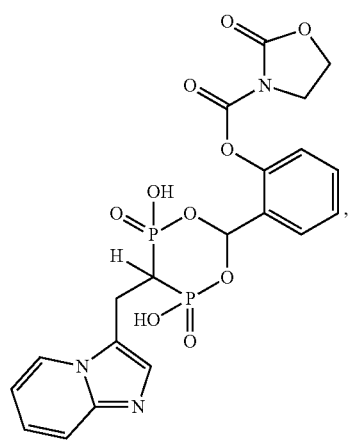
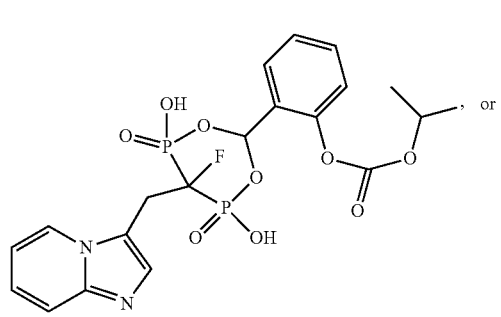
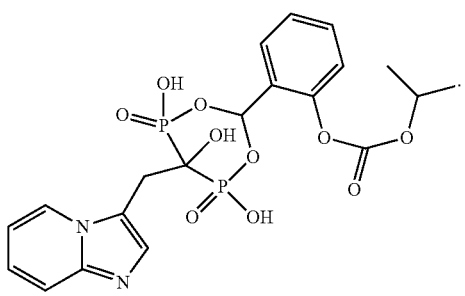
In some embodiments, specific examples of compounds or pharmaceutically acceptable salts or hydrates of the compounds of Formula III and Formula IV include, without limitation:
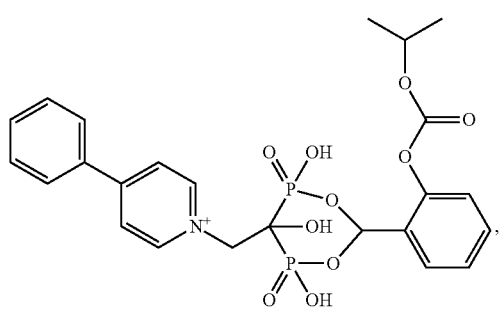
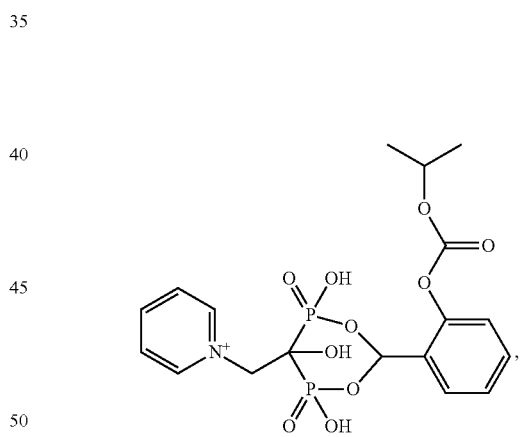
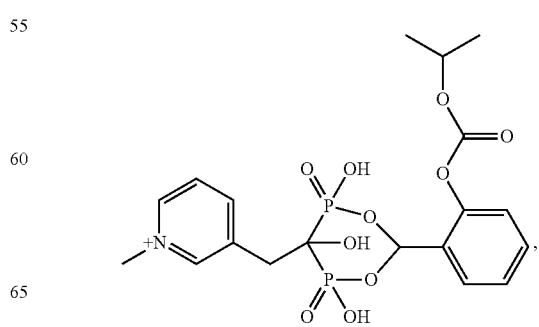

85
-continued

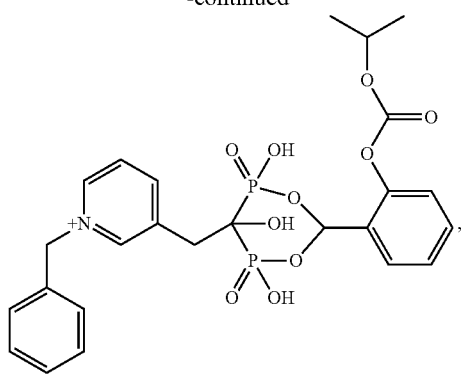

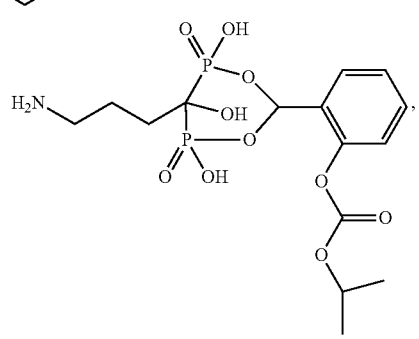

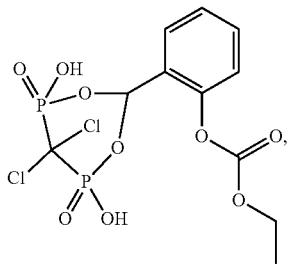

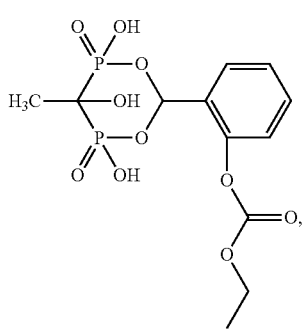

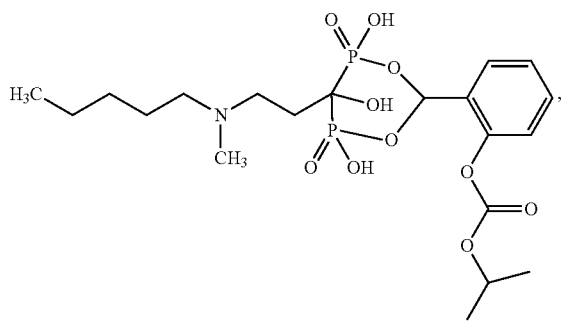

86
-continued

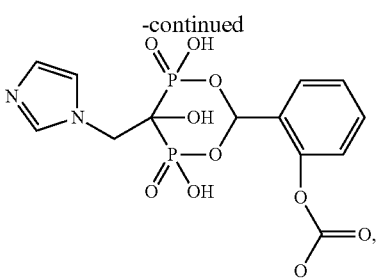

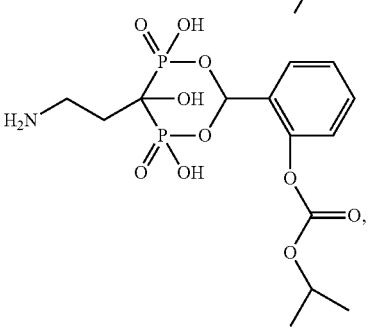

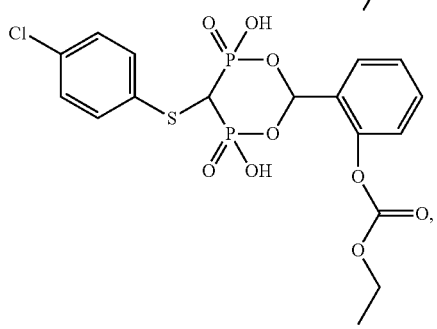

or

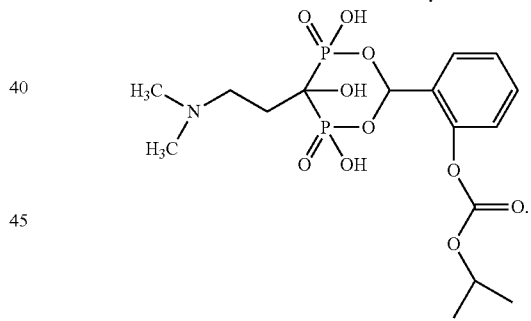

In some embodiments, a pharmaceutical composition including a compound or a pharmaceutically acceptable salt or hydrate of a compound of Formula III or IV and a pharmaceutically acceptable carrier is provided. Preferably, the compound of Formula III or Formula IV is selected from one of the specific embodiments disclosed above, and, more preferably, the compound is selected from the examples of compounds listed above.

In some embodiments, the pharmaceutical composition further comprises at least one pharmaceutically active ingredient selected from the group consisting of: an anti-inflammatory, an immunomodulator, a chelator, a musculoskeletal anabolic agent, and a combination thereof.

In yet another aspect, a method of treating or preventing disorders associated with abnormal calcium and phosphate metabolism is disclosed, including administering an effective amount of a compound or a pharmaceutically acceptable salt or hydrate of a compound of Formula III, IV, IVa, IVb, IVc, IVd, IVe or IVf to a patient in need of such treatment. Preferably, the compound of Formula III, IV, IVa, IVb, IVc, IVd, IVe or IVf is selected from one of the of the specific embodiments disclosed above, and, more preferably, the compound is selected from the examples of compounds listed above.

In certain specific embodiments of the method of treating or preventing disorders associated with abnormal calcium and phosphate metabolism, the disorder associated with abnormal calcium and phosphate metabolism is osteoporosis, rheumatoid arthritis, osteoarthritis, Paget's disease, alveolar bone loss, bone related cancer therapy, or an orthopedic disorder. In other embodiments, the disorder is a non-skeletal disorder selected from the group consisting of; a non-bone cancer, an inflammatory disorder, an immunomodulatory disorder, and a parasitic disorder. In some embodiments, the parasitic disorder is selected from the group consisting of malaria, leishmaniasis, a trypanasomal disease, an entamoebal infection, a giardia infection, and a cryptosporidial infection.

In some embodiments, the compound or a pharmaceutically acceptable salt or hydrate of a compound of Formula III, IV, IVa, IVb, IVc, IVd, IVe or IVf administered to the subject animal or human modifies the activity of farnesyl pyrophosphate synthase in the subject animal or human.

In some embodiments, the method includes administering an effective amount of a compound of Formula III or a pharmaceutically acceptable salt or hydrate thereof to a patient in need of such treatment, where $R_9$ is hydrogen, —F, or —Cl; $R_{10}$ is

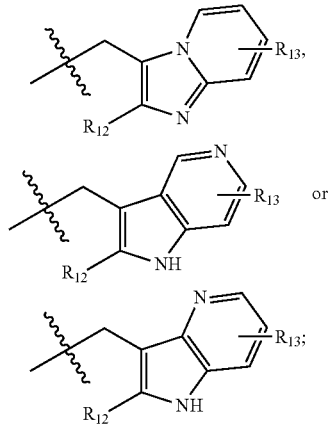

$R_{12}$ is hydrogen, —OH, $C_1$-$C_8$ alkyl, —OCH$_3$, or —F; and $R_{13}$ is hydrogen, —OH, $C_1$-$C_8$ alkyl, or —F. In some embodiments, the method includes administering an effective amount of a compound or a pharmaceutically acceptable salt or hydrate of a compound of Formula III to a patient in need of such treatment, where $R_1$ and $R_5$ are each independently halogen; and $R_3$ is —OR$_6$, —O-L-OC(O)R$_6$, —O-L—OC(O)OR$_6$, —OC(O)R$_6$, —OC(O)-L—OC(O)R$_6$, —OC(O)OR$_6$, —OC(O)O-L-C(O)R$_7$, —OC(O)NR$_6$R$_7$, —OC(O)N(R$_6$)-L-OC(O)R$_7$, —OC(O)N(-L-OC(O)R$_7$)(-L-OC(O)R$_8$),

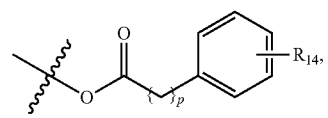

-continued

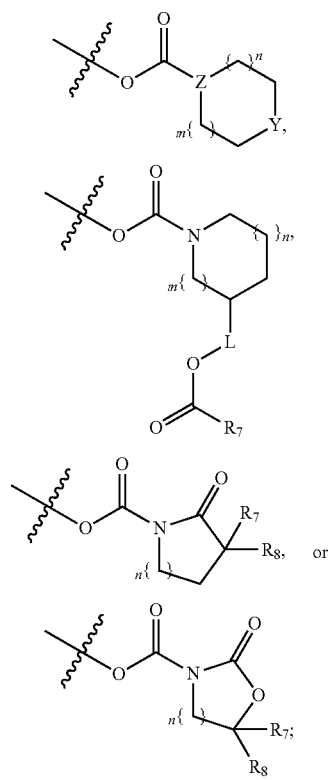

the $R_2$ and $R_4$ are each hydrogen; and $R_6$, $R_7$, $R_8$, L, m and n are as defined above. In some embodiments, $R_1$ is —OR$_6$, —O-L-OC(O)R$_6$, —O-L—OC(O)OR$_6$, —OC(O)R$_6$, —OC(O)-L-OC(O)R$_6$, —OC(O)OR$_6$, —OC(O)O-L-C(O)R$_7$, —OC(O)NR$_6$R$_7$, —OC(O)N(R$_6$)-L-OC(O)R$_7$, —OC(O)N(-L-OC(O)R$_7$)(-L-OC(O)R$_8$),

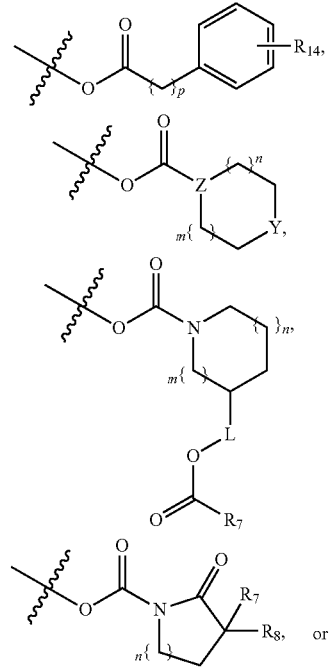

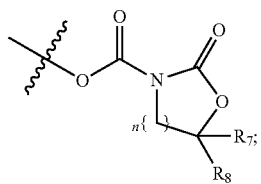

one of $R_2$, $R_3$, $R_4$ and $R_5$ is halogen, —$CF_3$, $C_1$-$C_8$ alkyl, phenyl, —$OR_6$, or —$C(O)OR_6$; each remaining R-group of $R_1$, $R_2$, $R_3$, $R_4$, and $R_5$ is hydrogen; and $R_6$, $R_7$, $R_8$, L, m and n are as defined above.

In some embodiments, $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

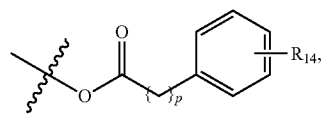

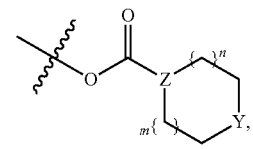

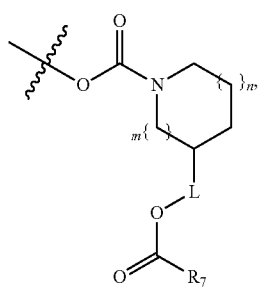

one of $R_1$, $R_2$, $R_4$ and $R_5$ is halogen, —$CF_3$, $C_1$-$C_8$ alkyl, phenyl, —$OR_6$, or —$C(O)OR_6$; each remaining R-group of $R_1$, $R_2$, $R_4$ and $R_5$ is hydrogen; and $R_6$, $R_7$, $R_8$, L, m and n are as defined above.

In some embodiments, $R_1$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

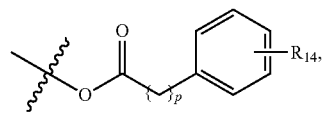

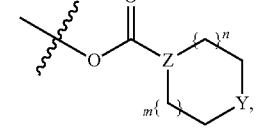

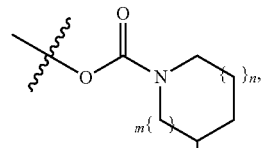

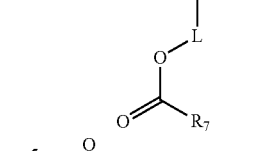

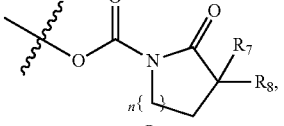

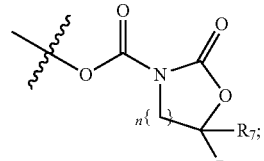

$R_2$, $R_3$, $R_4$, and $R_5$ are each hydrogen; and $R_6$, $R_7$, $R_8$, L, m and n are as defined above. In some embodiments, the method includes administering an effective amount of a compound or a pharmaceutically acceptable salt or hydrate of a compound of Formula III to a patient in need of such treatment, where $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

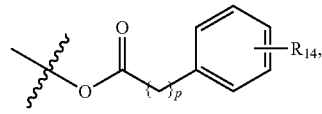

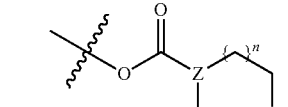

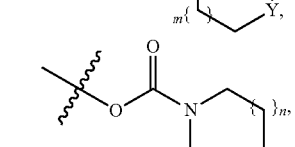

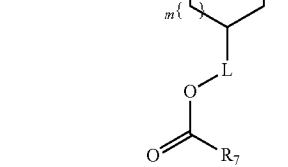

-continued

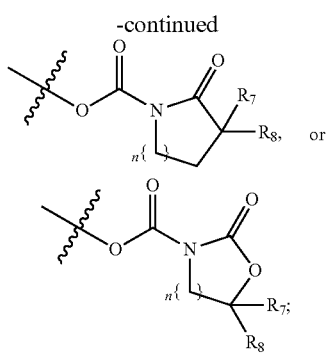

$R_1$, $R_2$, $R_4$, and $R_5$ are each hydrogen; and $R_6$, $R_7$, $R_8$, L, m and n are as defined above. In some embodiments, the method includes administering an effective amount of a compound or a pharmaceutically acceptable salt or hydrate of a compound of Formula IV to a patient in need of such treatment. In some embodiments, the method includes administering an effective amount of a compound or a pharmaceutically acceptable salt or hydrate of a compound of Formula IV, IVa, IVb, IVc, IVd, IVe or IVf to a patient in need of such treatment.

In some embodiments, a method of treating or preventing disorders associated with abnormal calcium and phosphate metabolism is disclosed. The method includes administering an effective amount of a compound or a pharmaceutically acceptable salt or hydrate of a compound of Formula IV, and the compound is selected from:

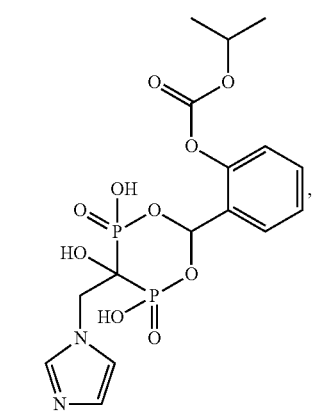

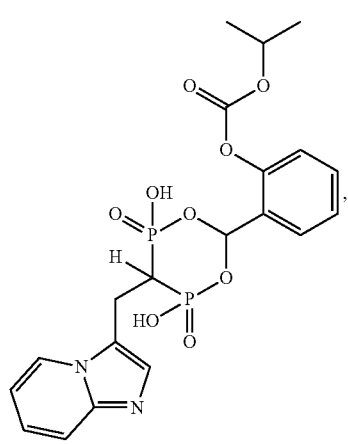

-continued

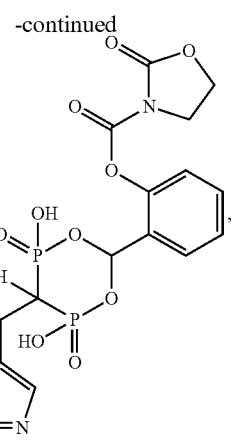

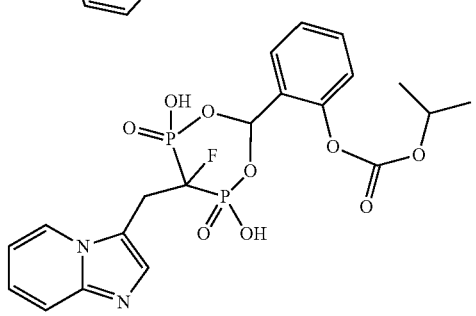

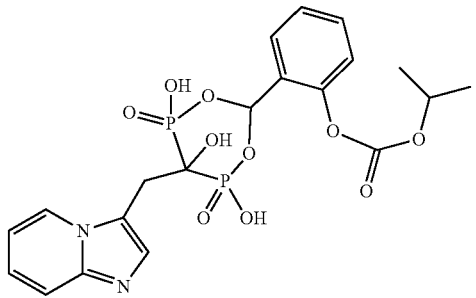

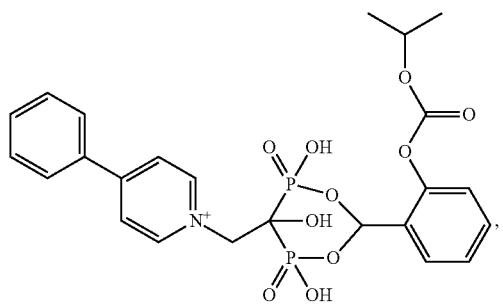

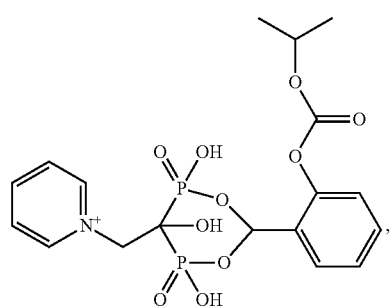

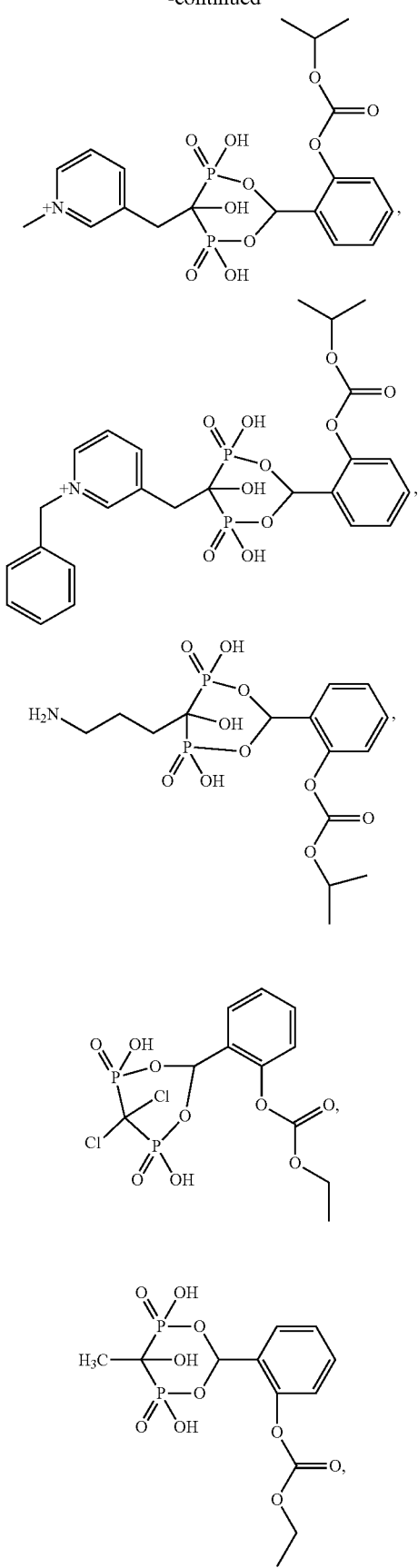
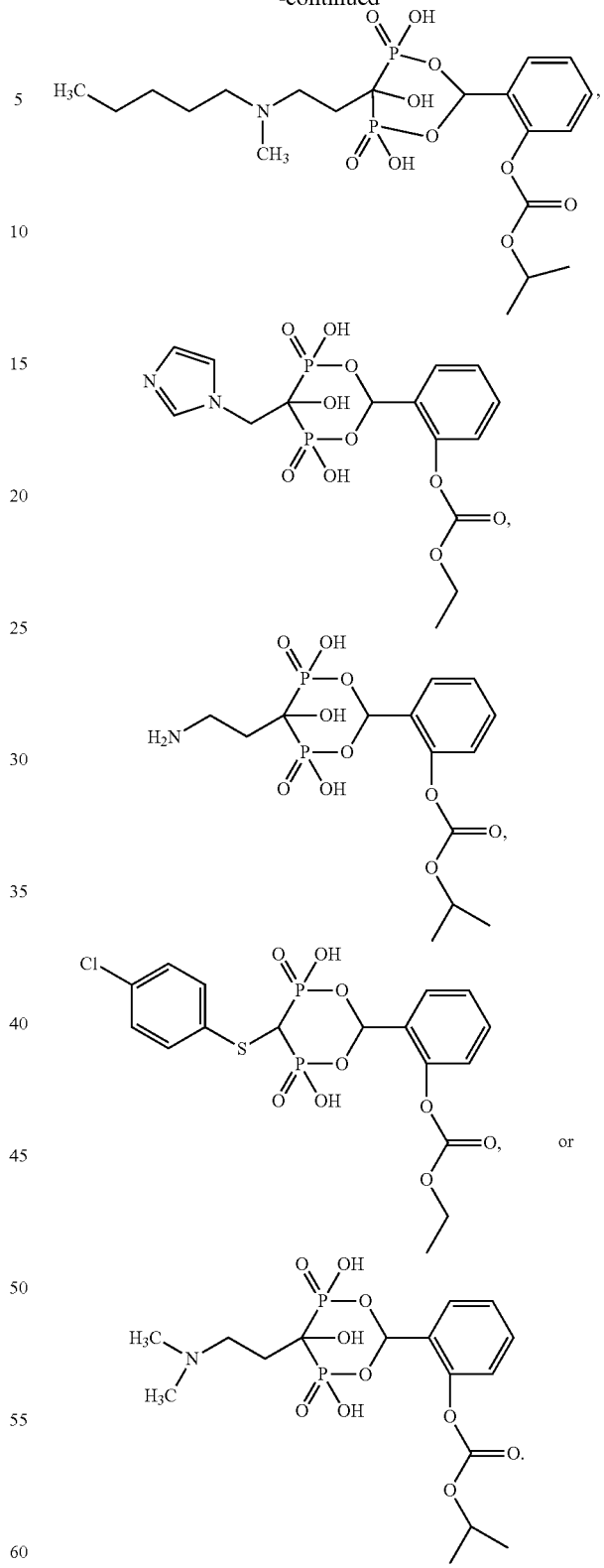
Summary of Properties
The bisphosphonate cyclic acetal compounds described herein demonstrate improved absorption, especially under oral administration, compared with the tetra acid bisphosphonates. During oral administration, a very low percentage, e.g., from about 0.2% to about 5%, of the dosed bisphosphonates is absorbed. Due to the polar nature of the molecule, bisphosphonates generally have low affinity to lipids, thus making it difficult for them to cross the cell membranes. In addition, paracellular transportation is difficult because bisphosphonates are polar and can easily become charged under physiological conditions. In comparison, bisphosphonate cyclic acetal compounds disclosed herein utilize a bisphosphonate cyclic acetal to "mask" a portion of the bisphosphonic acid functionality. Thus, the lipophilicity of the resulting bisphosphonate cyclic acetal compounds is greatly increased, which facilitates their transportation through the lipid-containing membrane and results in improved absorption. In some embodiments, the bisphosphonate cyclic acetal compounds described herein result in up to five times better absorption than the tetra acid bisphosphonates.

The bisphosphonate cyclic acetal compounds described herein also exhibit improved absorption in the presence of food when compared with the tetra acid bisphosphonates. During oral administration in the presence of food, especially with food rich in calcium, the absorption of the tetra acid bisphosphonates is further dramatically reduced, because bisphosphonates form stable and insoluble chelates with calcium in food, resulting in very low or virtually no absorption. Because of this food effect, most bisphosphonates have a food restriction during oral administration. The bisphosphonate cyclic acetal compounds contain a six-membered bisphosphonate cyclic acetal ring. The bisphosphonate cyclic acetal masks one hydroxyl group from each phosphonate constraining them in a six-membered ring conformation, thereby hindering (and in some cases preventing) any bisphosphonate-calcium chelation. In some embodiments, the bisphosphonate cyclic acetal compounds are stable in the gastrointestinal tract. As a result, the bisphosphonate cyclic acetal compounds described herein exhibit improved absorption when administered with food.

Once absorbed, the bisphosphonate cyclic acetal compounds described herein are converted to the tetra acid bisphosphonates. During this conversion, the cyclic acetal moiety of the bisphosphonate cyclic acetal compounds is cleaved under in vivo conditions and the tetra acid bisphosphonates are released while generating certain byproducts of the cyclic acetal moiety. In some embodiments, the byproducts generated are those a generally recognized as GRAS, a status designated for substances considered safe in foods. In some embodiments, the byproduct generated is salicyclic acid or salicyclic aldehyde, both of which are generally recognized as safe (GRAS). In some embodiments, the process of the conversion utilizes enzymes. Exemplary enzymes include, but are not limited to, hydrolases. An exemplary mechanism, without limitation, of the conversion from the bisphosphonate cyclic acetal to the tetra acid bisphosphonate is shown in Scheme 1. In Scheme 1, bisphosphonate cyclic acetal 1 is used to demonstrate a proposed mechanism of the conversion, where $R_9$ and $R_{10}$ are as defined herein and non-limiting examples of R' include $R_6$, and as defined herein. The R'C(O) moiety is cleaved by certain enzymes, e.g., a hydrolase, to provide intermediate 2, which undergoes spontaneous disintegration to release the tetra acid bisphosphonate 3, while generating salicyclic byproduct 4 (R" is H or OH). Ideally, this conversion occurs after the absorption of the bisphosphonate cyclic acetal compounds, thus resulting in the release of the bisphosphonate after absorption.

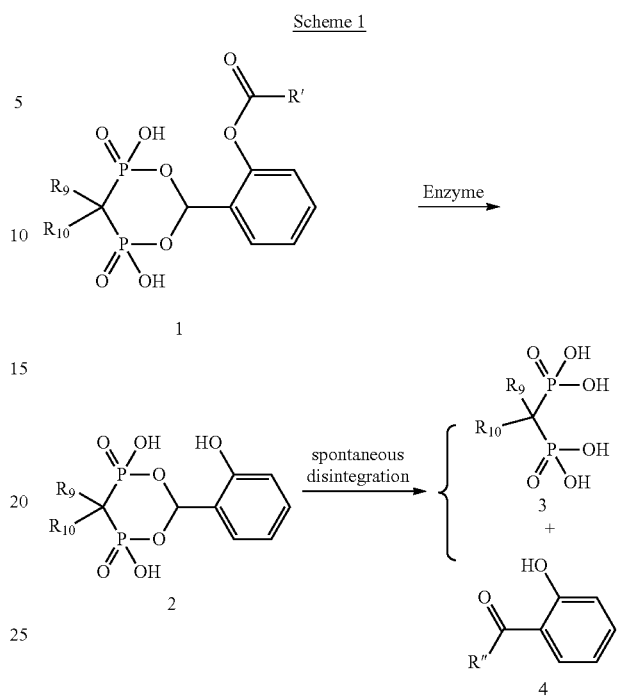

Scheme 1

Thus, the bisphosphonate cyclic acetal compounds described herein demonstrate improved lipophilicity and oral administration absorption, especially when administered with food. The cyclic acetal compounds are converted to the tetra acid bisphosphonates after absorption, thus resulting in an increase exposure of bisphosphonate. Other potential advantages of the bisphosphonate cyclic acetal compounds include fewer esophagus side effects and fewer administration restrictions. In some embodiments, the bisphosphonate cyclic acetal compounds described herein demonstrates improved safety or tolerability during IV administration.

Synthesis

The compounds and their pharmaceutically acceptable salts or hydrates described herein are prepared using a variety of methods starting from commercially available compounds, known compounds, or compounds prepared by known methods. General synthetic routes to many of the compounds described herein are included in the following schemes. It is understood by those skilled in the art that protection and deprotection steps not shown in the Schemes may be required for these syntheses, and that the order of steps may be changed to accommodate functionality in the target molecule. The need for protection and deprotection, and the selection of appropriate protecting groups are found, for example, in Greene and Wuts, Protecting Groups in Organic Synthesis, Second Edition, John Wiley & Sons (1991), which is incorporated herein by reference in its entirety.

In the schemes described herein, appropriate solvents include, but are not limited to, dimethyl sulfoxide, dimethylformamide, tetrahydrofuran, methanol, ethanol, methylene chloride, toluene, and acetone. Suitable acid binding agents include, but are not limited to, organic bases, such as, for example, pyridine, triethylamine, triethanolamine, 1,8-diazabicyclo[5.4.0]undec-7-ene (DBU), and diisopropylethylamine (DIPEA); and inorganic bases, such as, for example, sodium hydride, potassium carbonate, and sodium carbonates. Suitable reducing agents include, but are not limited to, sodium cyanoborohydride and sodium triacetoxyborohydride.

Firstly, substituted benzylaldehydes are provided. In some embodiments, the substituted benzylaldehydes are commercially available. In other embodiments, the substituted benzylaldehydes are prepared by methods known in the art, as illustrated in the following schemes.

In some embodiments, benzylaldehydes bearing an ether linkage are synthesized. Scheme 2 illustrates one process for making substituted benzaldehyde 6 bearing an ether linkage, where $R_a$ is any of $R_1$, $R_2$, $R_3$, $R_4$, and $R_5$, which are as defined herein. r is an integer from 0 to 4. The hydroxyl group is ortho, meta, or para with respect to the aldehyde group. LG is a leaving group and $R_b$ is an optionally substituted alkyl group. Non-limiting examples of $R_b$ include —$R_6$, -L-OC(O)$R_6$, and -L—OC(O)O$R_6$, where $R_6$ and L are as defined herein. Exemplary leaving groups include, without limitation, Cl, Br, I, OTf (OSO$_2$CF$_3$), and OTs (OSO$_2$C$_6$H$_4$CH$_3$). As shown in Scheme 2, substituted hydroxybenzaldehyde 5 is reacted with $R_b$-LG under conditions effective to produce substituted hydroxybenzaldehyde 6, where O$R_b$ occupies a position on the phenyl ring which is ortho, meta, or para relative to the aldehyde group. The reaction is carried out in an appropriate solvent, e.g., acetone, acetonitrile, dimethylformide, or a mixture thereof. An acid binding agent is used in this reaction. Exemplary appropriate acid binding agents include, without limitation, inorganic bases, such as, for example, sodium hydride, potassium carbonate, and sodium carbonates and organic bases, such as, for example, pyridine, triethylamine, triethanolamine, 1,8-diazabicyclo[5.4.0]undec-7-ene (DBU), and diisopropylethylamine (DIPEA). This reaction is carried out at low temperature, e.g., 0° C., at room temperature, under heating conditions, or a combination thereof.

Scheme 2

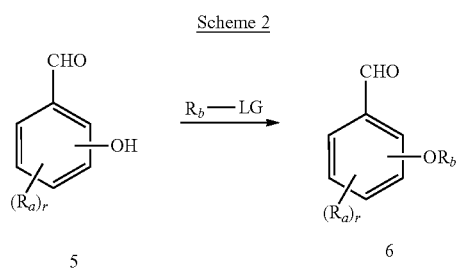

In other embodiments, benzylaldehydes bearing an ester linkage are synthesized. Scheme 3 illustrates one process for making substituted benzaldehyde 7 bearing an ester linkage, where $R_a$ and r are as defined herein and $R_c$ is an optionally substituted alkyl group. Non-limiting examples of $R_c$ include —$R_6$ and -L-OC(O)$R_6$, where $R_6$ and L are as defined herein. The hydroxyl group is ortho, meta, or para with respect to the aldehyde group. As shown in Scheme 3, substituted hydroxybenzaldehyde 5 is reacted under conditions effective to produce substituted hydroxybenzaldehyde 7, where —OC(O)$R_c$ occupies a position on the phenyl ring which is ortho, meta, or para relative to the aldehyde group. An acylating agent is used in this process. Exemplary acylating agents include, without limitation, $R_c$C(O)OH, $R_c$C(O)Cl, and ($R_c$C(O))$_2$O. When $R_c$C(O)OH is used as the acylating agent, coupling agents are used to promote the esterification reaction. Exemplary coupling agents include, without limitation, DCC (Dicyclohexylcarbodiimide), DIC (N,N'-Diisopropylcarbodiimide), and EDC (1-Ethyl-3-(3-dimethylaminopropyl)carbodiimide). When ($R_c$C(O))$_2$O is used as the acylating agent, a catalyst is used to promote the esterification reaction. Exemplary catalysts include, without limitation, DMAP (4-Dimethylaminopyridine). The reaction is carried out in an appropriate solvent, e.g., methylene chloride, toluene, dimethylformide, or a mixture thereof. An acid binding agent is used in this reaction. Appropriate acid binding agents include, without limitation, organic bases, such as, for example, pyridine, triethylamine, triethanolamine, 1,8-diazabicyclo[5.4.0]undec-7-ene (DBU), and diisopropylethylamine (DIPEA). This reaction is carried out at low temperature, e.g., 0° C., at room temperature, under heating conditions, or a combination thereof.

Scheme 3

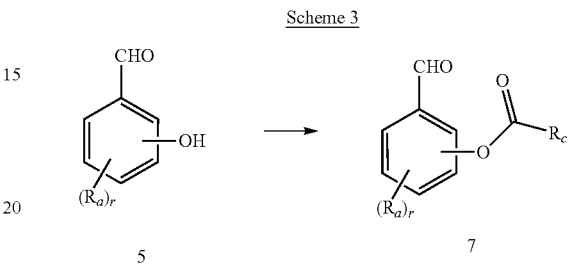

In yet other embodiments, benzylaldehydes bearing a carbonate linkage are synthesized. Scheme 4 illustrates one process for making substituted benzaldehyde 8 bearing a carbonate linkage, where $R_a$ and r are defined herein and $R_d$ is an optionally substituted alkyl group. Non-limiting examples of $R_d$ include —$R_6$, and -L-OC(O)$R_7$, where $R_6$, $R_7$ and L are defined herein. The hydroxyl group is ortho, meta, or para with respect to the aldehyde group. As shown in Scheme 4, substituted hydroxybenzaldehyde 5 is reacted under conditions effective to produce substituted hydroxybenzaldehyde 8, where —OC(O)O$R_d$ can occupy a position on the phenyl ring which is ortho, meta, or para relative to the aldehyde group. A derivatizing reagent is used in this process. Exemplary derivatizing reagents include, without limitation, $R_d$OC(O)Cl. The derivatizing reagent $R_d$C(O)Cl is commercially available or is produced by methods known in the art. The reaction is carried out in an appropriate solvent, e.g., methylene chloride, toluene, dimethylformide, or a mixture thereof. An acid binding agent is used in this reaction. Exemplary appropriate acid binding agents include, without limitation, organic bases, such as, for example, pyridine, triethylamine, triethanolamine, 1,8-diazabicyclo[5.4.0]undec-7-ene (DBU), and diisopropylethylamine (DIPEA). This reaction is carried out at low temperature, e.g., 0° C., at room temperature, under heating conditions, or a combination thereof.

Scheme 4

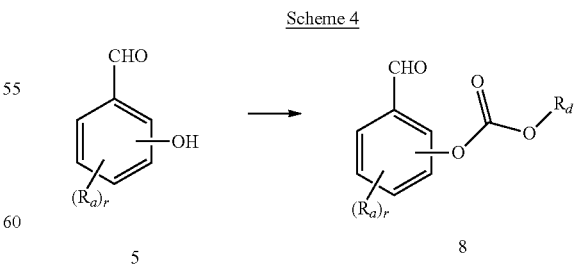

In yet other embodiments, benzylaldehydes bearing a carbamate linkage are synthesized. Scheme 5 illustrates one process for making substituted benzaldehyde 9 bearing a carbamate linkage, where $R_a$ and r are defined herein and $R_c$ is an optionally substituted amino group. Non-limiting examples of $R_c$ include —$NR_6R_7$, —$N(R_6)$-L-OC(O)$R_7$, —N(-L-OC(O)$R_7$)(-L-OC(O)$R_8$),

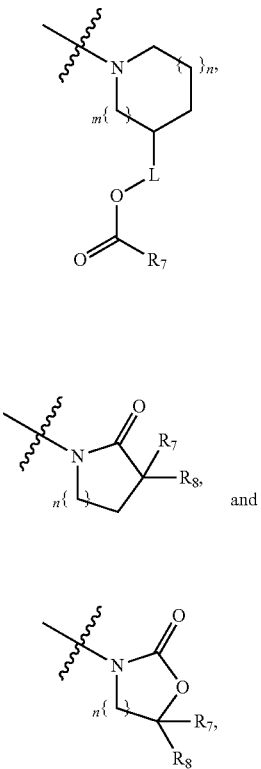

and where $R_6$, $R_7$, $R_8$, L, m, and n are defined herein. The hydroxyl group is ortho, meta, or para with respect to the aldehyde group. As shown in Scheme 5, substituted hydroxybenzaldehyde 5 is reacted under conditions effective to produce substituted hydroxybenzaldehyde 9, where —OC(O)$R_c$ occupies a position on the phenyl ring which is ortho, meta, or para relative to the aldehyde group. A derivatizing reagent is used in this process. Exemplary derivatizing reagents include, without limitation, $R_cC(O)Cl$. The derivatizing reagent $R_cC(O)Cl$ is commercially available or is produced by methods known in the art. The reaction is carried out in an appropriate solvent, e.g., methylene chloride, toluene, dimethylformide, or a mixture thereof. An acid binding agent is used in this reaction. Exemplary appropriate acid binding agents include, without limitation, pyridine, triethylamine, triethanolamine, 1,8-diazabicyclo[5.4.0]undec-7-ene (DBU), diisopropylethylamine (DIPEA), and sodium hydride. This reaction is carried out at low temperature, e.g., 0° C., at room temperature, under heating conditions, or a combination thereof Scheme 5

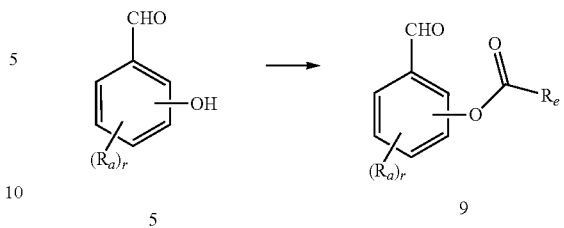

Secondly, as shown in Scheme 6, bisphosphonate cyclic acetal compounds are synthesized from substituted benzaldehyde 10. Substituted benzaldehyde 10 is any commercially available benzaldehyde or any benzaldehyde synthesized by methods known in the art, e.g., benzaldehydes 6-9 as shown in Schemes 2-5. In Scheme 6, $R_1$, $R_2$, $R_3$, $R_4$, $R_5$, $R_9$ and $R_{10}$ are defined herein, X and Y are halogens including, without limitation, Cl, Br, and I, and $R_f$ is $C_1$-$C_8$ alkyl, $C_2$-$C_8$ alkenyl, or $C_2$-$C_8$ alkynyl. As illustrated in Scheme 6, substituted benzaldehyde 10 is converted to intermediate 11. In some embodiments, X and Y are both Cl and benzaldehyde 10 is reacted with reagent such as triphosgene under conditions effective to produce intermediate 11. Other exemplary reagents to convert benzaldehyde 10 to intermediate 11 (where X and Y are each Cl) include, without limitation, phosgene. The reaction is carried out in an appropriate solvent, e.g., tetrahydrofuran, toluene, or a mixture thereof. An acid binding agent is used in this reaction. Exemplary appropriate acid binding agents include, without limitation, pyridine, triethylamine, triethanolamine, 1,8-diazabicyclo[5.4.0] undec-7-ene (DBU), and diisopropylethylamine (DIPEA). This reaction is carried out at low temperature, e.g., 0° C., at room temperature, under heating conditions, or a combination thereof.

Intermediate 11 is then reacted with $R_f$OH under conditions effective to produce carbonate 12. In some embodiments, $R_f$ is $C_1$-$C_8$ alkyl and X and Y are each Cl and intermediate 11 is reacted with t-BuOH to produce carbonate 12. This reaction is carried out in an appropriate solvent, e.g., tetrahydrofuran, methylene chloride, toluene, or a mixture thereof. An acid binding agent is used in this reaction. Exemplary appropriate acid binding agents include, without limitation, pyridine, triethylamine, triethanolamine, 1,8-diazabicyclo[5.4.0]undec-7-ene (DBU), and diisopropylethylamine (DIPEA). This reaction is carried out at low temperature, e.g., 0° C., at room temperature, under heating conditions, or a combination thereof.

Carbonate 12 is then reacted with bisphosphonate 13 under conditions effective to produce bisphosphonate cyclic acetal 14. The reaction is carried out in an appropriate solvent, e.g., acetonitrile. An acid binding agent is used in this reaction. Appropriate acid binding agents include, without limitation, pyridine, triethylamine, triethanolamine, 1,8-diazabicyclo [5.4.0]undec-7-ene (DBU), and diisopropylethylamine (DIPEA). This reaction is carried out under inert atmosphere. Exemplary inert atmospheres include, without limitation, nitrogen and argon atmosphere. This reaction is carried out at room temperature, under heating conditions, or a combination thereof. In some embodiments, the produced bisphosphonate cyclic acetal 14 is purified by purification methods known in the art, e.g., silica gel column chromatography. In some embodiments, carbonate 12 where $R_f$ is tert-butyl and X is Cl is reacted with bisphosphonate 13 to produce bisphosphonate cyclic acetal 14.

In some embodiments, bisphosphonate 13 where $R_9$ is OH and $R_{10}$ is

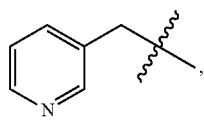 [SMILES: *Cc1cccnc1]

i.e., risedronate, is reacted with carbonate 12 under conditions effective to produce risedronate cyclic acetal 14, where $R_9$ is OH and $R_{10}$ is

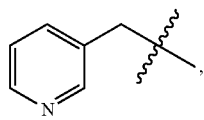

In some embodiments, a mixture of risedronate (bisphosphonate 13 where $R_9$ is OH and $R_{10}$ is

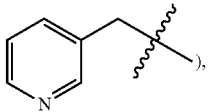

diisopropylethylamine, and acetonitrile is heated at 40° C. for 1 hour and then cooled to room temperature. Carbonate 12 where $R_f$ is tert-butyl and X is Cl is then added to the mixture and the mixture is heated at 35° C. for 16 hours under nitrogen atmosphere to produce risedronate cyclic acetal, (cyclic acetal 14 where $R_9$ is OH and $R_{10}$ is

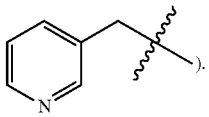 [SMILES: *Cc1cccnc1]

In some embodiments, bisphosphonate 13 where $R_9$ is OH and $R_{10}$ is

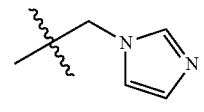 [SMILES: *Cn1ccnc1]

is reacted with carbonate 12 under conditions effective to produce risedronate cyclic acetal 14, where $R_9$ is OH and $R_{10}$ is

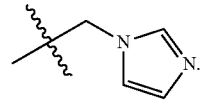 [SMILES: *Cn1ccnc1]

In some embodiments, a mixture of risedronate (bisphosphonate 13 where $R_9$ is OH and $R_{10}$ is

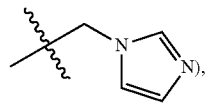

diisopropylethylamine, and acetonitrile is heated at 40° C. for 1 hour and then cooled to room temperature. Carbonate 12 where $R_f$ is tert-butyl and X is Cl is then added to the mixture and the mixture is heated at 35° C. for 16 hours under nitrogen atmosphere to produce risedronate cyclic acetal, (cyclic acetal 14 where $R_9$ is OH and $R_{10}$ is

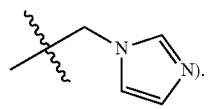

In some embodiments, bisphosphonate 13 where $R_9$ is H and $R_{10}$ is

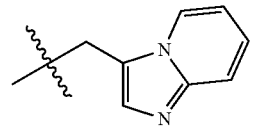 [SMILES: *Cc1cnc2ccccn12]

is reacted with carbonate 12 under conditions effective to produce risedronate cyclic acetal 14, where $R_9$ is H and $R_{10}$ is

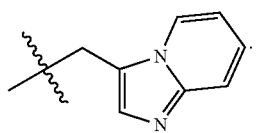

In some embodiments, a mixture of risedronate (bisphosphonate 13 where $R_9$ is H and $R_{10}$ is

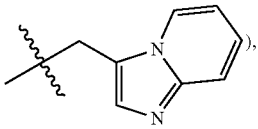

diisopropylethylamine, and acetonitrile is heated at 40° C. for 1 hour and then cooled to room temperature. Carbonate 12 where $R_f$ is tert-butyl and X is Cl is then added to the mixture and the mixture is heated at 35° C. for 16 hours under nitrogen atmosphere to produce risedronate cyclic acetal, (cyclic acetal 14 where $R_9$ is H and $R_{10}$ is

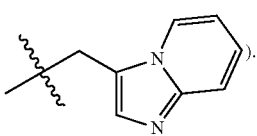 [SMILES: *Cc1cnc2ccccn12]

Scheme 6

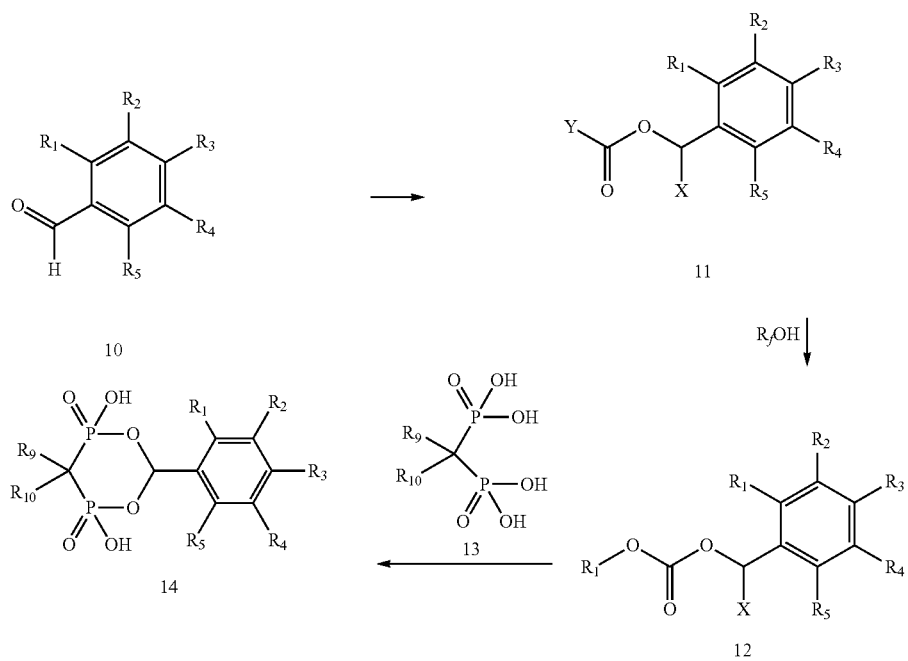

The compounds and pharmaceutically acceptable salts or hydrates of the compounds described herein are also useful in the manufacture of medicaments for treating or preventing disorder associated with abnormal calcium and phosphate metabolism in a mammal.

The cyclic acetal bisphosphonate compounds may exist in two isomeric forms, i.e., cis-isomer and trans-isomer. As shown in Scheme 7, when the α-hydroxy group and the substituted phenyl group are on the opposite side of the six-membered cyclic acetal ring, the isomer is assigned as a trans-isomer. If the α-hydroxy group and the substituted phenyl group are on the same side of the six-membered cyclic acetal ring, the isomer is assigned as a cis-isomer. In some embodiments, the two isomers are separated and the configuration of each isomer is assigned using analogy to the NMR characteristics of reported similar systems (see (1). V. A. Pavlov, J. A. S. Smith, T. A. Zjablikova, Magnetic Resonance in Chemistry, 1992, 30, 716-722; (2) G. C. Levy, G. L. Nelson, Carbon-13 Nuclear Magnetic Resonance for Organic Chemists, Wiley-Interscience, New York, 1972).

Scheme 7

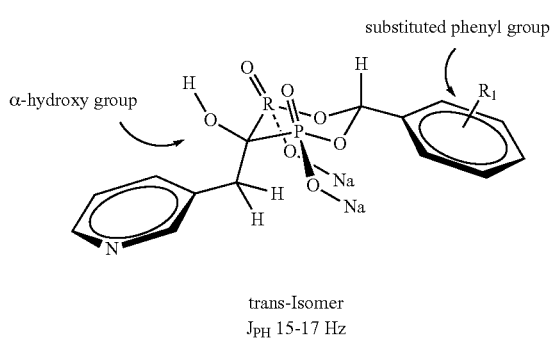

trans-Isomer
J$_{PH}$ 15-17 Hz

-continued

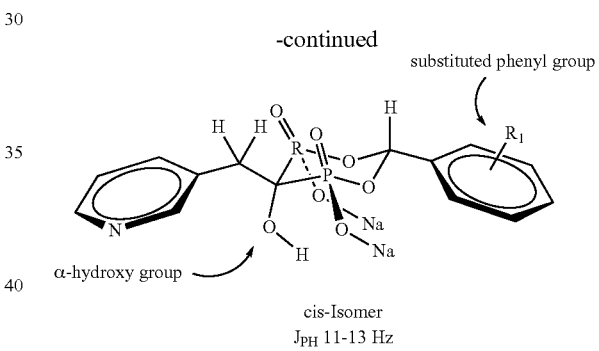

cis-Isomer
J$_{PH}$ 11-13 Hz

Pharmaceutical Compositions

In some embodiments, the compounds or pharmaceutically acceptable salts or hydrates of the compounds described herein are a component of a composition that includes one or more pharmaceutically acceptable excipients.

In some embodiments, the composition further comprises a pharmaceutically-acceptable excipient. The term "pharmaceutically-acceptable excipient," as used herein, means any physiologically inert, pharmacologically inactive material known to one skilled in the art, which is compatible with the physical and chemical characteristics of the isomer herein. Pharmaceutically-acceptable excipients include, but are not limited to, polymers, resins, plasticizers, fillers, lubricants, diluents, binders, disintegrants, solvents, co-solvents, surfactants, preservatives, sweetening agents, flavoring agents, pharmaceutical grade dyes or pigments, and viscosity agents.

Flavoring agents and dyes and pigments among those useful herein include those described in *Handbook of Pharmaceutical Excipients* (4$^{th}$ ed., Pharmaceutical Press 2003).

Suitable co-solvents include, but are not limited to, ethanol, isopropanol, and acetone.

Suitable surfactants include, but are not limited to, polyoxyethylene sorbitan fatty acid esters, polyoxyethylene monoalkyl ethers, sucrose monoesters, sodium lauryl sulfate, Tween 80®, and lanolin esters and ethers.

Suitable preservatives include, but are not limited to, phenol, alkyl esters of parahydroxybenzoic acid, benzoic acid and the salts thereof, boric acid and the salts thereof, sorbic acid and the salts thereof, chlorobutanol, benzyl alcohol, thimerosal, phenylmercuric acetate and nitrate, nitromersol, benzoalkonium chloride, cetylypridinium chloride, methyl paraben, and propyl paraben.

Suitable fillers include, but are not limited to, starch, lactose, sucrose, maltodextrin, and microcrystalline cellulose.

Suitable plasticizers include, but are not limited to, triethyl citrate, polyethylene glycol, propylene glycol, dibutyl phthalate, castor oil, acetylated monoglycerides, and triacetin.

Suitable polymers include, but are not limited to, ethylcellulose, cellulose acetate trimellitate, hydroxypropylmethylcellulose phthalate, cellulose acetate phthalate, polyvinyl acetate phthalate, and Eudragit® L 30-D, Eudragit® L 100-55, and Eudragit® S100 (Rohm Pharma GmbH and Co. KG, Darmstadt, Germany), and Acryl-EZE® and Sureteric® (Colorcon, Inc., West Point, Pa.).

Suitable lubricants include, but are not limited to, magnesium stearate, stearic acid, and talc.

The pharmaceutical compositions described herein, in some embodiments, optionally comprise a chelating agent. The term "chelating agent," as used herein, means a molecule containing two or more electron donor atoms that can form coordinate bonds to a single metal ion. The term "chelating agent" is understood to include the chelating agent as well as salts thereof. For example, the term "chelating agent" includes citric acid as well as its salt forms.

The most common and widely used chelating agents coordinate to metal atoms through oxygen or nitrogen donor atoms, or both. Other less common chelating agents coordinate through sulfur in the form of —SH (thiol or mercapto) groups. After the first coordinate bond is framed, each successive donor atom that binds creates a ring containing the metal atom. A chelating agent may be bidentate, tridentate, tetradentate, etc., depending upon whether it contains two, three, four, or more donor atoms capable of binding to the metal atom. See Kirk-Othmer Encyclopedia of Chemical Technology ($4^{th}$ ed. 2001).

Chelating agents suitable for use in the compositions described herein include any pharmaceutically-acceptable chelating agent. Non-limiting examples of chelating agents suitable for use in the present invention include ethylenediaminetetraacetic acid (EDTA), citric acid, malic acid, tartaric acid, lactic acid, aspartic acid, glutamic acid, lysine, sodium hexametaphosphate, and combinations thereof. In one embodiment of the present invention, the chelating agent is EDTA, citric acid, or sodium hexametaphosphate. In certain preferred embodiments, the chelating agent is EDTA or salts thereof, in more preferred embodiments, the chelating agent is disodium EDTA. In certain embodiments, the bisphosphonate compounds described herein are formulated as oral dosage forms disclosed in U.S. Pat. No. 7,645,459 or U.S. Pat. No. 7,645,460, which are incorporated herein by reference in their entirety.

In another embodiment, a monodentate complexing agent is used in place of a polydentate chelating agent. Suitable monodentate complexing agents include, but are not limited to, phosphates (e.g., sodium phosphate, sodium aluminum phosphate, sodium acid phosphate, dipotassium phosphate, disodium phosphate, monobasic) and carboxylic acids (e.g., fumaric acid, acetic acid). In one embodiment, the monodentate complexing agent is acetic acid.

The amount of chelating agent present in the oral dosage form of the present invention will depend on the particular chelating agent selected and the amount of bisphosphonate compound present in the oral dosage form. Generally, the oral dosage forms of the present invention will contain a safe and effective amount of a chelating agent suitable for achieving the desired chelating effect. In one embodiment, the oral dosage form contains from about 10 mg to about 1000 mg of a chelating agent per unit dose. In another embodiment, the oral dosage forms contain from about 10 mg to about 500 mg of a chelating agent per unit dose. When the chelating agent is EDTA or salts thereof, the preferred range is from about 10 mg to about 500 mg, preferably from about 75 mg to about 250 mg, and more preferably from about 25 mg to about 250 mg per unit dose. When the chelating agent is citric acid or any other chelating agent, the preferred range is from about 25 mg to about 1000 mg, preferably from about 50 mg to about 500 mg per unit dose.

In some embodiments, the pharmaceutical compositions described herein optionally comprise a delayed release mechanism. The term "delayed release," as used herein, refers to a delivery of a bisphosphonate active ingredient and a chelating agent which is achieved by formulating the pharmaceutical composition comprising the bisphosphonate and the chelating agent so that they will be released at a generally predictable location in the lower GI tract, more distal to that which would have been accomplished had there been no alteration in the delivery of the bisphosphonate and the chelating agent. In certain embodiments, the delayed release mechanism is selected from the group consisting of pH triggered delivery systems, bacterial enzyme triggered delivery systems, time dependent delivery systems and combinations thereof. In pH triggered delivery systems, the delayed release of the pharmaceutical composition may be achieved by coating the tablet, capsule, or particles, granules, or beads of the bisphosphonate and the chelating agent with a substance which is pH dependent, i.e., broken down or dissolves at a pH which is generally present in the lower GI tract, but not present in the upper GI tract (i.e., the mouth, buccal cavity, pharynx, esophagus, or stomach).

In some embodiments, the pharmaceutical compositions described herein optionally comprise a pH triggered delivery system of a film coating or an enteric coating. In some embodiments, the enteric coating enables the bisphosphonate compounds to avoid contacts with stomach acidic fluids. Excipients suitable for use in a film coating include, but are not limited to, hydroxypropylmethylcellulose, hydroxypropylcellulose, gelatin, polyvinylpyrrolidone, lactose, polyethylene glycol, talc, microcrystalline cellulose, and polyvinyl alcohol. Excipients suitable for use in an enteric coating include, but are not limited to, cellulose acetate trimelliate, hydroxypropylmethylcellulose phthalate, cellulose acetate phthalate, polyvinyl acetate phthalate, Eudragit® L 30-D, Eudragit® L 100-55, Eudragit® S100 (Rohm Pharma GmbH and Co. KG, Darmstadt, Germany), Acryl-EZE® and Sureteric® (Colorcon, Inc., West Point, Pa.), triethyl citrate, polyethylene glycol, propylene glycol, dibutyl phthalate, castor oil, acetylated monoglycerides, triacetin, and talc.

Such pharmaceutical compositions are prepared, for example, using a method including admixing the compound or pharmaceutically acceptable salt or hydrate of the compound and a pharmaceutically acceptable excipient. Admixing is accomplished using methods well known for admixing a compound or a pharmaceutically acceptable salt or hydrate of a compound and a physiologically acceptable excipient. Examples of such excipients are well known to those skilled in the art and are prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Satisfactory pharmaceutically acceptable excipients include those that are compatible with the other ingredients in the formulation and that are biologically acceptable.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule.

The compounds or pharmaceutically acceptable salts or hydrates of the compounds described herein may be administered orally or parenterally, neat or in combination with conventional pharmaceutical carriers as described above. The compounds or pharmaceutically acceptable salts or hydrates of the compounds described herein can also be administered by any convenient route, for example, orally, by infusion or bolus injection, by absorption through epithelial or mucocutaneous linings (e.g., oral, rectal, vaginal, and intestinal mucosa, etc.) and can be administered together with another therapeutic agent.

In some embodiments, the bisphosphonate cyclic acetal compounds described herein are administered as an adjuvant with one or more anti-inflammatory or immunomodulatory compounds. The use of higher affinity bisphosphonate compounds known in the art with anti-inflammatory compounds is limited due to toxicity issues related to the combination of these compounds. In particular, higher dosages of anti-inflammatory compounds are required to protect bone, when co-administered with known bisphosphonate compounds. Because of the higher dosages, however, side effects and other toxicity-related effects are quickly observed and the co-administration can be stopped. Because the bisphosphonate cyclic acetal compounds described herein have improved absorption which allows for lower dosage, however, they can be used effectively to protect bone in combination with anti-inflammatories or immunomodulatory agents at dosage levels that are low enough to not trigger toxic effects. Accordingly, the compounds described herein provide improved protection against bone erosion, while at the same time offering improved joint preservation, while inducing less overall skeletal turnover reduction than traditional bisphosphonates. In one embodiment, the compounds described herein are useful for inhibiting bone erosion. In another embodiment, the compounds described herein are useful for inhibiting both inflammation and bone erosion. For example, such anti-inflammatory, immunomodulatory and anti-erosion properties are achieved in some embodiments when the bisphosphonate cyclic acetal compounds described herein are co-administered with an anti-inflammatory or immunomodulatory agent. In these embodiments, the anti-inflammatory or immunomodulatory agent can be administered at lower doses than when administered on its own. Thus, in some embodiments, the bisphosphonate cyclic acetal compound is administered in combination or in sequence with the one or more anti-inflammatory or immunomodulatory compounds. Exemplary anti-inflammatory compounds include, without limitation, biologic anti-inflammatory compounds such as tumor necrosis factor antagonists (e.g., Enbrel®), NSAIDs, and methotrexate.

The synergy of the bisphosphonate cyclic acetal compounds described herein is also beneficial for treatment of osteoarthritis. In osteoarthritis, the afflicted joints are known to exhibit higher bone turnover. Treatment with a combination of one or more of the bisphosphonate cyclic acetal compounds described herein and an anti-inflammatory compound can normalize the turnover at these sites without producing excessive bone turnover in the remaining skeleton. In addition, the co-administration minimizes any potential antiapoptotic effects on chondrocytes that are delivered to this joint by the virtue of these lower affinity bisphosphonate analogs. The compounds described herein are useful for improvement of joint function.

Similarly, the compounds described herein can also be co-administered with anabolic compounds. With bisphosphonate compounds known in the art, a wash out phase is necessary when treating patients who have been previously administered anabolic compounds, such as parathyroid hormone and prostaglandins. The lower bone affinity of the compounds described herein, however, results in less interference with these anabolic agents. Accordingly, the compounds described herein can be administered to patients treated with anabolic agents with little or no washout period. In one embodiment, the compounds described herein are co-administered with one or more anabolic compounds. One exemplary anabolic compound is a compound based on parathyroid hormones (PTH) such as PTH 1-34 (Forteo®). Anabolic therapy is often prescribed to patients with very serious osteoporotic disease and/or those who do not respond to bisphosphonate therapy. Accordingly, the bisphosphonate cyclic acetal compounds described herein are useful for treatment of osteoporotic disease, as well as subjects who respond poorly to bisphosphonate therapy.

It is understood that the dosage, regimen and mode of administration of the bisphosphonate cyclic acetal compounds will vary according to the malady and the individual being treated and will be subject to the judgment of the medical practitioner involved. In some embodiments, administration of one or more of the compounds or pharmaceutically acceptable salts or hydrates of the compounds described herein begins at a low dose and is increased until the desired effects are achieved.

The bisphosphonate cyclic acetal compound or a pharmaceutically acceptable salt or hydrate thereof of this invention is delivered in an amount that is effective for treating or preventing bone metabolism disorder. In addition, in vitro or in vivo assays are optionally employed to help identify optimal dosage ranges. The precise dose to be employed will also depend on the route of administration, the condition, the seriousness of the condition being treated, as well as various physical factors related to the individual being treated, and should be decided according to the judgment of a health-care practitioner. The number and frequency of dosages corresponding to a completed course of therapy will be determined according to the judgment of a health-care practitioner.

The amount of the bisphosphonate cyclic acetal compound or a pharmaceutically acceptable salt or hydrate thereof of this invention that is effective for treating or preventing a central nervous system disorder will typically range from about 0.01 mg/kg to about 1 g/kg of body weight per day; in another embodiment, from about 1 mg/kg to about 600 mg/kg body weight per day; in another embodiment, from about 1 mg/kg to about 250 mg/kg body weight per day; in another embodiment, from about 10 mg/kg to about 400 mg/kg body weight per day; in another embodiment, from about 10 mg/kg to about 200 mg/kg of body weight per day; in another embodiment, from about 10 mg/kg to about 100 mg/kg of body weight per day; in one embodiment, from about 10 mg/kg to about 25 mg/kg body weight per day; in another embodiment, from about 1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day.

In one embodiment, the pharmaceutical composition is in unit dosage form. In such form, the composition is sub-divided in unit dose containing appropriate quantities of the compound or pharmaceutically acceptable salt or hydrate of the compound; the unit dosage form can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage forms may contain from about 0.01 mg/kg to about 250 mg/kg, in one embodiment from about 1 mg/kg to about 250 mg/kg, in another embodiment from about 10 mg/kg to about 25 mg/kg, and may be given in a single dose or in two or more divided doses. Variations in the dosage will necessarily depend upon the species, weight and condition of the patient being treated and the patient's individual response to the medicament.

In one embodiment, the unit dosage form is about 0.01 to about 1000 mg. In another embodiment, the unit dosage form is about 0.01 to about 500 mg; in another embodiment, the unit dosage form is about 0.01 to about 250 mg; in another embodiment, the unit dosage form is about 0.01 to about 100 mg; in another embodiment, the unit dosage form is about 0.01 to about 50 mg; in another embodiment, the unit dosage form is about 0.01 to about 25 mg; in another embodiment, the unit dosage form is about 0.01 to about 10 mg; in another embodiment, the unit dosage form is about 0.01 to about 5 mg; and in another embodiment, the unit dosage form is about 0.01 to about 10 mg.

An enteric coating can be applied to the compressed tablet, the capsule (e.g., gelatin, starch, or hydroxypropylmethylcellulose) and/or the beads, particles or granules of active ingredient in a sufficient thickness so that the entire coating does not dissolve in gastrointestinal fluids at a pH below 5.5, but does dissolve at a pH of 5.5 or above. The dissolution or disintegration of the excipient coating generally does not occur until the entry of the coated dosage form into the small intestine.

It is expected that any anionic polymer exhibiting the requisite pH-dependent solubility profile can be used as an enteric coating in the practice of the present invention to achieve delivery of the bisphosphonate and chelating agent to the lower GI tract. The coating is chosen dependent upon compatibility with the particular bisphosphonate cyclic acetal compound selected. The preferred polymers for use in the present invention are anionic carboxylic polymers. It is particularly preferred that the polymers are acrylic polymers, and, more preferably, partly methyl-esterified methacrylic acid polymers, in which the ratio of free anionic carboxyl groups to ester groups is about 1:1.

A particularly suitable methacrylic acid copolymer is Eudragit L.R™, particularly Eudragit L 30 D-55.R™ and Eudragit L 100-55.R™, manufactured by Rohm Pharma GmbH and Co. KG, Darmstadt, Germany. In Eudragit L 30 D-55.R™, the ratio of free carboxyl groups to ester groups is approximately 1:1. Further, said copolymer is known to be insoluble in GI fluids having a pH below 5.5. That is, it is generally insoluble in the fluid of the upper GI tract having a pH of about 1.5 to 5.5, but readily soluble at pH above 5.5, which corresponds to the pH of the fluid in the lower GI tract.

Other methacrylic acid copolymer which are suitable for use in coating the oral dosage forms and/or the granules, particles, or beads of active ingredient which can be employed in the method of treatment described herein, either alone or in combination with other coatings, is Eudragit S.R™ and Eudragit FS30D.R™, manufactured by Rohm Pharma GmbH and Co. KG, Darmstadt, Germany. Eudragit S.R™ differs from Eudragit L 30 D-55.R™ only insofar as the ratio of free carboxyl groups to ester groups is approximately 1:2. Eudragit S.R™ is also, like Eudragit L 30 D-55.R™, substantially insoluble at pH below 5.5, but unlike Eudragit L 30 D-55.R™, is poorly soluble in GI fluids having a pH of 5.5-7.0, such as that present in small intestinal fluids. Eudragit S.R™ is soluble at pH 7.0 and above, such as that present in the terminal ileum and colon.

Eudragit S.R™ can also be used alone as a coating which would provide delivery of the bisphosphonate active ingredient beginning primarily at the large intestine (more distal than the terminal ileum) via a delayed-release mechanism. In addition, Eudragit S.R™, being poorly soluble in intestinal fluids below pH 7.0, can be used in combination with Eudragit L 30 D-55.R™, soluble in intestinal fluids above pH 5.5, in order to effect a delayed release composition which can be formulated to deliver the active ingredient at various segments of the intestinal tract; the more Eudragit L 30 D-55.R™ used, the more proximal release and delivery begins and the more Eudragit S.R™ used, the more distal release and delivery begins.

The coating can, and usually will, contain a plasticizer and possibly other coating excipients such as coloring agents, surfactant, talc, and/or magnesium stearate, many of which are well known in the coating art. In particular, anionic carboxylic acrylic polymers usually will contain 10-25% by weight of a plasticizer, especially triethyl citrate, tributyl citrate, acteyltriethyl citrate, dibutyl phthalate, diethyl phthalate, polyethylene glycol, acetylated monoglycerides propylene glycol, and triacetin. Conventional coating techniques such as fluid-bed or pan coating are employed to apply the coating. Coating thickness are sufficient to ensure that the oral dosage form remains essentially intact until the desired site of delivery in the lower GI tract is reached.

The solid oral dosage form may be in the form of a coated compressed tablet which contains particles or granules of the bisphosphonate active ingredient and the chelating agent, or of a soft or hard capsule (e.g., gelatin, starch, or hydroxypropylmethylcellulose), coated or uncoated, which contains beads or particles of the bisphosphonate active ingredient and the chelating agent, which themselves are enterically coated.

For sustained release of the bisphosphonate and chelating agent a sustained release polymer is required to control the dissolution rate of the bisphosphonate and chelating agent from the dosage form. If the bisphosphonate and chelating agent are both soluble (defined as 33 mg/ml or greater in water) then high levels of sustained release polymers are required. Sustained release polymers include but are not limited to, hydroxypropylmethylcellulose, hydroxypropylcellulose and Carbomer.

Methods of Use

The present invention further relates to a method of treating, preventing or ameliorating disorders of bone metabolism, such as those characterized by abnormal calcium and phosphate metabolism. These methods include the step of administering to a human or other mammal in need thereof a safe and effective amount of a pharmaceutical composition delivered to said human or other mammal via the oral dosage forms described herein.

Diseases characterized by abnormal calcium and phosphate metabolism include, but are not limited to, osteoporosis, secondary osteoporosis, secondary osteoporosis stemming from osteoporosis, osteoarthritis, Paget's disease (osteitis deformans), hyperparathyroidism, hypercalcemia of malignancy, osteolytic bone metastasis, myositis ossificans progressiva, calcinosis universalis, and such afflictions as arthritis, neuritis, bursitis, tendonitis, bone pain, and other inflammatory conditions which predispose involved tissue to loss or deposition of calcium phosphates. The compounds described herein are also useful for other bone disorders and conditions such as, without limitation, fracture repair, prosthesis integration, and osteonecrosis (e.g., of hip or knee). The compounds described herein are also useful for the prevention and treatment of skeletal related events associated with cancer such as metastasis, tumor growth, bone pain, fractures, and such afflictions as arthritis (including bone disease and joint function in osteoarthritis). Further, the compounds described herein are also useful for treatment and prevention of additional skeletal related events induced during the treatment of cancer, such as hormone ablation therapy, aromatase inhibitor therapy, and androgen ablation therapy, particularly in patients suffering from breast or cancer patients.

In other embodiments, the disorder may be a non-skeletal disorder such as, but not limited to, a non-bone cancer, an immunomodulatory disorder, an inflammatory disorder, or a parasitic disorder. In these embodiments, the parasitic disorder can be, but is not limited to, malaria, leishmaniasis, a trypanasomal disease, an entamoebal infection, a giardia infection, and a cryptosporidial infection.

The compounds described herein are also useful for the prevention and treatment of parasitic disorders such as malaria and Chagas disease, and disorders of the gastrointestinal tract such as intestinal parasites, and irritable bowel disease. In some embodiments, the compounds described herein are, in some embodiments, useful to inhibit or treat parasitic infections, such as protozoan infections and diseases including malaria trypanasomes leishmania, entomaeba, cryptosporidium, and giardia.

In some embodiments, the compounds described herein are useful for treating or preventing inflammation disorders. Such disorders include, without limitation, rheumatoid arthritis, and irritable bowel disease. In some embodiments, when used for treating or preventing inflammation disorders, the compounds described herein are used in combination with one or more anti-inflammatory compounds.

In some embodiments, the compounds described herein are useful for treating, preventing or ameliorating dental disorders. Exemplary disorders include, without limitation, cavities and periodontal disease. In some embodiments, the compounds described herein are useful for treatment related to dental surgical procedures, such as tooth implantation.

In some embodiments, the compounds described herein are useful for treatment related to orthopedic joint implants, for example, to improve fixation of artificial joins, or to prevent loosening of implanted joints. In further embodiments, the compounds described herein have orthopedic uses, such as to promote or facilitate fracture repair and bone regeneration, either when used as a sole therapy on in conjunction with other pharmaceutical or non-pharmaceutical orthopedic therapy.

In further embodiments, the bisphosphonate cyclic acetal compounds described herein offer orthopedic utility in the outcomes of hip, knee or other skeletal sites in both pediatric and adult populations.

The oral dosage forms described herein are suitable for administration to pediatric or adult patients in need of such treatment.

In some embodiments, the bisphosphonate cyclic acetal compounds described herein are useful as part of hormone ablation therapy, for example, in patients suffering from breast cancer or prostate cancer. In some embodiments, the bisphosphonate cyclic acetal compounds described herein are useful as part of aromatase inhibitor therapy, for example, in patients suffering from cancer. In some embodiments, the bisphosphonate cyclic acetal compounds described herein are useful as part of androgen ablation therapy, for example, in patients suffering from prostate cancer or other diseases.

Administration of the bisphosphonate cyclic acetal compounds described herein can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the compositions containing the bisphosphonate cyclic acetal compounds described herein can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, in all manners known to those skilled in the pharmaceutical arts.

The oral dosage forms of the present invention are suitable for administration to a patient according to a continuous dosing interval of daily, weekly, three times per month, twice monthly, and monthly.

When administered for the treatment or inhibition of a particular disease state or disorder, it is understood that the effective dosage may vary depending upon the particular the bisphosphonate cyclic acetal compounds or pharmaceutically acceptable salts or hydrates thereof of this invention utilized, the mode of administration, the condition, and severity thereof, of the condition being treated, as well as the various physical factors related to the individual being treated. In therapeutic application, the bisphosphonate cyclic acetal compounds and pharmaceutically acceptable salts or hydrates thereof described herein are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case can be subjectively determined by the attending physician. The variables involved include the specific condition and the size, age and response pattern of the patient.

The bisphosphonate cyclic acetal compounds and pharmaceutically acceptable salts or hydrates thereof described herein are also useful in the manufacture of medicaments for treating a bone metabolism disorder in a mammal. Similarly, the bisphosphonate cyclic acetal compounds and pharmaceutically acceptable salts or hydrates thereof described herein are also useful in the manufacture of medicaments for treating a bone metabolism disorder.

The following examples illustrate the production of representative compounds described herein.

EXAMPLES

The following examples illustrate the production of representative compounds described herein. In some instances, it will be readily understood that the products may have included the monosodium salt in combination with the disodium salt.

Section 1. Synthesis of Substituted Benzaldehydes.

Substituted benzaldehydes were either commercially available or synthesized accordingly to the following procedures.

Example 1

4-Formylphenyl octanoate

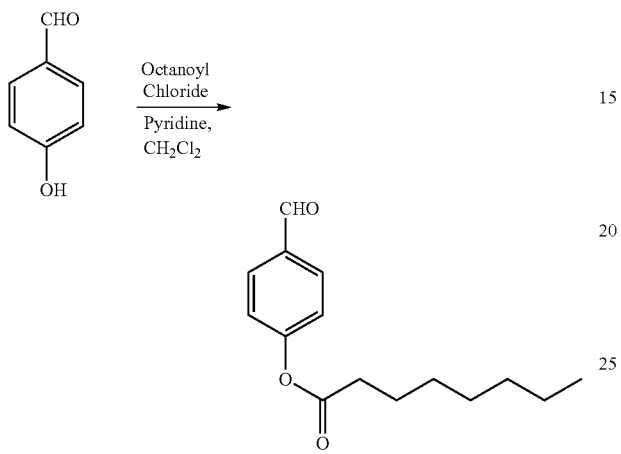

To a 250 mL dry round bottom flask were added 4-hydroxybenzaldehyde (6.11 g, 50.0 mmol) and anhydrous $CH_2Cl_2$ (50 mL). The solution was cooled in an ice-water bath, then pyridine (8.09 mL, 100 mmol) was added. To the resulting solution, octanoyl chloride (10.3 mL, 60 mmol) was added slowly under stirring and $N_2$. The mixture was first stirred at 0° C. for 2 hours, then at room temperature for 20 hours. To the reaction mixture, water (100 mL) was added and the $CH_2Cl_2$ layer was separated. The aqueous layer was extracted continually with $CH_2Cl_2$ (100 mL×2). The combined $CH_2Cl_2$ solution was dried over $Na_2SO_4$. After removal of the solvent, the residue was purified with a silica gel chromatography (heptane/ethyl acetate, gradient eluting) to give 4-formylphenyl octanoate (10.7 g) as colorless oil. Yield: 86%. $^1$H NMR ($CDCl_3$, 300 MHz): δ=9.98 (s, 1H), 7.91 (d, J=8.7 Hz, 2H), 7.26 (d, J=8.4 Hz, 2H), 2.58 (t, J=6.9 Hz, 2H), 1.38-0.86 (m, 13H). $^{13}$C NMR ($CDCl_3$, 75.5 MHz): δ=191.0, 171.7, 155.6, 134.0, 131.3, 122.5, 34.5, 31.7, 29.1, 29.0, 24.9, 22.7, 14.2.

Example 2

4-Formylphenyl isopropyl carbonate

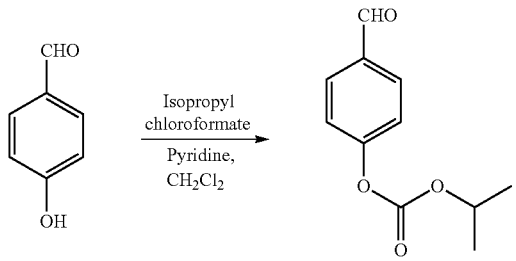

To a 250 mL dry round bottom flask were added 4-hydroxybenzaldehyde (4.88 g, 40.0 mmol), anhydrous $CH_2Cl_2$ (40 mL) and pyridine (4.2 mL, 52.0 mmol). The mixture was stirred in an ice-water bath, then a solution of isopropyl chloroformate in toluene (1.0 M, 48.0 mL) was added. After stirring at 0° C. for 2 hours, water (100 mL) and MTBE (300 mL) were added to the reaction mixture. The aqueous layer was separated, and the MTBE layer was washed, respectively, with cold water (80 mL), cold 5% NaOH aqueous solution (80 mL), cold water (80 mL), cold 0.5 N HCl aqueous solution (80 mL) and cold water (80 mL). The organic layer was dried over $Na_2SO_4$, and the solvent was evaporated to give 4-formylphenyl isopropyl carbonate (8.50 g) as pale yellow oil. Yield: 100%. $^1$H NMR ($CDCl_3$, 300 MHz): δ=9.71 (s, 1H), 7.64 (d, J=8.4 Hz, 2H), 7.10 (d, J=8.7 Hz, 2H), 4.73 (seventet, J=6.0 Hz, 1H), 1.12 (d, J=6.3 Hz, 6H).

Example 3

3,5-Difluoro-4-formylphenyl 2-oxooxazolidine-3-carboxylate

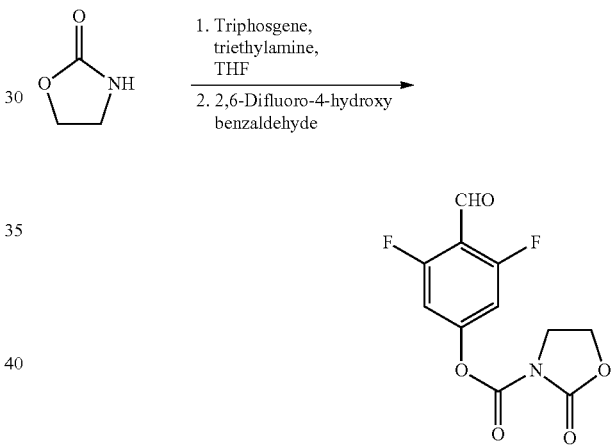

To a 250 mL dry round bottom flask were added 2-oxazolidinone (4.35 g, 50.0 mmol), triphosgene (5.49 g, 18.5 mmol) and anhydrous THF (80 mL). The mixture was stirred in an ice-water bath, then triethylamine (9.8 mL, 70.0 mmol) was added slowly. After stirring at 0° C. for 1 hour, the mixture was stirred continually at room temperature overnight. The reaction mixture was filtered and the filtrate was concentrated. The residue was dissolved in 20 mL of $CH_2Cl_2$, and this solution was added slowly to a stirring mixture of 2,6-difluoro-4-hydroxybenzaldehyde (5.93 g, 27.5 mmol) and pyridine (4.44 mL, 55.0 mmol) in 30 mL of anhydrous $CH_2Cl_2$ at 0° C. After stirring at room temperature for 10 hours, water (100 mL) was added to the reaction mixture. The $CH_2Cl_2$ layer was separated, and the aqueous layer was extracted continually with $CH_2Cl_2$ (50 mL×4). The combined $CH_2Cl_2$ solution was dried over $Na_2SO_4$. After removal of the solvent, the residue was purified with a silica gel chromatography (heptane/ethyl acetate, gradient eluting) to give 3,5-difluoro-4-formylphenyl 2-oxooxazolidine-3-carboxylate (4.92 g) as a white solid. Yield: 33%. $^1$H NMR ($CDCl_3$, 300 MHz): δ=10.29 (s, 1H), 6.98 (dd, J=10.8, 2.1 Hz, 2H), 4.51 (t, J=7.8 Hz, 2H), 4.18 (t, J=7.6 Hz, 2H). $^{13}$C NMR ($CDCl_3$, 75.5

MHz): δ=183.5, 163.7 (dd, J=263.6, 8.00 Hz), 151.2, 148.0, 112.6, 106.8 (dd, J=25.7, 3.70 Hz), 62.1, 43.7.

Example 4

3-Formylphenyl butyrate

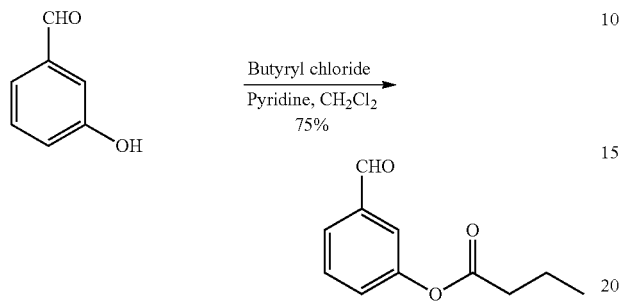

To a 250 mL dry round bottom flask were added 3-hydroxybenzaldehyde (5.0 g, 41.0 mmol), anhydrous CH$_2$Cl$_2$ (50 mL). The solution was cooled in an ice-water bath, then pyridine (6.64 mL, 82.0 mmol) was added. To the resulting solution, butyryl chloride (5.15 mL, 49.2 mmol) was added slowly under stirring and N$_2$. The mixture was first stirred at 0° C. for 2 hours, then at room temperature for 20 hours. To the reaction mixture, water (80 mL) was added and the CH$_2$Cl$_2$ layer was separated. The aqueous layer was extracted continually with CH$_2$Cl$_2$ (50 mL×3). The combined CH$_2$Cl$_2$ solution was dried over Na$_2$SO$_4$. After removal of the solvent, the residue was purified with a silica gel chromatography (heptane/ethyl acetate, gradient eluting) to give 3-formylphenyl butyrate (5.9 g) as colorless oil. Yield: 75%. $^1$H NMR (CDCl$_3$, 300 MHz): δ=9.96 (s, 1H), 7.72 (t of d, J=1.2, 7.5 Hz, 1H), 7.60 (t, J=2.4 Hz, 1H), 7.52 (t, J=8.1 Hz, 1H), 7.36-7.32 (m, 1H), 2.56 (t, J=7.5 Hz, 2H), 1.78 (sextet, J=7.2 Hz, 2H), 1.04 (t, J=7.5 Hz, 3H). $^{13}$C NMR (CDCl$_3$, 75.5 MHz): δ=191.2, 171.7, 151.3, 137.7, 130.1, 127.8, 127.2, 122.2, 36.0, 18.3, 13.5.

Example 5

Ethyl 4-formylphenyl carbonate

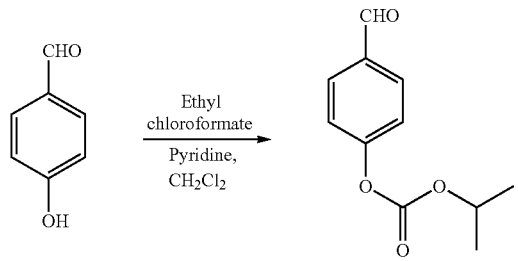

To a 250 mL dry round bottom flask were added 4-hydroxybenzaldehyde (6.11 g, 50.0 mmol), anhydrous CH$_2$Cl$_2$ (150 mL). The solution was cooled in an ice-water bath, then pyridine (4.86 mL, 60.0 mmol) was added. To the resulting solution, ethyl chloroformate (4.78 mL, 50.0 mmol) was added slowly under stirring and N$_2$. The mixture was stirred and warmed to room temperature, then stirred at room temperature overnight. To the reaction mixture, water (100 mL) was added and the CH$_2$Cl$_2$ layer was separated. The aqueous layer was extracted continually with CH$_2$Cl$_2$ (100 mL×2). The combined CH$_2$Cl$_2$ solution was dried over Na$_2$SO$_4$. After removal of the solvent, the residue was purified with a silica gel chromatography (heptane/ethyl acetate, gradient eluting) to give ethyl 4-formylphenyl carbonate (8.92 g) as colorless oil. Yield: 92%. $^1$H NMR (CDCl$_3$, 300 MHz): δ=10.07 (s, 1H), 8.00 (d, J=8.7 Hz, 2H), 7.45 (d, J=8.7 Hz, 2H), 4.42 (q, J=7.2 Hz, 2H), 1.47 (t, J=7.2 Hz, 3H). $^{13}$C NMR (CDCl$_3$, 75.5 MHz): δ=191.0, 155.7, 152.9, 134.2, 131.4, 121.9, 65.4, 14.3.

Example 6

4-Formylphenyl tetrahydro-2H-pyran-4-carboxylate

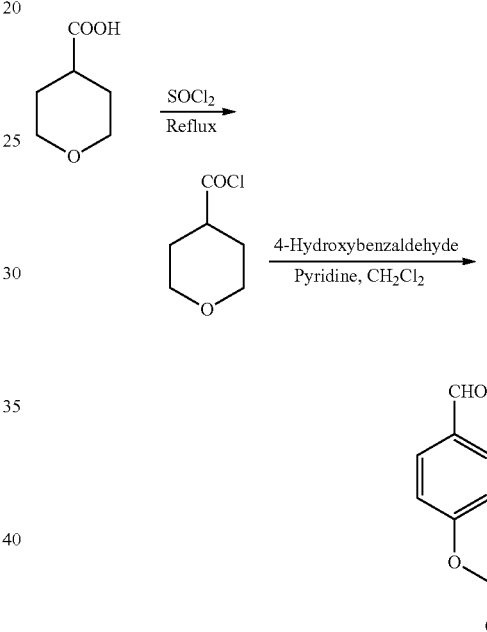
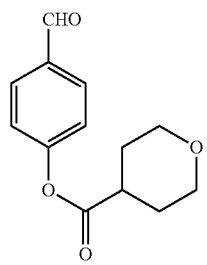

To a 100 mL dry round bottom flask were added tetrahydro-pyran-4-carboxylic acid (2.8 g, 21.5 mmol), thionyl chloride (2.8 mL, 34.4 mmol). The mixture was refluxed for 45 minutes, then all the volatile materials were rotary-evaporated. To the residue, anhydrous CH$_2$Cl$_2$ (10 mL) was added. The resulting solution was cooled to 0° C., and pyridine (2.63 g, 21.5 mmol) was added, followed by a solution of 4-hydroxybenzaldehyde (2.04 g, 25.8 mmol) in anhydrous CH$_2$Cl$_2$ (30 mL). The reaction mixture was stirred and warmed from 0° C. to room temperature slowly, then at room temperature overnight. To the reaction mixture, water (60 mL) was added and the CH$_2$Cl$_2$ layer was separated. The aqueous layer was extracted continually with CH$_2$Cl$_2$ (50 mL×3). The combined CH$_2$Cl$_2$ solution was washed with a cold aqueous solution of saturated NaHCO$_3$ (80 mL). After drying and removal of the solvent, the residue was purified with a silica gel chromatography (heptane/ethyl acetate, gradient eluting) to give 4-formylphenyl tetrahydro-2H-pyran-4-carboxylate (4.40 g) as colorless oil. Yield: 87%. $^1$H NMR (CDCl$_3$, 300 MHz): δ=9.97 (s, 1H), 7.91 (d, J=8.7 Hz, 2H), 7.27 (d, J=8.4 Hz, 2H), 4.06-4.00 (m, 2H), 3.55-3.47 (m, 2H), 2.88-2.81 (m, 1H), 2.03-1.88 (m, 4H). $^{13}$C NMR (CDCl$_3$, 75.5 MHz): δ=190.9, 172.2, 155.3, 133.9, 131.1, 122.2, 115.9, 66.8, 40.1, 28.4.

Example 7

4-Formylphenyl morpholine-4-carboxylate

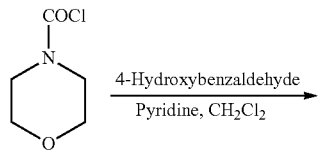

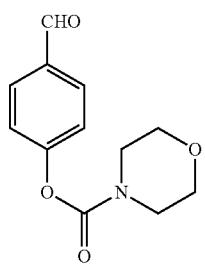

To a 250 mL dry round bottom flask were added 4-hydroxybenzaldehyde (6.11 g, 50.0 mmol), anhydrous CH$_2$Cl$_2$ (80 mL) and pyridine (4.86 mL, 60.0 mmol). The mixture was stirred in an ice-water, then 4-morpholinecarbonyl chloride (6.12 mL, 52.5 mmol) was added. The mixture was stirred and warmed slowly to room temperature, then stirred at room temperature overnight. An aqueous solution of 5% NaHCO$_3$ (100 mL) was added to the reaction mixture. The CH$_2$Cl$_2$ layer was separated, and the aqueous layer was extracted continually with CH$_2$Cl$_2$ (50 mL×2). The combined CH$_2$Cl$_2$ solution was dried over Na$_2$SO$_4$. Removal of the solvent gave 4-formylphenyl morpholine-4-carboxylate (8.80 g) as white solid. Yield: 75%. $^1$H NMR (CDCl$_3$, 300 MHz): δ=9.97 (s, 1H), 7.90 (d, J=9.0 Hz, 2H), 7.30 (d, J=9.0 Hz, 2H), 3.77-3.57 (m, 6H). $^{13}$C NMR (CDCl$_3$, 75.5 MHz, mixture of two isomers): δ=191.0, 156.0, 152.6, 133.6, 131.1, 122.3, 66.5, 66.4, 45.0, 44.2.

Example 8

2-Fluoro-4-formylphenyl morpholine-4-carboxylate

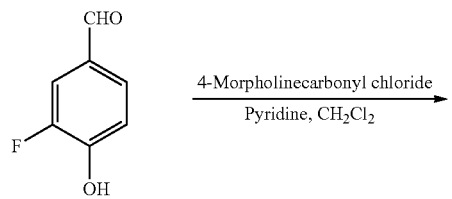

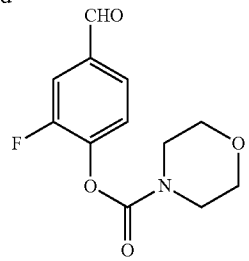

To a 250 mL dry round bottom flask were added 3-fluoro-4-hydroxybenzaldehyde (4.76 g, 34.0 mmol), anhydrous CH$_2$Cl$_2$ (40 mL) and pyridine (3.6 mL, 44.2 mmol). The mixture was stirred in an ice-water bath, then 4-morpholinecarbonyl chloride (4.4 mL, 37.4 mmol) was added. The mixture was stirred and warmed slowly to room temperature, then at room temperature overnight. Water (80 mL) was added to the reaction mixture. The CH$_2$Cl$_2$ layer was separated, and the aqueous layer was extracted continually with CH$_2$Cl$_2$ (50 mL×3). The combined CH$_2$Cl$_2$ solution was dried over Na$_2$SO$_4$. After removal of the solvent, the residue was purified with a silica gel chromatography (heptane/ethyl acetate, gradient eluting) to give 2-fluoro-4-formylphenyl morpholine-4-carboxylate (7.45 g) as white solid. Yield: 87%. $^1$H NMR (CDCl$_3$, 300 MHz): δ=9.97 (s, 1H), 7.74-7.70 (m, 2H), 7.45 (t, J=7.8 Hz, 1H), 3.81-3.61 (m, 8H). $^{13}$C NMR (CDCl$_3$, 75.5 MHz, mixture of two isomers): δ=189.9, 156.5, 153.1, 151.8, 144.0, 143.8, 135.0, 134.9, 126.7, 126.6, 124.8, 116.7, 116.4, 66.4, 66.3, 45.2, 44.4.

Example 9

3,5-Difluoro-4-formylphenyl morpholine-4-carboxylate

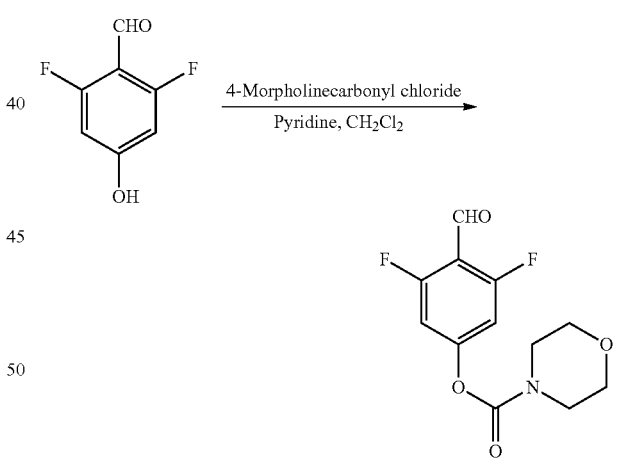

To a 250 mL dry round bottom flask were added 2,6-difluoro-4-hydroxybenzaldehyde (5.53 g, 35.0 mmol), anhydrous CH$_2$Cl$_2$ (40 mL) and pyridine (3.68 mL, 45.5 mmol). The mixture was stirred in an ice-water bath, then 4-morpholinecarbonyl chloride (4.4 mL, 37.4 mmol) was added. After stirring at 0° C. for 1 hour, the mixture was stirred at room temperature overnight. Water (80 mL) and CH$_2$Cl$_2$ (50 mL) were added to the reaction mixture. The CH$_2$Cl$_2$ layer was separated, and the aqueous layer was extracted continually with CH$_2$Cl$_2$ (50 mL×3). The combined CH$_2$Cl$_2$ solution was dried over Na$_2$SO$_4$. After removal of the solvent, the residue was purified with a silica gel chromatography (heptane/ethyl acetate, gradient eluting) to give 3,5-difluoro-4-formylphenyl morpholine-4-carboxylate (8.90 g) as white solid. Yield:

94%. ¹H NMR (CDCl₃, 300 MHz): δ=10.28 (s, 1H), 6.91 (dd, J=10.8, 1.5 Hz, 2H), 3.77-3.58 (m, 8H). ¹³C NMR (CDCl₃, 75.5 MHz, mixture of two isomers): δ=183.7, 163.8 (dd, J=263.1, 8.53 Hz), 157.0 (t, J=15.3 Hz), 151.8, 111.7 (t, J=11.5 Hz), 106.6 (dd, J=25.1, 3.70 Hz), 66.6, 66.5, 45.2, 44.5.

Example 10

2-Fluoro-4-formylphenyl dimethylcarbamate

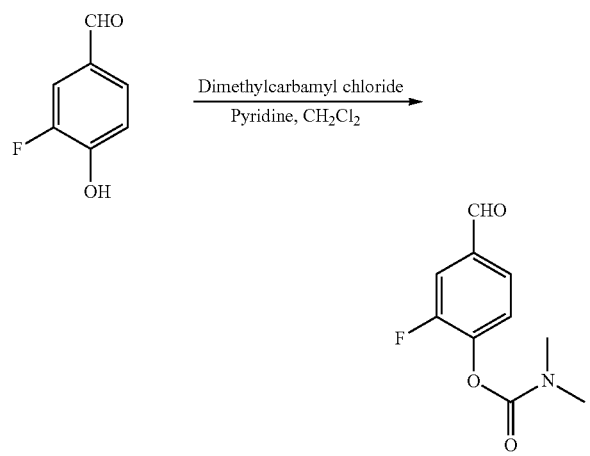

To a 250 mL dry round bottom flask were added 3-fluoro-4-hydroxybenzaldehyde (4.90 g, 35.0 mmol), anhydrous CH₂Cl₂ (20 mL) and pyridine (3.68 mL, 45.5 mmol). The mixture was stirred in an ice-water bath, then dimethylcarbamic chloride (3.54 mL, 38.5 mmol) was added. The mixture was stirred at room temperature for 62 hours. Water (80 mL) and CH₂Cl₂ (50 mL) were added to the reaction mixture. The CH₂Cl₂ layer was separated, and the aqueous layer was extracted continually with CH₂Cl₂ (50 mL×3). The combined CH₂Cl₂ solution was dried over Na₂SO₄. After removal of the solvent, the residue was purified with a silica gel chromatography (heptane/ethyl acetate, gradient eluting) to give 2-fluoro-4-formylphenyl dimethylcarbamate (7.10 g) as white solid. Yield: 96%. ¹H NMR (CDCl₃, 300 MHz): δ=9.92 (d, J=1.8 Hz, 1H), 7.69-7.64 (m, 2H), 7.40 (t, J=7.5 Hz, 1H), 3.13 (s, 3H), 3.03 (s, 3H). ¹³C NMR (CDCl₃, 75.5 MHz): δ=190.0, 156.5, 153.0 (d, J=17.1 Hz), 144.2 (d, J=12.8 Hz), 134.7 (d, J=5.5 Hz), 126.6 (d, J=3.6 Hz), 124.8, 116.5, 116.2, 36.8, 36.5. ¹⁹F NMR (CDCl₃, 282.3 MHz): δ=−127.5.

Example 11

2-Fluoro-6-formylphenyl morpholine-4-carboxylate

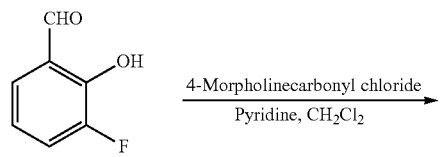

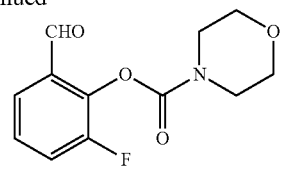

To a 250 mL dry round bottom flask were added 3-fluoro-2-hydroxybenzaldehyde (4.90 g, 35.0 mmol), anhydrous CH₂Cl₂ (50 mL) and pyridine (3.40 mL, 42.0 mmol). The mixture was stirred in an ice-water bath, then 4-morpholinecarbonyl chloride (4.50 mL, 38.5 mmol) was added. The mixture was stirred at room temperature for 24 hours. Water (80 mL) was added to the reaction mixture. The CH₂Cl₂ layer was separated, and the aqueous layer was extracted continually with CH₂Cl₂ (100 mL×2). The combined CH₂Cl₂ solution was dried over Na₂SO₄. After removal of the solvent, the residue was purified with a silica gel chromatography (heptane/ethyl acetate, gradient eluting) to give 2-fluoro-6-formylphenyl morpholine-4-carboxylate (8.34 g) as white solid. Yield: 94%. ¹H NMR (CDCl₃, 300 MHz): δ=10.06 (s, 1H), 7.58 (dt, J=7.8, 1.5 Hz, 1H), 7.39-7.22 (m, 2H), 3.69 (br, 6H), 3.50 (br, 2H). ¹³C NMR (CDCl₃, 75.5 MHz, mixture of two isomers): δ=187.6, 187.5, 170.5, 156.4, 152.4 (d, J=100.7 Hz), 139.9 (d, J=12.8 Hz), 130.5, 126.5 (d, J=7.3 Hz), 125.2 (d, J=3.1 Hz), 121.7 (d, J=17.4 Hz), 66.1, 45.0, 44.3.

Example 12

3,5-Difluoro-4-formylphenyl isopropyl carbonate

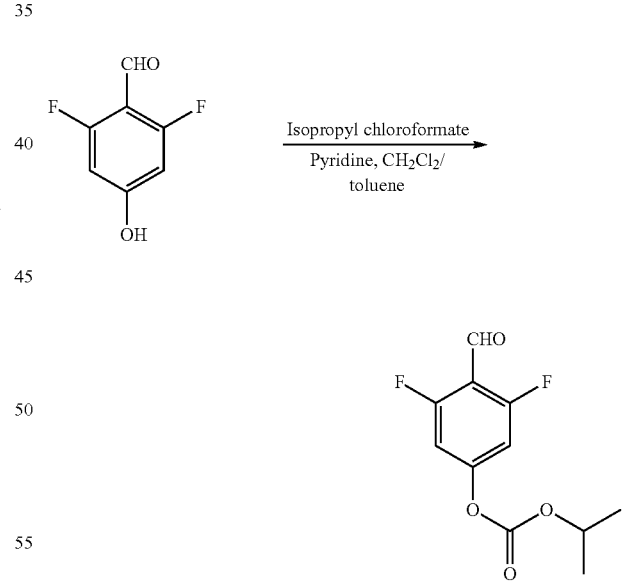

To a 250 mL dry round bottom flask were added 2,6-difluoro-4-hydroxybenzaldehyde (4.80 g, 30.4 mmol), anhydrous CH₂Cl₂ (30 mL) and pyridine (3.0 mL, 36.5 mmol). The mixture was stirred in an ice-water bath, then a solution of isopropyl chloroformate in toluene (1.0 M, 33.4 mL) was added. After stirring at 0° C. for 2 hours, the mixture was stirred at room temperature overnight. Water (80 mL) was added to the reaction mixture. The CH$_2$Cl$_2$ layer was separated, and the aqueous layer was extracted continually with CH$_2$Cl$_2$ (80 mL×3). The combined CH$_2$Cl$_2$ solution was dried over Na$_2$SO$_4$. After removal of the solvent, the residue was purified with a silica gel chromatography (heptane/ethyl acetate, gradient eluting) to give 3,5-difluoro-4-formylphenyl isopropyl carbonate (6.20 g) as a colorless oil. Yield: 84%. $^1$H NMR (CDCl$_3$, 300 MHz): δ=10.30 (s, 1H), 7.02-6.96 (m, 2H), 5.03 (seventet, J=6.3 Hz, 1H), 1.43 (d, J=6.3 Hz, 6H). $^{13}$C NMR (CDCl$_3$, 75.5 MHz): δ=183.3, 163.6 (dd, J=262.5, 7.92 Hz), 156.3 (t, J=15.2 Hz), 151.1, 111.9 (t, J=11.5 Hz), 106.0 (dd, J=25.1, 3.62 Hz), 74.5, 21.5. $^{19}$F NMR (CDCl$_3$, 282.3 MHz): δ=−113.0 (d, J=9.0 Hz).

Example 13

3,5-Difluoro-4-formylphenyl octan-2-yl carbonate

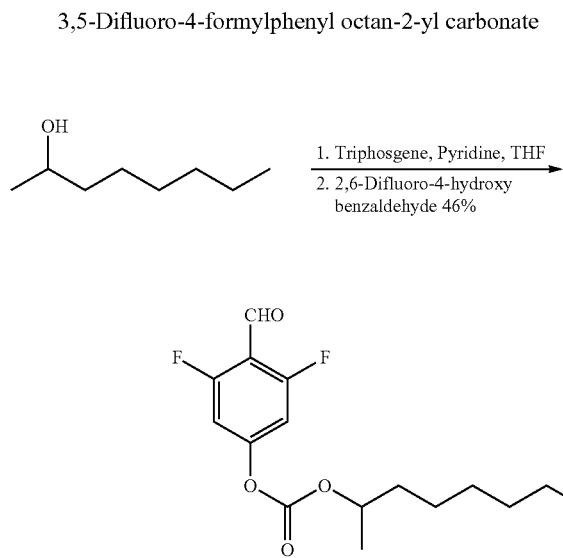

To a 250 mL dry round bottom flask were added 2-octanol (4.51 g, 34.6 mmol), triphosgene (3.44 g, 11.6 mmol) and anhydrous THF (100 mL). The mixture was stirred in an ice-water bath, then pyridine (5.6 mL, 69.2 mmol) was injected slowly. After stirring at room temperature for 30 minutes, the mixture was filtered, and the filtrate was concentrated. The residue was dissolved in 15 mL of CH$_2$Cl$_2$ and cooled in an ice-water bath. To this stirring solution, a solution of 2,6-difluoro-4-hydroxybenzaldehyde (4.2 g, 26.6 mmol) and pyridine (2.80 mL, 34.6 mmol) in 20 mL of anhydrous CH$_2$Cl$_2$ was added slowly. After stirring at room temperature for 2 hours, water (80 mL) was added to the reaction mixture. The CH$_2$Cl$_2$ layer was separated, and the aqueous layer was extracted continually with CH$_2$Cl$_2$ (100 mL×3). The combined CH$_2$Cl$_2$ solution was dried over Na$_2$SO$_4$. After removal of the solvent, the residue was purified with a silica gel chromatography (heptane/ethyl acetate, gradient eluting) to give 3,5-difluoro-4-formylphenyl octan-2-yl carbonate (5.0 g) as a colorless oil. Yield: 46%. $^{13}$C NMR (CDCl$_3$, 75.5 MHz): δ=183.2, 163.4 (dd, J=263.0, 8.53 Hz), 156.3 (t, J=15.2 Hz), 151.2, 111.8 (t, J=11.0 Hz), 105.9 (dd, J=25.7, 3.62 Hz), 78.0, 35.6, 31.6, 28.9, 25.1, 22.4, 19.6, 13.9.

Example 14

(3-Fluoro-4-formylphenoxy)methyl butyrate

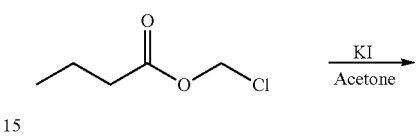

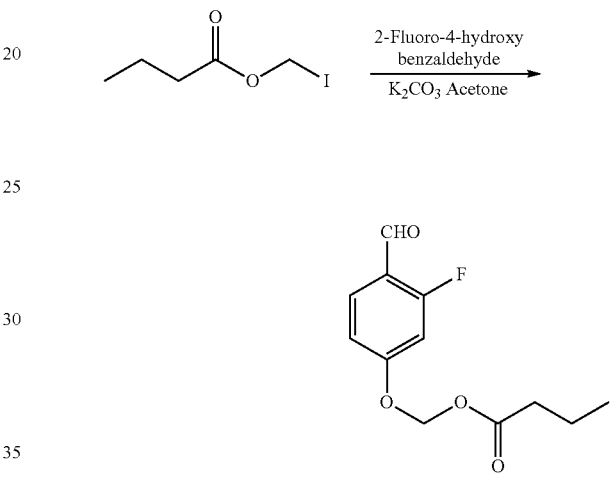

To a 500 mL dry round bottom flask a were added 2-fluoro-4-hydroxybenzaldehyde (5.60 g, 40 mmol), anhydrous K$_2$CO$_3$ (10.6 g, 76.9 mmol) and acetone (200 mL). The mixture was stirred at room temperature for 30 minutes. To another 500 mL dry round bottom flask b were added chloromethyl butyrate (9.33 g, 61.5 mmol), KI (14.2 g, 66.6 mmol) and acetone (150 mL). This mixture was also stirred at room temperature for 30 minutes. After the solid settled down on the glassware bottom, the top yellow acetone solution in flask b was decanted into the stirring solution in the round bottom flask a. The resulting mixture was refluxed for 4 hours. Most acetone was rotary evaporated, and the residual solid was triturated with methyl tert-butyl ether (MTBE) three times (100 mL, 50 mL, 50 mL). The MTBE extract was concentrated, and the residue was purified with a silica gel chromatography (heptane/ethyl acetate, gradient eluting) to give (3-fluoro-4-formylphenoxy)methyl butyrate (6.40 g) as a colorless oil. Yield: 43%. $^1$H NMR (CDCl$_3$, 300 MHz): δ=10.18 (s, 1H), 7.80 (t, J=8.7 Hz, 1H), 6.93-6.89 (m, 1H), 6.82 (dd, J=12.3, 2.1 Hz, 1H), 5.83 (s, 2H), 2.36 (t, J=7.5 Hz, 2H), 1.64 (sextet, J=7.5 Hz, 2H), 0.92 (t, J=7.5 Hz, 3H). $^{13}$C NMR (CDCl$_3$, 75.5 MHz): δ=185.5 (d, J=6.1 Hz), 169.7 (d, J=258.8 Hz), 162.8 (d, J=12.2 Hz), 130.2 (d, J=3.7 Hz), 119.1 (d, J=8.5Hz), 112.4 (d, J=3.1 Hz), 103.5 (d, J=24.4 Hz), 84.1, 35.7, 18.0, 13.3.

Example 15

3,5-Dichloro-4-formylphenyl isopropyl carbonate

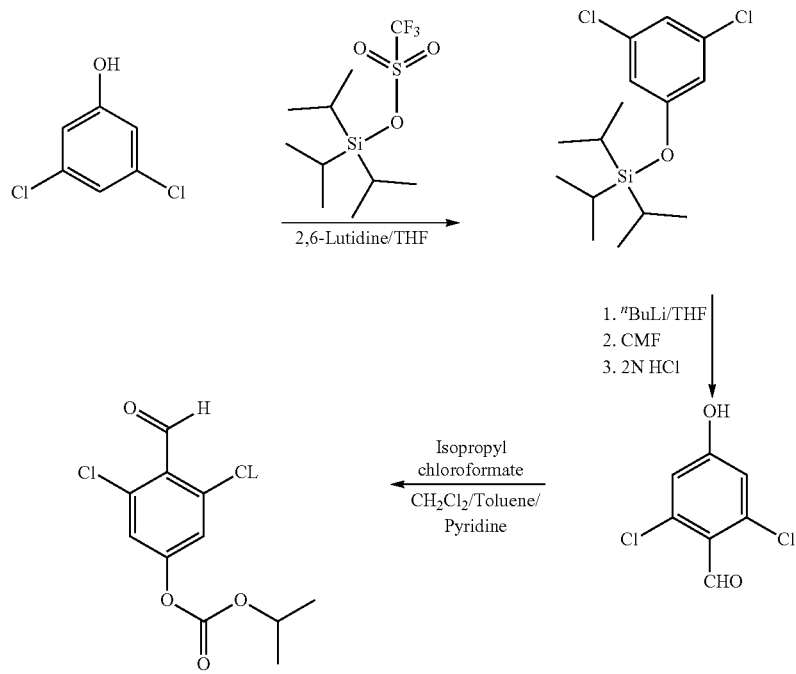

The synthesis of 2,6-dichloro-4-hydroxybenzaldehyde as depicted in the above scheme followed the procedures disclosed in: Hirschheydt, T. V.; Voss, E. *Synthesis* 2004, 12, 2062.

To a 250 mL dry round bottom flask were added 2,6-dichloro-4-hydroxybenzaldehyde (5.73 g, 30.0 mmol), anhydrous $CH_2Cl_2$ (30 mL) and pyridine (3.0 mL, 36.5 mmol). The mixture was stirred in an ice-water bath, then a solution of isopropyl chloroformate in toluene (1.0 M, 33.4 mL) was added. After stirring at 0° C. for 2 hours, water (100 mL) and $CH_2Cl_2$ (50 mL) were added to the reaction mixture. The $CH_2Cl_2$ layer was separated, and the aqueous layer was extracted continually with $CH_2Cl_2$ (40 mL×3). The combined $CH_2Cl_2$ solution was dried over $Na_2SO_4$. After removal of the solvent, the residue was purified with a silica gel chromatography (heptane/ethyl acetate, gradient eluting) to give 3,5-dichloro-4-formylphenyl isopropyl carbonate (6.72 g) as a colorless oil. Yield: 81%. $^1H$ NMR ($CDCl_3$, 300 MHz): δ=10.53 (s, 1H), 7.41 (s, 2H), 5.09 (seventet, J=6.3 Hz, 1H), 1.48 (d, J=6.3 Hz, 6H). $^{13}C$ NMR ($CDCl_3$, 75.5 MHz): δ=187.8, 153.8, 151.5, 138.0, 127.8, 122.8, 74.6, 21.8.

Example 16

3,5-Difluoro-4-formylphenyl 5,5-dimethyl-2-oxooxazolidine-3-carboxylate

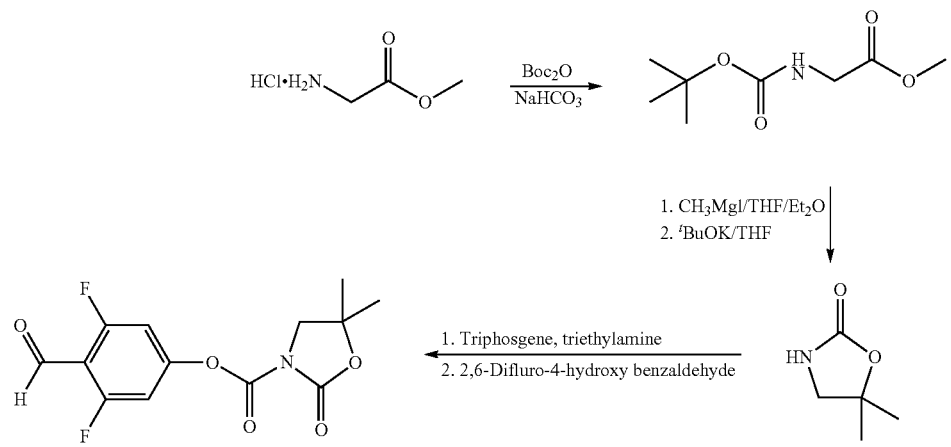

The synthesis of 5,5-Dimethyl-oxazolidin-2-one as depicted in the above scheme followed the procedures disclosed in: Bull, S. D.; Davies, S. G.; Jones, S.; Sanganee, H. J. *J. Chem. Soc. Perkin Trans.* 1 1999, 4, 387.

To a 250 mL dry round bottom flask were added 5,5-dimethyl-oxazolidin-2-one (5.10 g, 44.3 mmol), triphosgene (5.26 g, 17.7 mmol) and anhydrous THF (80 mL). The mixture was stirred in an ice-water bath, then triethylamine (8.6 mL, 62.0 mmol) was added slowly. The resulting mixture was stirred at room temperature overnight. The reaction mixture was filtered and the filtrate was concentrated. To the residue was added 2,6-difluoro-4-hydroxybenzaldehyde (5.03 g, 31.9 mmol) and 80 mL of $CH_2Cl_2$. The resulting solution was cooled in an ice-water bath, then triethylamine (6.0 mL, 42.5 mmol) was added. After stirring at room temperature for 7 hours, water (100 mL) was added to the reaction mixture. The $CH_2Cl_2$ layer was separated, and the aqueous layer was extracted continually with $CH_2Cl_2$ (50 mL×3). The combined $CH_2Cl_2$ solution was dried over $Na_2SO_4$. After removal of the solvent, the residue was purified with a silica gel chromatography (heptane/ethyl acetate, gradient eluting) to give 3,5-difluoro-4-formylphenyl 5,5-dimethyl-2-oxooxazolidine-3-carboxylate (6.9 g) as a pale yellow crystal. Yield: 52%. $^1$H NMR (CDCl$_3$, 300 MHz): δ=10.39 (s, 1H), 7.09 (d, J=9.0 Hz, 2H), 3.97 (s, 2H), 1.67 (s, 6H).

Example 18

(S)-3,5-Difluoro-4-formylphenyl 2-(acetoxymethyl) pyrrolidine-1-carboxylate

The synthesis of (S)-(−)-1-benzyl-2-pyrrolidinemethyl acetate as depicted in the above scheme followed the procedures disclosed in: Zhao, S.; Freeman, J. P.; Bacon, C. L.; Fox, G. B.; O'Driscoll, E.; Foley, A. G.; Kelly, J.; Farrell, U.; Regan, C.; Mizsac, S. A.; Szmuszkovicz, J. *Bioorg. Med. Chem.* 1999, 7, 1647.

To a 500 mL dry round bottom flask were added triphosgene (8.90 g, 30.0 mmol) and anhydrous $CH_2Cl_2$ (300 mL). The mixture was stirred in an dry ice-acetone bath, then a solution of (S)-(−)-1-benzyl-2-pyrrolidinemethyl acetate (21.0 g, 90.0 mmol) in 50 mL of $CH_2Cl_2$ was added slowly. After the addition, the resulting mixture was cooled in an ice-water bath, then warmed slowly to room temperature and was stirred at room temperature overnight. After removal of the volatile materials, the residue was purified with a silica gel chromatography (heptane/ethyl acetate, gradient eluting) to give (S)-(1-(chlorocarbonyl)pyrrolidin-2-yl)methyl acetate (15.3 g) as a colorless oil. Yield: 83%. $^1$H NMR (CDCl$_3$, 300 MHz, mixture of two isomers): δ=4.30-4.07 (m, 3H), 3.65-3.50 (m, 2H), 2.11-1.90 (m, 7H). $^{13}$C NMR (CDCl$_3$, 75.5 MHz, mixture of two isomers): δ=170.4, 170.3, 146.9, 146.1, 63.9, 63.0, 59.2, 58.1, 50.7, 48.9, 28.1, 27.6, 22.9, 22.8, 20.6.

To a 250 mL dry round bottom flask were added (S)-(1-(chlorocarbonyl)pyrrolidin-2-yl)methyl acetate (6.79 g, 33.0 mmol), 2,6-difluoro-4-hydroxybenzaldehyde (4.74 g, 30 mmol), triethylamine (5.40 mL, 39.0 mmol) and anhydrous $CH_2Cl_2$ (40 mL). The resulting mixture was stirred at room temperature for 2 days, then water (80 mL) was added to the reaction mixture. The $CH_2Cl_2$ layer was separated, and the aqueous layer was extracted continually with $CH_2Cl_2$ (80 mL×2). The combined $CH_2Cl_2$ solution was dried over $Na_2SO_4$. After removal of the solvent, the residue was purified with a silica gel chromatography (heptane/ethyl acetate, gradient eluting) to give (S)-3,5-difluoro-4-formylphenyl 2-(acetoxymethyl)pyrrolidine-1-carboxylate (4.92 g) as a colorless oil. Yield: 46%. $^1$H NMR (CDCl$_3$, 300 MHz, mixture of two isomers): δ=10.28 (s, 1H), 6.97 (t, J=11.4 Hz, 2H), 4.33-4.12 (m, 3H), 3.65-3.55 (m, 2H), 2.10-2.01 (m, 7H). $^{13}$C NMR (CDCl$_3$, 75.5 MHz, mixture of two isomers): δ=183.5, 170.7 (d, J=7.3 Hz), 163.6 (dd, J=262.5, 8.6 Hz), 157.0, 150.8 (d, J=14.6 Hz), 112.6, 106.2 (d, J=25.0 Hz), 64.4, 63.8, 56.8, 56.4, 47.4, 47.3, 28.7, 27.8, 23.8, 22.9, 20.8.

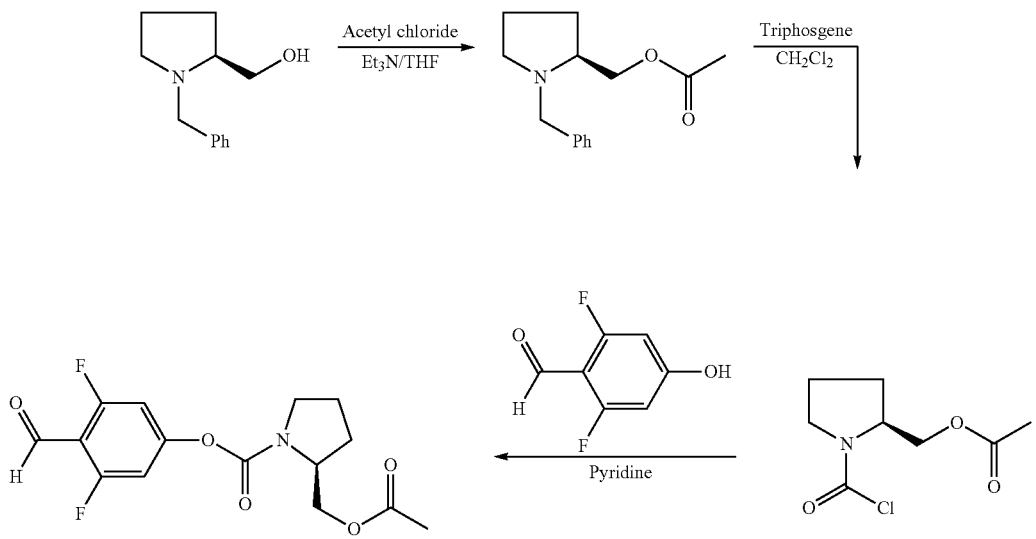

Example 19

3-Fluoro-4-formylphenyl 2-oxooxazolidine-3-carboxylate

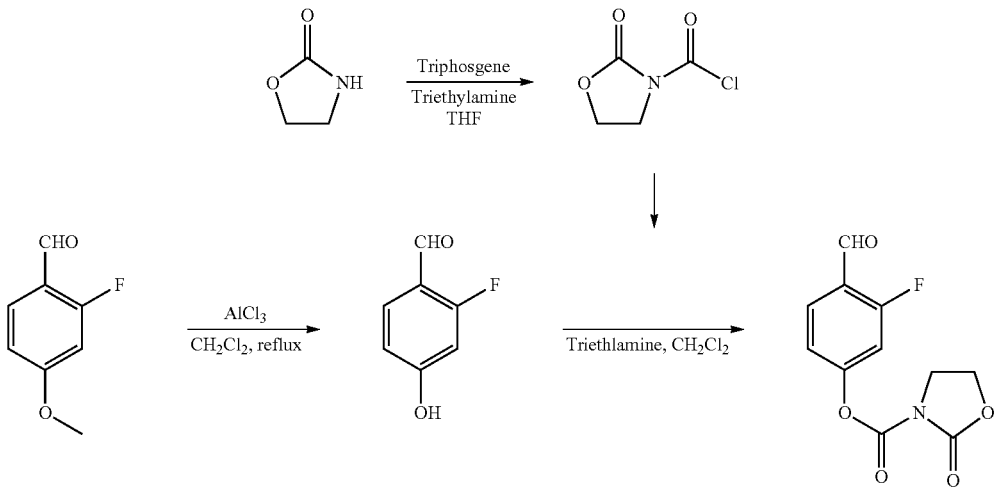

To a 2000 mL dry round bottom flask were added 2-fluoro-4-methoxybenzaldehyde (25.0 g, 162.2 mmol), anhydrous AlCl$_3$ (64.8 g, 486.8 mmol) and anhydrous CH$_2$Cl$_2$ (1000 mL). The mixture was stirred and refluxed for 3 days. The reaction mixture was cooled in an ice-water bath, then ice (100 g) was added very carefully into the reaction mixture to quench the excess AlCl$_3$. Another 800 mL of cold water was added. The organic layer was separated, and the aqueous solution was extracted with MTBE (300 mL×2). The combined organic layer was concentrated, and the residual solid was dissolved in 400 mL of cold 2N aqueous NaOH and 200 mL of water. The resulting aqueous solution was extracted with MTBE (200 mL×2). The basic aqueous solution then was acidified with concentrated HCl. After filtration and drying, 2-fluoro-4-hydroxybenzaldehyde (21.5 g) was obtained as a white solid. Yield: 95%. $^1$H NMR (Acetone-d$_6$, 300 MHz): δ=10.12 (s, 1H), 9.87 (s, 1H), 7.74 (t, J=8.4 Hz, 1H), 6.83 (dd, J=8.4, 1.8 Hz, 1H), 7.70 (dd, J=12.3, 2.1 Hz, 1H).

To a 250 mL dry round bottom flask were added 2-oxazolidinone (4.35 g, 50.0 mmol), triphosgene (5.49 g, 18.5 mmol) and anhydrous THF (100 mL). The mixture was stirred in an ice-water bath, then triethylamine (9.8 mL, 70.0 mmol) was added slowly. After stirring at 0° C. for 1 hour, the mixture was stirred continually at room temperature overnight. The reaction mixture was filtered and the filtrate was concentrated. The residue was dissolved in 10 mL of CH$_2$Cl$_2$, and this solution was added slowly to a stirring mixture of 2-fluoro-4-hydroxybenzaldehyde (3.78 g, 27.0 mmol) and triethylamine (5.63 mL, 40.4 mmol) in 20 mL of anhydrous CH$_2$Cl$_2$ at 0° C. After stirring at room temperature for 2 days, water (80 mL) and MTBE (100 mL) were added to the reaction mixture. The mixture was filtered and the solid was washed with cold water (50 mL×2), followed by extraction using MTBE (50 mL×4). After drying, 3-fluoro-4-formylphenyl 2-oxooxazolidine-3-carboxylate (5.90 g) was obtained as a white solid. Yield: 86%. $^1$H NMR (CDCl$_3$, 300 MHz): δ=10.42 (s, 1H), 8.03 (t, J=8.1 Hz, 1H), 7.27-7.23 (m, 2H), 4.61 (t, J=7.8 Hz, 2H), 4.29 (t, J=7.5 Hz, 2H). $^{13}$C NMR (CDCl$_3$, 75.5 MHz): δ=186.3 (d, J=6.0 Hz), 166.9, 155.0 (d, J=260 Hz), 130.2, 122.6, 118.3, 110.7 (d, J=24.4 Hz), 62.2, 43.9. $^{19}$F NMR (CDCl$_3$, 282.3 MHz): δ=−118.6.

Example 20

2-Formyl-4-methylphenyl 2-oxooxazolidine-3-carboxylate

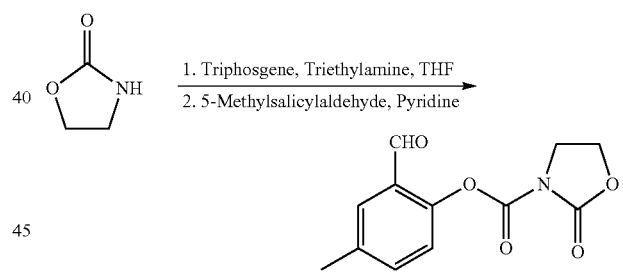

To a 500 mL dry round bottom flask were added 2-oxazolidinone (9.13 g, 104.9 mmol), triphosgene (10.9 g, 36.7 mmol) and anhydrous THF (100 mL). The mixture was stirred in an ice-water bath, then triethylamine (15.8 mL, 115.4 mmol) was added slowly. The resulting mixture was stirred at room temperature overnight. The reaction mixture was filtered and the filtrate was concentrated. The residue was dissolved in 20 mL of CH$_2$Cl$_2$, and this solution was added slowly to a stirring mixture of 5-methylsalicylaldehyde (10.0 g, 73.4 mmol) and pyridine (8.5 mL, 104.9 mmol) in 30 mL of anhydrous CH$_2$Cl$_2$ at 0° C. After stirring at room temperature overnight, water (50 mL) and MTBE (100 mL) were added to the reaction mixture. The mixture was filtered and the solid was washed with cold water (20 mL×2), followed by MTBE (20 mL×2). After drying, 2-formyl-4-methylphenyl 2-oxooxazolidine-3-carboxylate (13.3 g) was obtained as a white solid. Yield: 73%. $^1$H NMR (Acetone-d$_6$, 300 MHz): δ=10.25 (s, 1H), 7.78 (s, 1H), 7.62 (d, J=8.1 Hz, 1H), 7.35 (d, J=8.4 Hz, 1H), 4.58 (t, J=7.8 Hz, 2H), 4.32 (t, J=7.5 Hz, 2H), 2.47 (s, 3H).

Example 21

2-(((4-Formylphenoxy)carbonyl)(methyl)amino)ethyl acetate

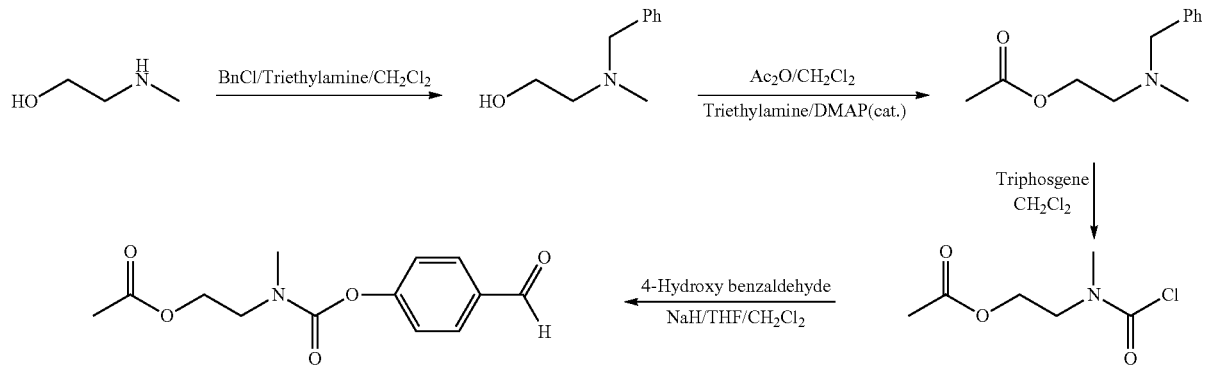

The synthesis of 2-(benzyl(methyl)amino)ethanol as depicted in the above scheme followed the procedures disclosed in Jones, G. C.; Hauser, C. R. *J. Org. Chem.* 1962, 27, 802.

To a 500 mL dry round bottom flask were added 2-(benzyl(methyl)amino)ethanol (46.3 g, 280.2 mmol), triethylamine (150 mL, 1.08 mol), acetic anhydride (31.8 mL, 336.2 mmol), anhydrous $CH_2Cl_2$ (100 mL) and a crystal piece of DMAP (4-Dimethylaminopyridine). The mixture was stirred at room temperature for 3 hours. MTBE (700 mL) was added into the reaction mixture, and this mixture was washed, respectively, with cold 2N NaOH (150 mL), water (100 mL), brine (150 mL). The MTBE layer was concentrated, and the residue was poured onto a silica gel pad (200.0 g). The pad was eluted with a co-solvents of ethyl acetate: heptane=3:1 to give 2-(benzyl(methyl)amino)ethyl acetate (50.8 g) as a yellow oil. Yield: 87%. $^1$H NMR (CDCl$_3$, 300 MHz): δ=7.41-7.25 (m, 5H), 4.29 (t, J=6.3 Hz, 2H), 3.65 (s, 2H), 2.74 (t, J=6.0 Hz, 2H), 2.38 (s, 3H), 2.14 (s, 3H). $^{13}$C NMR (CDCl$_3$, 75.5 MHz): δ=170.9, 138.7, 128.9, 128.2, 127.1, 62.5, 62.2, 55.3, 42.6, 21.0.

To a 1000 mL dry round bottom flask were added triphosgene (24.2 g, 81.5 mmol) and anhydrous $CH_2Cl_2$ (500 mL). The mixture was stirred in a dry ice-acetone bath, then a solution of 2-(benzyl(methyl)amino)ethyl acetate (50.7 g, 244.6 mmol) in 150 mL of anhydrous $CH_2Cl_2$ was added slowly. After the addition, the resulting mixture was cooled in an ice-water bath, then warmed slowly to room temperature, followed being stirred at room temperature overnight. After removal of the volatile materials, the residue was purified with a silica gel chromatography (heptane/ethyl acetate, gradient eluting) to give 2-(chlorocarbonyl(methyl)amino)ethyl acetate (40.2 g) as a yellow oil. Yield: 92%. $^1$H NMR (CDCl$_3$, 300 MHz, mixture of two isomers): isomer 1: δ=4.27 (t, J=5.7 Hz, 2H), 3.76 (t, J=5.7 Hz, 2H), 3.10 (s, 3H), 2.09 (s, 3H); isomer 2: δ=4.26 (t, J=5.1 Hz, 2H), 3.66 (t, J=5.1 Hz, 2H), 3.20 (s, 3H), 2.07 (s, 3H). $^{13}$C NMR (CDCl$_3$, 75.5 MHz, mixture of two isomers): δ=170.5, 149.9, 149.0, 61.2, 61.1, 51.4, 50.0, 39.4, 37.4, 20.7.

To a 250 mL dry round bottom flask were added sodium hydride (2.08 g, 60%, 52 mmol), anhydrous THF (40 mL) and 4-hydroxybenzaldehyde (4.88 g, 40.0 mmol). The resulting mixture was stirred at room temperature for 1 hour. To this mixture, a solution of 2-(chloro-carbonyl(methyl)amino) ethyl acetate (8.98 g, 50 mmol) in 10 mL of anhydrous $CH_2Cl_2$ was added. The resulting mixture was stirred at room temperature overnight. The volatile materials were removed, then cold water (100 mL) was added to the residue. The aqueous solution was extracted with $CH_2Cl_2$ (60 mL×4). The combined $CH_2Cl_2$ solution was dried over $Na_2SO_4$. After removal of the solvent, the residue was purified with a silica gel chromatography (heptane/ethyl acetate, gradient eluting) to give 2-(((4-formylphenoxy)carbonyl)(methyl)amino) ethyl acetate (10.4 g) as a colorless oil. Yield: 98%. $^1$H NMR (CDCl$_3$, 300 MHz, mixture of two isomers), isomer 1: δ=9.92 (s, 1H), 7.85 (d, J=8.4 Hz, 2H), 7.27 (d, J=8.4 Hz, 2H), 4.26 (t, J=5.4 Hz, 2H), 3.66 (t, J=5.4 Hz, 2H), 3.12 (s, 3H), 2.03 (s, 3H); isomer 2: δ=9.92 (s, 1H), 7.85 (d, J=8.4 Hz, 2H), 7.27 (d, J=8.4 Hz, 2H), 4.24 (t, J=5.1 Hz, 2H), 3.57 (t, J=5.1 Hz, 2H), 3.02 (s, 3H), 2.01 (s, 3H). $^{13}$C NMR (CDCl$_3$, 75.5 MHz, mixture of two isomers): δ=190.7, 170.5, 170.4, 156.0, 155.9, 153.6, 153.2, 133.2, 130.8, 130.7, 61.6, 61.5, 48.3, 47.9, 35.5, 20.5.

Example 22

2,2'-((4-formylphenoxy)carbonylazanediyl)bis(ethane-2,1-diyl)diacetate

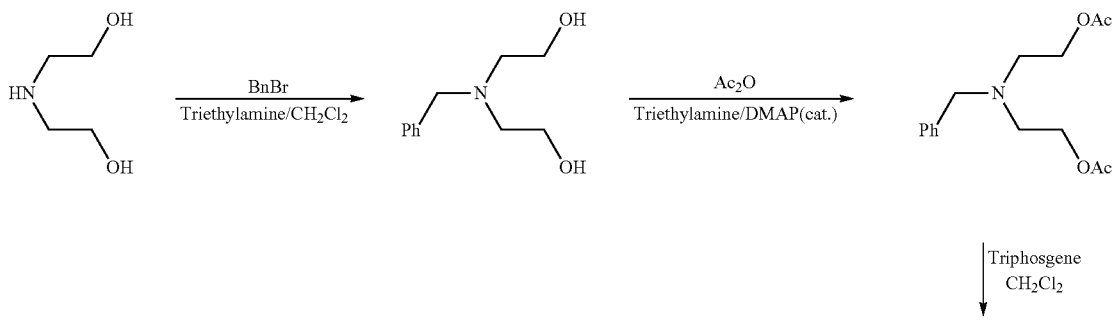

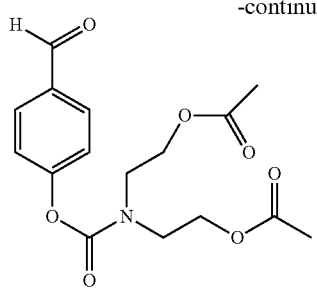 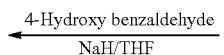 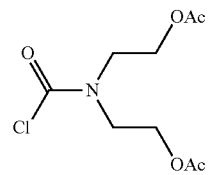

The synthesis of 2,2'-benzylazanediyl-bis-ethanol as depicted in the above scheme followed procedures disclosed in Shen, Y.; Feng, X.; Li, Y.; Zhang, G.; Jiang, Y. *Tetrahedron* 2003, 59, 5667.

To a 500 mL dry round bottom flask were added 2,2'-benzylazanediyl-bis-ethanol (45.2 g, 231.0 mmol), triethylamine (200 mL), acetic anhydride (52.4 mL, 554.4 mmol), anhydrous $CH_2Cl_2$ (100 mL) and a crystal piece of DMAP. The mixture was stirred in an ice-water bath for 1 hour, then at room temperature for 2 hours. Most volatile materials were evaporated, then MTBE (700 mL) was added into the residue, and this mixture was washed, respectively, with water (100 mL), cold 2N NaOH (200 mL), water (150 mL), brine (100 mL). The MTBE layer was concentrated, and the residue was poured onto a silica gel pad (200.0 g). The pad was eluted with a co-solvents of ethyl acetate:heptane (1:1) to give 2,2'-(benzy-lazanediyl)bis(ethane-2,1-diyl)diacetate (53.0 g) as a yellow oil. Yield: 82%. $^1H$ NMR ($CDCl_3$, 300 MHz): δ=7.38-7.25 (m, 5H), 4.20 (t, J=6.3 Hz, 4H), 3.77 (s, 2H), 2.86 (t, J=6.3 Hz, 4H), 2.09 (s, 6H). $^{13}C$ NMR ($CDCl_3$, 75.5 MHz): δ=170.7, 139.0, 128.6, 128.2, 127.0, 62.4, 59.2, 52.5, 20.8.

To a 1000 mL dry round bottom flask were added triphosgene (18.8 g, 63.2 mmol) and anhydrous $CH_2Cl_2$ (500 mL). The mixture was stirred in a dry ice-acetone bath, then a solution of 2,2'-(benzylazanediyl)bis(ethane-2,1-diyl)diacetate (53.0 g, 189.7 mmol) in 100 mL of anhydrous $CH_2Cl_2$ was added slowly. After the addition, the resulting mixture was cooled in an ice-water bath, then warmed slowly to room temperature, followed being stirred at room temperature overnight. After removal of the volatile materials, the residue was purified with a silica gel chromatography (heptane/ethyl acetate, gradient eluting) to give 2,2'-(chlorocarbony-lazanediyl)bis(ethane-2,1-diyl)diacetate (45.7 g) as a yellow oil. Yield: 96%. $^1H$ NMR ($CDCl_3$, 300 MHz): δ=4.27 (t, J=5.7 Hz, 2H), 4.25 (t, J=5.4 Hz, 2H); 3.79 (t, J=5.7 Hz, 2H), 3.68 (t, J=5.4 Hz, 2H), 2.08 (s, 3H); 2.06 (s, 3H). $^{13}C$ NMR ($CDCl_3$, 75.5 MHz): δ=170.5, 149.4, 61.5, 61.0, 50.4, 49.1, 20.6.

To a 250 mL dry round bottom flask were added sodium hydride (2.08 g, 60%, 52 mmol), anhydrous THF (40 mL) and 4-hydroxybenzaldehyde (4.88 g, 40.0 mmol). The resulting mixture was stirred at room temperature for 1 hour. To this mixture, a solution of 2,2'-(chloro-carbonylazanediyl)bis(ethane-2,1-diyl)diacetate (12.6 g, 50 mmol) in 10 mL of anhydrous THF was added. The resulting mixture was stirred at room temperature overnight. The volatile materials were removed, then cold water (100 mL) was added to the residue. The aqueous solution was extracted with MTBE (50 mL×3). The combined MTBE solution was dried over $Na_2SO_4$. After removal of the solvent, the residue was purified with a silica gel chromatography (heptane/ethyl acetate, gradient eluting) to give 2,2'((4-formylphenoxy)carbonylazanediyl)bis(ethane-2,1-diyl)diacetate (12.8 g) as a white solid. Yield: 95%. $^1H$ NMR ($CDCl_3$, 300 MHz): δ=9.88 (s, 1H), 7.83-7.79 (m, 2H), 7.25-7.22 (m, 2H), 4.25 (t, J=5.7 Hz, 2H), 4.20 (t, J=5.4 Hz, 2H), 3.66 (t, J=5.7 Hz, 2H), 3.56 (t, J=5.4 Hz, 2H), 1.98 (s, 3H), 1.96 (s, 3H). $^{13}C$ NMR ($CDCl_3$, 75.5 MHz): δ=190.5, 170.3, 170.2, 155.7, 153.3, 133.5, 130.8, 62.0, 61.6, 47.6, 47.3, 20.4.

Section 2. Synthesis of Bisphosphonate Cyclic Acetals.

The bisphosphonate cyclic acetals were synthesized following the general procedures shown below for Risedronate cyclic acetal Example 26.

Example 25 tert-Butyl chlorobenzylcarbonate

The substituted benzaldehyde 23 was converted to tert-butyl chlorobenzylcarbonate 25 using the general procedures shown below.

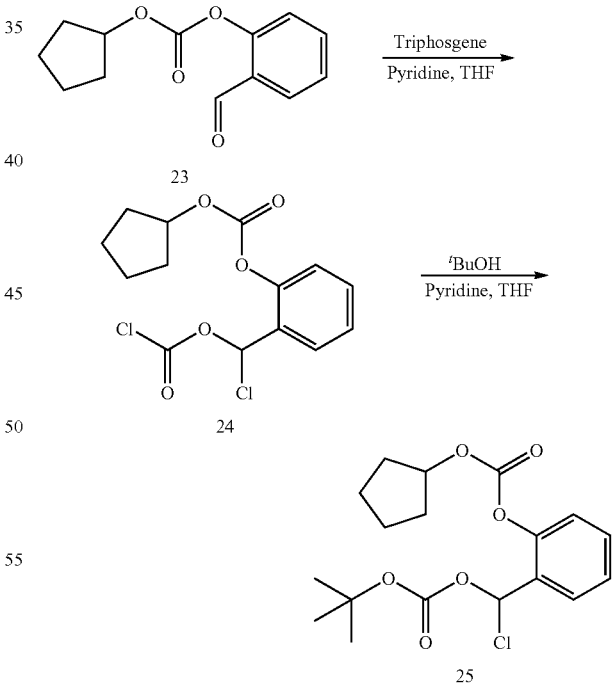

To a dry 250 mL round bottom flask was added substituted benzaldehyde 23 (468 mg, 20.0 mmol), anhydrous THF (15 mL) and triphosgene (2.96 g, 10.0 mmol), and pyridine (0.79 mL, 0.63 mmol). The mixture was stirred for 1 hour at 40° C.-45° C. The completion of the reaction was monitored by $^{13}C$ NMR, peak at δ=80-87 indicated the formation of carbonyl chloride 24. This reaction mixture was used in the next step without work-up and purification. To a solution of carbonyl chloride 24 in THF was added dichloromethane (10 ml) followed by drop-wise addition of $^t$BuOH (25 mmol) and pyridine (25 mmol) at 0° C. The resulted mixture was stirred at 0° C. for 1.5 hours. The reaction mixture was diluted with MTBE (100 mL) and filtered through a pad of glass microfibre filter to remove the pyridine hydrochloride salt precipitated. The filtrate was collected and washed with ice cold water (100 mL) and the organic layer was dried over $MgSO_4$. The solvents were removed by evaporation to give the carbonate 25 (18 mmol) as a pale yellow oil. This oil was used for next step without further purification.

Example 26

Risedronate Cyclic Acetal

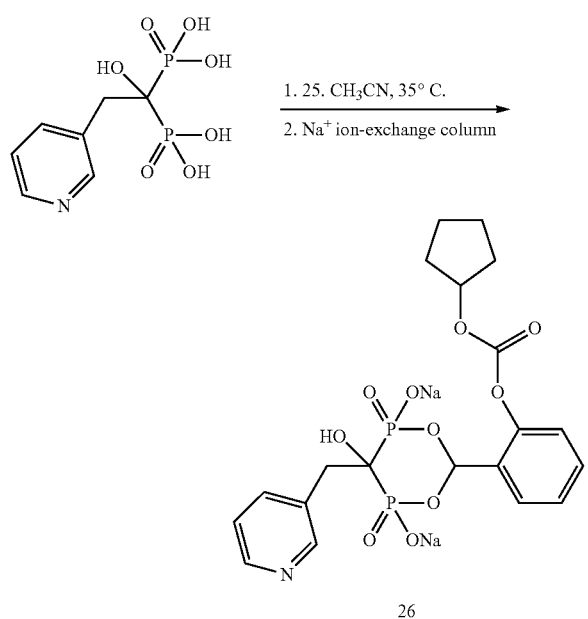

To a suspension of risedronate (8 mmol) in MeCN (10 mL) was added DIPEA (40 mmol) and the mixture was heated at 40° C. for 10 minutes. The resulting clear solution was cooled to room temperature and a solution of the carbonate 25 in MeCN (5 mL) was added under inert atmosphere. The mixture was then stirred at 40° C.-45° C. for 18 hours. The reaction mixture was then cooled to room temperature and evaporated to dryness. The residue obtained was purified by combi-flash system (120 g silica column, Isco or Silicycle) with gradient eluting by acetonitrile-MeOH (0-30%). The fractions containing cis and trans isomers of DIPEA-salt of the product were separately collected (monitored by $^{31}$P NMR). The earlier fractions contained trans-isomer (chemical shift of phosphorus in $^{31}$P NMR was in stronger field). Later fractions are cis-isomer ($\delta_P$—in a weaker field). DIPEA-salt of the product was converted to a sodium-salt 26 in Na$^+$ ion-exchange column (5 g of resin). Lyophilization of collected fractions afforded 0.4 mmol of trans-isomer, 0.3 mmol of cis-isomer, and 0.5 mmol of mixture cis/trans isomers. Mixture of isomers (Na-salt) are further separated by combi-flash chromatography (water-acetonitrile eluting system).

trans-Isomer: yield 200 mg (2.7%). $^1$H NMR ($D_2O$, 300 MHz): δ=8.38 (s, 1H), 8.06 (d, 1H), 7.87 (d, J=9.9 Hz, 1H), 7.15 (m, 3H), 7.01 (t, 1H), 6.89 (t, 1H), 6.23 (t, 1H), 4.87 (m, 1H), 3.07 (t, 2H, J=16.2 Hz), 1.55-1.28 (m, 8H). $^{31}$P NMR ($D_2O$, 121.5 MHz): δS=15.835. MS (M−1) m/z: 498. Elemental analysis (%) calculated for $C_{20}H_{23}N_1O_{10}P_2Na_2 \cdot 2.5H_2O$ (587): C, 40.69; H, 4.78; N, 2.37. Found: C, 40.57; H, 4.61; N, 2.47.

cis-Isomer Yield 150 mg (2%). NMR ($D_2O$, 300 MHz): δ=8.37 (s, 1H), 8.22 (d, 1H), 8.10 (d, J=8.1 Hz, 1H), 7.41-7.45 (m, 2H), 7.18 (t, 1H), 7.07 (t, 1H), 6.90 (d, J=8.1 Hz, 1H), 6.37 (t, 1H), 4.87 (m, 1H), 3.15 (t, 2H, J=12.6 Hz), 1.63-1.28 (m, 8H). $^{31}$P NMR ($D_2O$, 121.5 MHz): δ=15.338. MS (M−1) m/z: 498. Elemental analysis (%) calculated for $C_{20}H_{23}N_1O_{10}P_2Na_2 2.5H_2O \cdot 0.1CH_3CN$ (591.1): C, 37.84; H, 4.45; N, 2.40. Found: C, 37.59; H, 4.75; N, 2.75.

Example 27

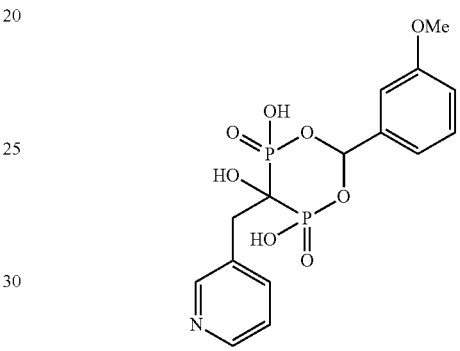

Example 27 was synthesized following the general synthetic procedures of Example 26 starting from 3-methoxybenzaldehyde.

Yield: 405 mg (17%). Elemental analysis (%) calculated for $C_{15}H_{17}N_1O_8P_2 \cdot 0.9NaCl \cdot 1.9NH_4Cl$ (555.49): C, 32.43; H, 4.46; N, 7.31. Found: C, 32.50; H, 4.13; N, 7.26. ESI MS ($H_2O$) m/z 400 (M$^+$−1). $^1$H NMR ($D_2O$, 300 MHz): δ=8.80-8.45 (m, 3H), 7.95-7.05 (m, 5H), 5.95 (m, 1H), 3.90 (s, 3H), 3.60-3.45 (m, 2H). $^{31}$P NMR ($D_2O$, 121.5 MHz): δ=16.2, 16.0.

Example 28

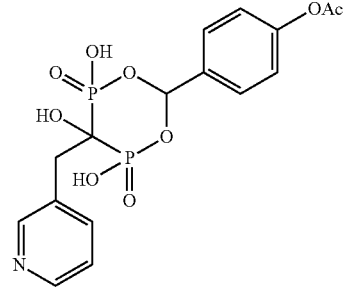 [SMILES: CC(=O)Oc1ccc(C2OP(=O)(O)C(O)(Cc3cccnc3)P(=O)(O)O2)cc1]

Example 28 was synthesized following the general synthetic procedures of Example 26 starting from 4-formylphenyl acetate.

Yield 0.720 g (22%) as white powder, mixture of cis (55%) and trans (45%) isomers, contaminated with Risedronate (16%). $^1$H NMR ($D_2O$): δ=8.75 (s, 0.45H-trans), 8.61 (s, 0.55H-cis), 8.44 (m, 1H-trans,cis), 8.36 (d, J=7.8, 0.45H-trans), 8.21 (d, J=7.8 Hz, 0.55H-cis), 7.63 (d, J=8.9 Hz for AB-system, 1.1H-cis), 7.61 (m, 1H, trans, cis), 7.29 (d, J=8.5 Hz for AB-system, 0.9H-trans), 7.18 (d, J=8.9 Hz for AB-system, 1.1H-cis), 7.11 (d, J=8.5 Hz for AB-system, 0.9H-trans), 6.55 (t, 0.55H, cis), 6.41 (t, 0.45H, trans), 3.40 (m, J=16.5 Hz-trans, 2H-trans, cis), 2.3 (s, 3H). $^{31}$P NMR (D$_2$O): δ=16.55-cis, 16.29-trans. LC-MS (ESI) for C$_{16}$H$_{17}$NO$_9$P$_2$ m/z 428 [M-H]$^-$ Calc. for 0.84C$_{16}$H$_{15}$NNa$_2$O$_9$P$_2$.0.16C$_7$H$_7$NNa$_4$O$_7$P$_2$.2.5H$_2$O (%): C, 34.84; H, 3.76; N, 2.79. Found (%): C, 34.36; H, 3.46; N, 2.78.

Example 29

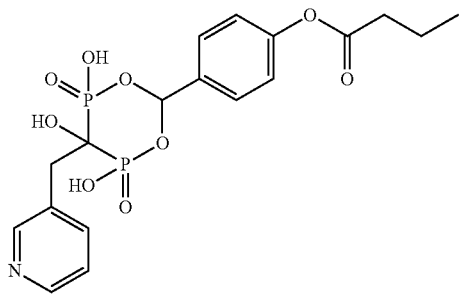

Example 29 was synthesized following the general synthetic procedures of Example 26 starting from 4-formylphenyl butyrate.

cis-Isomer: yield 0.63 g (18%). $^1$H NMR (D$_2$O): δ=8.64 (s, 1H), 8.50 (d, J=5.7 Hz, 1H), 8.16 (d, J=7.5 Hz, 1H), 7.70 (d, J=9.0 Hz for AB-system, 2H), 7.59 (dd, J=5.7, 7.5 Hz, 1H), 7.24 (d, J=9.0 Hz for AB-system, 2H), 6.62 (t, J=4.9 Hz, 1H), 3.45 (t, J=12.4 Hz, 2H), 2.66 (t, J=7.2 Hz, 2H), 1.77 (m, J=7.2 Hz, 2H), 1.03 (t, J=7.2 Hz, 3H). $^{31}$P NMR (D$_2$O): δ=16.68. LC-MS (ESI) for C$_{18}$H$_{21}$NO$_9$P$_2$ m/z 456 [M-H]$^-$ Calc. for C$_{18}$H$_{19}$NNa$_2$O$_9$P$_2$.3H$_2$O (%): C, 38.93; H, 4.54; N, 2.52. Found (%): C, 38.62; H, 4.12; N, 2.64.

trans-Isomer: yield 0.647 g (18%). $^1$H NMR (D$_2$O): =8.79 (s, 1H), 8.46 (d, J=4.8 Hz, 1H), 8.32 (d, J=8.1 Hz, 1H), 7.56 (t, J=5.7 Hz, 1H), 7.33 (d, J=8.5 Hz for AB-system, 2H), 7.17 (d, J=8.5 Hz for AB-system, 2H), 6.48 (t, J=4.8 Hz, 1H), 3.45 (t, J=16.5 Hz, 2H), 2.67 (t, J=7.2 Hz, 2H), 1.78 (m, J=7.2 Hz, 2H), 1.04 (t, J=7.2 Hz, 3H). $^{31}$P NMR (D$_2$O): δ=16.40. LC-MS (ESI) for C$_{18}$H$_{21}$NO$_9$P$_2$ m/z 456 [M-H]$^-$ Calc. for C$_{18}$H$_{19}$NNa$_2$O$_9$P$_2$.1.5H$_2$O.1NaCl (%): C, 36.85; H, 3.78; N, 2.39. Found (%): C, 36.98; H, 3.90; N, 2.53.

Example 30

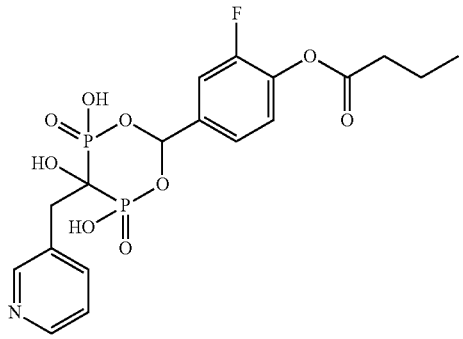 [SMILES: CCCC(=O)Oc1ccc(C2OP(=O)(O)C(O)(Cc3cccnc3)P(=O)(O)O2)cc1F]

Example 30 was synthesized following the general synthetic procedures of Example 26 starting from 2-fluoro-4-formylphenyl butyrate.

Yield: 0.18 g (3%). Elemental analysis (%) calculated for C$_{18}$H$_{18}$FNNa$_2$O$_9$P$_2$.1.5NaCl.2H$_2$O (606.97): C, 33.62; H, 3.45; N, 2.18. Found C, 33.45; H, 3.21; N, 2.29. ESI MS (CH$_3$CN): m/z 474 (100), 475 (15), calculated m/z 475.31. $^1$H NMR (D$_2$O, 300 MHz): δ=0.98 (t, 3H, J=7.2 Hz), 1.91 (q, 2H, J=7.2 Hz), 2.65 (t, 2H, J=7.2 Hz), 3.44 (t, 2H, J=12.3 Hz), 6.53 (m, 1H), 7.26 (m, 1H), 7.48 (m, 1H), 7.50 (d, 2H, J=10.5 Hz), 7.71 (m, 1H), 8.32 (m, 1H), 8.52 (m, 1H), 8.65 (m, 1H). $^{31}$P NMR (D$_2$O, 121.5 MHz): δ=16.46. $^{19}$F NMR (D$_2$O, 282 MHz): δ=−128.75.

Example 31

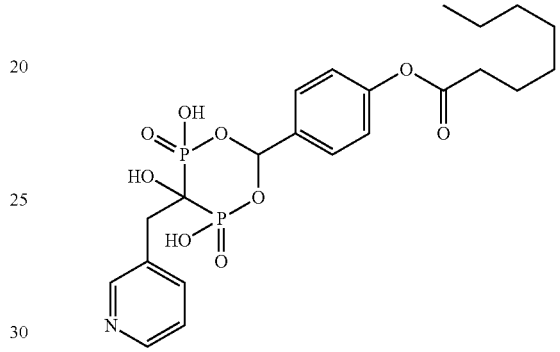

Example 31 was synthesized following the general synthetic procedures of Example 26 starting from 4-formylphenyl octanoate (Example 1).

Yield: 725 mg (26%); elemental analysis (%) calculated for C$_{22}$H$_{27}$N$_1$Na$_2$O$_9$P$_2$.0.70NaCl.1.0H$_2$O (616.34): C, 42.87; H, 4.74; N, 2.27. Found: C, 42.91; H, 4.87; N, 2.21. ESI MS (H$_2$O): m/z: 512 (M$^+$−1). $^1$H NMR (D$_2$O, 300 MHz): δ=8.60-6.80 (m, 8H), 6.62-6.38 (m, 1H), 3.58-3.24 (m, 2H), 2.42 (t, 2H), 1.76-0.82 (m, 13H). $^{31}$P NMR (D$_2$O, 121.5 MHz): δ=16.5, 16.0.

Example 32

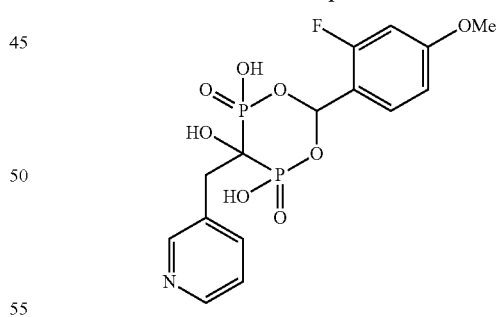

Example 32 was synthesized following the general synthetic procedures of Example 26 starting from 2-fluoro-4-methoxybenzaldehyde.

trans-Isomer: yield 1.0 g (20%). Elemental analysis (%) calculated for C$_{15}$H$_{14}$FNNa$_2$O$_8$P$_2$.0.3NaCl.2.3H$_2$O (522.19): C, 34.50; H, 3.59; N, 2.68. Found C, 34.40; H, 3.41; N, 2.80. ESI MS (CH$_3$CN): m/z 418 (100), 419 (80), 420 (10) calculated m/z 419.24. $^1$H NMR (D$_2$O, 300 MHz): δ=3.39 (t, 2H, J=8.7 Hz), 3.79 (s, 1H), 6.73 (m, 2H), 6.78 (m, 1H), 7.52 (m, 1H), 7.60 (m, 2H), 8.10 (s, 1H), 8.42 (m, 1H), 8.57 (m, 1H). $^{31}$P NMR (D$_2$O, 121.5 MHz): δ=16.57. $^{19}$F NMR (D$_2$O, 282 MHz): δ=−121.84.

cis-Isomer, yield: 1.5 g (31%). Elemental analysis (%) calculated for $C_{15}H_{14}FNNa_2O_8P_2 \cdot 0.4NaCl \cdot 2H_2O$ (504.62): C, 35.70; H, 3.20; N, 2.78. Found C, 35.52; H, 3.23; N, 2.83. ESI MS (CH$_3$CN): m/z 418 (100), 419 (8), calculated m/z 419.24. $^1$H NMR (D$_2$O, 300 MHz): δ=3.43 (t, 2H, J=15.6 Hz), 3.76 (s, 3H), 6.58 (m, 1H), 6.71 (m, 3H), 6.89 (m, 1H), 7.48 (m, 2H), 8.24 (m, 1H), 8.40 (m, 1H), 8.73 (m, 1H). $^{31}$P NMR (D$_2$O, 121.5 MHz): δ=16.36. $^{19}$F NMR (D$_2$O, 282 MHz): δ=−121.23.

Example 33

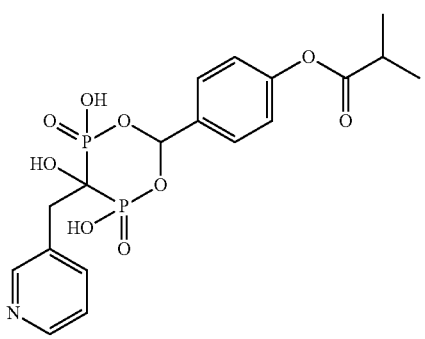

Example 33 was synthesized following the general synthetic procedures of Example 26 starting from 4-formylphenyl isobutyrate.

trans-Isomer, yield: 0.9 g (17%). Elemental analysis (%) calculated for $C_{15}H_{14}FNNa_2O_8P_2 \cdot 0.8NaCl \cdot 0.2H_2O$ (546.40): C, 39.57; H, 3.80; N, 2.56. Found C, 39.29; H, 4.10; N, 2.76. ESI MS (CH$_3$CN): m/z 456 (100), 457 (22) calculated m/z 457.32. $^1$H NMR (D$_2$O, 300 MHz): δ=1.25 (d, 6H, J=6 Hz), 2.88 (sept, 1H, J=6 Hz), 3.37 (t, 2H, J=8.7 Hz), 3.79 (s, 1H), 6.41 (m, 1H), 7.10 (m, 1H), 7.25 (m, 2H), 7.50 (m, 1H), 8.25 (s, 1H), 8.40 (m, 1H) 8.61 (m, 1H), 8.72 (m, 1H). $^{31}$P NMR (D$_2$O, 121.5 MHz): δ=16.41.cis-Isomer, yield: 0.9 g (15.5%). Elemental analysis (%) calculated for $C_{18}H_{19}NNa_2O_9P_2 \cdot 0.9NaCl \cdot 2.1H_2O$ (610.74): C, 35.40; H, 3.83; N, 2.29. Found C, 35.24; H, 3.53; N, 2.44. ESI MS (CH$_3$CN): m/z 456 (100), 457 (30), calculated m/z 457.32. $^1$H NMR (D$_2$O, 300 MHz): δ=1.27 (d, 6H, J=6 Hz), 2.87 (sept., 1H, J=6 Hz), 3.41 (t, 2H, J=10.8 Hz), 6.57 (m, 1H), 7.10 (m, 1H), 7.18 (d, 1H, J=7.8 Hz), 7.54 (m, 1H), 7.65 (d, 1H, J=9.0 Hz), 8.09 (m, 1H), 8.43 (m, 1H), 8.59 (m, 1H). $^{31}$P NMR (D$_2$O, 121.5 MHz): δ=16.70.

Example 34

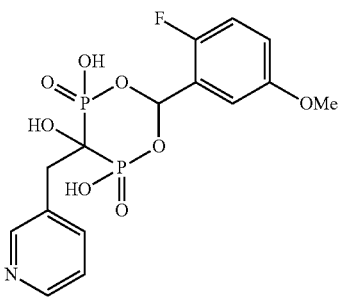 [SMILES: COc1ccc(F)c(C2OP(=O)(O)C(O)(Cc3cccnc3)P(=O)(O)O2)c1]

Example 34 was synthesized following the general synthetic procedures of Example 26 starting from 2-fluoro-5-methoxybenzaldehyde.

trans-Isomer yield: 1.25 g (24%). Elemental analysis (%) calculated for $C_{15}H_{14}FNNa_2O_8P_2 \cdot 0.3NaCl \cdot 2.3H_2O$ (522.19): C, 29.85; H, 3.21; N, 2.32. Found C, 29.84; H, 2.91; N, 2.40. ESI MS (CH$_3$CN): m/z 418 (100), 419 (20), 420 (1) calculated m/z 419.24. $^1$H NMR (D$_2$O, 300 MHz): δ=3.37 (t, 2H, J=17.2 Hz), 3.74 (s, 1H), 6.58 (m, 1H), 6.91 (m, 1H), 7.00 (m, 2H), 7.54 (d, 1H, J=5.4 Hz), 8.30 (d, 1H, J=8.1 Hz), 8.40 (d, 1H, J=7.5 Hz), 8.73 (s, 1H). $^{31}$P NMR (D$_2$O, 121.5 MHz): δ=16.38. $^{19}$F NMR (D$_2$O, 282 MHz): δ=−130.08.

Example 35

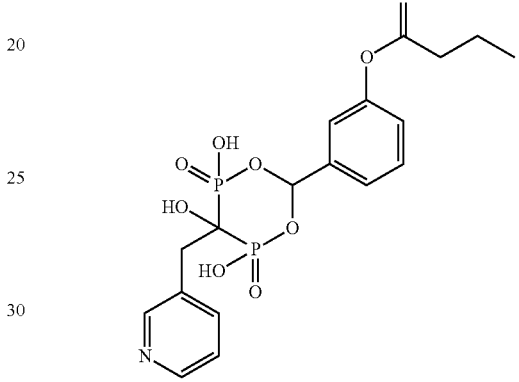

Example 35 was synthesized following the general synthetic procedures of Example 26 starting from 3-formylphenyl butyrate (Example 4).

Yield: 215 mg (11%). Elemental analysis (%) calculated for $C_{18}H_{19}N_1Na_2O_9P_2 \cdot 1.10NaCl \cdot 2.0H_2O$ (601.63): C, 35.94; H, 3.85; N, 2.33. Found: C, 35.80; H, 3.83; N, 2.28. ESI MS (H$_2$O): m/z: 456 (M$^+$−1). $^1$H NMR (D$_2$O, 300 MHz): δ=8.72-7.05 (m, 8H), 6.56-6.32 (m, 1H), 3.42-3.22 (m, 2H), 2.60 (m, 2H), 1.74 (m, 2H), 0.96 (m, 3H). $^{31}$P NMR (D$_2$O, 121.5 MHz): δ=16.8, 16.4.

Example 36

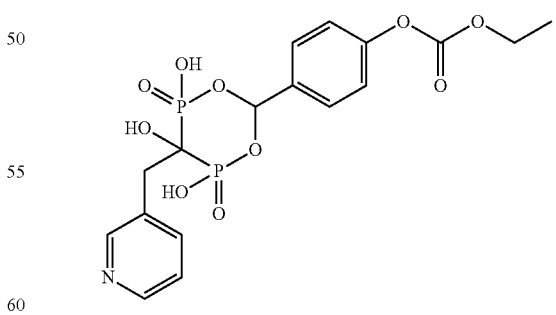

Example 36 was synthesized following the general synthetic procedures of Example 26 starting from ethyl 4-formylphenyl carbonate (Example 5).

Yield: 215 mg (9%); elemental analysis (%) calculated for $C_{17}H_{17}N_1Na_2O_{10}P_2 \cdot 0.9NaCl \cdot 0.8H_2O$ (570.29): C, 35.80; H, 3.29; N, 2.46. Found: C, 35.86; H, 3.29; N, 2.54. ESI MS (H₂O): m/z: 458 (M⁺−1). ¹H NMR (D₂O, 300 MHz): δ=8.62-7.21 (m, 8H), 6.60-6.52 (m, 1H), 4.36-4.24 (m, 2H), 3.46-3.26 (m, 2H), 1.36-1.28 (m, 3H). ³¹P NMR (D₂O, 121.5 MHz): δ=16.7.

Example 37

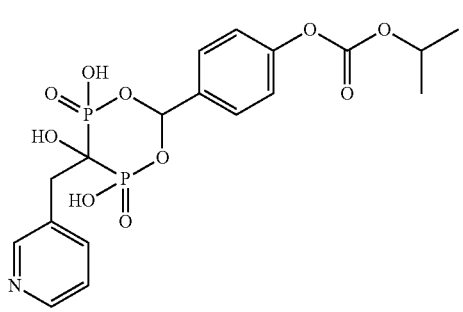 [SMILES: CC(C)OC(=O)Oc1ccc(C2OP(=O)(O)C(O)(Cc3cccnc3)P(=O)(O)O2)cc1]

Example 37 was synthesized following the general synthetic procedures of Example 26 starting from 4-formylphenyl 3-methylbutanoate.

cis-Isomer, yield: 0.31 g (5.0%). Elemental analysis (%) calculated for $C_{19}H_{21}NNa_2O_9P_2 \cdot 1.1NaCl \cdot 2.4H_2O$ (622.86): C, 36.64; H, 4.17; N, 2.25. Found C, 36.64; H, 3.87; N, 2.33. ESI MS (CH₃CN): m/z 470 (100), 471 (20) calculated m/z 471.34. ¹H NMR (D₂O, 300 MHz): δ=1.00 (d, 6H, J=6.0 Hz), 2.13 (m, 1H, J=6.6 Hz), 2.5 (m, 2H), 3.37 (t, 2H, J=12.1 Hz), 6.55 (t, 1H, J=4.3 Hz), 7.17 (m, 1H), 7.48 (m, 2H), 7.62 (m, 2H), 8.03 (m, 1H), 8.39 (s, 1H), 8.55 (s, 1H). ³¹P NMR (D₂O, 121.5 MHz): δ=16.72.

Example 38

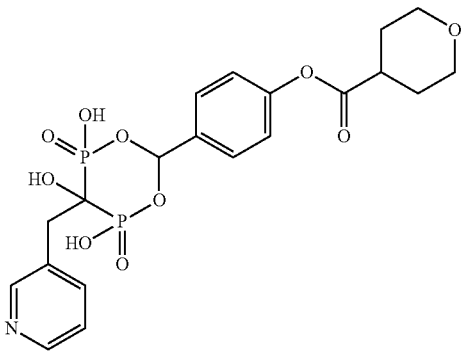 [SMILES: O=C(Oc1ccc(C2OP(=O)(O)C(O)(Cc3cccnc3)P(=O)(O)O2)cc1)C1CCOCC1]

Example 38 was synthesized following the general synthetic procedures of Example 26 starting from 4-formylphenyl tetrahydro-2H-pyran-4-carboxylate (Example 6).

Yield: 385 mg (14%); elemental analysis (%) calculated for $C_{20}H_{21}N_1Na_2O_{10}P_2 \cdot 0.8NaCl \cdot 1.6H_2O$ (618.92): C, 38.81; H, 3.94; N, 2.26. Found: C, 38.79; H, 4.15; N, 2.45. ESI MS (H₂O) m/z 498 (M⁺−1). ¹H NMR (D₂O, 300 MHz): δ=8.88-7.16 (m, 8H), 6.62-6.50 (m, 1H), 4.06-4.02 (m, 2H), 3.63-3.49 (m, 4H), 2.98 (m, 1H), 2.07-1.81 (m, 4H). ³¹P NMR (D₂O, 121.5 MHz): δ=16.0, 15.9.

Example 39

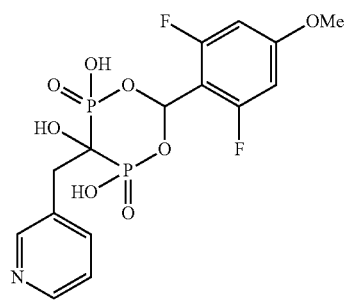 [SMILES: COc1cc(F)c(C2OP(=O)(O)C(O)(Cc3cccnc3)P(=O)(O)O2)c(F)c1]

Example 39 was synthesized following the general synthetic procedures of Example 26 starting from 2,6-difluoro-4-methoxybenzaldehyde.

Yield: 256 mg (11%); elemental analysis (%) calculated for $C_{15}H_{13}F_2N_1Na_2O_8P_2 \cdot 1.2NaCl \cdot 0.5H_2O$ (560.36): C, 32.15; H, 2.52; N, 2.50. Found: C, 32.04; H, 2.52; N, 2.53. ESI MS (H₂O) m/z 436 (M⁺−1). ¹H NMR (D₂O, 300 MHz): δ=8.72-7.40 (m, 4H), 6.82-6.52 (m, 3H), 3.80 (s, 3H), 3.42-3.26 (m, 2H). ³¹P NMR (D₂O, 121.5 MHz): δ=16.6. ¹⁹F NMR (CDCl₃, 282.3 MHz): δ=−113.

Example 40

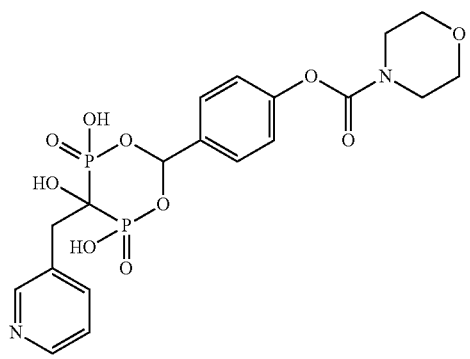

Example 40 was synthesized following the general synthetic procedures of Example 26 starting from 4-formylphenyl morpholine-4-carboxylate (Example 7).

Yield: 342 mg (13%); elemental analysis (%) calculated for $C_{19}H_{20}N_2Na_2O_{10}P_2 \cdot 1.0NaCl \cdot 1.0H_2O$ (620.79): C, 36.76; H, 3.57; N, 4.51. Found: C, 36.89; H, 3.50; N, 4.48. ESI MS (H₂O) m/z 499 (M⁺−1). ¹H NMR (D₂O, 300 MHz): δ=8.58-

7.16 (m, 8H), 6.56 (m, 1H), 3.80-3.45 (m, 8H), 3.43-3.28 (m, 2H). $^{31}$P NMR (D$_2$O, 121.5 MHz): δ=16.8, 16.5.

Example 41

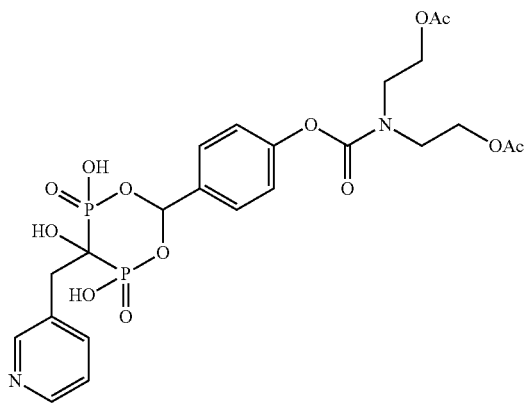 [SMILES: CC(=O)OCCN(CCOC(C)=O)C(=O)Oc1ccc(C2OP(=O)(O)C(O)(Cc3cccnc3)P(=O)(O)O2)cc1]

Example 41 was synthesized following the general synthetic procedures of Example 26 starting from 2,2'-((4-formylphenoxy)carbonylazanediyl)bis(ethane-2,1-diyl)diacetate (Example 22).

trans-Isomer, yield: 677 mg (15%). Elemental analysis (%) calculated for C$_{23}$H$_{26}$N$_2$Na$_2$O$_{13}$P$_2$.0.8H$_2$O (660.82): C, 41.80; H, 4.21; N, 4.24. Found: C, 41.76; H, 4.30; N, 4.03. ESI MS (H$_2$O) m/z 601 (M$^+$−1). $^1$H NMR (D$_2$O, 300 MHz): δ=8.64-7.03 (m, 8H), 6.40-6.28 (m, 1H), 4.27-4.22 (m, 4H), 3.69-3.56 (m, 4H), 3.30 (t, J=16.5 Hz, 2H), 1.99 (s, 6H). $^{31}$P NMR (D$_2$O, 121.5 MHz): δ=16.5.

cis-Isomer, yield: 294 mg (7%). Elemental analysis (%) calculated for C$_{23}$H$_{26}$N$_2$Na$_2$O$_{13}$P$_2$.0.5 NaCl.1.2H$_2$O (697.26): C, 39.62; H, 4.11; N, 4.02. Found: C, 39.51; H, 4.11; N, 4.02. ESI MS (H$_2$O): m/z: 601 (M$^+$−1). $^1$H NMR (D$_2$O, 300 MHz): δ=8.60-7.10 (m, 8H), 6.58 (br, 1H), 4.29 (br, 4H), 3.75-3.62 (m, 4H), 3.39 (br, 2H), 2.06 (s, 6H). $^{31}$P NMR (D$_2$O, 121.5 MHz): δ=16.8.

Example 42

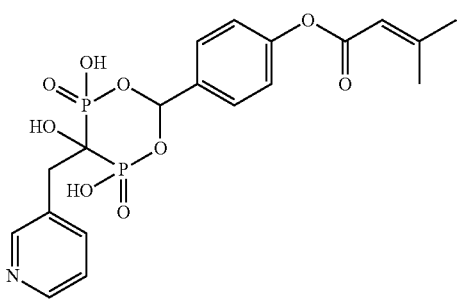 [SMILES: CC(C)=CC(=O)Oc1ccc(C2OP(=O)(O)C(O)(Cc3cccnc3)P(=O)(O)O2)cc1]

Example 42 was synthesized following the general synthetic procedures of Example 26 starting from 4-formylphenyl 3-methylbut-2-enoate.

Yield: 0.12 g (2%). Elemental analysis (%) calculated for C$_{19}$H$_{19}$NNa$_2$O$_9$P$_2$.0.5NaCl.2.2H$_2$O (582.17): C, 39.20; H, 4.05; N, 2.41. Found C, 39.00; H, 3.88; N, 2.73. ESI MS (CH$_3$CN): m/z 468 (100), 469 (20) calculated m/z 469.33. $^1$H NMR (D$_2$O, 300 MHz): δ=1.97 (m, 3H), 2.13 (m, 1H), 3.36 (t, 2H, J=16.6 Hz), 5.96 (s, 1H), 6.41 (t, 1H, J=4.5 Hz), 7.09 (m, 2H), 7.24 (m, 2H), 7.45 (m, 1H), 8.21 (m, 1H), 8.38 (m, 1H), 8.71 (s, 1H). $^{31}$P NMR (D$_2$O, 121.5 MHz): δ=16.43.

Example 43

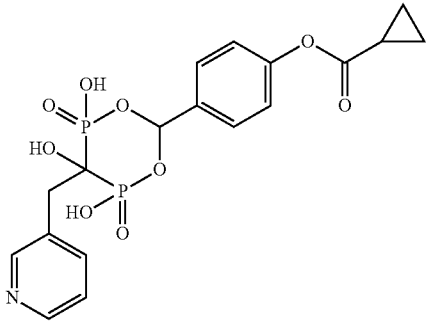 [SMILES: O=C(Oc1ccc(C2OP(=O)(O)C(O)(Cc3cccnc3)P(=O)(O)O2)cc1)C1CC1]

Example 43 was synthesized following the general synthetic procedures of Example 26 starting from 4-formylphenyl cyclopropanecarboxylate.

trans-Isomer, yield: 0.11 g (2.1%). Elemental analysis (%) calculated for C$_{18}$H$_{17}$NNa$_2$O$_9$P$_2$.0.05NaCl.1.3H$_2$O (525.62): C, 41.13; H, 3.76; N, 2.66. Found C, 41.17; H, 3.84; N, 2.70. ESI MS (CH$_3$CN): m/z 454 (100), 455 (30) calculated m/z 455.30. $^1$H NMR (D$_2$O, 300 MHz): δ=1.09 (m, 4H), 1.89 (m, 1H), 3.33 (t, 2H, J=17.1 Hz), 6.37 (t, 1H, J=4.8 Hz), 7.08 (m, 2H), 7.17 (m, 2H), 7.34 (m, 1H), 8.09 (m, 1H, J=7.8 Hz), 8.33 (d, 1H, J=5.4 Hz), 8.67 (s, 1H). $^{31}$P NMR (D$_2$O, 121.5 MHz): δ=16.57.

cis-Isomer, yield: 0.12 g (2.3%). Elemental analysis (%) calculated for C$_{18}$H$_{17}$NNa$_2$O$_9$P$_2$.0.2NaCl.2.4H$_2$O (525.62): C, 41.13; H, 3.76; N, 2.66. Found C, 38.93; H, 3.68; N, 2.64. ESI MS (CH$_3$CN): m/z 454 (100), 455 (20) calculated m/z 455.30. $^1$H NMR (D$_2$O, 300 MHz): δ=1.11 (m, 4H), 1.91 (m, 1H), 3.38 (t, 2H, J=12.6 Hz), 6.56 (t, 1H, J=4.4 Hz), 7.18 (m, 2H), 7.44 (m, 1H), 7.63 (d, 2H, J=7.8 Hz), 8.00 (m, 1H, J=7.8 Hz), 8.39 (m, 1H), 8.54 (s, 1H). $^{31}$P NMR (D$_2$O, 121.5 MHz): δ=14.65.

Example 44

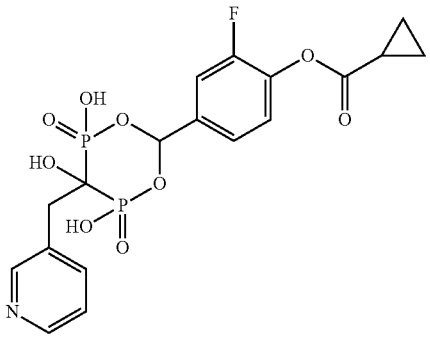 [SMILES: O=C(Oc1ccc(C2OP(=O)(O)C(O)(Cc3cccnc3)P(=O)(O)O2)cc1F)C1CC1]

Example 44 was synthesized following the general synthetic procedures of Example 26 starting from 2-fluoro-4-formylphenyl cyclopropanecarboxylate.

trans-Isomer, yield: 0.14 g (2.6%). Elemental analysis (%) calculated for $C_{18}H_{16}FNNa_2O_9P_2.0.2NaCl.1.3H_2O$ (552.38): C, 41.80; H, 3.12; N, 2.71. Found C, 39.39; H, 3.71; N, 2.71. ESI MS ($CH_3CN$): m/z 472 (100), 473 (20) calculated m/z 473.29. $^1H$ NMR ($D_2O$, 300 MHz): δ=1.14 (m, 4H), 1.94 (m, 1H), 3.32 (t, 2H, J=17.5 Hz), 6.35 (t, 1H, J=4.5 Hz), 7.04 (m, 2H), 7.17 (t, 1H, J=8.1 Hz), 7.35 (m, 1H), 8.08 (m, 1H, J=7.5 Hz), 8.33 (d, 1H, J=4.5 Hz), 8.67 (s, 1H). $^{31}P$ NMR ($D_2O$, 121.5 MHz): δ=16.45. $^{19}F$ NMR ($D_2O$, 282 MHz): δ=−129.18.

cis-Isomer, yield: 0.06 g (1.2%). Elemental analysis (%) calculated for $C_{18}H_{16}FNNa_2O_9P_2.0.8NaCl.1.8H_2O$ (525.62): C, 41.80; H, 3.12; N, 2.71. Found C, 35.99; H, 3.36; N, 2.68. ESI MS ($CH_3CN$): m/z 472 (100), 473 (30) calculated m/z 473.29. $^1H$ NMR ($D_2O$, 300 MHz): δ=1.14 (m, 4H), 1.94 (m, 1H), 3.34 (t, 2H, J=12.6 Hz), 6.52 (t, 1H, J=3.3 Hz), 7.18 (m, 2H), 7.44 (m, 1H), 7.63 (d, 2H, J=7.8 Hz), 8.00 (m, 1H, J=7.8 Hz), 8.39 (m, 1H), 8.54 (s, 1H). $^{31}P$ NMR ($D_2O$, 121.5 MHz): δ=14.87. $^{19}F$ NMR ($D_2O$, 282 MHz): δ=−129.13.

Example 45

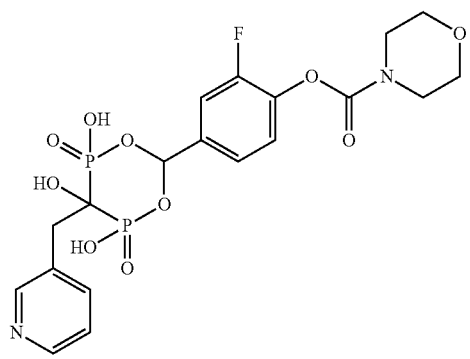

Example 45 was synthesized following the general synthetic procedures of Example 26 starting from 2-fluoro-4-formylphenyl morpholine-4-carboxylate (Example 8).

trans-Isomer, yield: 203 mg (7%); elemental analysis (%) calculated for $C_{19}H_{19}F_1N_2Na_2O_{10}P_2.0.2NaCl.1.0H_2O$ (592.02): C, 38.55; H, 3.58; N, 4.73. Found: C, 38.44; H, 3.61; N, 4.50; ESI MS ($H_2O$): m/z: 517 ($M^+$−1). $^1H$ NMR ($D_2O$, 300 MHz): δ=8.67-6.93 (m, 8H), 6.35 (t, J=4.5 Hz, 1H), 3.75-3.50 (m, 8H), 3.32 (t, J=17.4 Hz, 2H). $^{31}P$ NMR ($D_2O$, 121.5 MHz): δ=16.5. $^{19}F$ NMR ($CDCl_3$, 282.3 MHz): δ=−130.0.

cis-Isomer, yield: 298 mg (11%); elemental analysis (%) calculated for $C_{19}H_{19}F_1N_2Na_2O_{10}P_2.2.2NaCl.1.2H_2O$ (712.53): C, 32.03; H, 3.03; N, 3.93. Found: C, 31.92; H, 3.06; N, 3.88; ESI MS ($H_2O$): m/z: 517 ($M^+$−1). $^1H$ NMR ($D_2O$, 300 MHz): δ=8.52-7.25 (m, 8H), 6.54 (t, J=5.4 Hz, 1H), 3.77-3.53 (m, 8H), 3.37 (t, J=12.6 Hz, 2H). $^{31}P$ NMR ($D_2O$, 121.5 MHz): δ=16.8. $^{19}F$ NMR ($CDCl_3$, 282.3 MHz): δ=−129.9.

Example 46

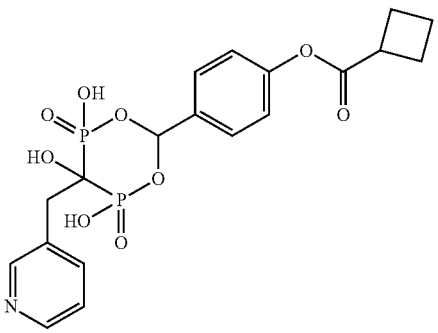 [SMILES: O=C(Oc1ccc(C2OP(=O)(O)C(O)(Cc3cccnc3)P(=O)(O)O2)cc1)C1CCC1]

Example 46 was synthesized following the general synthetic procedures of Example 26 starting from 4-formylphenyl cyclobutanecarboxylate.

cis-Isomer: yield 0.581 g (26%), contaminated with Risedronate (6%). $^1H$ NMR ($D_2O$): δ=8.64 (s, 1H), 8.50 (d, J=4.5 Hz, 1H), 8.18 (d, J=8.2 Hz, 1H), 7.69 (d, J=8.4 Hz for AB-system, 2H), 7.60 (dd, J=4.5, 8.2 Hz, 1H), 7.22 (d, J=8.4 Hz for AB-system, 2H), 6.61 (t, J=5.1 Hz, 1H), 3.53 (m, 1H), 3.46 (t, J=12.5 Hz, 2H), 2.38 (m, 4H), 2.20-1.88 (m, 2H). $^{31}P$ NMR ($D_2O$): δ=16.64. Calc. for $0.94C_{19}H_{19}NNa_2O_9P_2.0.06C_7H_7NNa_4O_7P_2.0.5H_2O.0.5NaCl$ (%): C, 40.43; H, 3.58; N, 2.58. Found (%): C, 40.31; H, 3.65; N, 2.93.

trans-Isomer: yield 0.596 g (27%), contaminated with Risedronate (9.6%). $^1H$ NMR ($D_2O$): δ=8.77 (s, 1H), 8.44 (d, J=5.0 Hz, 1H), 8.26 (d, J=8.0 Hz, 1H), 7.51 (dd, J=5.0, 8.0 Hz, 1H), 7.31 (d, J=8.5 Hz for AB-system, 2H), 7.15 (d, J=8.5 Hz for AB-system, 2H), 6.46 (t, J=4.95 Hz, 1H), 3.52 (m, 1H), 3.42 (t, J=17.0 Hz, 2H), 2.37 (m, 4H), 2.18-1.88 (m, 2H). $^{31}P$ NMR ($D_2O$): δ=16.42. Calc. for $0.9C_{19}H_{19}NNa_2O_9P_2.0.1C_7H_7NNa_4O_7P_2.0.5H_2O$ (%): C, 42.14; H, 3.73; N, 2.75. Found (%): C, 41.85; H, 3.97; N, 2.37.

Example 47

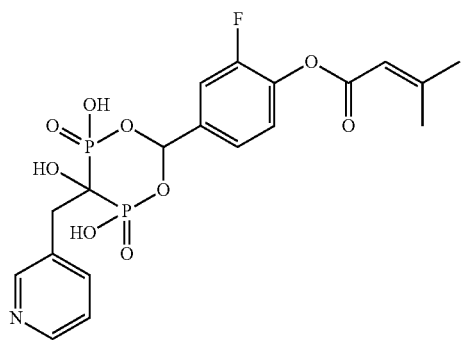 [SMILES: CC(C)=CC(=O)Oc1ccc(C2OP(=O)(O)C(O)(Cc3cccnc3)P(=O)(O)O2)cc1F]

Example 47 was synthesized following the general synthetic procedures of Example 26 starting from 2-fluoro-4-formylphenyl 3-methylbut-2-enoate.

trans-Isomer, yield: 0.26 g (4.5%). Elemental analysis (%) calculated for $C_{19}H_{18}FNNa_2O_9P_2 \cdot 0.02NaCl \cdot 0.45H_2O$ (582.17): C, 42.34; H, 3.55; N, 2.83. Found C, 42.61; H, 4.19; N, 2.53. ESI MS ($CH_3CN$): m/z 486 (100), 487 (35) calculated m/z 487.32. $^1H$ NMR ($D_2O$, 300 MHz): δ=1.95 (m, 3H), 2.19 (m, 1H), 3.33 (t, 2H, J=17.4 Hz), 5.95 (s, 1H), 6.36 (t, 1H, J=4.8 Hz), 6.95 (m, 1H), 7.09 (m, 1H), 7.18 (m, 1H), 7.33 (m, 1H), 8.08 (m, 1H, J=7.8 Hz), 8.33 (d, 1H, J=4.5 Hz), 8.68 (s, 1H). $^{31}P$ NMR ($D_2O$, 121.5 MHz): δ=16.24. $^{19}F$ NMR ($D_2O$, 282 MHz): δ=−128.84.

cis-Isomer, yield: 0.11 g (1.9%). Elemental analysis (%) calculated for $C_{19}H_{18}FNNa_2O_9P_2 \cdot 0.04NaCl \cdot 2.8H_2O$ (584.08): C, 39.07; H, 4.07; N, 2.40. Found C, 38.80; H, 3.77; N, 2.44. ESI MS ($CH_3CN$): m/z 486 (100), 487 (23) calculated m/z 487.32. $^1H$ NMR ($D_2O$, 300 MHz): δ=1.98 (s, 3H), 2.14 (s, 3H), 3.37 (t, 2H, J=12.5 Hz), 5.99 (s, 1H), 6.53 (t, 1H, J=4.4 Hz), 7.10 (m, 1H), 7.25 (m, 1H), 7.51 (m, 2H), 8.10 (m, 1H), 8.44 (m, 1H), 8.58 (s, 1H). $^{31}P$ NMR ($D_2O$, 121.5 MHz): δ=16.58. $^{19}F$ NMR ($D_2O$, 282 MHz): δ=−128.83.

Example 48

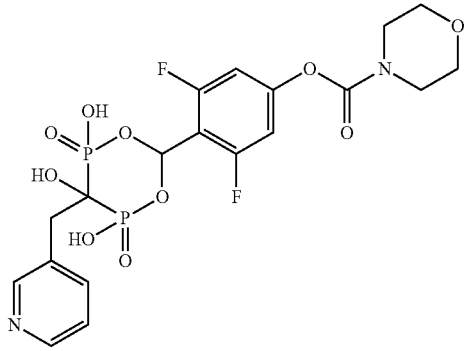 [SMILES: O=C(Oc1cc(F)c(C2OP(=O)(O)C(O)(Cc3cccnc3)P(=O)(O)O2)c(F)c1)N1CCOCC1]

Example 48 was synthesized following the general synthetic procedures of Example 26 starting from 3,5-difluoro-4-formylphenyl morpholine-4-carboxylate (Example 9).

Yield: 209 mg (5%); elemental analysis (%) calculated for $C_{19}H_{18}F_2N_2Na_2O_{10}P_2 \cdot 1.5NaCl \cdot 2.2H_2O$ (707.60): C, 32.25; H, 3.19; N, 3.96. Found: C, 32.08; H, 3.34; N, 3.90. ESI MS ($H_2O$) m/z 535 ($M^+$−1). $^1H$ NMR ($D_2O$, 300 MHz): δ=8.74-6.81 (m, 7H), 3.76-3.39 (m, 10H). $^{31}P$ NMR ($D_2O$, 121.5 MHz): δ=16.5. $^{19}F$ NMR ($CDCl_3$, 282.3 MHz, mixture of two-Isomers): δ=−112.8 (d, J=9.0 Hz), −113.2 (d, J=9.3 Hz).

Example 49

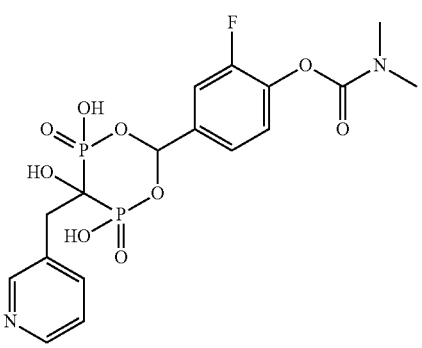 [SMILES: CN(C)C(=O)Oc1ccc(C2OP(=O)(O)C(O)(Cc3cccnc3)P(=O)(O)O2)cc1F]

Example 49 was synthesized following the general synthetic procedures of Example 26 starting from 2-fluoro-4-formylphenyl dimethylcarbamate (Example 10).

Yield: 518 mg (14%); elemental analysis (%) calculated for $C_{17}H_{17}F_1N_2Na_2O_9P_2 \cdot 1.0NaCl \cdot 2.0H_2O$ (614.76): C, 33.21; H, 3.44; N, 4.56. Found: C, 33.20; H, 3.64; N, 4.49. ESI MS ($H_2O$): m/z: 475 ($M^+$−1). $^1H$ NMR ($D_2O$, 300 MHz): δ=8.71-6.97 (m, 7H), 6.55-6.37 (m, 1H), 3.42-3.30 (m, 2H), 3.11 (s, 3H), 2.96 (s, 3H). $^{31}P$ NMR ($D_2O$, 121.5 MHz): δ=16.8, 16.5. $^{19}F$ NMR ($CDCl_3$, 282.3 MHz): δ=−130.0.

Example 50

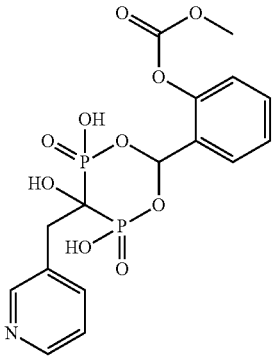 [SMILES: COC(=O)Oc1ccccc1C1OP(=O)(O)C(O)(Cc2cccnc2)P(=O)(O)O1]

Example 50 was synthesized following the general synthetic procedures of Example 26 starting from 2-formylphenyl methyl carbonate.

trans-Isomer, yield: 0.19 g (3.7%). Elemental analysis (%) calculated for $C_{16}H_{15}NNa_2O_{10}P_2 \cdot 0.09NaCl \cdot 2.2H_2O$ (534.14): C, 35.98; H, 3.66; N, 2.62. Found C, 35.74; H, 3.45; N, 2.89. ESI MS ($CH_3CN$): m/z 444 (100), 445 (10) calculated m/z 445.26. $^1H$ NMR ($D_2O$, 300 MHz): δ=3.37 (t, 2H, J=16.4 Hz), 3.88 (s, 3H), 6.55 (t, 1H, J=5.4 Hz), 7.21 (m, 1H), 7.33 (m, 2H), 7.48 (m, 2H), 8.23 (m, 1H), 8.38 (m, 1H), 8.75 (s, 1H). $^{31}P$ NMR ($D_2O$, 121.5 MHz): δ=16.21.

Example 51

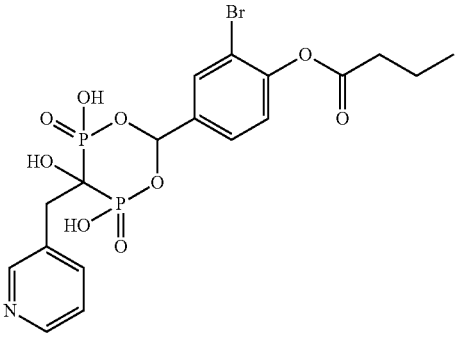 [SMILES: CCCC(=O)Oc1ccc(C2OP(=O)(O)C(O)(Cc3cccnc3)P(=O)(O)O2)cc1Br]

Example 51 was synthesized following the general synthetic procedures of Example 26 starting from 2-bromo-4-formylphenyl butyrate.

cis-Isomer: yield 0.201 g (6.7%) of title compound as white powder. $^1H$ NMR ($D_2O$): δ=8.57 (s, 1H), 8.43 (d, J=5.1 Hz, 1H), 7.99 (s, 1H), 7.96 (d, J=8.2 Hz, 1H), 7.67 (d, J=7.8 Hz, 1H), 7.43 (t, J=5.4 Hz, 1H), 7.31 (d, J=7.8 Hz, 1H), 6.59 (t, J=4.8 Hz, 1H), 3.41 (t, J=12.7 Hz, 2H), 2.73 (t, J=7.2 Hz, 2H), 1.80 (m, J=7.2 Hz, 2H), 1.05 (t, J=7.2 Hz, 3H). $^{31}P$ NMR ($D_2O$): δ=16.84. LC-MS (ESI) for $C_{18}H_{20}BrNO_9P_2$ m/z 534

[M-2H]⁻, 536 [M]⁻. Elemental analysis (%) calculated for C₁₈H₁₈BrNNa₂O₉P₂.1H₂O.2NaCl (%): C, 30.23; H, 2.82; N, 1.96. Found (%): C, 30.42; H, 3.33; N, 2.35.

Example 52

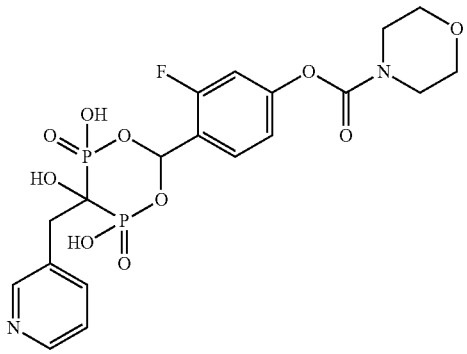 [SMILES: O=C(Oc1ccc(C2OP(=O)(O)C(O)(Cc3cccnc3)P(=O)(O)O2)c(F)c1)N1CCOCC1]

Example 52 was synthesized following the general synthetic procedures of Example 26 starting from 3-fluoro-4-formylphenyl morpholine-4-carboxylate.

Yield: 0.135 g (3%). Na-salt of title compound as white powder, trans-isomer. ¹H NMR (D₂O): δ=8.78 (s, 1H), 8.45 (d, J=5.1 Hz, 1H), 8.26 (d, J=8.4 Hz, 1H), 7.50 (dd, J=5.1, 8.4 Hz, 1H), 7.17 (t, J=8.7 Hz, 1H), 7.01 (d, J=9.3 Hz, 2H), 6.70 (t, J=6.0 Hz, 1H), 3.90-3.50 (m, 8H), 3.44 (t, J=17.0 Hz, 2H). ³¹P NMR (D₂O): δ=16.42. ¹⁹F NMR (D₂O): δ=−117.27. LC-MS (ESI) for C₁₉H₂₁FN₂O₁₀P₂ m/z 517 [M-H]⁻. Elemental analysis (%) calculated for C₁₉H₁₉FN₂Na₂O₁₀P₂.3.0H₂O (%): C, 37.03; H, 4.09; N, 4.54. Found (%): C, 36.89; H, 3.91; N, 4.71.

Example 53

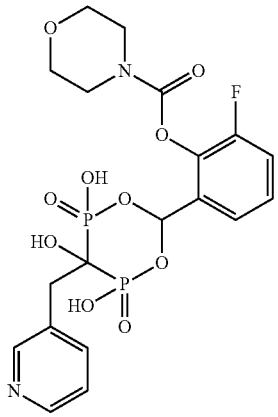 [SMILES: O=C(Oc1c(F)cccc1C1OP(=O)(O)C(O)(Cc2cccnc2)P(=O)(O)O1)N1CCOCC1]

Example 53 was synthesized following the general synthetic procedures of Example 26 starting from 2-fluoro-6-formylphenyl morpholine-4-carboxylate (Example 11).

Yield: 253 mg (7%). Elemental analysis (%) calculated for C₁₉H₁₉Ca₁F₁N₂O₁₀P₂.1.0NaCl.6.0H₂O (775.47): C, 29.43; H, 4.03; N, 3.61. Found: C, 29.61; H, 4.01; N, 3.43. ESI MS (H₂O) m/z 517 (M⁺−1). ³¹P NMR (D₂O, 121.5 MHz): δ=16.0, 15.8. (The solubility of this calcium salt in water is very low, and only ³¹P NMR was available).

Example 54

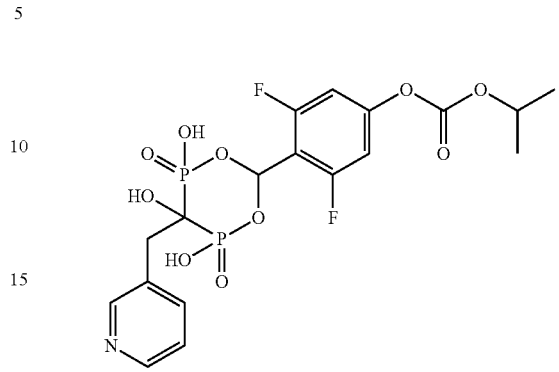

Example 54 was synthesized following the general synthetic procedures of Example 26 starting from 3,5-difluoro-4-formylphenyl isopropyl carbonate (Example 12).

Yield 0.52 g (27%), white solid, contaminated with Risedronate (5%). NMR (D₂O): δ=8.67 (s, 1H), 8.51 (d, J=5.7 Hz, 1H), 8.24 (d, J=7.8 Hz, 1H), 7.65 (dd, J=5.7, 7.8 Hz, 1H), 7.02 (d, ³J_{FH}=9.0 Hz, 2H), 6.92 (t, J=5.4 Hz, 1H), 5.02 (m, J=6.3 Hz, 1H), 3.47 (t, J=12.6 Hz, 2H), 1.37 (d, J=6.3 Hz, 6H). ³¹P NMR (D₂O): δ=16.40. ¹⁹F NMR (D₂O): δ=−112.324 (d, J_{FF}=9.0 Hz). LC-MS (ESI) for C₁₈H₁₉F₂NO₁₀P₂ m/z 508 [M-H]⁻. Elemental analysis (%) calculated for 0.95C₁₈H₁₇F₂NNa₂O₁₀P₂.0.05C₇H₇NNa₄O₇P₂.2H₂O.0.5NaCl (%): C, 34.39; H, 3.39; N, 2.30. Found (%): C, 34.02; H, 3.59; N, 2.25.

Example 55

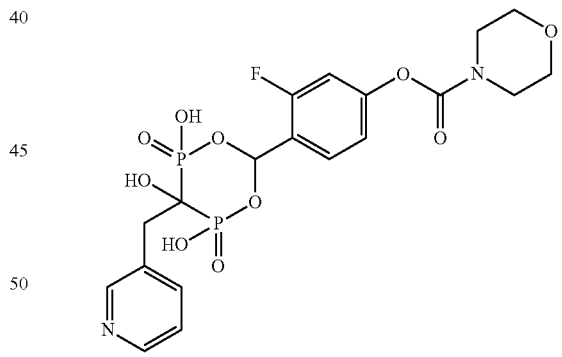

Example 55 was synthesized following the general synthetic procedures of Example 26 starting from 3-fluoro-4-formylphenyl morpholine-4-carboxylate.

Yield: 0.655 g (14%) of Ca-salt of title compound as white powder, mixture of cis- (64%) and trans- (36%) isomers. ¹HNMR (D₂O): δ=8.77 (s, 0.36H-trans), 8.65 (s, 0.64H-cis), 8.50 (d, 0.64H-cis), 8.44 (d, 0.36H-trans), 8.17 (m, 1H-trans, cis), 7.80 (t, J=8.4 Hz, 0.64H-cis), 7.56 (m, 0.64H-cis), 7.48 (m, 0.36H-trans), 7.20-6.84 (m, 2.36H-trans, cis), 6.70 (m, 1H-trans, cis), 3.90-3.50 (m, 8H), 3.46 (m, J=12.0 Hz for cis, 2H-trans, cis). ³¹P NMR (D₂O): δ=16.53-trans, 16.36-cis. LC-MS (ESI) for C₁₉H₂₁FN₂O₁₀P₂ m/z 517 [M-H]⁻. Elemental analysis (%) calculated for $C_{19}H_{19}CaFN_2O_{10}P_2 \cdot 0.1CaCl_2 \cdot 4.0H_2O$ (%): C, 35.68; H, 4.26; N, 4.38, Ca, 6.89. Found (%): C, 35.46; H, 3.86; N, 4.39; Ca, 6.80.

Example 56

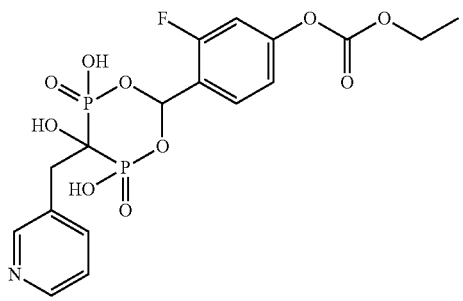 [SMILES: CCOC(=O)Oc1ccc(C2OP(=O)(O)C(O)(Cc3cccnc3)P(=O)(O)O2)c(F)c1]

Example 56 was synthesized following the general synthetic procedures of Example 26 starting from ethyl 3-fluoro-4-formylphenyl carbonate.

Yield: 0.128 g (3.5%). Na-salt of title compound as white powder, mixture of cis- (70%) and trans- (30%) isomers, contaminated with Risedronate (12%). $^1H$ NMR ($D_2O$): δ=8.77 (s, 0.3H-trans), 8.61 (s, 0.7H-cis), 8.46 (d, J=3.3 Hz, 1H-trans,cis), 8.22 (d, J=6.9 Hz, 0.3H-trans), 8.18 (t, 0.3H-trans), 8.07 (d, J=7.2 Hz, 0.7H-cis), 7.82 (t, J=8.5 Hz, 0.7H-cis), 7.57 (m, 0.7H-cis), 7.51 (m), 7.46 (m, 0.3H-trans), 7.15 (m), 7.08 (m), 6.84 (t, J=5.1 Hz, 0.7H-cis), 6.69 (t, J=5.0 Hz, 0.3H-trans), 4.36 (q, J=7.2 Hz, 2H), 3.43 (t, J=12.3 Hz, 1.4H-cis), 3.36 (t, J=16.2 Hz, 0.6H-trans), 1.36 (t, J=7.2 Hz, 3H). $^{31}P$ NMR ($D_2O$): δ=16.68-cis, 16.46-trans. $^{19}F$ NMR ($D_2O$): δ=−116.32 (cis), −116.84 (trans). LC-MS (ESI) for $C_{17}H_{18}FNO_{10}P_2$ m/z 476 [M-H]$^-$. Elemental analysis (%) calculated for $0.88C_{17}H_{16}FNNa_2O_{10}P_2 \cdot 0.12C_7H_7NNa_4O_7P_2 \cdot 3H_2O \cdot NaCl$ (%): C, 30.82; H, 3.42; N, 2.27. Found (%): C, 30.50; H, 3.49; N, 2.86.

Example 57

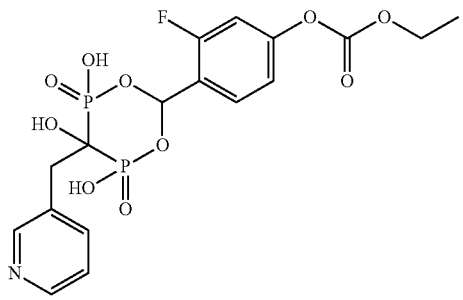 [SMILES: CCOC(=O)Oc1ccc(C2OP(=O)(O)C(O)(Cc3cccnc3)P(=O)(O)O2)c(F)c1]

Example 57 was synthesized following the general synthetic procedures of Example 26 starting from ethyl 3-fluoro-4-formylphenyl carbonate.

Yield: 0.100 g (3%). Ca-salt of title compound as white solid, mixture of cis- (78%) and trans- (22%) isomers. $^1H$ NMR ($D_2O$): δ=8.79 (s, 0.22H-trans), 8.69 (s, 0.78H-cis), 8.53 (m, 1H-trans, cis), 8.46 (d, 0.22H-trans), 8.32 (d, 0.78H-cis), 7.80 (t, J=8.4 Hz, 0.78H-cis), 7.71 (m, 1H), 7.59 (m, 0.22H-trans), 7.20-7.00 (m, 2H), 6.85 (t, 0.78H-cis), 6.69 (t, 0.22H-trans), 4.36 (q, J=7.2 Hz, 2H), 3.50 (m, J=11.0 Hz for cis, 2H-trans, cis), 1.36 (t, J=7.2 Hz, 3H). $^{31}P$ NMR ($D_2O$): δ=16.32-trans, 16.11-cis. $^{19}F$ NMR ($D_2O$): δ=−116.31 (cis). LC-MS (ESI) for $C_{17}H_{18}FNO_{10}P_2$ m/z 476 [M-H]$^-$. Elemental analysis (%) calculated for $C_{17}H_{16}CaFNO_{10}P_2 \cdot 2H_2O \cdot CaCl_2$ (%): C, 30.83; H, 3.04; N, 2.11. Found (%): C, 30.74; H, 3.42; N, 2.77.

Example 58

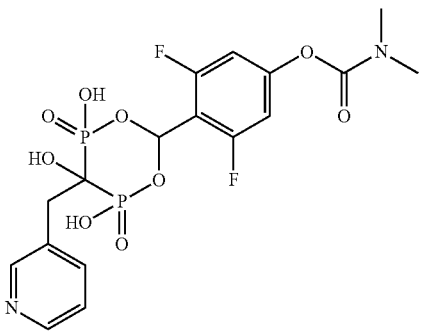 [SMILES: CN(C)C(=O)Oc1cc(F)c(C2OP(=O)(O)C(O)(Cc3cccnc3)P(=O)(O)O2)c(F)c1]

Example 58 was synthesized following the general synthetic procedures of Example 26 starting from 3,5-difluoro-4-formylphenyl dimethylcarbamate.

Yield: 200 mg, (3%). $^1H$ NMR ($D_2O$): δ=2.94 (3H, s), 3.05 (3H, s), 3.37-3.48 (2H, m), 6.80-6.88 (3H, m), 7.47-7.54 (1H, m), 8.05-8.26 (1H, m), 8.42-8.71 (1H, m). $^{31}P$ NMR ($D_2O$): δ=16.59. Elemental analysis. Found C, 34.70%; H, 3.45%; N, 4.7%, calculated for $C_{17}H_{16}F_2N_2Na_2O_9P_2(H_2O)_{2.7}$ C, 34.79%; H, 3.68%; N, 4.77%. LC-MS: (M−1) m/z 493 calculated for $C_{17}H_{18}F_2N_2O_9P_2$ 494.29.

Example 59

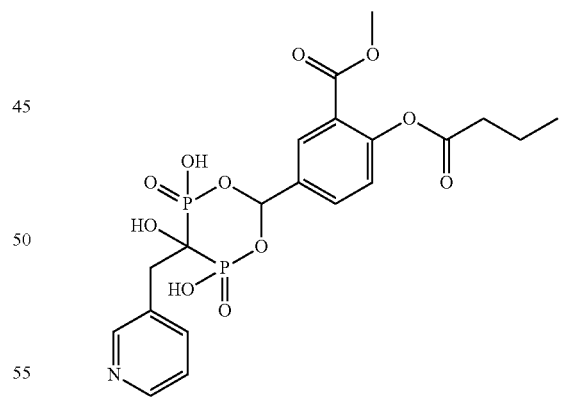

Example 59 was synthesized following the general synthetic procedures of Example 26 starting from methyl 2-(butyryloxy)-5-formylbenzoate.

trans-Isomer, yield: 0.68 g (11.5%). Elemental analysis (%) calculated for $C_{18}H_{19}NNa_2O_{10}P_2 \cdot 0.09NaCl \cdot 1.5H_2O$ (591.62): C, 40.60; H, 4.09; N, 2.37. Found C, 40.54; H, 4.07; N, 2.32. ESI MS ($CH_3CN$): m/z 514 (100), 515 (25) calculated m/z 515.35. $^1H$ NMR ($D_2O$, 300 MHz): δ=0.98 (t, 3H, J=7.5 Hz), 1.69 (d, 2H, J=8.1 Hz), 2.63 (d, 2H, J=8.0 Hz), 3.45 (t, 2H, J=16.5 Hz), 3.88 (s, 3H), 6.41 (t, 1H, J=4.5 Hz), 7.18 (m, 1H), 7.40 (m, 1H), 7.47 (m, 1H), 7.73 (m, 1H), 8.18 (m, 1H), 8.33 (m, 1H), 8.69 (s, 1H). $^{31}$P NMR (D$_2$O, 121.5 MHz): δ=16.42.

Example 60

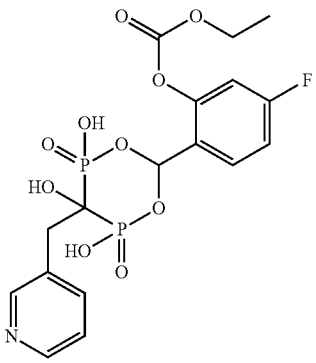 [SMILES: CCOC(=O)Oc1cc(F)ccc1C1OP(=O)(O)C(O)(Cc2cccnc2)P(=O)(O)O1]

Example 60 was synthesized following the general synthetic procedures of Example 26 starting from ethyl 5-fluoro-2-formylphenyl carbonate.

trans-Isomer, yield: 0.231 g (6%), contaminated with Risedronate (9%). $^1$H NMR (D$_2$O): δ=8.72 (s, 1H), 8.40 (d, J=4.5 Hz, 1H), 8.16 (d, J=8.1 Hz, 1H), 7.44 (dd, J=4.5, 8.1 Hz, 1H), 7.30-7.20 (m, 1H), 7.18-7.05 (m, 2H), 6.58 (t, J=4.7 Hz, 1H), 4.39 (q, J=7.2 Hz, 2H), 3.40 (t, J=16.5 Hz, 2H), 1.37 (t, J=7.2 Hz, 3H). $^{31}$P NMR (D$_2$O): δ=16.19. $^{19}$F NMR (D$_2$O): δ=−110.025. LC-MS (ESI) for C$_{17}$H$_{18}$FNO$_{10}$P$_2$ m/z 476 [M-H]$^-$. Elemental analysis (%) calculated for 0.91C$_{17}$H$_{16}$FNNa$_2$O$_{10}$P$_2$.0.09C$_7$H$_7$NNa$_4$O$_7$P$_2$.3H$_2$O (%): C, 34.42; H, 3.80; N, 2.49. Found (%): C, 34.82; H, 3.50; N, 2.46 cis-Isomer: yield 0.438 g (12%). $^1$H NMR (D$_2$O): δ=8.62 (s, 1H), 8.47 (s, 1H), 8.10 (d, J=7.8 Hz, 1H), 7.83 (t, J=7.8 Hz, 1H), 7.53 (m, 1H), 7.30-7.09 (m, 2H), 6.72 (t, J=5.1 Hz, 1H), 4.40 (q, J=6.9 Hz, 2H), 3.43 (t, J=12.3 Hz, 2H), 1.40 (t, J=6.9 Hz, 3H). $^{31}$P NMR (D$_2$O): δ 16.16. $^{19}$F NMR (D$_2$O): δ −110.124. LC-MS (ESI) for C$_{17}$H$_{18}$FNO$_{10}$P$_2$ m/z 476 [M-H]$^-$. Elemental analysis (%) calculated for C$_{17}$H$_{16}$FNNa$_2$O$_{10}$P$_2$.3NaCl (%): C, 29.31; H, 2.31; N, 2.01. Found (%): C, 28.94; H, 2.67; N, 2.47.

Example 61

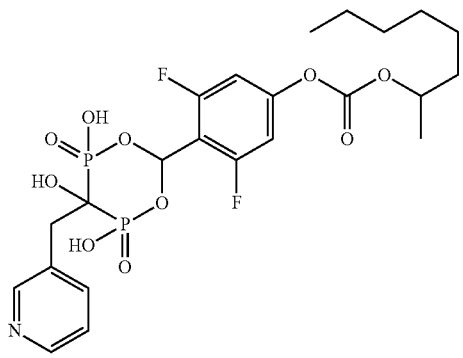 [SMILES: CCCCCCC(C)OC(=O)Oc1cc(F)c(C2OP(=O)(O)C(O)(Cc3cccnc3)P(=O)(O)O2)c(F)c1]

Example 61 was synthesized following the general synthetic procedures of Example 26 starting from 3,5-difluoro-4-formylphenyl octan-2-yl carbonate (Example 13).

Yield: 394 mg (13%). Elemental analysis (%) calculated for C$_{23}$H$_{27}$F$_2$N$_1$Na$_2$O$_{10}$P$_2$.0.3NaCl.0.6H$_2$O (651.76): C, 42.39; H, 4.36; N, 2.15. Found: C, 42.27; H, 4.32; N, 2.32; ESI MS (H$_2$O): m/z: 578 (M$^+$−1). $^1$H NMR (D$_2$O, 300 MHz): δ=8.56-6.73 (m, 7H), 4.82 (m, 1H), 3.45-3.29 (m, 2H), 1.66-0.60 (m, 16H). $^{31}$P NMR (D$_2$O, 121.5 MHz): δ=16.6, 16.5. $^{19}$F NMR (CDCl$_3$, 282.3 MHz): δ=−112.5.

Example 62

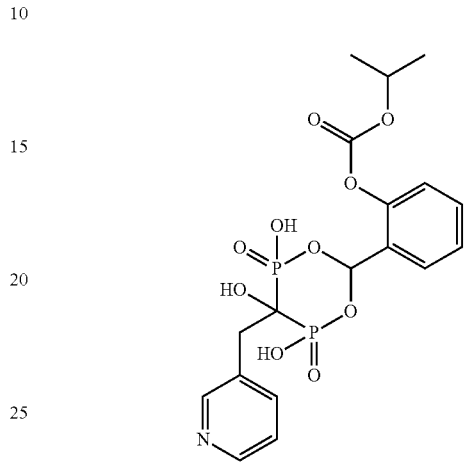

Example 62 was synthesized following the general synthetic procedures of Example 26 starting from 2-formylphenyl isopropyl carbonate.

cis-Isomer, yield: 0.46 g (7.4%). Elemental analysis (%) calculated for C$_{18}$H$_{19}$NNa$_2$O$_{10}$P$_2$.0.9NaCl.2.9H$_2$O.0.2CH$_3$CN. (630.36): C, 35.06; H, 4.06; N, 2.67. Found C, 34.81; H, 3.95; N, 2.83. ESI MS (CH$_3$CN): m/z 472 (100), 473 (25) calculated m/z 473.32. $^1$H NMR (D$_2$O, 300 MHz): δ=1.33 (d, 3H, J=6.3 Hz), 3.36 (t, 2H, J=12.3 Hz), 4.95 (sept, 1H, J=6.0 Hz), 6.67 (t, 1H, J=4.5 Hz), 7.21 (d, 1H, J=8.4 Hz), 7.39 (m, 1H), 7.47 (m, 2H, J=7.8 Hz), 7.74 (d, 1H, J=7.8 Hz), 8.05 (m, 1H, J=8.1 Hz), 8.40 (m, 1H), 8.54 (s, 1H). $^{31}$P NMR (D$_2$O, 121.5 MHz): δ=16.08.

trans-Isomer, yield: 0.46 g (8.1%). Elemental analysis (%) calculated for C$_{18}$H$_{19}$NNa$_2$O$_{10}$P$_2$.0.7NaCl.2.5H$_2$O (564.38): C, 38.29; H, 4.21; N, 2.48. Found C, 38.03; H, 4.16; N, 2.49. ESI MS (CH$_3$CN): m/z 472 (100), 473 (25) calculated m/z 473.32. $^1$H NMR (D$_2$O, 300 MHz): δ=1.32 (d, 3H, J=6.3 Hz), 3.36 (t, 2H, J=16.6 Hz), 4.96 (sept, 1H, J=5.5 Hz), 6.55 (t, 1H, J=5.1 Hz), 7.18 (m, 2H), 7.31 (m, 1H), 7.43 (m, 2H), 8.16 (m, 1H, J=7.2 Hz), 8.36 (d, 1H, J=5.4 Hz), 8.67 (s, 1H). $^{31}$P NMR (D$_2$O, 121.5 MHz): δ=16.22.

Example 62a (trans)(monosodium salt)

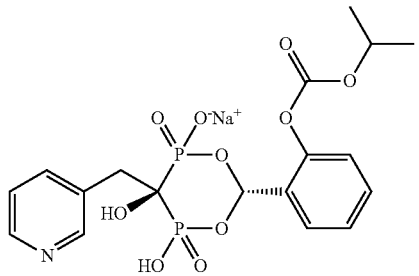

Example 62a (PG 990) was produced as follows to obtain the monosodium salt of Example 62 (trans):

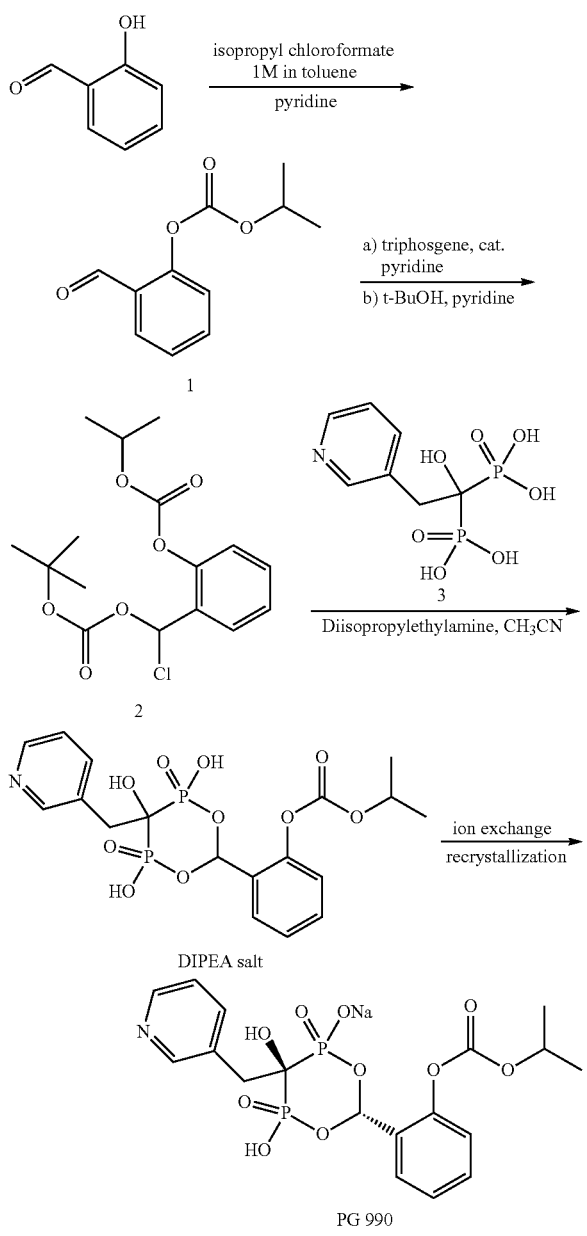

i) Isopropoxycarbonylsalicylaldehyde

A solution of salicylaldehyde (444 g, 3.64 mol) in acetonitrile (3.6 L) was treated with potassium carbonate (powder, 753 g, 5.45 mol) and isopropyl chloroformate (1 M in toluene, 4 L, 4 mol) was added over 1 hour. The temperature of the mixture rose to 28° C. during the addition. The resulting suspension was mechanically stirred for 3-4 days. The mixture was filtered and the filtrate was concentrated on a rotary evaporator (rotovap). The residue was taken up in 1.6 L total volume of 1:1 ethyl acetate:heptane, washed with 2×250 mL of half-saturated ice-brine followed by brine, dried over magnesium sulfate, filtered and concentrated on the rotovap finishing at 60° C./~5 mm Hg to give 763.9 grams (~100% yield) of 1, GC purity 98.5%.

ii) BOC-Chlorobenzyl Intermediate

Triphosgene (359.6 g, 1.212 mol) was dissolved in 2 L of toluene under nitrogen and the solution was added over about 1 hour to a mixture of pyridine (30 mL, 0.369 mol) in 2 L of toluene in a 12 L 4-neck flask equipped with mechanical stirrer, addition funnel with nitrogen inlet, and thermocouple probe, with ice-bath cooling, keeping the temperature below 9° C. Compound 1 (designated as #1 in the schematic diagram directly above) (763.9 g, about 3.635 mol) was then added over about 3 minutes with a 100 mL toluene rinse, while the temperature remained between 6.3-6.9° C. The mixture was then warmed to room temperature over a period of 30 minutes, warmed to 40° C. for 1 hour, and chilled in an ice bath. Tert-butanol (277.6 g, 3.745 mol) in toluene (300 mL) was added over about 10 minutes whilst maintaining a temperature below 10° C. Pyridine (273 mL, 3.354 mol) was then added slowly over 35 minutes, maintaining the temperature between 14-15° C. The mixture was then warmed to room temperature and stirred for 2 hours, then filtered. The filter cake was washed with 500 mL toluene, and the filtrate was concentrated on the rotary evaporator to give the intermediate compound 2 (designated as #2 in the schematic diagram directly above) (1.201 kg, 96% yield, NMR purity ~90-95%).

iii) Drying of Risedronic Acid

Risedronic acid (designated as #3 in the schematic diagram directly above) (923.6 g) was suspended in 1.5 L of mesitylene in a 3 L 3-neck flask equipped with a mechanical stirrer and Dean-Stark trap, and was heated at reflux until was removed from the distillate and about 60 mL of water had been collected. This process took about 1.5 hours. The mixture was cooled and filtered, and the filter cake was washed with heptane and pulled dry under a filter dam. The precipitate was transferred to a 3 L flask and further dried on the rotary evaporator at maximum vacuum (ca 1-5 mm Hg) and 100° C. until no additional solvent distilled. 862.6 grams of dried risedronic acid were obtained.

Dried risedronic acid (500 g, 1.766 mol) and diisopropylethylamine (913 g, 7.06 mol) were suspended in acetonitrile (5 L) in a 12 L, 3-necked flask, and the mixture was heated at 70° C. for 2 hours until the solution became clear. The mixture was cooled to room temperature, treated with the intermediate, compound 2 (1.201 kg, ~3.24 mol), and the mixture heated at 35° C. for 38 hours. The reaction mixture was concentrated to give 2.11 kg of a thick oil. This crude reaction mixture was diluted with 1 L of acetonitrile and was applied to a silica gel column (Sorbent Technologies 60 Å, 40-75 cat. no. 52500-20, 6.1 kg, ca. 19×47 cm) packed in acetonitrile, and eluted successively with 20 L acetonitrile, 20 L 10% methanol/acetonitrile, 4 L 30% methanol/acetonitrile, 8 L 35% methanol/acetonitrile, and 28 L 37.5% methanol/acetonitrile.

Approximately 1 gallon fractions were collected and analyzed by MS and NMR. Product began eluting in fraction 15, and fraction 22 was mostly impurities. Fractions 15-21 were combined and evaporated to give 305.6 grams of a thick oil. This oil was dissolved with agitation in 300 mL of distilled water and applied to an Amberlite IR120(plus) sodium form column (2.1 kg, 2.4 L bed volume in an 11 cm diameter column). The product was eluted with distilled water, collecting the main band of product in 1.1 L of water and tailing fractions in 400 mL of water. The fractions were kept cold with an ice bath. The fractions were divided into 6×1200 mL lyophilization flasks, frozen, and lyophilized for 3 days. The main band fractions weighed 194.23 g, and the tailing fractions weighed 3.65 g. The combined fractions were treated with methanol and water (30 mL) (total volume was about 1.1 L). A white precipitate began to form before the crude product had entirely dissolved. The mixture was stirred mechanically at room temperature until all of the gummy material had converted to free-flowing solids, then was stirred an additional hour, then chilled in an ice bath with stirring for 2 hours. The solids were collected by filtration and washed with about 200 mL of cold methanol followed by about 200 mL of ether. It was then air-dried in the funnel and allowed to reach room temperature. It was transferred to a tared bottle and further dried for two days on a lyophilizer to give 59.11 g of PG 990 (Example 62a (trans)) as a white powder. NMR analysis indicated that this product was a mixture of about 85:15 trans-:cis-isomers ($^{31}$P) and contained about 0.4 mol of methanol.

iv) Purification 47.9 grams of this white powder was recrystallized by dissolving it in 720 mL of water, filtering it through a glass microfiber filter, and subsequent dilution to 2.3 L with acetone. The resulting suspension was stirred at room temperature for 1 hour, then cooled in an ice bath for 2 hours, and the product collected by filtration and washed with 200 mL of acetone. The solids were dried in the filter under suction overnight to give 38.13 grams (79.6% recovery) of product at >about 98% purity with <0.5% risedronate, <0.5% of the cis-compound, and about 1.1 mol % acetone by NMR.

Specifically, the trans isomer of Example 62 was synthesized according to the following procedures.

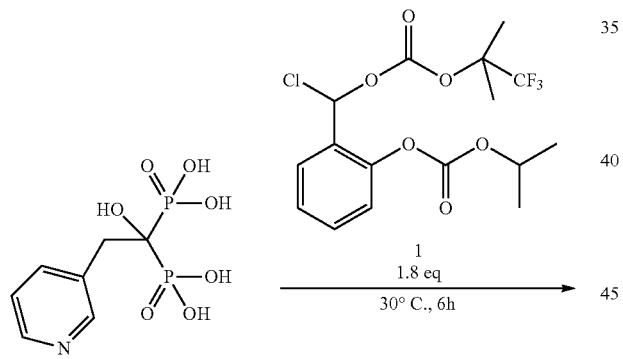

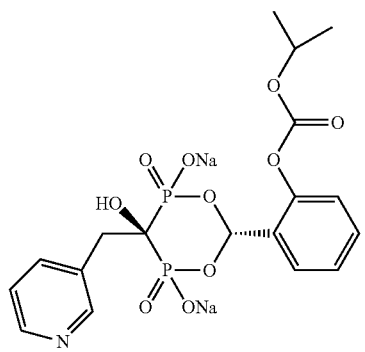

To a 300 mL dry round bottom flask was added risedronate (12.2 g, 43.2 mmol), anhydrous acetonitrile (75 mL) and diisopropylethylamine (30 mL, 172.8 mmol). After stirring at 45° C. under $N_2$ for 1 hour, this mixture became clear, and then was stirred in an ice-water bath and cooled to 5° C. A solution of chlorocarbonate (designated as #1 in the schematic diagram directly above) (31.0 g, 77.7 mmol) in 35 mL of anhydrous acetonitrile was injected into the cooled mixture. The cold bath was removed and the resulting mixture was stirred at 30° C. under $N_2$ atmosphere for 6 hours. This reaction mixture was poured into a 250 g of silica gel chromatography (10.5 cm height). The column was eluted with 1.5 L of acetonitrile, then 1.5 L of 50% methanol/acetonitrile. The second fraction (50% methanol/acetonitrile) was concentrated to give 28.96 g of brown gummy oil. This DIPEA salt then was passed through a 200 g of Amberlite Na$^+$ ion-exchange column.

The resultant mixture was then lyophilized and produced 18.15 g of orange solid. To this solid, methanol (60 mL) was added and the resulting mixture was first stirred at room temperature for 2 hours, then further cooled in the ice-water bath for 2 hours. The resulting solid was collected by filtration and washed with cold methanol (5 mL×2), then acetonitrile (10 mL).

After further drying in the lyophilizer, 3.35 g of product (Example 62 (trans)) was obtained as a white powder, pure trans-isomer, by $^{31}$P NMR. Yield: 15%.

Example 63

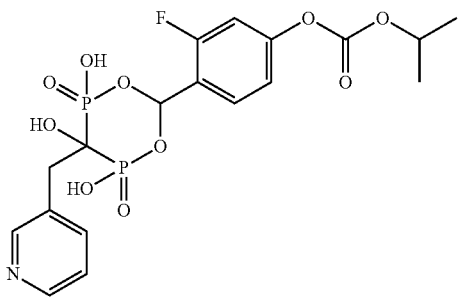 [SMILES: CC(C)OC(=O)Oc1ccc(C2OP(=O)(O)C(O)(Cc3cccnc3)P(=O)(O)O2)c(F)c1]

Example 63 was synthesized following the general synthetic procedures of Example 26 starting from 3-fluoro-4-formylphenyl isopropyl carbonate.

trans-Isomer: yield 0.259 g (7%). $^1$H NMR (D$_2$O): δ=8.76 (s, 1H), 8.41 (d, J=4.8 Hz, 1H), 8.15 (d, J=7.8 Hz, 1H), 7.41 (dd, J=4.8, 7.8 Hz, 1H), 7.20-7.04 (m, 3H), 6.70 (t, J=4.5 Hz, 1H), 5.03 (m, J=6.0 Hz, 1H), 3.41 (t, J=17.1 Hz, 2H), 1.40 (d, J=6.0 Hz, 6H). $^{31}$P NMR (D$_2$O): δ=16.54. $^{19}$F NMR (D$_2$O): δ -117.032. LC-MS (ESI) for C$_{18}$H$_{20}$FNO$_{10}$P$_2$ m/z 490 [M-H]$^-$. Calc. for C$_{18}$H$_{18}$FNNa$_2$O$_{10}$P$_2$·2H$_2$O (%): C, 37.84; H, 3.88; N, 2.45. Found (%): C, 37.83; H, 4.19; N, 2.19.

cis-Isomer: yield 0.4 g (10.5%), contaminated with Risedronate (5%). $^1$H NMR (D$_2$O): δ=8.57 (s, 1H), 8.43 (d, J=5.1 Hz, 1H), 7.98 (d, J=7.2 Hz, 1H), 7.82 (t, J=8.1 Hz, 1H), 7.43 (m, 1H), 7.22-7.10 (m, 2H), 6.83 (t, J=5.1 Hz, 1H), 5.00 (m, J=6.3 Hz, 1H), 3.41 (t, J=12.3 Hz, 2H), 1.37 (d, J=6.3 Hz, 6H). $^{31}$P NMR (D$_2$O): δ=16.78. $^{19}$F NMR (D$_2$O): δ=-116.361. LC-MS (ESI) for C$_{18}$H$_{20}$FNO$_{10}$P$_2$ m/z 490 [M-H]$^-$ Calc. for 0.95C$_{18}$H$_{18}$FNNa$_2$O$_{10}$P$_2$· 0.05C$_7$H$_7$NNa$_4$O$_7$P$_2$·0.6H$_2$O·2NaCl (%): C, 32.23; H, 2.92; N, 2.15. Found (%): C, 32.60; H, 3.34; N, 2.29.

Example 64

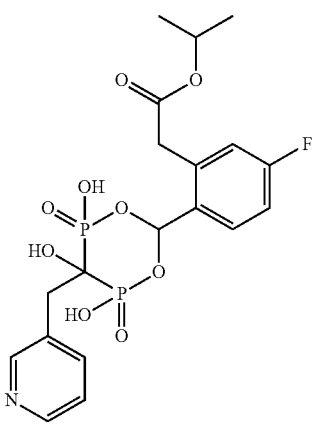 [SMILES: CC(C)OC(=O)Cc1cc(F)ccc1C1OP(=O)(O)C(O)(Cc2cccnc2)P(=O)(O)O1]

Example 64 was synthesized following the general synthetic procedures of Example 26 starting from 5-fluoro-2-formylphenyl isopropyl carbonate.

trans-Isomer: yield 0.774 g (20.5%). $^1$H NMR (D$_2$O): δ=8.71 (s, 1H), 8.40 (d, J=4.5 Hz, 1H), 8.14 (d, J=8.4 Hz, 1H), 7.42 (dd, J=4.5, 8.4 Hz, 1H), 7.23 (m, 1H), 7.11 (m, 2H), 6.58 (t, J=4.5 Hz, 1H), 5.03 (m, 1H), 3.40 (t, J=16.2 Hz, 2H), 1.39 (d, J=6.3 Hz, 6H). $^{31}$P NMR (D$_2$O): δ=16.15. $^{19}$F NMR (D$_2$O): δ −110.102. LC-MS (ESI) for C$_{18}$H$_{20}$FNO$_{10}$P$_2$ m/z 490 [M-H]$^-$. Elemental analysis (%) calculated for C$_{18}$H$_{18}$FNNa$_2$O$_{10}$P$_2$.1.8H$_2$O (%): C, 38.08; H, 3.83; N, 2.47. Found (%): C, 38.32; H, 3.98; N, 2.30.

cis-Isomer: yield 0.25 g (6.5%), contaminated with Risedronate (5%) and 5-member ring product (10%). $^1$H NMR (D$_2$O): δ=8.59 (s, 1H), 8.45 (d, J=3.9 Hz, 1H), 8.04 (d, J=8.1 Hz, 1H), 7.83 (dd, J=3.9, 8.1 Hz, 1H), 7.48 (m, 1H), 7.26-7.08 (m, 2H), 6.72 (t, J=5.0 Hz, 1H), 5.03 (m, J=6.3 Hz, 1H), 3.41 (t, J=12.5 Hz, 2H), 1.41 (t, J=6.3 Hz, 6H). $^{31}$P NMR (D$_2$O): δ=16.15. $^{19}$F NMR (D$_2$O): δ=−110.189. LC-MS (ESI) for C$_{18}$H$_{20}$FNO$_{10}$P$_2$ m/z 490 [M-H]$^-$. Elemental analysis (%) calculated for 0.85C$_{18}$H$_{18}$FNNa$_2$O$_{10}$P$_2$.0.1C$_{18}$H$_{17}$FNNa$_3$O$_{10}$P$_2$.0.05C$_7$H$_7$NNa$_4$O$_7$P$_2$—H$_2$O.NaCl (%): C, 34.60; H, 3.22; N, 2.31. Found (%): C, 34.34; H, 3.41; N, 2.52.

Example 65

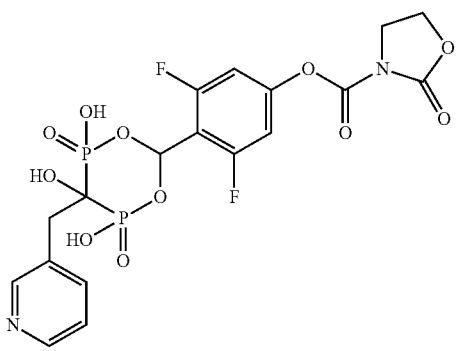 [SMILES: O=C1OCCN1C(=O)Oc1cc(F)c(C2OP(=O)(O)C(O)(Cc3cccnc3)P(=O)(O)O2)c(F)c1]

Example 65 was synthesized following the general synthetic procedures of Example 26 starting from 3,5-difluoro-4-formylphenyl 2-oxooxazolidine-3-carboxylate (Example 3).

Yield: 545 mg (19%). Elemental analysis (%) calculated for C$_{18}$H$_{16}$F$_2$N$_2$Na$_2$O$_{11}$P$_2$.0.3NaCl.1.3H$_2$O (621.22): C, 34.80; H, 2.69; N, 4.51. Found: C, 34.88; H, 2.71; N, 4.41; ESI MS (H$_2$O) m/z 535 (M$^+$-1). $^1$H NMR (D$_2$O, 300 MHz): δ=8.55-6.87 (m, 7H), 4.51 (t, J=7.2 Hz, 2H), 4.20 (t, J=7.2 Hz, 2H), 3.36 (t, J=12.3 Hz, 2H). $^{31}$P NMR (D$_2$O, 121.5 MHz): δ=16.6. $^{19}$F NMR (CDCl$_3$, 282.3 MHz): δ=−112.0 (d, J=9.0 Hz).

Example 66

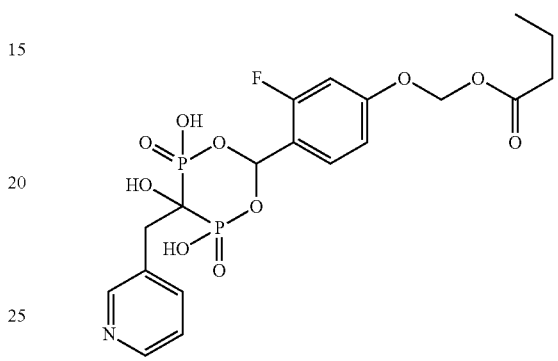

Example 66 was synthesized following the general synthetic procedures of Example 26 starting from (3-fluoro-4-formylphenoxy)methyl butyrate (Example 14).

Yield: 195 mg (7%); elemental analysis (%) calculated for C$_{19}$H$_{20}$F$_1$N$_1$Na$_2$O$_{10}$P$_2$.1.0NaCl.0.8H$_2$O (622.18): C, 36.68; H, 3.50; N, 2.25. Found: C, 36.77; H, 3.49; N, 2.28; ESI MS (H$_2$O): m/z: 504 (M$^+$-1). $^1$H NMR (D$_2$O, 300 MHz): δ=8.70-6.61 (m, 8H), 5.80-5.77 (m, 2H), 3.40-3.25 (m, 2H), 2.37 (t, J=7.5 Hz, 2H), 1.56 (sextet, J=7.5 Hz, 2H), 0.82 (t, J=7.5 Hz, 3H). $^{31}$P NMR (D$_2$O, 121.5 MHz): δ=16.8, 16.6. $^{19}$F NMR (CDCl$_3$, 282.3 MHz): δ=−116.9.

Example 67

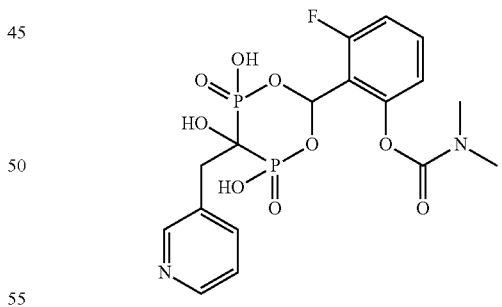

Example 67 was synthesized following the general synthetic procedures of Example 26 starting from 3-fluoro-2-formylphenyl dimethylcarbamate.

Yield: 0.12 g (2%). Elemental analysis (%) calculated for C$_{17}$H$_{17}$FN$_2$Na$_2$O$_9$P$_2$.0.7NaCl.2.5H$_2$O (606.23): C, 33.68; H, 3.66; N, 4.62. Found C; 33.43; H, 3.41; N, 4.39. ESI MS (CH$_3$CN): m/z 475 (100), 476 (20) calculated m/z 476.29. $^1$H NMR (D$_2$O, 300 MHz): δ=2.94 (d, 3H, J=12.3 Hz), 3.12 (d, 3H, J=10.8 Hz), 3.36 (m, 2H), 6.80 (t, 1H, J=5.1 Hz), 6.85 (t, 1H, J=6.0 Hz), 6.91 (m, 1H), 7.14 (m, 1H), 7.33 (m, 1H), 7.47 (m, 2H), 8.05 (m, 1H), 8.18 (m, 1H), 8.42 (m, 1H), 8.55 (s, 1H), 8.61 (s, 1H). $^{31}$P NMR (D$_2$O, 121.5 MHz): δ=16.50 (trans); 16.74 (cis). $^{19}$F NMR (D$_2$O, 282 MHz): δ=−116.65, −115.81.

Example 68

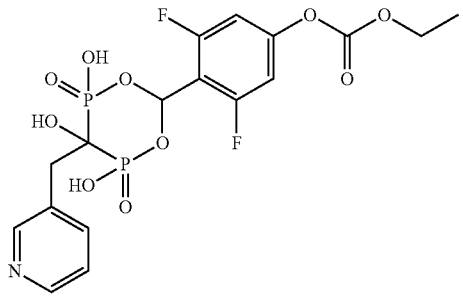 [SMILES: CCOC(=O)Oc1cc(F)c(C2OP(=O)(O)C(O)(Cc3cccnc3)P(=O)(O)O2)c(F)c1]

Example 68 was synthesized following the general synthetic procedures of Example 26 starting from 3,5-difluoro-4-formylphenyl ethyl carbonate.

cis-Isomer: yield 0.265 g, white solid, contaminated with Risedronate (3.5%) and 5-member ring product (11%). $^1$H NMR (D$_2$O): δ=8.68 (s, 1H), 8.54 (d, J=5.1 Hz, 1H), 8.29 (d, J=6.6 Hz, 1H), 7.69 (t, 1H), 7.03 (d, J=9.9 Hz, 2H), 6.92 (t, J=5.5 Hz, 1H), 4.37 (q, J=7.2 Hz, 2H), 3.48 (t, J=12.3 Hz, 2H), 1.36 (t, J=7.2 Hz, 3H). $^{31}$P NMR (D$_2$O): δ=16.36. $^{19}$F NMR (D$_2$O): δ=−112.291 (d, J$_{FF}$=9.3 Hz). LC-MS (ESI) for C$_{17}$H$_{17}$F$_2$NO$_{10}$P$_2$ m/z 494 [M−H]$^−$.

Elemental analysis (%) calculated for 0.855C$_{17}$H$_{15}$F$_2$NNa$_2$O$_{10}$P$_2$.0.11C$_{17}$H$_{14}$F$_2$NNa$_3$O$_{10}$P$_2$. 0.035C$_7$H$_7$NNa$_4$O$_7$P$_2$—H$_2$O.Na Cl (%): C, 32.66; H, 2.73; N, 2.29. Found (%): C, 33.00; H, 3.08; N, 2.38.

Example 69

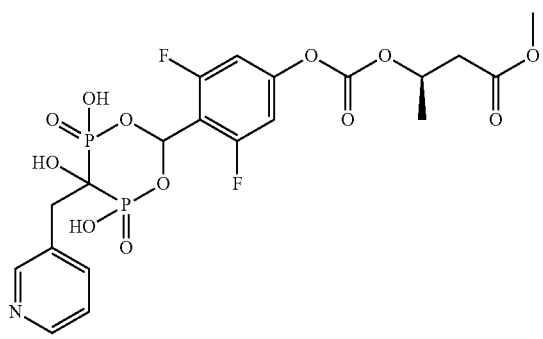 [SMILES: COC(=O)C[C@@H](C)OC(=O)Oc1cc(F)c(C2OP(=O)(O)C(O)(Cc3cccnc3)P(=O)(O)O2)c(F)c1]

Example 69 was synthesized following the general synthetic procedures of Example 26 starting from (R)-methyl 3-((3,5-difluoro-4-formylphenoxy)carbonyloxy)butanoate.

cis-Isomer, yield: 0.35 g (4.7%). Elemental analysis (%) calculated for C$_{20}$H$_{19}$F$_2$NNa$_2$O$_{12}$P$_2$.1.3NaCl.3.0H$_2$O (741.35): C, 32.40; H, 3.40; N, 1.89. Found C, 32.15; H, 3.14; N, 2.15. ESI MS (CH$_3$CN): m/z 566 (100), 568 (35) calculated m/z 567.33. $^1$H NMR (D$_2$O, 300 MHz): δ=1.37 (d, 3H, J=6.3 Hz), 2.76 (d, 2H, J=6.3 Hz), 3.40 (t, 2H, J=12.1 Hz), 3.67 (s, 3H), 5.22 (sext, 1H, J=6.6 Hz), 6.18 (d, 1H, J=13.2 Hz), 6.84 (t, 1H, J=4.5 Hz), 6.95 (1H, d, J=8.7 Hz), 7.61 (m, 1H), 8.19 (d, 1H, J=7.8 Hz), 8.47 (m, 1H), 8.61 (s, 1H). $^{31}$P NMR (D$_2$O, 121.5 MHz): δ=16.35. $^{19}$F NMR (D$_2$O, 282 MHz): δ=−112.13, −115.61.

Example 70

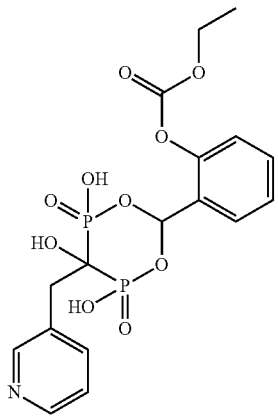 [SMILES: CCOC(=O)Oc1ccccc1C1OP(=O)(O)C(O)(Cc2cccnc2)P(=O)(O)O1]

Example 70 was synthesized following the general synthetic procedures of Example 26 starting from ethyl 2-formylphenyl carbonate.

Yield: 0.16 g (3.0%). Elemental analysis (%) calculated for C$_{17}$H$_{17}$NNa$_2$O$_{10}$P$_2$.0.1NaCl.2.2H$_2$O (548.75): C, 37.21; H, 3.93; N, 2.55. Found C, 36.98; H, 3.81; N, 2.47. ESI MS (CH$_3$CN): m/z 458 (100), 459 (20) calculated m/z 459.29. $^1$H NMR (D$_2$O, 300 MHz): δ=1.30 (t, 3H, J=7.2 Hz), 3.35 (t, 2H, J=16.2 Hz), 4.31 (q, 4H, J=7.1 Hz), 6.54 (t, 1H, J=4.8 Hz), 7.18 (d, 1H, J=8.4 Hz), 7.31 (m, 2H), 7.43 (m, 2H), 8.11 (d, 1H, J=7.8 Hz), 8.34 (d, 1H, J=8.34 Hz), 8.65 (s, 1H). $^{31}$P NMR (D$_2$O, 121.5 MHz): δ=16.25.

Example 71

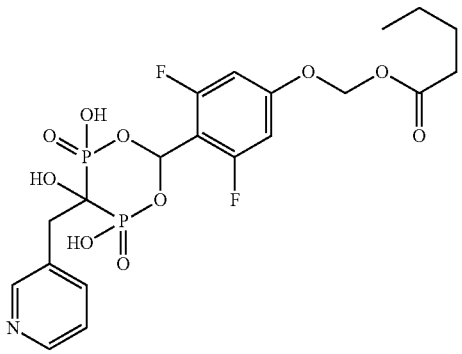 [SMILES: CCCCC(=O)OCOc1cc(F)c(C2OP(=O)(O)C(O)(Cc3cccnc3)P(=O)(O)O2)c(F)c1]

Example 71 was synthesized following the general synthetic procedures of Example 26 starting from (3,5-difluoro-4-formylphenoxy)methyl pentanoate.

Yield 400 mg (10%) for cis- and trans-isomers. $^1$H NMR (D$_2$O, 300 MHz): δ=8.64-8.52 (m, 2H), 8.11-7.93 (m, 1H), 7.41 (m, 1H), 6.82-6.70 (m, 3H), 4.75 (s, 2H), 3.43-3.3.0 (m, 2H), 2.36 (t, 2H), 1.59-1.51 (m, 2H), 0.81 (t, 3H). $^{31}$P NMR (D$_2$O, 121.5 MHz): δ=16.748, 16.688. MS (M−1) m/z: 522. Elemental analysis (%) calculated for $C_{19}H_{21}NO_{10}P_2Na_2.2H_2O.NaCl$ (567): C, 34.38; H, 3.80; N, 2.11. Found: C, 34.57; H, 3.54; N, 2.17.

Example 72

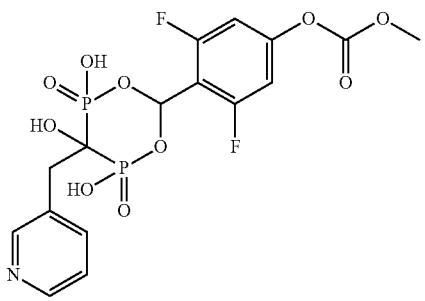 [SMILES: COC(=O)Oc1cc(F)c(C2OP(=O)(O)C(O)(Cc3cccnc3)P(=O)(O)O2)c(F)c1]

Example 72 was synthesized following the general synthetic procedures of Example 26 starting from 3,5-difluoro-4-formylphenyl methyl carbonate.

Yield: 0.23 g (4.3%). Elemental analysis (%) calculated for $C_{16}H_{15}F_2NNa_2O_{10}P_2.0.2NaCl.0.97H_2O$ (554.39): C, 34.66; H, 2.72; N, 2.53. Found C, 34.96; H, 3.14; N, 2.17. ESI MS ($CH_3CN$): m/z 480 (100), 481 (50), 484 (40) calculated m/z 481.24. $^1H$ NMR ($D_2O$, 300 MHz): δ=3.40 (t, 2H, J=12.6 Hz), 3.86 (s, 3H), 6.17 (m, 1H), 6.49 (t, 1H, J=5.3 Hz), 6.96 (m, 1H), 7.59 (m, 1H), 8.18 (m, 1H), 8.46 (m, 1H), 8.60 (s, 1H). $^{31}P$ NMR ($D_2O$, 121.5 MHz): δ=16.43. $^{19}F$ NMR ($D_2O$, 282 MHz): δ=−112.24.

Example 73

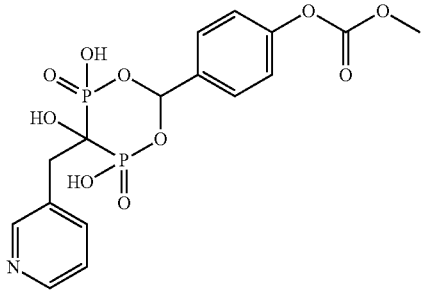 [SMILES: COC(=O)Oc1ccc(C2OP(=O)(O)C(O)(Cc3cccnc3)P(=O)(O)O2)cc1]

Example 73 was synthesized following the general synthetic procedures of Example 26 starting from 4-formylphenyl methyl carbonate.

trans-Isomer: yield 0.327 g (11%) of title compound as white solid. $^1H$ NMR ($D_2O$): δ=8.77 (s, 1H), 8.43 (d, J=5.1 Hz, 1H), 8.20 (d, J=7.2 Hz, 1H), 7.46 (dd, J=5.1, 7.2 Hz, 1H), 7.30 (d, J=8.8 Hz for AB-system, 2H), 7.25 (d, J=8.8 Hz for AB-system, 2H), 6.47 (t, J=4.7 Hz, 1H), 3.94 (s, 3H), 3.42 (t, J=17.1 Hz, 2H). $^{31}P$ NMR ($D_2O$): δ=16.53. LC-MS (ESI) for $C_{16}H_{17}NO_{10}P_2$ m/z 444 [M-H]$^-$. Calc. for $C_{16}H_{15}NNa_2O_{10}P_2.3H_2O$ (%): C, 35.37; H, 3.90; N, 2.58. Found (%): C, 35.50; H, 3.94; N, 2.54.

Example 74

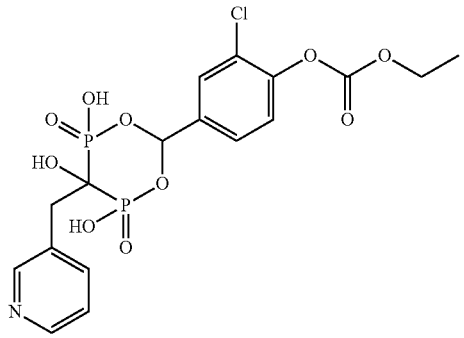

Example 74 was synthesized following the general synthetic procedures of Example 26 starting from 2-chloro-4-formylphenyl ethyl carbonate.

trans-Isomer: yield 0.156 g (5.5%) of title compound as white powder. $^1H$ NMR ($D_2O$): δ=8.79 (s, 1H), 8.47 (d, J=4.5 Hz, 1H), 8.24 (d, J=8.1 Hz, 1H), 7.49 (dd, J=5.0, 8.1 Hz, 1H), 7.39-7.23 (m, 3H), 6.43 (t, J=4.9 Hz, 1H), 4.42 (q, J=7.2 Hz, 2H), 3.43 (t, J=17.4 Hz, 21-1), 1.40 (t, J=7.2 Hz, 3H). $^{31}P$ NMR ($D_2O$): δ=16.31. LC-MS (ESI) for $C_{17}H_{18}ClNO_{10}P_2$ m/z 492 [M-2H]$^-$, 494 [M]$^-$. Elemental analysis (%) calculated for $C_{17}H_{16}ClNNa_2O_{10}P_2.2H_2O.0.5NaCl$ (%): C, 33.86; H, 3.34; N, 2.32. Found (%): C, 34.18; H, 3.14; N, 1.80.

Example 75

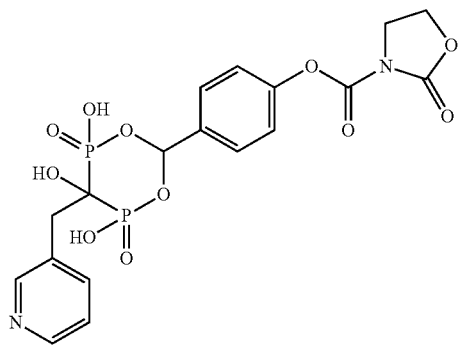 [SMILES: O=C1OCCN1C(=O)Oc1ccc(C2OP(=O)(O)C(O)(Cc3cccnc3)P(=O)(O)O2)cc1]

Example 75 was synthesized following the general synthetic procedures of Example 26 starting from 4-formylphenyl 2-oxoxazolidine-3-carboxylate.

Yield 217 mg (10%). $^1H$ NMR ($D_2O$, 300 MHz): δ=8.42 (s, 1H), 8.29 (m, 1H), 8.14 (m, 1H), 7.96-7.81 (m, 1H), 7.36 (d, 2H), 7.24 (m, 1H), 6.87 (d, 2H), 6.52 (t, 2H), 6.21-6.05 (m, 1H), 4.24 (t, 2H), 3.94 (t, 2H), 3.14-3.01 (m, 2H). $^{31}P$ NMR ($D_2O$, 121.5 MHz): δ=16.343, 16.051. MS (M−1) m/z: 499. Elemental analysis (%) calculated for $C_{18}H_{18}N_2O_{11}P_2Na_2.11\%$ risedronate.$1.2H_2O.0.2NaCl$ (563.3): C, 36.56; H, 3.68; N, 4.79. Found: C, 36.25; H, 3.30; N, 4.64.

Example 76

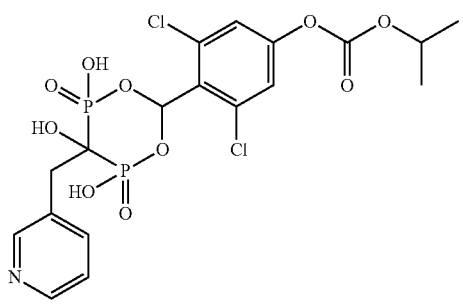

Example 76 was synthesized following the general synthetic procedures of Example 26 starting from 3,5-dichloro-4-formylphenyl isopropyl carbonate (Example 15).

cis-Isomer, yield: 258 mg (9%). Elemental analysis (%) calculated for $C_{18}H_{17}Cl_2N_1Na_2O_{10}P_2 \cdot 1.0NaCl \cdot 2.0H_2O$ (680.67): C, 31.76; H, 3.11; N, 2.06. Found: C, 31.30; H, 3.20; N, 2.52. ESI MS (H$_2$O) m/z 540 (M$^+$−1). $^1$H NMR (D$_2$O, 300 MHz): δ=8.56-7.18 (m, 7H), 4.90 (m, 1H), 3.38 (t, J=12.5 Hz, 2H), 1.30 (d, J=6.0 Hz, 6H). $^{31}$P NMR (D$_2$O, 121.5 MHz): δ=16.5.

Example 77

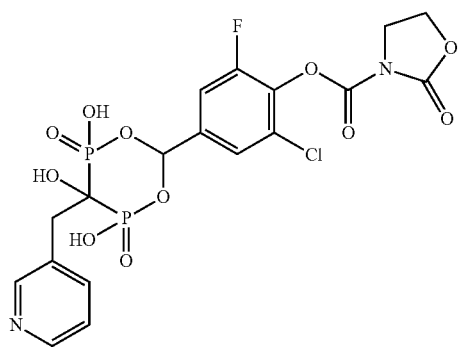 [SMILES: O=C1OCCN1C(=O)Oc1c(F)cc(C2OP(=O)(O)C(O)(Cc3cccnc3)P(=O)(O)O2)cc1Cl]

Example 77 was synthesized following the general synthetic procedures of Example 26 starting from 2-chloro-6-fluoro-4-formylphenyl 2-oxooxazolidine-3-carboxylate.

trans-Isomer, yield: 0.15 g (2%). Elemental analysis (%) calculated for $C_{18}H_{15}ClFN_2Na_2O_{11}P_2 \cdot 1.1NaCl \cdot 4.3H_2O$ (750.17): C, 28.82; H, 3.04; N, 3.73. Found: C, 29.10; H, 3.05; N, 3.12. ESI MS (CH$_3$CN): m/z 551 (100), 553 (75), 555 (30) calculated m/z 552.73. NMR (D$_2$O, 300 MHz): δ=3.30 (t, 3H, J=15.9 Hz), 4.30 (t, 2H, J=7.7 Hz), 4.55 (t, 2H, J=8.3 Hz), 6.50 (t, 1H, J=5.2 Hz), 7.41 (m, 1H), 7.62 (m, 1H), 7.68 (s, 1H), 7.94 (s, 1H), 8.34 (m, 1H), 8.45 (s, 1H). $^{31}$P NMR (D$_2$O, 121.5 MHz): δ=16.82. $^{19}$F NMR (D$_2$O, 282 MHz): δ=−125.56.

Example 78

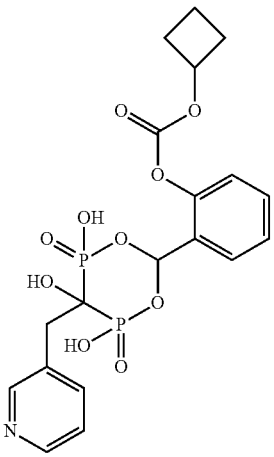 [SMILES: O=C(Oc1ccccc1C1OP(=O)(O)C(O)(Cc2cccnc2)P(=O)(O)O1)OC1CCC1]

Example 78 was synthesized following the general synthetic procedures of Example 26 starting from cyclobutyl 2-formylphenyl carbonate.

trans-Isomer: yield 0.129 g (4.6%). $^1$H NMR (D$_2$O): δ=8.82 (s, 1H), 8.54 (m, 2H), 7.77 (dd, J=5.4, 7.8 Hz, 1H), 7.53 (m, 1H), 7.38 (m, 2H), 7.26 (d, J=8.7 Hz, 1H), 6.61 (t, J=5.1 Hz, 1H), 5.06 (m, J=7.0 Hz, 1H), 3.51 (t, J=15.3 Hz, 2H), 2.45-2.20 (m, 4H), 1.84 (m, 1H), 1.65 (m, 1H). $^{31}$P NMR (D$_2$O): δ=15.80. LC-MS (ESI) for $C_{19}H_{21}NO_{10}P_2$ m/z 484 [M-H]$^-$. Elemental analysis (%) calculated for $C_{19}H_{19}NNa_2O_{10}P_2 \cdot 3H_2O$ (%): C, 39.12; H, 4.32; N, 2.40. Found (%): C, 39.39; H, 3.98; N, 2.31.

cis-Isomer: yield 0.143 g (5.1%). $^1$H NMR (D$_2$O): δ=8.75 (s, 1H), 8.66-8.44 (m, 2H), 7.82 (m, 2H), 7.64-7.24 (m, 3H), 6.75 (t, J=5.2 Hz, 1H), 5.07 (m, J=7.2 Hz, 1H), 3.53 (t, J=12.3 Hz, 2H), 2.50-2.20 (m, 4H), 1.86 (m, 1H), 1.68 (m, 1H). $^{31}$P NMR (D$_2$O): δ=15.71. LC-MS (ESI) for $C_{19}H_{21}NO_{10}P_2$ m/z 484 [M-H]$^-$. Elemental analysis (%) calculated for $C_{19}H_{19}NNa_2O_{10}P_2 \cdot 1.5H_2O \cdot 2NaCl$ (%): C, 33.90; H, 3.29; N, 2.08. Found (%): C, 34.10; H, 3.60; N, 2.28.

Example 79

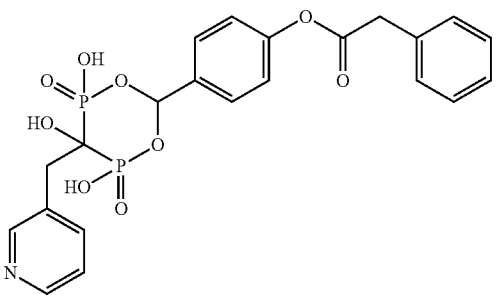 [SMILES: O=C(Cc1ccccc1)Oc1ccc(C2OP(=O)(O)C(O)(Cc3cccnc3)P(=O)(O)O2)cc1]

Example 79 was synthesized following the general synthetic procedures of Example 26 starting from 4-formylphenyl 2-phenylacetate.

trans-Isomer, yield: 0.12 g (2%). Elemental analysis (%) calculated for $C_{22}H_{19}NNa_2O_9P_2.0.2NaCl.3.3H_2O$ (620.48): C, 36.61; H, 4.24; N, 2.25. Found C, 36.54; H, 4.53; N, 2.15. ESI MS (CH$_3$CN): m/z 504 (100), 505 (50), 506 (5) calculated m/z 505.36. $^1$H NMR (D$_2$O, 300 MHz): δ=3.35 (t, 2H, J=17.2 Hz), 3.98 (s, 2H), 6.39 (t, 1H, J=6.3 Hz), 7.07 (d, 2H, J=7.5 Hz), 7.23 (d, 2H, J=8.1 Hz), 7.39 (m, 5H), 8.14 (m, 1H, J=6.3 Hz), 8.35 (m, 2H), 8.68 (s, 1H). $^{31}$P NMR (D$_2$O, 121.5 MHz): δ=16.49.

cis-Isomer, yield: 0.33 g (5.3%). Elemental analysis (%) calculated for $C_{22}H_{19}NNa_2O_9P_2.0.2NaCl.3.3H_2O$ (620.48): C, 41.07; H, 3.70; N, 2.18. Found C, 40.78; H, 3.83; N, 2.59. ESI MS (CH$_3$CN): 504 (100), 505 (50), 506 (5) calculated m/z 505.36. $^1$H NMR (D$_2$O, 300 MHz): δ=3.38 (t, 2H, J=12.3 Hz), 3.99 (s, 2H), 6.55 (t, 1H, J=4.5 Hz), 7.15 (d, 2H, J=7.5 Hz), 7.40 (m, 5H), 7.51 (m, 2H), 7.62 (d, 1H, J=8.4 Hz), 8.08 (m, 1H, J=7.5 Hz), 8.43 (m, 1H), 8.57 (s, 1H). $^{31}$P NMR (D$_2$O, 121.5 MHz): δ=16.69.

Example 80

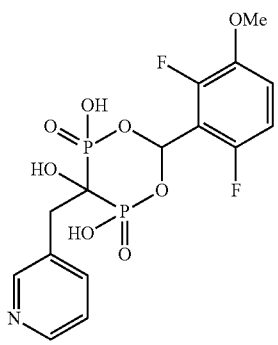 [SMILES: COc1ccc(F)c(C2OP(=O)(O)C(O)(Cc3cccnc3)P(=O)(O)O2)c1F]

Example 80 was synthesized following the general synthetic procedures of Example 26 starting from 2,6-difluoro-3-methoxybenzaldehyde.

Yield 0.135 g (4%) of title compound as white solid, mixture of cis (40%) and trans (60%) isomers. $^1$H NMR (D$_2$O): δ=8.81 (s, 0.6H-trans), 8.65 (s, 0.4H-cis), 8.54 (d, J=5.7 Hz, 0.6H-trans), 8.50 (d, J=5.7 Hz, 0.4H-cis), 8.44 (d, J=7.5 Hz, 0.6H-trans), 8.18 (d, J=7.8 Hz, 0.4H-cis), 7.69 (dd, J=5.7 Hz, J=7.5 Hz, 0.6H-trans), 7.60 (dd, J=5.7, 7.8 Hz, 0.4H-cis), 7.28-6.90 (m, 2H), 6.84 (t, J=5.1 Hz, 1H-trans,cis), 6.38 (t, 0.44H-trans), 3.90 (s, 1.2H-cis), 3.88 (s, 1.8H-trans), 3.51 (t, J=15.9 Hz, 1.2H-trans), 3.46 (t, J=12.9 Hz, 0.8H-cis). $^{31}$P NMR (D$_2$O): δ=16.48-cis, 16.44-trans. $^{19}$F NMR (D$_2$O): δ=−136.074 (J=9.3 Hz, cis), −136.560 (J=9.3 Hz, trans), −125.182 (J=7.9 Hz, cis), −125.636 (J=7.9 Hz, trans). LC-MS (ESI) for $C_{15}H_{15}F_2NO_8P_2$ m/z 436 [M-H]$^-$. Elemental analysis (%) calculated for $C_{15}H_{13}P_2NNa_2O_8P_2.3H_2O.0.5NaCl$ (%): C, 31.92; H, 3.39; N, 2.48. Found (%): C, 32.11; H, 3.48; N, 2.45.

Example 81

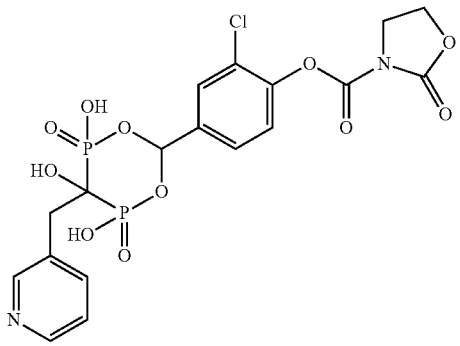

Example 81 was synthesized following the general synthetic procedures of Example 26 starting from 2-chloro-4-formylphenyl 2-oxooxazolidine-3-carboxylate.

Yield: 0.33 g (5%). Elemental analysis (%) calculated for $C_{18}H_{15}ClN_2Na_2O_{11}P_2.1.1NaCl.3.8H_2O$ (676.03): C, 31.98; H, 3.37; N, 4.14. Found: C, 31.76; H, 3.13; N, 4.11. ESI MS (CH$_3$CN): m/z 533 (100), 535 (30) calculated m/z 534.74. $^1$H NMR (D$_2$O, 300 MHz): δ=3.37 (t, 3H, J=12.7 Hz), 4.25 (t, 2H, J=7.8 Hz), 4.52 (t, 2H, J=8.4 Hz), 6.54 (t, 1H, J=5.1 Hz), 7.26 (m, 1H), 7.39 (m, 1H), 7.60 (s, 1H), 7.80 (s, 1H), 7.94 (d, 1H, J=7.8 Hz), 8.39 (m, 1H), 8.52 (s, 1H). $^{31}$P NMR (D$_2$O, 121.5 MHz): δ=16.82.

Example 82

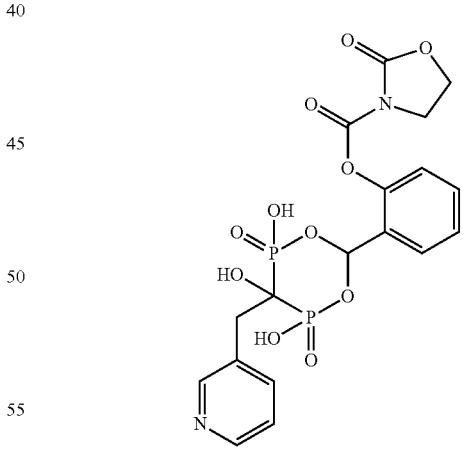

Example 82 was synthesized following the general synthetic procedures of Example 26 starting from 2-formylphenyl 2-oxooxazolidine-3-carboxylate.

Yield: 0.33 g (5.3%). Elemental analysis (%) calculated for $C_{18}H_{19}N_2Na_2O_{11}P_2.0.3NaCl.3.7H_2O$ (628.47): C, 34.40; H, 3.75; N, 4.46. Found C, 34.39; H, 4.07; N, 4.66. ESI MS (CH$_3$CN): m/z 499 (100), 500 (24) calculated m/z 500.30. $^1$H NMR (D$_2$O, 300 MHz): δ=3.04 (t, 3H, J=16.5 Hz), 3.99 (t, 2H, J=8.1 Hz), 4.21 (t, 2H, J=16.3 Hz), 6.24 (t, 1H, J=4.5 Hz), 6.91 (m, 1H), 6.98 (m, 2H), 7.17 (m, 1H), 7.92 (m, 2H), 8.11 (m, 1H), 8.37 (s, 1H). $^{31}$P NMR (D$_2$O, 121.5 MHz): δ=15.88.

Example 83

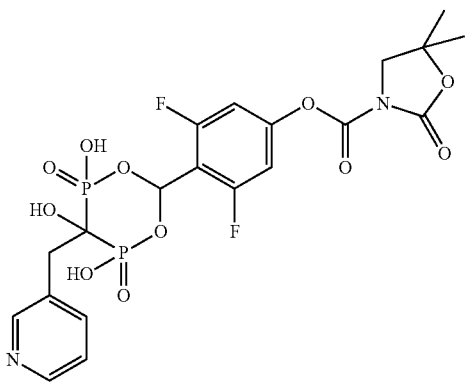 [SMILES: CC1(C)CN(C(=O)Oc2cc(F)c(C3OP(=O)(O)C(O)(Cc4cccnc4)P(=O)(O)O3)c(F)c2)C(=O)O1]

Example 83 was synthesized following the general synthetic procedures of Example 26 starting from 3,5-difluoro-4-formylphenyl 5,5-dimethyl-2-oxooxazolidine-3-carboxylate (Example 16).

cis-Isomer, yield: 312 mg (10%). Elemental analysis (%) calculated for C$_{20}$H$_{18}$F$_2$N$_2$Na$_2$O$_{11}$P$_2$·0.5NaCl·1.8H$_2$O (669.97): C, 35.86; H, 3.25; N, 4.18. Found: C, 35.86; H, 3.16; N, 4.15. ESI MS (H$_2$O) m/z 563 (M$^+$−1). $^1$H NMR (D$_2$O, 300 MHz): δ=8.54-6.99 (m, 6H), 6.87 (t, J=5.7 Hz, 1H), 3.40 (s, 2H), 3.36 (t, J=12.3 Hz, 2H), 1.52 (s, 6H). $^{31}$P NMR (D$_2$O, 121.5 MHz): δ=16.7. $^{19}$F NMR (CDCl$_3$, 282.3 MHz): δ=−112.0 (d, J=9.3 Hz).

Example 84

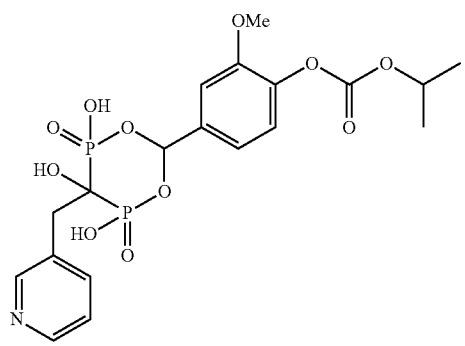 [SMILES: COc1cc(C2OP(=O)(O)C(O)(Cc3cccnc3)P(=O)(O)O2)ccc1OC(=O)OC(C)C]

Example 84 was synthesized following the general synthetic procedures of Example 26 starting from 4-formyl-2-methoxyphenyl isopropyl carbonate.

trans-Isomer, yield: 0.93 g (15%). Elemental analysis (%) calculated for C$_{19}$H$_{21}$NNa$_2$O$_{11}$P$_2$·0.5NaCl·2.6H$_2$O (623.39): C, 36.61; H, 4.24; N, 2.25. Found C, 36.54; H, 4.53; N, 2.15. ESI MS (CH$_3$CN): m/z 502 (100), 503 (22) calculated m/z 503.34. $^1$H NMR (D$_2$O, 300 MHz): δ=1.32 (d, 3H, J=6.3 Hz), 3.34 (t, 2H, J=17.2 Hz), 3.83 (s, 3H), 4.91 (sept, 1H, J=5.9 Hz), 6.38 (t, 1H, J=5.4 Hz), 6.87 (m, 2H), 7.13 (d, 1H, J=8.1 Hz), 7.37 (m, 1H), 8.14 (m, 1H, J=8.1 Hz), 8.34 (d, 1H, J=5.1 Hz), 8.71 (s, 1H). $^{31}$P NMR (D$_2$O, 121.5 MHz): δ=16.57.

cis-Isomer: yield 0.62 g (10%). Elemental analysis (%) calculated for C$_{19}$H$_{21}$NNa$_2$O$_{11}$P$_2$·0.5NaCl·2.5H$_2$O (621.59): C, 36.71; H, 4.22; N, 2.25. Found C, 36.45; H, 4.38; N, 2.22. ESI MS (CH$_3$CN): m/z 502 (100), 503 (23) calculated m/z 503.34. $^1$H NMR (D$_2$O, 300 MHz): δ=1.33 (d, 3H, J=6.3 Hz), 3.38 (t, 2H, J=12.3 Hz), 3.85 (s, 3H), 4.43 (sept, 1H, J=6.0 Hz), 6.54 (t, 1H, J=4.8 Hz), 7.21 (m, 2H), 7.43 (m, 2H), 8.02 (m, 1H, J=7.5 Hz), 8.39 (m, 1H), 8.54 (s, 1H). $^{31}$P NMR (D$_2$O, 121.5 MHz): 16.08.

Example 85

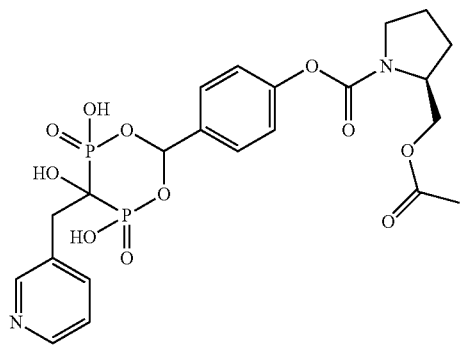 [SMILES: CC(=O)OC[C@@H]1CCCN1C(=O)Oc1ccc(C2OP(=O)(O)C(O)(Cc3cccnc3)P(=O)(O)O2)cc1]

Example 85 was synthesized following the general synthetic procedures of Example 26 starting from (S)-4-formylphenyl 2-(acetoxymethyl)pyrrolidine-1-carboxylate (Example 17).

Yield: 856 mg (29%). Elemental analysis (%) calculated for C$_{22}$H$_{24}$N$_2$Na$_2$O$_{11}$P$_2$·2.5H$_2$O (645.42): C, 40.94; H, 4.53; N, 4.34. Found: C, 40.93; H, 4.47; N, 4.31. ESI MS (H$_2$O): m/z 555 (M$^+$−1). $^1$H NMR (D$_2$O, 300 MHz): δ=8.73-7.12 (m, 8H), 6.59-6.42 (m, 1H), 4.40-4.12 (m, 3H), 3.64-3.30 (m, 4H), 2.06-1.85 (m, 7H). $^{31}$P NMR (D$_2$O, 121.5 MHz): δ=16.8, 16.5.

Example 86

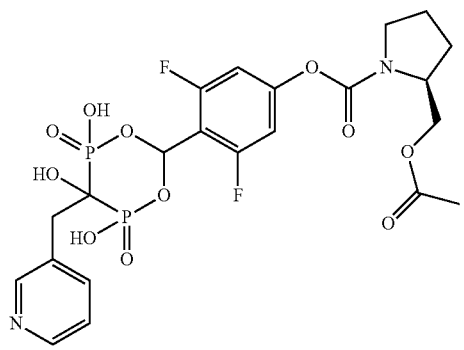 [SMILES: CC(=O)OC[C@@H]1CCCN1C(=O)Oc1cc(F)c(C2OP(=O)(O)C(O)(Cc3cccnc3)P(=O)(O)O2)c(F)c1]

Example 86 was synthesized following the general synthetic procedures of Example 26 starting from (S)-3,5-difluoro-4-formylphenyl 2-(acetoxymethyl)pyrrolidine-1-carboxylate (Example 18).

Yield: 87 mg (3%). Elemental analysis (%) calculated for C$_{22}$H$_{22}$F$_2$N$_2$Na$_2$O$_{11}$P$_2$·1.8NaCl·3.3H$_2$O (801.03): C, 32.99; H, 3.60; N, 3.50. Found: C, 32.96; H, 3.75; N, 3.42. ESI MS (H$_2$O) m/z 591 (M$^+$−1). $^1$H NMR (D$_2$O, 300 MHz): δ=8.66-6.80 (m, 7H), 4.36-4.12 (m, 3H), 3.57-3.25 (m, 4H), 2.06-

1.87 (m, 7H). $^{31}$P NMR (D$_2$O, 121.5 MHz): δ=16.8, 16.7. $^{19}$F NMR (CDCl$_3$, 282.3 MHz): δ=−112.8.

Example 87

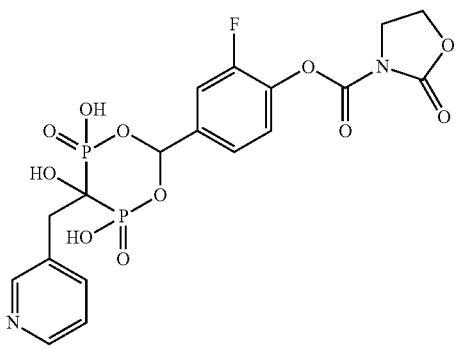 [SMILES: O=C1OCCN1C(=O)Oc1ccc(C2OP(=O)(O)C(O)(Cc3cccnc3)P(=O)(O)O2)cc1F]

Example 87 was synthesized following the general synthetic procedures of Example 26 starting from 2-fluoro-4-formylphenyl 2-oxooxazolidine-3-carboxylate.

trans-Isomer: yield 0.267 g (12%). $^1$H NMR (D$_2$O): δ=8.76 (s, 1H), 8.42 (d, J=4.0 Hz, 1H), 8.19 (d, J=7.5 Hz, 1H), 7.45 (dd, J=4.0, 7.5 Hz, 1H), 7.36 (t, J=8.1 Hz, 1H), 7.15 (m, 2H), 6.45 (t, J=4.8 Hz, 1H), 4.59 (t, J=8.25 Hz, 2H), 4.30 (t, J=8.25 Hz, 2H), 3.41 (t, J=17.2 Hz, 2H). $^{31}$P NMR (D$_2$O): δ=16.45. $^{19}$F NMR (D$_2$O): δ=−129.192. LC-MS (ESI) for C$_{18}$H$_{17}$FN$_2$O$_{11}$P$_2$ m/z 517 [M-H]$^-$. Elemental analysis (%) calc. for C$_{18}$H$_{15}$FN$_2$Na$_2$O$_{11}$P$_2$.3H$_2$O (%): C, 35.08; H, 3.43; N, 4.55. Found (%): C, 35.49; H, 3.63; N, 4.20.

cis-Isomer: yield 0.302 g (14%). $^1$H NMR (D$_2$O): δ=8.64 (s, 1H), 8.49 (m, 1H), 8.19 (d, J=8.1 Hz, 1H), 7.66-7.37 (m, 4H), 6.60 (t, J=4.5 Hz, 1H), 4.59 (t, J=8.2 Hz, 2H), 4.30 (t, J=8.2 Hz, 2H), 3.46 (t, J=12.6 Hz, 2H). $^{31}$P NMR (D$_2$O): δ=16.61. $^{19}$F NMR (D$_2$O): δ=−129.084. LC-MS (ESI) for C$_{18}$H$_{17}$FN$_2$O$_{11}$P$_2$ m/z 517 [M-H]$^-$. Elemental analysis (%) calc. for C$_{18}$H$_{15}$FN$_2$Na$_2$O$_{11}$P$_2$.2.5H$_2$O.1.5NaCl (%): C, 31.11; H, 2.90; N, 4.03. Found (%): C, 31.53; H, 3.17; N, 3.96.

Example 88

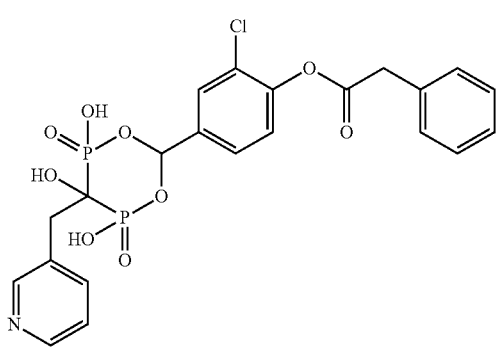 [SMILES: O=C(Cc1ccccc1)Oc1ccc(C2OP(=O)(O)C(O)(Cc3cccnc3)P(=O)(O)O2)cc1Cl]

Example 88 was synthesized following the general synthetic procedures of Example 26 starting from 2-chloro-4-formylphenyl 2-phenylacetate.

Yield: 0.29 g (4%). Elemental analysis (%) calculated for C$_{22}$H$_{18}$NNa$_2$ClO$_9$P$_2$.1.3NaCl.3.5H$_2$O.0.2CH$_3$CN (731.04): C, 36.80; H, 3.53; N, 2.30. Found C, 36.56; H, 3.26; N, 2.55. ESI MS (CH$_3$CN): m/z 538 (100), 540 (47) calculated m/z 539.81. $^1$H NMR (D$_2$O, 300 MHz): δ=3.38 (t, 2H, J=11.0 Hz), 3.40 (s, 1H), 6.50 (m, 2H), 7.26 (m, 1H), 7.41 (m, 7H), 7.72 (m, 1H), 8.03 (m, 1H), 8.42 (m, 1H), 8.55 (s, 1H). $^{31}$P NMR (D$_2$O, 121.5 MHz): δ=16.53.

Example 89

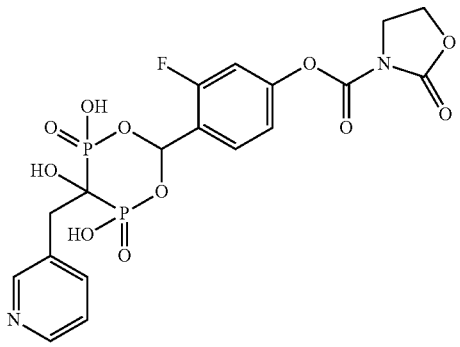 [SMILES: O=C1OCCN1C(=O)Oc1ccc(C2OP(=O)(O)C(O)(Cc3cccnc3)P(=O)(O)O2)c(F)c1]

Example 89 was synthesized following the general synthetic procedures of Example 26 starting from 3-fluoro-4-formylphenyl 2-oxooxazolidine-3-carboxylate (Example 19).

Yield: 370 mg (13%). Elemental analysis (%) calculated for C$_{18}$H$_{15}$F$_1$N$_2$Na$_2$O$_{11}$P$_2$.2.1H$_2$O (600.10): C, 36.03; H, 3.22; N, 4.67. Found: C, 36.17; H, 3.43; N, 4.81. ESI MS (H$_2$O): m/z 517 (M$^+$−1). $^1$H NMR (D$_2$O, 300 MHz): δ=8.70-7.02 (m, 7H), 6.80-6.60 (m, 1H), 4.53-4.47 (m, 2H), 4.21-4.10 (m, 2H), 3.42-3.28 (m, 2H). $^{31}$P NMR (D$_2$O, 121.5 MHz): δ=16.7, 16.5. $^{19}$F NMR (CDCl$_3$, 282.3 MHz): δ=−116.1, −116.7.

Example 90

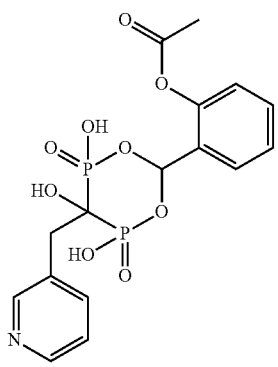 [SMILES: CC(=O)Oc1ccccc1C1OP(=O)(O)C(O)(Cc2cccnc2)P(=O)(O)O1]

Example 90 was synthesized following the general synthetic procedures of Example 26 starting from 2-formylphenyl acetate.

Yield 330 mg (10%); cis and trans isomers. $^1$H NMR (D$_2$O, 300 MHz): δ=8.73 (s, 1H), 8.37 (d, 1H), 8.25 (d, 1H), 8.10 (m, 1H) 7.59-7.13 (m, 4H), 6.59 (t, 1H), 3.36 (m, 2H), 2.36 (s, 3H). $^{31}$P NMR (D$_2$O, 121.5 MHz): δ=16.003. MS (M−1) m/z: 428. Elemental analysis (%) calculated for $C_{17}H_{19}NO_{10}P_2Na_2 \cdot 2.0H_2O \cdot 0.75NaCl$ (508.5): C, 34.62; H, 3.81; N, 2.52. Found: C, 34.37; H, 4.03; N, 2.48.

Example 91

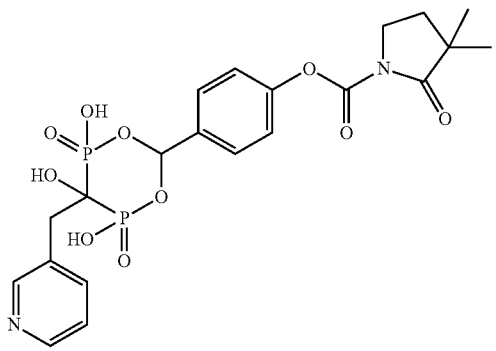 [SMILES: CC1(C)CCN(C(=O)Oc2ccc(C3OP(=O)(O)C(O)(Cc4cccnc4)P(=O)(O)O3)cc2)C1=O]

Example 91 was synthesized following the general synthetic procedures of Example 26 starting from 4-formylphenyl 4,4-dimethyl-2-oxopyrrolidine-1-carboxylate.

Yield 0.135 g (13%) of title compound as white solid, mixture of cis (59%) and trans (41%) isomers. $^1$H NMR (D$_2$O): δ=8.71 (s, 0.41H-trans), 8.55 (s, 0.59H-cis), 8.41 (d, J=4.8 Hz, 0.59H-cis), 8.37 (d, J=5.1 Hz, 0.41H-trans), 8.10 (d, J=7.5 Hz, 0.41H-trans), 7.96 (d, J=8.1 Hz, 0.59H-cis), 7.70 (d, J=8.4 Hz for AB-system, 1.18H-cis), 7.46-7.18 (m, 3.82H-trans,cis), 6.60 (t, J=5.1 Hz, 0.59H-cis), 6.43 (t, J=4.9 Hz, 0.41H-trans), 3.97 (t, J=6.9 Hz, 2H), 3.36 (m, 2H), 2.02 (t, J=6.9 Hz, 2H), 1.23 (s, 6H). $^{31}$P NMR (D$_2$O): δ=16.81-cis, 16.50-trans. LC-MS (ESI) for $C_{21}H_{24}N_2O_{10}P_2$ m/z 525 [M-H]$^-$. Elemental analysis (%) calculated for $C_{21}H_{22}N_2Na_2O_{10}P_2 \cdot 4H_2O$ (%): C, 39.26; H, 4.71; N, 4.36. Found (%): C, 38.92; H, 4.55; N, 4.03.

Example 92

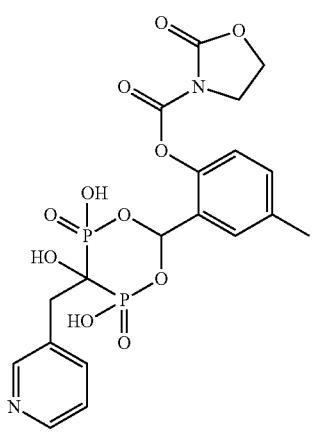 [SMILES: Cc1ccc(OC(=O)N2CCOC2=O)c(C2OP(=O)(O)C(O)(Cc3cccnc3)P(=O)(O)O2)c1]

Example 92 was synthesized following the general synthetic procedures of Example 26 starting from 2-formyl-4-methylphenyl 2-oxooxazolidine-3-carboxylate (Example 20).

cis-Isomer yield: 313 mg (7%). Elemental analysis (%) calculated for $C_{19}H_{18}N_2Na_2O_{11}P_2 \cdot 2.1H_2O$ (596.14): C, 38.28; H, 3.75; N, 4.70. Found: C, 38.23; H, 3.84; N, 4.84.

ESI MS (H$_2$O): m/z 513 (M$^+$-1). $^1$H NMR (D$_2$O, 300 MHz): δ=8.79-7.16 (m, 7H), 6.67 (t, J=5.4 Hz, 1H), 4.60 (t, J=7.5 Hz, 2H), 4.39 (t, J=7.5 Hz, 2H), 3.56 (t, J=11.7 Hz, 2H), 2.38 (s, 3H). $^{31}$P NMR (D$_2$O, 121.5 MHz): δ=15.3.

Example 93

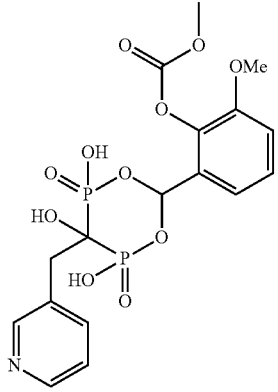 [SMILES: COC(=O)Oc1c(OC)cccc1C1OP(=O)(O)C(O)(Cc2cccnc2)P(=O)(O)O1]

Example 93 was synthesized following the general synthetic procedures of Example 26 starting from 2-formyl-6-methoxyphenyl methyl carbonate.

Yield 290 mg (8%), cis and trans isomers. $^1$H NMR (D$_2$O, 300 MHz): δ 8.70 (s, 1H), 8.4 (m, 2H), 7.75 (d, J=8.1 Hz, 1H), 7.25 (m, 2H), 7.15 (m, 1H), 6.46 (m, 1H), 4.87 (m, 1H), 3.78 (s, 3H), 3.73 (s, 3H), 3.25 (m, 2H). $^{31}$P NMR δ (D$_2$O, 121.5 MHz): δ=15.699. MS (M−1) m/z: 474. Elemental analysis (%) calculated for $C_{17}H_{19}NO_{11}P_2Na_2 \cdot 2.0H_2O \cdot 0.5$ NaCl (584): C, 34.81; H, 3.95; N, 2.39. Found: C, 34.41; H, 3.95; N, 2.37.

Example 94

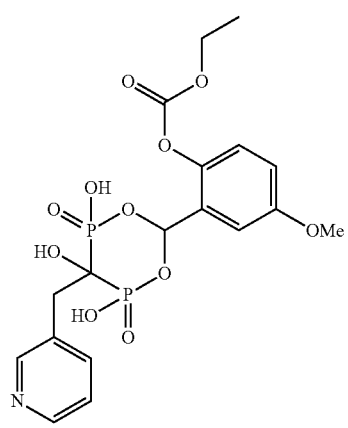 [SMILES: CCOC(=O)Oc1ccc(OC)cc1C1OP(=O)(O)C(O)(Cc2cccnc2)P(=O)(O)O1]

Example 94 was synthesized following the general synthetic procedures of Example 26 starting from ethyl 2-formyl-4-methoxyphenyl carbonate.

Yield 272.5 mg (5%) as the disodium salt.4.5H$_2$O. Elemental analysis (%) calculated for $C_{18}H_{19}NNa_2O_{11}P_2 \cdot 4.5H_2O$: C, 35.19; H, 4.59; N, 2.28. Found: C, 35.07; H, 4.28; N, 2.31. $^1$H NMR (D$_2$O): δ=1.20 (m, 3H), 3.27 (t, 2H), 3.71 (s, 3H), 4.20 (m, 2H), 6.39 (s, 1H), 6.66 (s, 1H), 6.9 (m, 1H), 7.0 (m, 1H), 7.38 (m, 1H), 8.11 (m, 1H), 8.28 (m, 1H), 8.59 (s, 1H). $^{31}$P NMR δ=16.573 (~5%), 16.003 (~95%). MS (ESI): m/e 488 (M-H$^+$).

Example 95

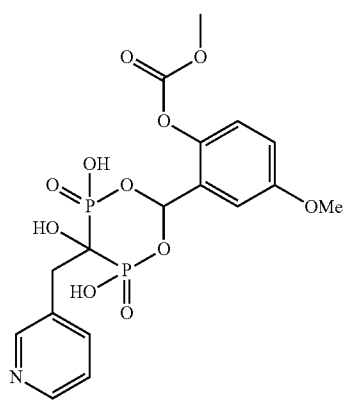 [SMILES: COC(=O)Oc1ccc(OC)cc1C1OP(=O)(O)C(O)(Cc2cccnc2)P(=O)(O)O1]

Example 95 was synthesized following the general synthetic procedures of Example 26 starting from 2-formyl-4-methoxyphenyl methyl carbonate.

Yield: 226 mg (6.5%); cis and trans isomers; $^1$H NMR (D$_2$O, 300 MHz): δ=8.65 (s, 1H), 8.52 (m, 2H), 7.85 (d, J=8.1 Hz, 1H), 7.25 (m, 2H), 7.15 (m, 1H), 6.46 (m, 1H), 4.87 (m, 1H), 3.77 (s, 3H), 3.71 (s, 3H), 3.37 (m, 2H). $^{31}$P NMR (D$_2$O, 121.5 MHz): δ=15.503, 15.415. MS (M-1) m/z: 474. Elemental analysis (%) calculated for C$_{17}$H$_{19}$NO$_{11}$P$_2$Na$_2$.2.0H$_2$O.0.6NaCl.6% risedronate (637.92): C, 34.34; H, 3.91; N, 2.44. Found: C, 34.23; H, 4.25; N, 2.78.

Example 96

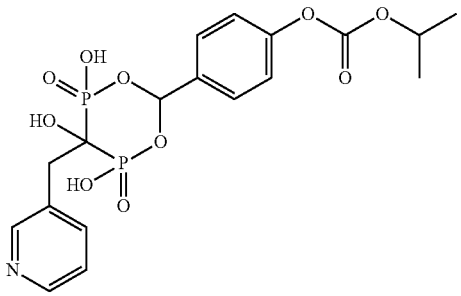 [SMILES: CC(C)OC(=O)Oc1ccc(C2OP(=O)(O)C(O)(Cc3cccnc3)P(=O)(O)O2)cc1]

Example 96 was synthesized following the general synthetic procedures of Example 26 starting from 4-formylphenyl isopropyl carbonate (Example 2).

Yield: 485 mg (12%). Elemental analysis (%) calculated for C$_{18}$H$_{19}$N$_1$Na$_2$O$_{10}$P$_2$.3.3H$_2$O (576.75): C, 37.49; H, 4.47; N, 2.43. Found: C, 37.56; H, 4.82; N, 2.57. ESI MS (H$_2$O): m/z 472 (M$^+$-1). $^1$H NMR (D$_2$O, 300 MHz): δ=8.61-7.06 (m, 8H), 6.48-6.30 (m, 1H), 4.80 (m, 1H), 3.32-3.20 (m, 2H), 1.22 (d, J=6.3 Hz, 6H). $^{31}$P NMR (D$_2$O, 121.5 MHz): δ=16.7, 16.4.

Example 97

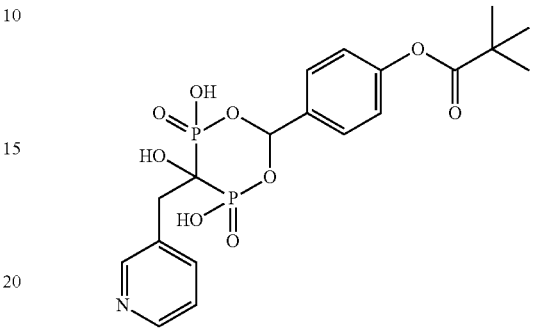

Example 97 was synthesized following the general synthetic procedures of Example 26 starting from 4-formylphenyl pivalate.

cis-Isomer yield: 100 mg (2%). Elemental analysis (%) calculated for C$_{19}$H$_{21}$N$_1$Na$_2$O$_9$P$_2$.0.9NaCl.2.5H$_2$O (612.97): C, 37.23; H, 4.28; N, 2.29. Found: C, 37.15; H, 4.30; N, 2.37. ESI MS (H$_2$O): m/z 470 (M$^+$-1). $^1$H NMR (D$_2$O, 300 MHz): δ=8.41-7.04 (m, 8H), 6.47 (br, 1H), 3.25 (t, J=12.3 Hz, 2H), 1.21 (s, 9H). $^{31}$P NMR (D$_2$O, 121.5 MHz): δ=16.8.

Example 98

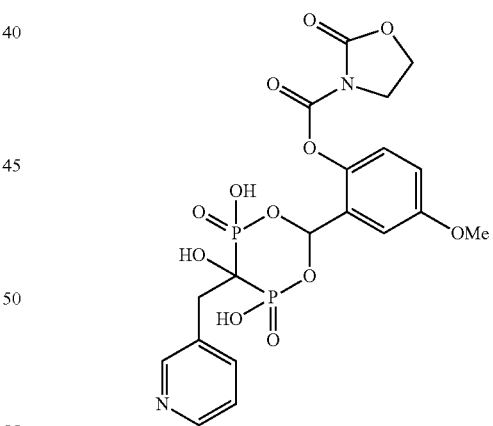

Example 98 was synthesized following the general synthetic procedures of Example 26 starting from 2-formyl-4-methoxyphenyl 2-oxooxazolidine-3-carboxylate.

Yield: 0.81 g (13.0%). Elemental analysis (%) calculated for C$_{19}$H$_{18}$N$_2$Na$_2$O$_{12}$P$_2$.0.1NaCl.4.2H$_2$O (628.47): C, 34.80; H, 4.06; N, 4.27. Found C, 35.09; H, 4.37; N, 3.76. ESI MS (CH$_3$CN): m/z 529 (100), 530 (23) calculated m/z 530.33. $^1$H NMR (D$_2$O, 300 MHz): δ=3.31 (m, 6H), 3.62 (s, 1H), 3.67 (s, 1H), 4.21 (m, 4H), 4.42 (m, 2H), 6.45 (t, 1H, J=5.5 Hz), 6.65 (t, 1H, J=4.8 Hz), 6.73 (m, 4H), 7.07 (m, 2H), 7.50 (m, 2H), 8.11 (m, 2H), 8.34 (m, 2H), 8.49 (m, 2H). $^{31}$P NMR (D$_2$O, 121.5 MHz): δ=15.99 (trans), 16.37 (cis).

Example 99

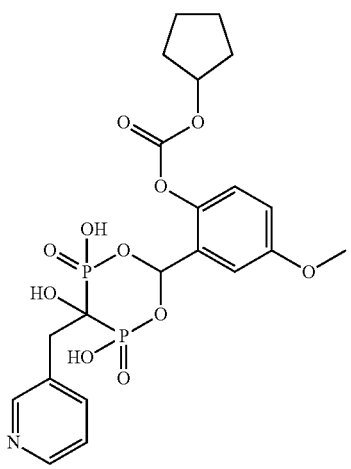 [SMILES: COc1ccc(OC(=O)OC2CCCC2)c(C2OP(=O)(O)C(O)(Cc3cccnc3)P(=O)(O)O2)c1]

Example 99 was synthesized following the general synthetic procedures of Example 26 starting from cyclopentyl 2-formyl-4-methoxyphenyl carbonate.

Yield 230 mg (10%); a mixture of cis and trans isomers. $^{31}$P NMR (D$_2$O, 121.5 MHz): δ=15.725. MS (M−1) m/z 529. Elemental analysis (%) calculated for C$_{21}$H$_{25}$N$_1$O$_{11}$P$_2$Na$_2$·2.5H$_2$O (618): C, 40.66; H, 4.87; N, 2.26. Found: C, 40.66; H, 4.87; N, 2.26.

Example 100

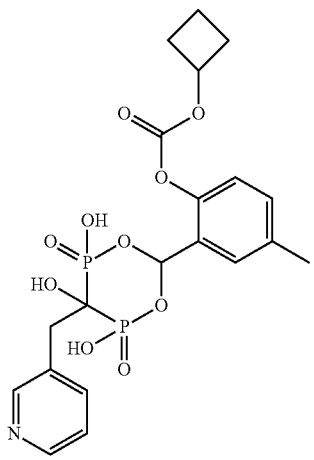 [SMILES: Cc1ccc(OC(=O)OC2CCC2)c(C2OP(=O)(O)C(O)(Cc3cccnc3)P(=O)(O)O2)c1]

Example 100 was synthesized following the general synthetic procedures of Example 26 starting from cyclobutyl 2-formyl-4-methylphenyl carbonate.

trans-Isomer: yield 170 mg (3%). $^1$H NMR (D$_2$O, 300 MHz): δ=8.41 (s, 1H), 8.10 (m, 1H), 7.89 (d, J=9.9 Hz, 1H), 7.15 (m, 2H), 6.95 (d, J=8.4 Hz, 1H), 6.74 (d, J=8.1 Hz, 1H), 6.55 (s, 1H), 6.17 (t, 1H), 4.68 (m, 1H), 3.06 (t, 2H, J=17.1 Hz), 1.90 (s, 3H), 2.02-1.84 (m, 4H), 1.45 (m, 1H), 1.29 (m, 1H). $^{31}$P NMR (D$_2$O, 121.5 MHz): δ=15.829. MS (M−1) m/z: 498. Elemental analysis (%) calculated for C$_{20}$H$_{23}$N$_1$O$_{10}$P$_2$Na$_2$·2H$_2$O (579): C, 41.32; H, 4.66; N, 2.41. Found: C, 41.18; H, 4.66; N, 2.74.

cis-Isomer: yield 136 mg (2.2%). $^1$H NMR (D$_2$O, 300 MHz): δ=8.31 (s, 1H), 8.16 (d, 1H), 7.91 (d, J=7.8 Hz, 1H), 7.34 (m, 2H), 7.26 (s, 1H), 6.98 (d, J=9.0 Hz, 1H), 6.77 (d, J=8.1 Hz, 1H), 6.32 (t, 1H), 4.69 (m, 1H), 3.10 (t, 2H, J=12.6 Hz), 1.99 (s, 3H), 2.02-1.84 (m, 4H), 1.51 (m, 1H), 1.30 (m, 1H). $^{31}$P NMR (D$_2$O, 121.5 MHz): δ=15.589. MS (M−1) m/z: 498. Elemental analysis (%) calculated for C$_{20}$H$_{23}$N$_1$O$_{10}$P$_2$Na$_2$·2H$_2$O (579): C, 41.32; H, 4.66; N, 2.41. Found: C, 41.44; H, 4.52; N, 2.68.

Example 102

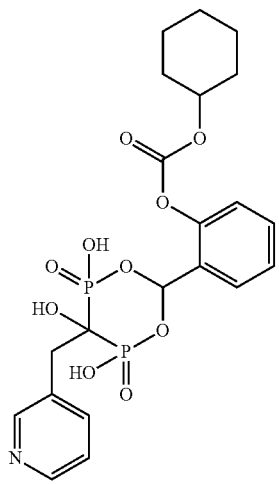 [SMILES: O=C(Oc1ccccc1C1OP(=O)(O)C(O)(Cc2cccnc2)P(=O)(O)O1)OC1CCCCC1]

Example 102 was synthesized following the general synthetic procedures of Example 26 starting from cyclohexyl 2-formylphenyl carbonate.

trans-Isomer, yield: 579 mg (8%). $^1$H NMR (D$_2$O, 300 MHz): δ=8.39 (s, 1H), 8.08 (d, 1H), 7.95 (d, J=8.1 Hz, 1H), 7.23-7.13 (m, 2H), 7.12-6.87 (m, 311), 6.24 (t, 1H), 4.45 (buried under D$_2$O, m, 1H), 3.08 (t, 211, J=15.9 Hz), 1.70-1.50 (m, 3H), 1.5-0.96 (m, 8H). $^{31}$P NMR (D$_2$O, 121.5 MHz): δ=15.715. MS (M−1) m/z: 512. Elemental analysis (%) calculated for C$_{17}$H$_{19}$NO$_{11}$P$_2$Na$_2$·2.0H$_2$O (593): C, 42.62; H, 4.87; N, 2.37. Found: C, 42.33; H, 4.48; N, 2.41.

cis-Isomer, yield: 434 mg (6%). $^1$H NMR (D$_2$O, 300 MHz): δ=8.25 (s, 1H), 8.11 (d, 1H), 7.77 (d, J=7.8 Hz, 1H), 7.45 (d, 1H), 7.21-7.16 (m, 2H), 7.09 (d, 1H), 6.92 (d, 1H), 6.38 (t, 1H), 4.45 (buried under D$_2$O, m, 1H), 3.07 (t, 2H, J=12.9 Hz), 1.72-1.58 (m, 3H), 1.40-0.84 (m, 10 μl). $^{31}$P NMR (D$_2$O, 121.5 MHz): δ=15.745. MS (M−1) m/z 512. Elemental analysis (%) calculated for C$_{20}$H$_{23}$NO$_{10}$P$_2$Na$_2$·2.0H$_2$O·0.3NaCl·0.1CH$_3$CN (611): C, 41.27; H, 4.79; N, 2.50. Found: C, 41.07; H, 4.52; N, 2.79.

Example 103

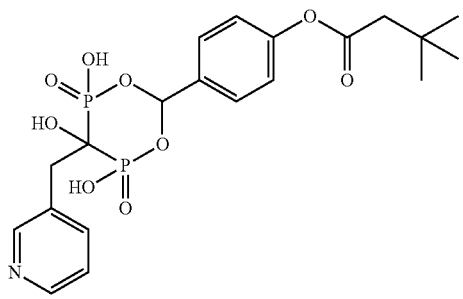

Example 103 was synthesized following the general synthetic procedures of Example 26 starting from 4-formylphenyl 3,3-dimethylbutanoate.

Yield: 220 mg (8%). Mixture of isomers with a ratio of 65:35. $^1$H NMR (D$_2$O): δ=1.08 (9H, s), 2.50 (2H, s), 3.33-3.47 (2H, m), 6.50-6.56 (1H, m), 7.11-7.38 (3H, m), 7.64-7.68 (1H, m), 7.94-8.69 (4H, m). $^{31}$P NMR (D$_2$O): δ=16.59 and 16.91 (1.00:0.35). Elemental analysis: found C, 39.98%; H, 4.89%; N, 2.45%; calculated for C$_{20}$H$_{23}$NCl$_{0.2}$Na$_2$.2O$_9$P$_2$(H$_2$O)$_{3.3}$ C, 40.00%, H, 4.97%, N, 2.33%. LC-MS: (M−1) m/z found 484; calculated for C$_{20}$H$_{25}$NO$_9$P$_2$ 485.37.

Example 104

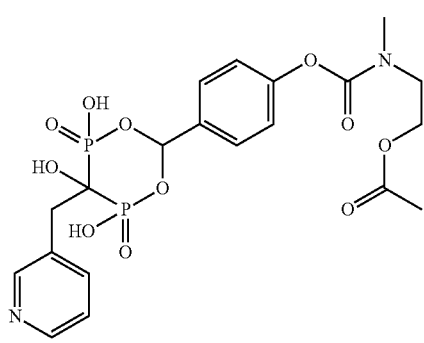 [SMILES: CC(=O)OCCN(C)C(=O)Oc1ccc(C2OP(=O)(O)C(O)(Cc3cccnc3)P(=O)(O)O2)cc1]

Example 104 was synthesized following the general synthetic procedures of Example 26 starting from 2-(((4-formylphenoxy)carbonyl)(methyl)amino)ethyl acetate (Example 21).

Yield: 972 mg (34%). Elemental analysis (%) calculated for C$_{20}$H$_{22}$N$_2$Na$_2$O$_{11}$P$_2$.2.1H$_2$O (612.18): C, 39.24; H, 4.31; N, 4.58. Found: C, 39.27; H, 4.47; N, 4.51. ESI MS (H$_2$O): m/z 529 (M$^+$−1). $^1$H NMR (D$_2$O, 300 MHz): δ=8.70-7.06 (m, 8H), 6.58-6.38 (m, 1H), 4.31-4.29 (m, 2H), 3.72-3.58 (m, 2H), 3.42-3.31 (m, 2H), 3.10-2.97 (2 singlets, 3H), 2.06 (s, 3H). $^{31}$P NMR (D$_2$O, 121.5 MHz): δ=16.8, 16.5.

Example 105

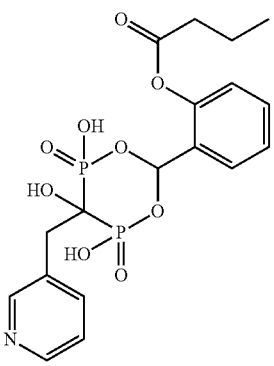 [SMILES: CCCC(=O)Oc1ccccc1C1OP(=O)(O)C(O)(Cc2cccnc2)P(=O)(O)O1]

Example 105 was synthesized following the general synthetic procedures of Example 26 starting from 2-formylphenyl butyrate.

trans-Isomer, yield: 0.52 g (8.8%). Elemental analysis (%) calculated for C$_{18}$H$_{19}$NNa$_2$O$_{10}$P$_2$.0.09NaCl.1.5H$_2$O (591.62): C, 40.60; H, 4.09; N, 2.37. Found C, 40.54; H, 4.07; N, 2.32. ESI MS (CH$_3$CN): m/z 456 (100), 457 (20) calculated m/z 457.32. $^1$H NMR (D$_2$O, 300 MHz): δ=0.95 (t, 3H, J=6.6 Hz), 1.67 (d, 2H, J=7.2 Hz), 2.65 (d, 2H, J=6.9 Hz), 3.35 (t, 2H, J=16.3 Hz), 6.48 (t, 1H, J=4.5 Hz), 7.07 (m, 1H), 7.28 (m, 2H), 7.47 (m, 2H), 8.24 (m, 1H), 8.35 (m, 1H), 8.61 (s, 1H). $^{31}$P NMR (D$_2$O, 121.5 MHz): δ=16.10.

Example 106

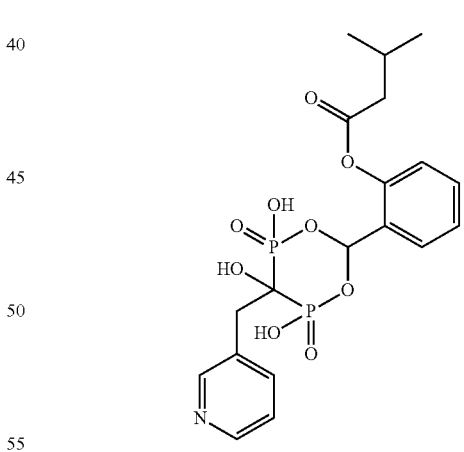

Example 106 was synthesized following the general synthetic procedures of Example 26 starting from 2-formylphenyl 3-methylbutanoate.

Yield: 0.58 g (10.0%), trans and cis isomers. Elemental analysis (%) calculated for C$_{19}$H$_{21}$NNa$_2$O$_9$P$_2$.0.7NaCl.1.3H$_2$O (579.66): C, 39.37; H, 4.10; N, 2.42. Found C, 39.26; H, 4.38; N, 2.58. ESI MS (CH$_3$CN): m/z 470 (100), 471 (20) calculated m/z 471.34. $^1$H NMR (D$_2$O, 300 MHz): δ=1.00 (d, 6+6H, J=6.0 Hz), 2.13 (m, 1+1H, J=6.6 Hz), 2.5 (m, 2+2H), 3.44 (m, 2+2H, J=15.9, 12.1 Hz), 6.51 (t, 1H, J=4.3 Hz), 6.62 (t, 1H, J=4.8 Hz), 7.14 (m, 2H), 7.32 (m, 4H), 7.45 (m, 4H), 7.81 (m, 2H), 8.49 (s, 1H), 8.58 (s, 1H), 8.76 (s, 1H), 8.78 (s, 1H). $^{31}$P NMR (D$_2$O, 121.5 MHz): δ=16.24, 16.20.

Example 107

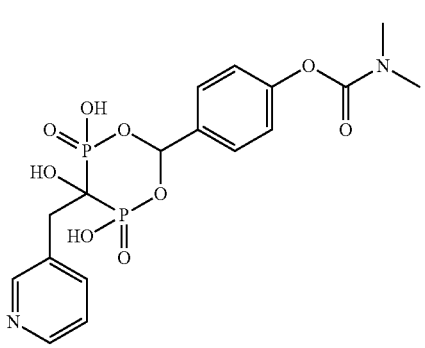 [SMILES: CN(C)C(=O)Oc1ccc(C2OP(=O)(O)C(O)(Cc3cccnc3)P(=O)(O)O2)cc1]

Example 107 was synthesized following the general synthetic procedures of Example 26 starting from 4-formylphenyl dimethylcarbamate.

Yield: 518 mg (14%); elemental analysis (%) calcd for C$_{17}$H$_{17}$F$_1$N$_2$Na$_2$O$_9$P$_2$.1.0NaCl.2.0H$_2$O (614.76): C, 33.21; H, 3.44; N, 4.56. Found: C, 33.20; H, 3.64; N, 4.49; ESI MS (H$_2$O): m/z: 475 (M$^+$−1). $^1$H NMR (D$_2$O; 300 MHz): δ=8.71-6.97 (m, 7H), 6.55-6.37 (m, 1H), 3.42-3.30 (m, 2H), 3.11 (s, 3H), 2.96 (s, 3H). $^{31}$P NMR (D$_2$O, 121.5 MHz): δ=16.8, 16.5. $^{19}$F NMR (CDCl$_3$, 282.3 MHz): δ=−130.0.

Example 108

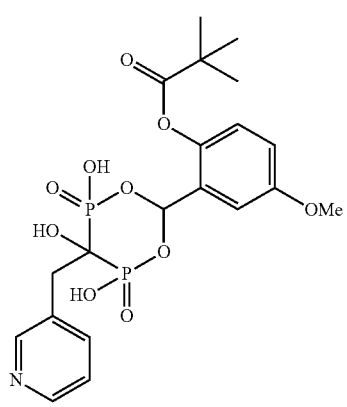 [SMILES: COc1ccc(OC(=O)C(C)(C)C)c(C2OP(=O)(O)C(O)(Cc3cccnc3)P(=O)(O)O2)c1]

Example 108 was synthesized following the general synthetic procedures of Example 26 starting from 2-formyl-4-methoxyphenyl pivalate.

Elemental analysis (%) calcd C$_{20}$H$_{23}$NNa$_2$O$_{10}$P$_2$.4 H$_2$O: C, 38.91; H, 5.06; N, 2.27. Found: C, 38.75, H, 4.93; N, 2.18. $^1$H NMR (D$_2$O), δ 1.223 (s, 9H), 3.241 (t, 3H, J$_{PH}$=16.5 Hz), 3.694 (s, 3H), 6.32 (t, 1H, J=5 Hz), 6.66 (s, 1H), 6.86 (m, 2H), 7.38 (m, 1H), 8.14 (d, J=7.8 Hz), 8.27 (m, 1H), 8.60 (m, 1H). $^{31}$P NMR δ=15.822. MS (ESI): m/e 500 (m-H$^+$).

Example 109

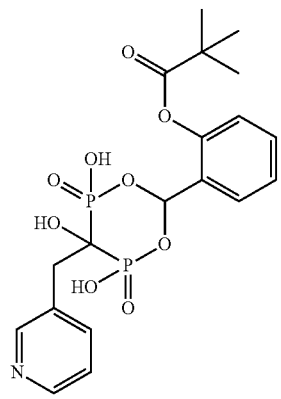 [SMILES: CC(C)(C)C(=O)Oc1ccccc1C1OP(=O)(O)C(O)(Cc2cccnc2)P(=O)(O)O1]

Example 109 was synthesized following the general synthetic procedures of Example 26 starting from 2-formylphenyl pivalate.

Trans isomer Yield: 105 mg. Elemental analysis (%) calcd for C$_{19}$H$_{21}$N$_1$O$_9$P$_2$Na$_2$ 2.0H$_2$O C, 41.39; H, 4.57; N, 254%. Found C, 41.67; H, 4.51; N, 2.55; ESI MS (H$_2$O): m/z 470 (M$^-$1). $^1$H NMR (D$_2$O; 300 MHz): δ=8.75 (s, 1H), 8.58 (m, 1H), 8.43 (s, 1H), 7.80 (m, 1H), 7.43 (m, 1H), 7.30 (m, 2H), 7.00 (m, 1H), 6.40 (s, 1H), 3.37 (t, J=15.0 Hz, 2H), 1.30 (s, 9H). $^{31}$P NMR (D$_2$O, 121.5 MHz): δ=15.35.

Example 110

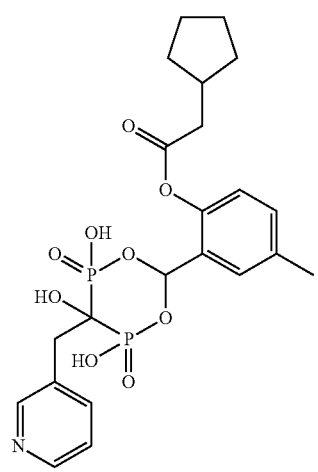 [SMILES: Cc1ccc(OC(=O)CC2CCCC2)c(C2OP(=O)(O)C(O)(Cc3cccnc3)P(=O)(O)O2)c1]

Example 110 was synthesized following the general synthetic procedures of Example 26 starting from cyclopentyl 2-formyl-4-methylphenyl carbonate.

Trans isomer 260 mg. Elemental analysis (%) calcd for C$_{21}$H$_{25}$N$_1$O$_{10}$P$_2$Na$_2$.2.5H$_2$O (604.4): C, 41.73; H, 5.00; N, 2.32. Found: C, 41.88; H, 5.15; N, 2.35. $^1$H NMR (D$_2$O; 300 MHz): δ=8.78, (s, 1H), 8.47 (m, 1H), 8.33 (d, 1H), 7.58 (m, 1H), 7.32 (1, 1H), 7.10 (t, 1H), 7.01 (s, 1H), 6.52 (t, 1H), 5.21 (m, 1H), 3.43 (t, 2H, J=17.1 Hz), 2.35 (s, 3H), 1.95-1.45 (m, 8H). m/z 512.

Example 111

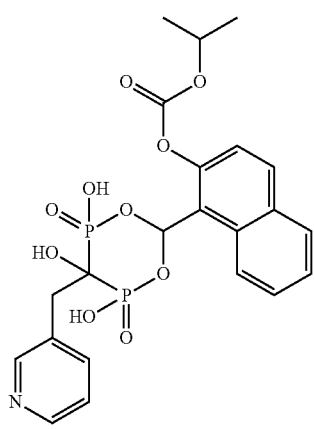 [SMILES: CC(C)OC(=O)Oc1ccc2ccccc2c1C1OP(=O)(O)C(O)(Cc2cccnc2)P(=O)(O)O1]

Example 111 was synthesized following the general synthetic procedures of Example 26 starting from 1-formylnaphthalen-2-yl isopropyl carbonate.

Yield: 201 mg, trans isomer. $^1$H NMR (D$_2$O), δ=1.18 (d, 6H), 3.47 (t, 2H, J$_{PH}$=14.1 Hz), 4.85 (m, 1H), 7.13 (m, 2H), 7.41 (m, 2H), 7.65-7.83 (m, 3H), 8.13 (d, 1H), 8.35 (d, 1H), 8.44 (d, 1H), 8.66 (s, 1H). Anal Calcd for C$_{22}$H$_{21}$NNa$_2$O$_{10}$P$_2$: C, 46.57; H, 3.73; N, 2.47. Found: C, 46.52; H, 3.98; N, 2.40. MS (ESI): m/e 522 (m-H$^+$).

Example 112

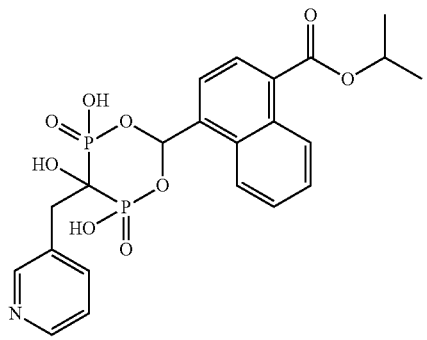 [SMILES: CC(C)OC(=O)c1ccc(C2OP(=O)(O)C(O)(Cc3cccnc3)P(=O)(O)O2)c2ccccc12]

Example 112 was synthesized following the general synthetic procedures of Example 26 starting from isopropyl 4-formyl-1-naphthoate.

Yield: 685 mg of a mixture of (100:4) trans-isomer:cis-isomer. Anal Calcd for C$_{22}$H$_{21}$NNa$_2$O$_{10}$P$_2$.2.4H$_2$O: C, 43.25; H, 4.26; N, 2.29. Found: C, 43.17; H, 3.83; N, 2.57. $^1$H NMR (D$_2$O), δ=1.26 (m, 6H), 3.41 (m, ~2H), 4.9 (m, ~1H), 7.0-8.6 (m, ~10H). $^{31}$P NMR (D$_2$O) δ 16.353, 16.239. MS (ESI): m/e 522 (m-H$^+$).

Example 113

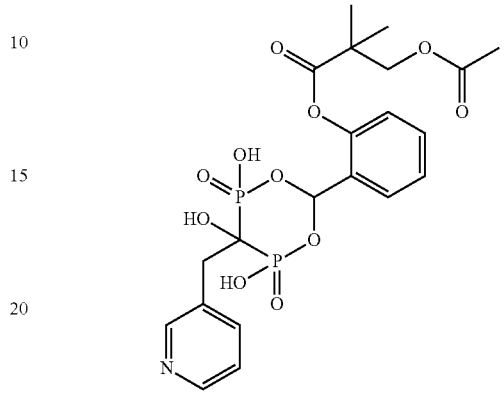

Example 113 was synthesized following the general synthetic procedures of Example 26 starting from 2-formylphenyl 3-acetoxy-2,2-dimethylpropanoate.

Yield: 65.7 mg as the disodium salt.0.5 H$_2$O, ~95:5 cis-isomer:trans-isomer. Anal. Calcd for C$_{18}$H$_{19}$NNa$_2$O$_{11}$P$_2$.4.5H$_2$O: C, 43.31; H, 4.15; N, 2.41. Found: C, 43.19, H, 4.28; N, 2.36. $^1$H NMR (D$_2$O), δ=1.4 (m, 6H), 2.14 (m, 3H), 3.36 (m, 2H), 4.32 (s, 2H), 6.66 (m, 1H), 7.08 (d, 1H), 7.5 (m, 2H), 7.82 (d, 1H), 7.95 (d, 1H), 8.40 (m, 1H), 8.53 (s, 1H). $^{31}$P NMR δ=16.347 (~5.5%), 16.151 (~94.5%). MS (ESI): m/e 528 (m-H$^+$).

Example 114

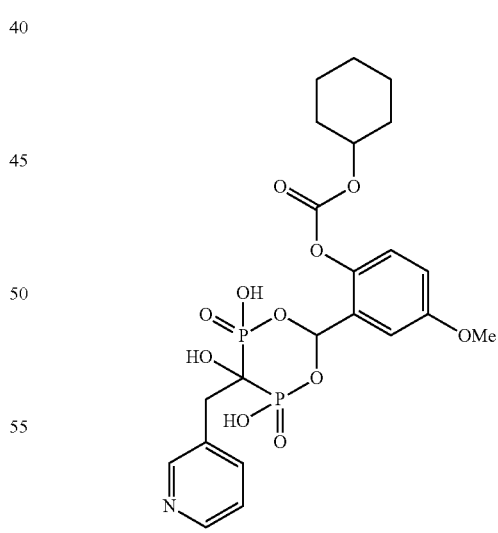

Example 114 was synthesized following the general synthetic procedures of Example 26 starting from cyclohexyl 2-formyl-4-methoxyphenyl carbonate.

Elemental analysis (%) calcd for C$_{21}$H$_{25}$N$_1$O$_{10}$P$_2$Na$_2$.1.5H$_2$O (616.4): C, 42.87; H, 4.91; N, 2.27. Found: C, 42.97; H, 4.99; N, 2.27. $^1$H NMR (D$_2$O; 300 MHz) δ=8.58 (s, 1H), 8.35 (d, 1H), 8.23 (1H), 7.56 (m, 1H), 6.84 (d, 1H), 6.73 (s, 1H), 6.63 (d, 1H), 6.20 (t, 1H), 4.45 (buried under D$_2$O, m, 1H), 3.52 (s, 3H), 3.22 (t, 2H, J=15.9 Hz), 1.70-1.50 (m, 3H), 1.5-0.96 (m, 8H). $^{31}$PNMR 8 (D$_2$O, 121.5 MHz):15.18. ESI m/z 542 (M−1).

Example 115

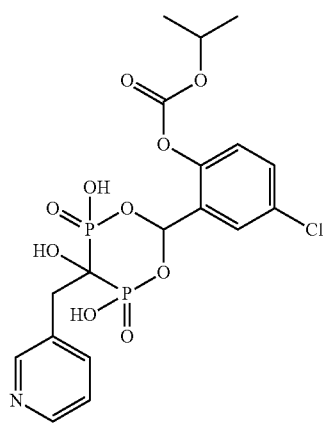 [SMILES: CC(C)OC(=O)Oc1ccc(Cl)cc1C1OP(=O)(O)C(O)(Cc2cccnc2)P(=O)(O)O1]

Example 115 was synthesized following the general synthetic procedures of Example 26 starting from 4-chloro-2-formylphenyl isopropyl carbonate.

Yield: 195 mg. Elemental analysis (%) calcd for C$_{18}$H$_{20}$N$_1$O$_{10}$P$_2$Na$_2$.1.5H$_2$O.0.3NaCl (602.4): C, 36.29; H, 3.90; N, 2.56. Found: C, 36.15; H, 3.54; N, 2.34. $^1$H NMR (D$_2$O; 300 MHz) δ=8.41 (s, 1H), 8.11 (d, 1H), 7.89 (1H), 7.14 (m, 3H), 7.02 (s, 1H), 6.86 (d, 1H), 6.70 (d, 1H), 6.17 (t, 1H), 4.65 (m, 1H), 3.05 (t, 2H), 1.01 (d, 6H). $^{31}$PNMR (D$_2$O, 121.5 MHz): δ=15.03. ESI m/z 506 (M−1).

Example 116

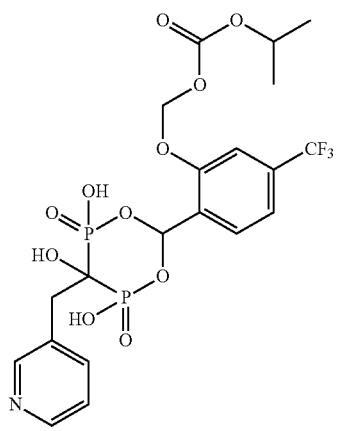 [SMILES: CC(C)OC(=O)OCOc1cc(C(F)(F)F)ccc1C1OP(=O)(O)C(O)(Cc2cccnc2)P(=O)(O)O1]

Example 116 was synthesized following the general synthetic procedures of Example 26 starting from (2-formyl-5-(trifluoromethyl)phenoxy)methyl isopropyl carbonate.

Trans isomer: yield: 259 mg (3.5%); elemental analysis (%) calcd for C$_{20}$H$_{20}$N$_1$Na$_2$O$_{11}$F$_3$P$_2$ (615.32): C, 39.04; H, 3.28; N, 2.28. Found: C, 39.24; H, 3.57; N, 1.95; ESI MS (H$_2$O): m/z: 570 (M$^+$−1). $^1$H NMR (D$_2$O; 300 MHz): δ=8.82-7.22 (m, 7H), 6.75-6.73 (m, 1H), 5.87 (s, 2H), 5.0-4.8 (m, 1H), 3.45 (t, J=17.1 Hz, 2H), 1.27 (m, 6H). $^{31}$P NMR (D$_2$O, 121.5 MHz): δ=15.9. $^{19}$F NMR (CDCl$_3$, 282.3 MHz): δ=−63.5.

Example 117

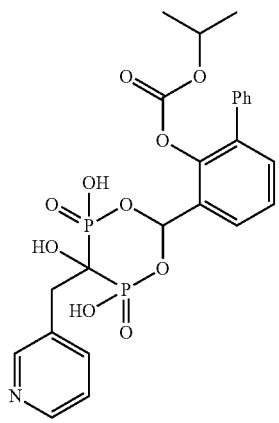 [SMILES: CC(C)OC(=O)Oc1c(-c2ccccc2)cccc1C1OP(=O)(O)C(O)(Cc2cccnc2)P(=O)(O)O1]

Example 117 was synthesized following the general synthetic procedures of Example 26 starting from 3-formylbiphenyl-2-yl isopropyl carbonate.

Yield: 400 mg, trans-isomer. Elemental analysis (%) calcd for C$_{24}$H$_{23}$NO$_{10}$P$_2$Na$_2$.2.0H$_2$O.0.4 NaCl (656.91): C, 44.25; H, 4.19; N, 2.35. Found: C, 43.97; H, 4.57; N, 2.22. $^1$HNMR (D$_2$O; 300 MHz) δ=8.36 (s, 1H), 8.10-8.06 (m, 1H), 7.85 (d, 1H), 7.15 (m, 8H), 6.92 (d, 1H), 6.29 (t, 1H), 3.05 (t, 2H), 0.68 (d, 6H). $^{31}$PNMR (D$_2$O, 121.5 MHz): δ=15.87. ESI m/z 548 (M−1).

Example 118

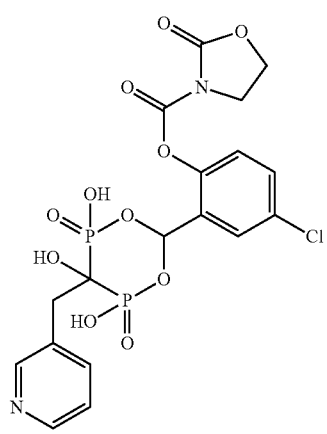 [SMILES: O=C1OCCN1C(=O)Oc1ccc(Cl)cc1C1OP(=O)(O)C(O)(Cc2cccnc2)P(=O)(O)O1]

Example 118 was synthesized following the general synthetic procedures of Example 26 starting from 4-chloro-2-formylphenyl 2-oxooxazolidine-3-carboxylate.

Yield: 120 mg Trans isomer Elemental analysis (%) calcd for C$_{18}$H$_{15}$ClN$_2$O$_{11}$P$_2$Na$_2$.2.5H$_2$O (635.78): C, 34.95; H, 3.36; N, 4.41. Found: C, 35.14; H, 3.64; N, 4.14. $^1$HNMR (D$_2$O; 300 MHz) δ=8.40 (s, 1H), 8.11 (m, 1H), 7.96 (d, 1H), 7.16 (m, 3H), 6.86 (d, 1H), 6.78 (s, 1H), 6.16 (t, 1H), 4.21 (t, 2H), 3.99 (t, 2H), 3.04 (t, 2H, J=16.8 Hz). ³¹PNMR (D₂O, 121.5 MHz): δ=15.51. ESI m/z 533 (M−1).

Example 119

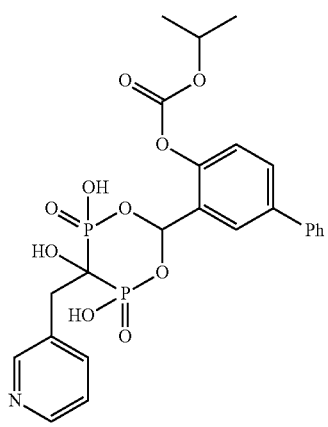 [SMILES: CC(C)OC(=O)Oc1ccc(-c2ccccc2)cc1C1OP(=O)(O)C(O)(Cc2cccnc2)P(=O)(O)O1]

Example 119 was synthesized following the general synthetic procedures of Example 26 starting from 3-formylbiphenyl-4-yl isopropyl carbonate.

Yield: 200 mg, trans-isomer. Elemental analysis (%) calcd for $C_{24}H_{23}NO_{10}P_2Na_2.0.8\,H_2O$ (611.91): C, 47.50; H, 4.10; N, 2.52. Found: C, 47.69; H, 4.23; N, 2.37. ¹HNMR (D₂O; 300 MHz) δ=8.47 (s, 1H), 8.26 (m, 1H), 7.79 (m, 1H), 7.31-7.15 (m, 8H), 6.96 (d, 1H), 6.27 (t, 1H), 3.13 (t, 2H), 1.04 (d, 6H). ³¹PNMR (D₂O, 121.5 MHz): δ=15.10. ESI m/z 548 (M−1).

Example 120

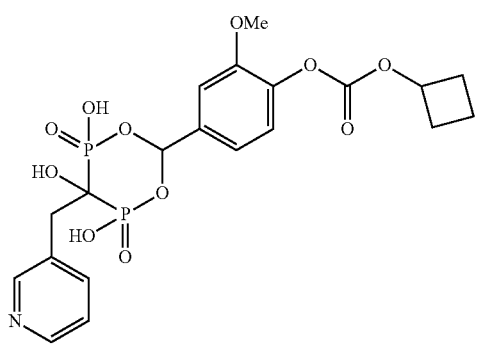 [SMILES: COc1cc(C2OP(=O)(O)C(O)(Cc3cccnc3)P(=O)(O)O2)ccc1OC(=O)OC1CCC1]

Example 120 was synthesized following the general synthetic procedures of Example 26 starting from cyclobutyl 4-formyl-2-methoxyphenyl carbonate.

Yield: 152 mg; trans-isomer. Elemental analysis (%) calcd for $C_{20}H_{24}NO_{11}P_2Na_2.0.4H_2O.0.1MeCN.0.1risedronate$ (600.97): C, 41.77; H, 4.23; N, 2.80. Found: C, 42.08; H, 4.59; N, 2.50. ¹HNMR (D₂O; 300 MHz) δ=8.52 (s, 1H), 8.38 (m, 1H), 8.21 (d, 1H), 7.57 (m, 2H), 6.85 (m, 2H), 6.66 (d, J=7.8 Hz, 1H), 6.11 (t, 1H), 4.67 (m, 1H), 3.53 (s, 3H), 3.06 (t, 2H, J=17.1 Hz), 2.02-1.84 (m, 4H), 1.50 (m, 1H), 1.28 (m, 1H). ³¹PNMR (D₂O, 121.5 MHz): δ=15.63. ESI m/z 514 (M−1).

Example 121

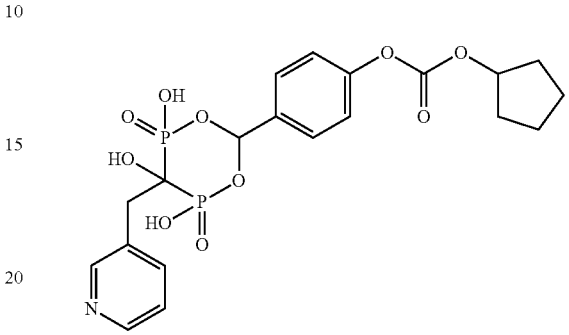

Example 121 was synthesized following the general synthetic procedures of Example 26 starting from cyclopentyl 4-formylphenyl carbonate.

Yield: 190 mg; trans-isomer. Elemental analysis (%) calcd for $C_{20}H_{23}NO_{10}P_2Na_2.1.0H_2O.0.5NaCl$ (592.59): C, 40.54; H, 4.25; N, 2.36. Found: C, 40.30; H, 4.22; N, 2.50. ¹HNMR (D₂O; 300 MHz) δ=8.38 (s, 1H), 8.06 (d, 1H), 7.87 (d, J=9.9 Hz, 1H), 7.15 (m, 3H), 7.01 (t, 1H), 6.89 (t, 1H), 6.23 (t, 1H), 4.87 (m, 1H), 3.07 (t, 2H, J=16.2 Hz), 1.55-1.28 (m, 8H). ³¹PNMR (D₂O, 121.5 MHz): δ=16.43. ESI m/z 498 (M−1).

Example 122

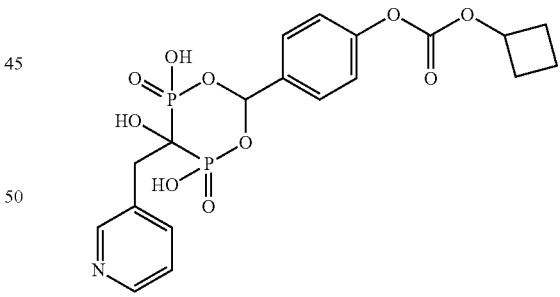

Example 122 was synthesized following the general synthetic procedures of Example 26 starting from cyclobutyl 4-formylphenyl carbonate.

Yield: 290 mg; trans-isomer. Elemental analysis (%) calcd for $C_{19}H_{21}NO_{10}P_2Na_2.1.0H_2O$ (553.44): C, 41.67; H, 4.24; N, 2.78. Found: C, 41.29; H, 4.28; N, 2.39. ¹HNMR (D₂O; 300 MHz) δ=8.45 (s, 1H), 8.15 (m, 1H), 7.95 (d, 1H), 7.15 (m, 2H), 6.95-6.85 (m, 3H), 6.12 (t, 1H), 4.67 (m, 1H), 3.04 (t, 2H, J=17.1 Hz), 2.02-1.84 (m, 4H), 1.45-1.20 (m, 2H). ³¹PNMR δ (D₂O, 121.5 MHz): 16.12. ESI m/z 484 (M−1).

Example 123

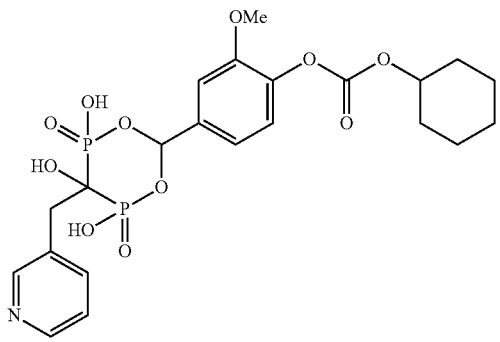 [SMILES: COc1cc(C2OP(=O)(O)C(O)(Cc3cccnc3)P(=O)(O)O2)ccc1OC(=O)OC1CCCCC1]

Example 123 was synthesized following the general synthetic procedures of Example 26 starting from cyclohexyl 4-formyl-2-methoxyphenyl carbonate.

Trans-isomer: Yield: 423 mg (7.0%); elemental analysis (%) calcd for C₂₂H₂₅N₁Na₂O₁₁P₂.0.1H₂O (600.81): C, 45.18; H, 4.43; N, 2.33. Found: C, 45.61; H, 4.96; N, 2.07. ESI MS (H₂O): m/z: 542 (M⁺−1). ¹H NMR (D₂O; 300 MHz): δ=8.79-6.93 (m, 7H), 6.45 (t, J=5.1 Hz, 1H), 3.89 (s, 3H), 3.43 (t, J=17.6 Hz, 2H), 1.96-1.26 (m, 10H). ³¹P NMR (D₂O, 121.5 MHz): δ=16.1.

Example 124

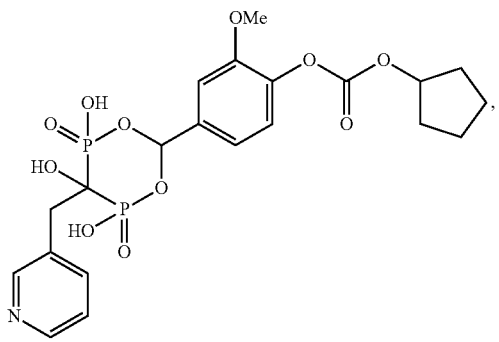 [SMILES: COc1cc(C2OP(=O)(O)C(O)(Cc3cccnc3)P(=O)(O)O2)ccc1OC(=O)OC1CCCC1]

Example 124 was synthesized following the general synthetic procedures of Example 26 starting from cyclopentyl 4-formyl-2-methoxyphenyl carbonate.

Trans isomer: Yield: 412 mg. Elemental analysis (%) calcd for C₂₁H₂₃N₁Na₂O₁₁P₂.1.2H₂O (594.98): C, 42.39; H, 4.30; N, 2.35. Found: C, 42.45; H, 4.55; N, 2.06. ESI MS (H₂O): m/z: 528 (M⁺−1). ¹H NMR (D₂O; 300 MHz): δ=8.77-6.90 (m, 7H), 6.44 (t, J=4.8 Hz, 1H), 5.20 (broad, 1H), 3.88 (s, 3H), 3.41 (t, J=16.7 Hz, 2H), 1.96-1.55 (m, 8H). ³¹P NMR (D₂O, 121.5 MHz): δ=16.2.

Example 125

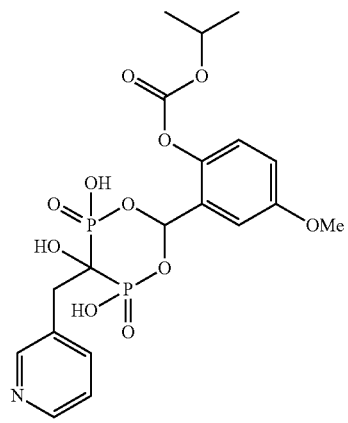 [SMILES: COc1ccc(OC(=O)OC(C)C)c(C2OP(=O)(O)C(O)(Cc3cccnc3)P(=O)(O)O2)c1]

Example 125 was synthesized following the general synthetic procedures of Example 26 starting from 2-formyl-4-methoxyphenyl isopropyl carbonate.

Yield: 150 mg; trans-isomer. Elemental analysis (%) calcd for C₁₉H₂₃NO₁₀P₂Na₂.1.0H₂O.0.3NaCl (584.89): C, 39.02; H, 4.31; N, 2.39. Found: C, 38.86; H, 4.00; N, 2.00. ¹H NMR (D₂O; 300 MHz) δ=8.36 (s, 1H), 8.03 (d, 1H), 7.82 (1H), 7.07 (m, 1H), 6.74 (d, 1H), 6.64 (d, 1H), 6.42 (m, 1H), 6.17 (t, 1H), 4.62 (m, 1H), 3.50 (s, 3H), 3.02 (t, 2H), 1.00 (d, 6H). ³¹P NMR (D₂O, 121.5 MHz): δ=15.82. ESI m/z 502 (M−1).

Example 126

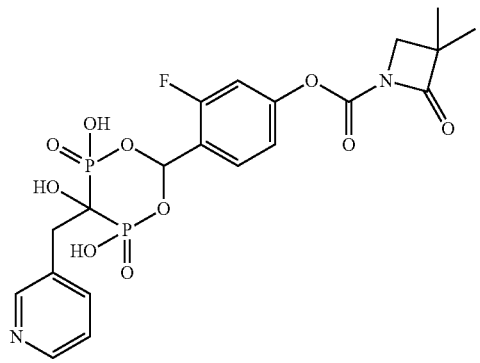 [SMILES: CC1(C)CN(C(=O)Oc2ccc(C3OP(=O)(O)C(O)(Cc4cccnc4)P(=O)(O)O3)c(F)c2)C1=O]

Example 126 was synthesized following the general synthetic procedures of Example 26 starting from 3-fluoro-4-formylphenyl 3,3-dimethyl-2-oxoazetidine-1-carboxylate.

Yield: trans-isomer, 105 mg (1.8%). Elemental analysis (%) calcd for C₂₀H₁₉F₁N₂Na₂O₁₀P₂ (574.32): C, 41.83; H, 3.33; N, 4.88. Found: C, 42.64; H, 3.69; N, 4.67. ESI MS (H₂O): m/z: 529 (M⁺−1). ¹H NMR (D₂O; 300 MHz): δ=8.73-7.06 (m, 7H), 6.68 (t, J=4.5 Hz, 1H), 3.72 (s, 2H), 3.39 (t, J=17.0 Hz, 2H), 1.41 (m, 6H). $^{31}$P NMR (D$_2$O, 121.5 MHz): δ=16.3. $^{19}$F NMR (CDCl$_3$, 282.3 MHz): δ=−116.6.

Example 127

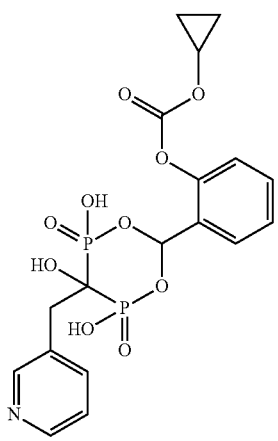 [SMILES: O=C(Oc1ccccc1C1OP(=O)(O)C(O)(Cc2cccnc2)P(=O)(O)O1)OC1CC1]

Example 127 was synthesized following the general synthetic procedures of Example 26 starting from cyclopropyl 2-formylphenyl carbonate.

Yield: trans-isomer: 98 mg (1.9%). Elemental analysis (%) calcd for C$_{18}$H$_{17}$N$_1$Na$_2$O$_{10}$P$_2$.0.3NaCl.1.0H$_2$O (550.83): C, 39.25; H, 3.48; N, 2.54. Found: C, 39.24; H, 3.56; N, 2.41. ESI MS (H$_2$O): m/z: 470 (M$^+$−1). $^1$H NMR (D$_2$O; 300 MHz): δ=8.69-7.23 (m, 8H), 6.57 (t, J=4.8 Hz, 1H), 4.26 (m, 1H), 3.38 (t, J=16.5 Hz, 2H), 0.94-0.77 (m, 4H). $^{31}$P NMR (D$_2$O, 121.5 MHz): δ=16.2.

Example 128

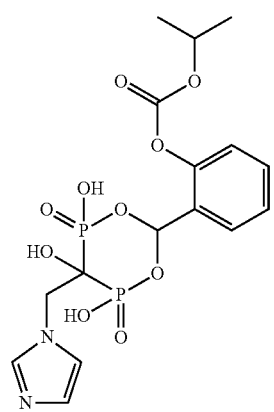 [SMILES: CC(C)OC(=O)Oc1ccccc1C1OP(=O)(O)C(O)(Cn2ccnc2)P(=O)(O)O1]

Example 128 was synthesized following the general synthetic procedures of Example 26 starting from 2-formylphenyl isopropyl carbonate.

Yield: 192 mg (3%). Elemental analysis (%) calcd for C$_{16}$H$_{18}$N$_2$Na$_2$O$_{10}$P$_2$.0.5H$_2$O (515.28): C, 37.30; H, 3.72; N, 5.44. Found: C, 37.66; H, 4.09; N, 5.19; ESI MS (H$_2$O): m/z: 461 (M$^+$−1). $^1$H NMR (D$_2$O; 300 MHz): δ=8.70-8.67 (m, 1H), 7.65-7.28 (m, 6H), 6.76-6.65 (m, 1H), 5.10-4.90 (m, 1H), 4.76-4.68 (m, 2H), 1.41-1.38 (m, 6H). $^{31}$P NMR (D$_2$O, 121.5 MHz): δ=12.67, 12.45.

Alternatively, Example 128 was synthesized according to the following synthetic procedure:

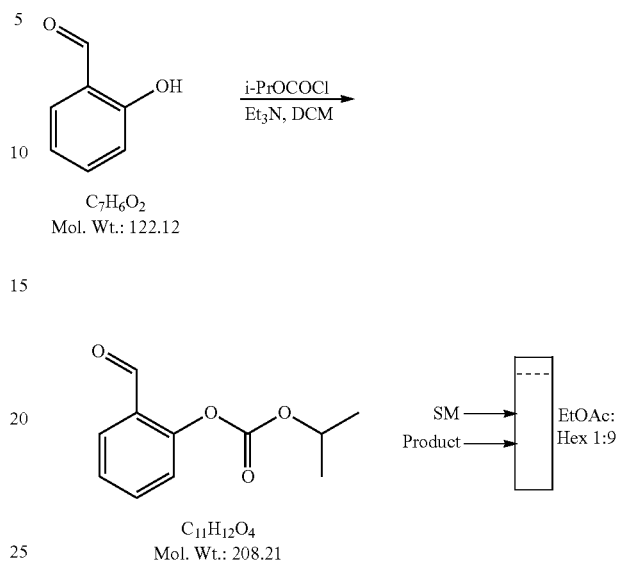

To a solution of salicylaldehyde (10.39 g, 85.08 mmol) and pyridine (7.57 mL, 1.1 eq.) in dichloromethane (40 mL) in a 250 mL round-bottom flask was added a solution of 1M isopropyl chloroformate in toluene (93.60 mL, 1.1 eq.) slowly in 20 minutes to maintain the internal temperature below −25° C. using a cold bath of dry ice/acetone. White precipitate began to form during the addition and more precipitate was seen after the addition was complete. The mixture was removed from the cold bath and stirred for 2 hours with the application of a slow increase of temperature. Subsequently, the reaction mixture was evaporated to half the volume on a rotary evaporator, diluted with ethyl acetate (50 mL), washed with ice cold water (2×100 mL), 1N NaOH (3×50 mL), ice water (2×50 mL) and cold brine (1×100 mL), dried over anhydrous MgSO$_4$ and evaporated on a rotary evaporator to produce 15.85 g (88%) of yellow oil. The carbonate (10.52 g) was distilled in high vacuum to yield 9.32 g of colorless oil (b.p. 101-103° C./0.8 torr). $^1$H NMR (300 MHz, CDCl$_3$): 810.22 (s, 1H), 7.92 (dd, J=2.1, 7.5 Hz, $^1$H), 7.68 (dt, J=2.1, 7.5 Hz, $^1$H), 7.47 (t, J=7.5 Hz, $^1$H), 7.32 (d, J=7.5 Hz, $^1$H), 5.04 (m, 1H), 1.45 (d, J=6.3 Hz, 6H).

The reaction was monitored by TLC analysis. The final step of distillation of the carbonate product is necessary to minimize moisture content therein as the synthesis of 1-tert-Butoxyformoxy-2'-isopropoxyformoxybenzylchloride below is conducted under exclusively anhydrous conditions.

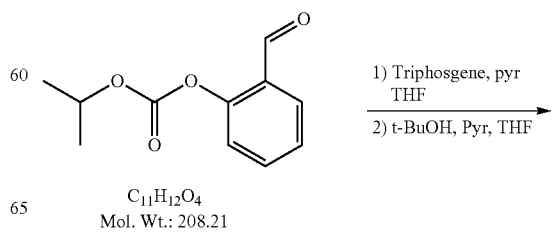

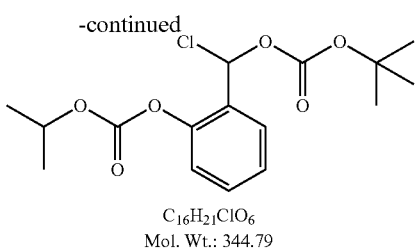

C₁₆H₂₁ClO₆
Mol. Wt.: 344.79

A 50-mL 3-neck round-bottom flask equipped with an argon line, a thermo couple and a rubber septum was charged with 2-Isopropoxyformoxy benzaldehyde (1.680 g, 8.069 mmol) and purged with vacuum-argon for 3 cycles. Freshly distilled THF (16 mL) was added followed by the addition of triphosgene (0.798 g, 1.0 eq. based on phosgene) at 3° C. and then a solution of 1.0M pyridine in THF (0.40 mL, 5 mol %). Freshly obtained triphosgene (Aldrich) was used to ensure high conversion. The mixture turned cloudy after the addition. The resultant mixture was warmed to room temperature over the course of 15 minutes and then heated at 44° C. in an oil bath for 1 hour. The mixture was cooled to −10° C. To it was added a solution of 1.6M tBuOH and 1.6M pyridine in THF (5.55 mL, 1.1 eq.) slowly to maintain the internal temperature<−7° C. The tBuOH, pyridine and THF solution was made in 1.6M concentration and dried and stored with molecular sieves under argon, which had been pre-dried in a drying oven at 145° C. in high vacuum for 2 days.

After the addition, the mixture was stirred and the temperature slowly raised to room temperature over the course of 1 hour. The solid was removed by filtration and rinsed with EtOAc:Hex (1:4). The volatiles were evaporated under reduce pressure to give 1.957 g of yellow thick oil. The intermediate was used for the next step without further purification subsequent to storing in an air moisture free environment freezer. This intermediate was relatively stable for up to 2 weeks when stored this freezer.

¹H NMR showed 3:1 ratio of the substituted benzylchloride vs. the aldehyde starting material.

iii) Drying (1-hydroxy-2-imidazol-1-yl)-ethyl-1,1-bisphosphonic acid (zoledronic acid)

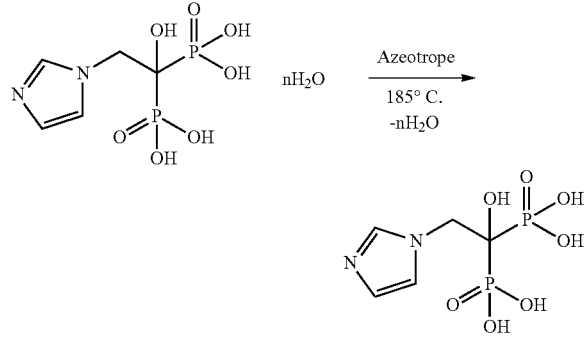

Since the supplied bisphosphonic acid contained hydrates, the water was removed by an azeotropic distillation procedure.

Zoledronic acid hydrate (24.00 g) was suspended in mesitylene (50 mL) in a 100 mL round-bottom flask equipped with a Dean-Stark trap. The suspension was heated at reflux until the distillate was free of water, which took approximately 2 hours and about 2 mL of water was collected. After cooling, the mixture was filtered and the solid was washed with hexane and dried in high vacuum overnight to produce 21.94 g of a white solid, which was stored under argon until further use.

iv) Carbonic acid isopropyl ester 2-(2,3,4-trihydroxy-3-imidazol-1-ylmethyl-2,4-dioxo-2λ⁵,4λ⁵-[1,5,2,4]dioxadiphosphinan-6-yl)-phenyl ester

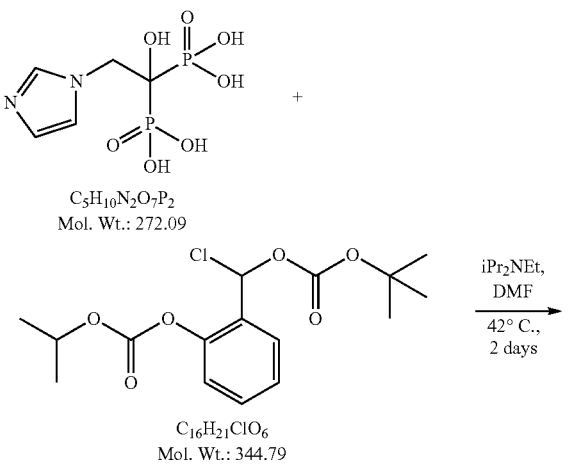

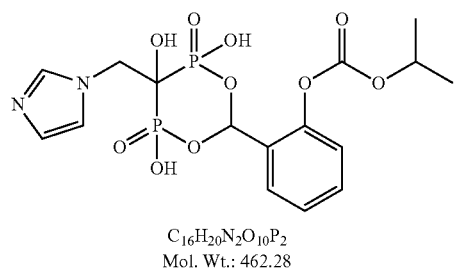

C₁₆H₂₀N₂O₁₀P₂
Mol. Wt.: 462.28

A 50-mL round bottom flask charged with zoledronic acid (1.098 g, 4.035 mmol) and EtNiPr₂ (2.81 mL, 4.0 eq.) in anhydrous DMF (25 mL) was heated at 42° C. for 15 min (during which n separation occurred) and to it was added a solution of 1-tert-butoxyformoxy-2'-isopropoxyformoxybenzylchloride (1.957 g, crude) in anhydrous DMF (10 mL). The resultant mixture was stirred and maintained at 42° C. for 24 hours as a heterogeneous suspension. A distillation head and a condenser were placed on the flask and the volatiles were distilled in high vacuum at 40° C. (oil bath). The residue was absorbed onto silica gel by mixing with MeOH (10 mL) and silica gel (15 g) followed by evaporation to dryness under high vacuum. This solid was added to a pre-packed column of silica gel (200 g) and eluded with CH₃CN:MeOH (10:0→10:1→4:1→2:1→0:10). The fractions collected were checked by TLC and MS analyses. Two poured fractions showed the product mass after evaporation under reduced pressure gave 80 mg and 170 mg, respectively.

The diacid (0.152 mg) was dissolved in CH₃CN and passed through an ion exchange resin column (containing Amberlite IR-120 (Na) ion exchange resin which had been washed with water before loading) (40 g), eluded with deionized water. The fraction with slight tan color was freeze-dried to give 64 mg of a white fluffy solid. The product showed cis/trans mixture and a strong signal in negative MS-ESI. $^{31}$P NMR (300 MHz, D$_2$O): δ13.85 (s) and 13.51 (s); MS (ESI): 461.0 (M-H$^+$).

Example 129

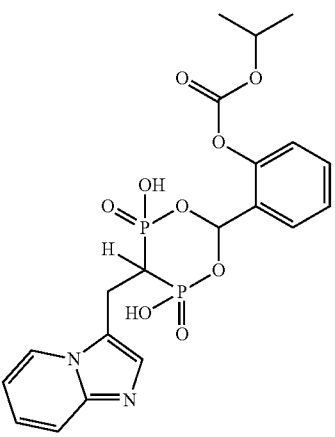 [SMILES: CC(C)OC(=O)Oc1ccccc1C1OP(=O)(O)C(Cc2cnc3ccccn23)P(=O)(O)O1]

Example 129 was synthesized following the general synthetic procedures of Example 26 starting from 2-formylphenyl isopropyl carbonate.

Yield 0.644 g (24%), white solid. $^1$H NMR (D$_2$O, δ ppm, J Hz): 8.64 (d, $^3J_{HH}$=7.2, 1H), 7.25-7.90 (m, 8H), 6.71 (t, $^3J_{HP}$=5.1, 0.5H), 6.68 (t, $^3J_{HP}$=5.1, 0.5H), 5.02 (m, 1H), 3.45-3.70 (m, 2H), 2.55-2.80 (m, 1H), 1.39 (d, $^3J_{HH}$=6.3, 3H), 1.38 (d, $^3J_{HH}$=6.3, 3H). $^{31}$P NMR (D$_2$O, δ ppm) 16.05, 15.97 (cis-isomer 84%); 15.77, 15.72 (trans-isomer 16%). LC-MS (ESI) for C$_{20}$H$_{22}$N$_2$O$_9$P$_2$ m/z 495 [M-H]$^-$. Calc. for C$_{20}$H$_{20}$N$_2$Na$_2$O$_9$P$_2$.2H$_2$O (%): C, 41.68; H, 4.20; N, 4.86. Found (%): C, 41.57; H, 4.62; N, 4.67.

Example 130

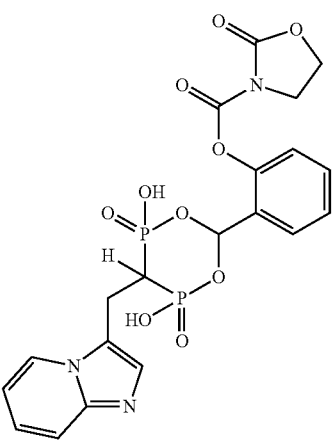 [SMILES: O=C1OCCN1C(=O)Oc1ccccc1C1OP(=O)(O)C(Cc2cnc3ccccn23)P(=O)(O)O1]

Example 130 was synthesized following the general synthetic procedures of Example 26 starting from 2-formylphenyl 2-oxooxazolidine-3-carboxylate.

Yield 0.355 g (15%), white solid. $^1$H NMR (D$_2$O, δ ppm, J Hz): 8.66 (d, $^3J_{HH}$=4.2, 1H), 7.30-7.90 (m, 8H), 6.72 (t, $^3J_{HP}$=4.2, 1H), 4.60 (t, $^3J_{HH}$=8.7, 2H), 4.39 (t, $^3J_{HH}$=8.7, 2H), 3.57 (td, $^3J_{HH}$=7.5, $^3J_{HP}$=21.3, 2H), 2.73 (m, 1H). $^{31}$P NMR (D$_2$O, δ ppm) 16.57 (cis-isomer 12%); 16.16, 16.10 (trans-isomer 88%). LC-MS (ESI) for C$_{20}$H$_{19}$N$_3$O$_{10}$P$_2$ m/z 522 [M-H]$^-$. Calc. for C$_{20}$H$_{17}$N$_3$Na$_2$O$_{10}$P$_2$.1.5H$_2$O (%): C, 40.42; H, 3.39; N, 7.07. Found (%): C, 41.03; H, 3.91; N, 6.56.

Example 131

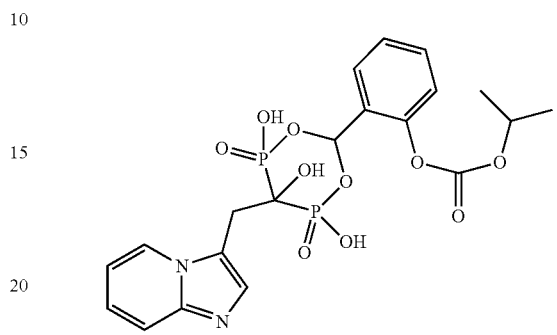

To a 500 ml dry round bottom flask were added minodronic acid (1.607 g, 4.989 mmol), carbonic acid 2-(tert-butoxycarbonyloxy-chloro-methyl)-phenyl ester isopropyl ester (3.44 g, 9.98 mmol, 2.0 eq.) and iPr$_2$Net (3.65 mL, 4.0 eq.) in anhydrous CH$_3$CN (20 mL). The mixture was stirred at 42° C. for 28 hours, at which point it turned to a homogenous brown solution. The solvent was evaporated to ½ of its volume and the remaining content was loaded to a pre-packed silica-gel column eluted with acetonitrile:water (10:0→10:1→10:2→10:3→10:4). Fractions showing product mass were combined and evaporated to ⅓ of its volume. The aqueous phase was passed through a column of Na+ ion-exchange resin and the eluent was lyophilized to give 0.826 g of the sodium salt. The solid was mixed with MeOH and stirred at room temperature for 2 hours. The suspension was centrifuged and an off-white solid 131 (0.219 g) remained. $^{31}$P NMR: 15.57 (s), 15.48 (s) (mixture of cis/trans isomers). LC-MS (ESI): 511.2 (M–Na$^+$).

Section 3. Conversion of Bisphosphonate Cyclic Acetals to Bisphosphonates After Intravenous (IV) Administration of Cyclic Acetals and Exposure of Bisphosphonate after Oral Administration of a Bisphosphonate Cyclic Acetal in Fasted and Fed Rats Male, Sprague-Dawley, rats weighing approximately 200-400 g were studied.

Formulations:

All formulations were prepared within approximately 1 hour of dosing.

Oral (PO) and Intraduodenal (ID) Dosing:

The appropriate test article formulation was administered to each animal as a 17 micromole/kg, 2 mL/kg dose solution in 0.6% methylcellulose/0.2% Tween 80® by oral gavage. Alternatively, animals were dosed with a 17 micromole/kg, 1 mL/kg dose solution in saline through a cannula into the duodenum. Animals in the fasted groups were fasted for approximately 4 hours after dosing and were returned to ad libitum access to food thereafter. Animals in the fed groups had access to food ad libitum for at least 2 hours prior to dosing, and throughout the day post dose.

IV Dosing:

Generally, animals were administered a 1.7 micromole/kg, 2 ml/kg IV dose (tail vein) of the appropriate formulation using a syringe and attached butterfly needle. All animals remained fasted for an additional 4 hours post dose and were returned to ad libitum access to food thereafter.

Urine Sample Collection:

Urine samples were collected into refrigerated plastic conical tubes at approximately 4, 8 and 24 hours post-dose. At the end of each collection period, samples were weighed and transferred to a −70° C. freezer for storage until analyzed.

Conversion of Risedronate Cyclic Acetal to Risedronate after IV Administration:

The absorbed risedronate is stable in vivo and is not metabolized. After IV administration of risedronate to rats, about 60% of risedronate binds to bone and about 40% of risedronate dosed is excreted in urine. When risedronate cyclic acetal compounds are administered intravenously to rats, a percentage of the cyclic acetal can remain intact and can be excreted in urine while a percentage of the cyclic acetal can be converted to risedronate in vivo. Assuming risedronate formed in vivo has the similar tissue distribution profile as described above, about 40% of risedronate generated in vivo will be excreted in urine and about 60% of risedronate generated in vivo will bind to bone. Thus, the percentage of the cyclic acetal which is converted to risedronate in vivo is estimated using Formula A:

$$\text{Amount (\%) Risedronate converted from Risedronate Cyclic Acetal} = \frac{\text{Amount of Risedronate recovered in urine}/0.4}{\text{Amount of Risedronate Cyclic Acetal dose}} \times 100\%$$

Formula A

Risedronate cyclic acetal compounds were administered intravenously in saline (0.9% sodium chloride). The amounts (percentage) of the cyclic acetal compounds converted to risedronate were calculated and are summarized in Table 1.

For example, when Example 82 was dosed in rats, 50% of the dosed cyclic acetal was recovered, and 43% of the dosed cyclic acetal was converted to risedronate (calculated using Formula A). In some cases, for example with Example 29, the percentage of cyclic acetal converted to risedronate was calculated to be more that 100%. While this may be caused by an inaccuracy in measuring small quantities of the compound in the samples, it, nonetheless, shows complete or nearly complete conversion to risedronate.

As summarized in Table 1, exemplary cyclic acetal compounds exhibited the spectrum (slow to fast) of conversion rates from risedronate cyclic acetal to risedronate in vivo after IV administration of the cyclic acetal compounds to rats. For example, dosing Examples 28, 29, 30, 33, 105, 47, 63, 79, and 83 in rats resulted in very low urinary recovery of the cyclic acetal, demonstrating rapid rate of conversion of the cyclic acetals to risedronate in vivo, i.e., conversion quickly to risedronate. In comparison, dosing Examples 32, 40, 45, and 82 in rats resulted in significant amounts of cyclic acetal recovery (about 50% or more of the cyclic acetal compounds were recovered after dosing) indicating relatively slow rates of systemic conversion of the cyclic acetal to risedronate. Examples 36, 50 and 62 (trans) demonstrated both systemic exposure of the cyclic acetal and risedronate suggesting both stability of the cyclic acetal and conversion to risedronate in vivo.

TABLE 1

Risedronate Cyclic Acetal Urinary Recovery and Amount Converted to Risedronate after IV Administration of Risedronate Cyclic Acetals to Rats

| Compound Administered[a] | Amount of Cyclic Acetal Excreted[b] | Amount Converted to Risedronate[c] |
|---|---|---|
| Example 28 | 0 | 106 (15)[d] |
| Example 29 (trans) | 1.0 (41) | 50 (13) |
| Example 30 | 0.1 (82) | 98 (52) |
| Example 32 (trans) | 77 (13) | 7.1 (7.0) |
| Example 33 (trans) | 0 | 84 (5.6) |
| Example 105 (trans) | 5.7 (52) | 81 (30) |
| Example 29 (cis) | 3.6 (37) | 130 (43) |
| Example 36 | 27 (17) | 69 (7.0) |
| Example 39 | 30 (28) | 12 (12) |
| Example 40 | 79 (10) | 4.0 (32) |
| Example 43 (mixture of cis/trans isomers) | 16 (19) | 72 (27) |
| Example 45 (mixture of cis/trans isomers) | 67 (6.6) | 9.3 (35) |
| Example 47 | 4.8 (27) | 16 (29) |
| Example 50 (trans) | 45 (9) | 76 (16) |
| Example 54 | 11 (26) | 42 (14) |
| Example 62 (trans) | 16 (17) 10(22) 13 | 80 (5.5) 75 (12) 87 |
| Example 63 (trans) | 3.3 (57) | 33 (26) |
| Example 70 | 22 (22) | 75 (37) |
| Example 75 | 48 (20) | 56 (31) |
| Example 79 (trans) | 0.3 (220) | 43 (27) |
| Example 81 | 25 (54) | 50 (24) |
| Example 82 | 50 (10) | 43 (10) |
| Example 83 | 2.3 (114) | 55 (16) |
| Example 96 | 16 (15) | 25 (27) |
| Example 98 | 31 (47) | 44 (68) |

[a]dose = 1.7 micromole/kg;
[b]values are % of administered dose excreted in urine;
[c]values are % dose converted from cyclic acetal as per Formula A;
[d]Coefficient of variation (% CV).

TABLE 2

Bisphosphonate Cyclic Acetal Urinary Recovery and Amount Converted to Bisphosphonate after IV Administration of Bisphosphonate Cyclic Acetals to Rats

| Bisphosphonate | Compound Administered[a] | Amount of Cyclic Acetal Excreted[b] | Amount Converted to Bisphosphonate[c] |
|---|---|---|---|
| Risedronate | Example 62 (trans) | 16 (17)[e] 10 (22) 13 | 80 (5.5) 75 (12) 87 |
| Unnamed | Example 129 | 7.1 | 17.5 |
| Zoledronate | Example 128 | 51.2 | 0 |

[a]dose = 1.7 micromole/kg;
[b]values are % of administered dose excreted in urine;
[c]values are % dose converted from cyclic acetal as per Formula A;
[e]Coefficient of variation (% CV).

In the experiment described above, risedronate urinary excretion data revealed a slower risedronate release rate into the bloodstream from Example 62 (trans) than from risedronate. After Example 62 (trans) administration, risedronate urinary excretion was significantly higher at later urine collection times (i.e., 4-8 or 8-24 hours) than after risedronate administration, see Table 3 and FIG. 1.

TABLE 3

Urinary recovery of Cyclic Acetal and
Risedronate after IV dosing in Rats

| Compound administered[a] | Compound measured | Amount excreted (nmol) by collection time | | |
|---|---|---|---|---|
| | | 0-4 hours | 4-8 hours | 8-24 hours |
| Example 62 (trans) | Risedronate | 105.6 | 23.3 | 33.2 |
| | Example 62 (trans) | 58.1 | 1.3 | 0.74 |
| Risedronate | Risedronate | 170.2 | 11.6 | 14.3 |

[a]dose = 1.7 micromole/kg.

Exposure of Risedronate after Oral Administration of Risedronate Cyclic Acetal

Example 62 (trans) and risedronate were administered via intraduodenal (ID) and oral administration to fasted and fed rats. Similar to the procedure described above in relation to the IV study, the urine of the rats was collected, and risedronate was recovered from urine. Risedronate exposure following ID and oral administration was calculated as percentage of the recovered risedronate from the dosed cyclic acetal (Formula A), and the results were compared to that from dosing with risedronate, See Table 4.

Administration of risedronate orally to fasted rats generally results in risedronate exposure of less than 1% of dose as estimated by urinary recovery. Administration with food (i.e., fed rats) causes an extensive reduction of risedronate exposure as compared to fasted rats.

ID administration of Example 62 (trans) to fed rats resulted in greater risedronate exposure (as percentage of the dose) than when risedronate was administered ID to fed rats. Thus, Example 62 (trans) was less susceptible to the food effect than risedronate.

Therefore, these experimental results suggest that oral administration of bisphosphonate cyclic acetal compounds results in improved bisphosphonate exposure under fed conditions.

TABLE 4

Summary of Urinary recovery of Cyclic Acetal and Risedronate after
IV, Intraduodenal (ID) and Oral (PO) (fasted and fed) dosing to Rats

| Compound Administered | Amount Excreted | IV[a] | ID[b] fasted | ID[b] fed | Oral[b] fast | Oral[b] fed |
|---|---|---|---|---|---|---|
| Risedronate | Risedronate[c] | 39<br>36 (13) | 0.49 (23)[e]<br>0.57 (4.5)<br>0.28 (29) | 0.012 (50) | 0.13 | 0.003 |
| Example 62 (trans) | Example 62[c] (trans) | 16 (17)<br>10 (22)<br>13 | 0.046 (118)<br>0.092 (36) | 0.028 (26)<br>0.33[f] (25) | 0.002 | 0.016 |
| | Risedronate[d] | 80 (5.5)<br>75 (12)<br>87 | 0.25 (44)<br>0.34 (14) | 0.07 (24)<br>0.53[f] (21) | 0.07 | 0.022 |

[a]dose = 1.7 micromole/kg;
[b]dose = 17 micromole/kg;
[c]values are % of administered dose excreted in urine;
[d]values are % dose converted from cyclic acetal as per Formula A;
[e]Coefficient of variation (% CV);
[f](dose = 85 micromole/kg.

Section 4. Bone Density Study of Risedronate and Risedronate Cyclic Acetal in Rats.

The effect of the compounds (Example 62 (trans) and Example 128) on in vivo bone resorption inhibition and mineralization inhibition was evaluated in the Schenk Model, an animal model system known in the field of bone metabolism. The general principles of this model are disclosed in Shinoda et al., *Calcif. Tissue Int.*, 35: 87-99 (1983); and in Schenk et al., *Calcif. Tissue Res.* 11: 196-214 (1973).

Male Sprague Dawley rats approximately 6 weeks old with weights ranging between 120 and 150 grams were placed into groups based on body weight, with 4-8 animals per group. All groups received treatment by subcutaneous injection (SQ) once daily for 7 days.

On day 7 after the start of dosing, all animals were euthanized via exsanguination under gas anesthesia and/or $CO_2$. The right tibia and femur were dissected free and placed in 70% ethyl alcohol.

The proximal metaphysis of the right tibia was analyzed using dual energy x-ray absorptiometry (DXA). This provides information on changes in both cortical and cancellous bone density. The primary end-point for this study was bone mineral density (BMD) in the tibia measured using Hologics QDR-4500 densitometer (Hologics, Inc). Statistical evaluation of data was made using parametric and non-parametric analysis of variance and Fisher's protected t-test to determine a statistically significant effect compared to control animals, defined as the lowest effective (significant anti-resorptive) dose (LED).

The dose which increased (BMD) 20% compared to the vehicle group (D20) was calculated via a logistic dose response relationship, which estimates an efficacy value using all animals in the study (Lundy et al., *J. Bone Min. Res.* 22 (Suppl. 1): S443, (2007)).

TABLE 5

Summary of efficacy parameters as estimated in the Schenk Model

| Compound | LED (mcg P/kg) | D20 (mcg P/kg) 20% > BMD than control |
|---|---|---|
| Risedronate | 1 | 1.8 |
| Example 62 (trans) | 3 | 5 |
| Zoledronic acid | 0.1 | 0.1 |
| Example 128 | 1 | 0.5 |

As confirmed in the Schenk Model, all four compounds increased bone density in the rat proximal tibial metaphysis. The fact that Example 62 (trans) and Example 128 were efficacious provides evidence that the active bisphosphonate was released into the blood prior to urinary excretion.

When ranges are used herein for physical properties, such as molecular weight, or chemical properties, such as chemical formulae, all combinations and subcombinations of ranges of specific embodiments therein are intended to be included.

The disclosure of each patent, patent application, and publication cited or described in this document are hereby incorporated herein by reference, in their entirety.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only a few variations of the present invention are exemplified herein, it is to be understood that the practice of such additional modifications and variations and the equivalents thereof, are within the spirit and scope of the invention as defined in the following claims.

We claim:

1. A method of treating osteoporosis, rheumatoid arthritis, osteoarthritis, Paget's disease, or alveolar bone loss comprising administering an effective amount of a compound of Formula I,

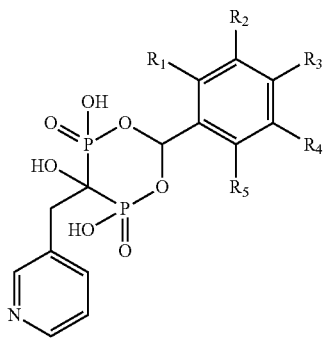

(I)

or a pharmaceutically acceptable salt thereof to a patient in need of such treatment, wherein $R_1$, $R_2$, $R_3$, $R_4$ and $R_5$ are each independently
a) hydrogen;
b) halogen, —CN, —$CF_3$, or —$NO_2$;
c) $C_1$-$C_8$ alkyl or $C_1$-$C_8$ haloalkyl;
d) $C_2$-$C_8$ alkenyl or $C_2$-$C_8$ haloalkenyl;
e) $C_2$-$C_8$ alkynyl or $C_2$-$C_8$ haloalkynyl;
f) optionally substituted aryl or optionally substituted heteroaryl;
g) —C(O)$R_6$;
h) —C(O)O$R_6$, or —$CO_2R_6$;
i) —$OR_6$, —O-L-OC(O)$R_6$, or —O-L-OC(O)O$R_6$;
j) —OC(O)$R_6$, or —OC(O)-L-OC(O)$R_6$;
k) —OC(O)O$R_6$, —OC(O)O-L-C(O)$R_7$, —OC(O)O-L-C(O)O$R_7$, or -L-OC(O)$R_6$;
l) —C(O)N$R_6R_7$, or —CN$R_6R_7$;
m) —OC(O)N$R_6R_7$, —OC(O)N($R_6$)-L-OC(O)$R_7$, —OC(O)O-L-($R_6$)-L-C(O)$R_7$, —OC(O)—C($R_6$)($R_7$)-L-OC(O)$R_8$, —OC(O)N(-L-OC(O)$R_7$)(-L-OC(O)$R_8$);
n) —$SR_6$, or —$NR_6R_7$;
o) —$NR_6$C(O)$R_7$;
p) —$NR_6$C(O)O$R_7$;
q) —$NR_6$C(O)$NR_7$;
r) —OS$O_2R_6$;
s) —S$O_2OR_6$;
t) —S$O_2R_6$;
u) —$NR_6$S$O_2R_7$;
v) —S$O_2NR_6R_7$;

w) 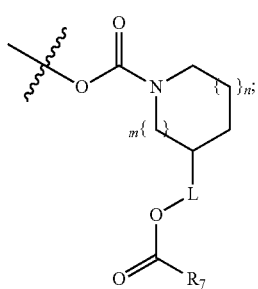

x) 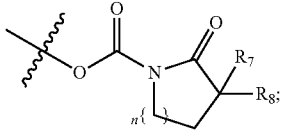

y) 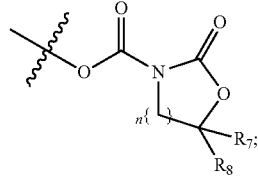

z) 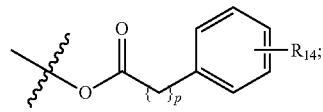

aa) 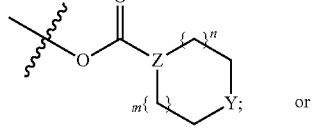

bb) $R_1$ and $R_2$, $R_2$ and $R_3$, $R_3$ and $R_4$, or $R_4$ and $R_5$ taken together form an optionally substituted 4- to 8-membered carbocyclic or heterocyclic ring, wherein the ring is saturated, unsaturated or aromatic;

wherein m and n are each independently an integer from 0 to 2;
Y is —$CH_2$—, —O—, —$NR_7$—, or —S—;
p is an integer from 1 to 3;
$R_{14}$ is hydrogen, halogen, $C_1$-$C_8$ alkyl, or $C_1$-$C_8$ alkoxyl;
Z is

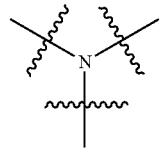 [SMILES: *N(*)*]

or

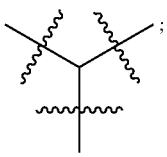 [SMILES: *C(*)*]

each $R_6$ is independently hydrogen, $C_1$-$C_8$ alkyl, $C_1$-$C_8$ haloalkyl, $C_2$-$C_8$ alkenyl, $C_2$-$C_8$ haloalkenyl, $C_2$-$C_8$ alkynyl, $C_2$-$C_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

$R_7$ and $R_8$ are each independently hydrogen or $C_1$-$C_8$ alkyl; and L is $C_1$-$C_8$ alkyl; or $R_6$ and $R_7$ taken together form an optionally substituted 4- to 8-membered carbocyclic or heterocyclic ring, wherein the ring is saturated, unsaturated or aromatic.

2. The method of claim 1, wherein $R_1$, $R_2$, $R_3$, $R_4$, and $R_5$ are each independently hydrogen, halogen, —CF$_3$, C$_1$-C$_8$ alkyl, optionally substituted phenyl, —OR$_6$, —O-L-OC(O)R$_6$, —O-L-OC(O)OR$_6$, —OC(O)R$_6$, —OC(O)-L—OC(O)R$_6$, —C(O)OR$_6$, —OC(O)OR$_6$, —OC(O)O-L-C(O)R$_7$, —OC(O)NR$_6$R$_7$, —OC(O)N(R$_6$)-L-OC(O)R$_7$, —OC(O)N(-L-OC(O)R$_7$)(-L-OC(O)R$_8$),

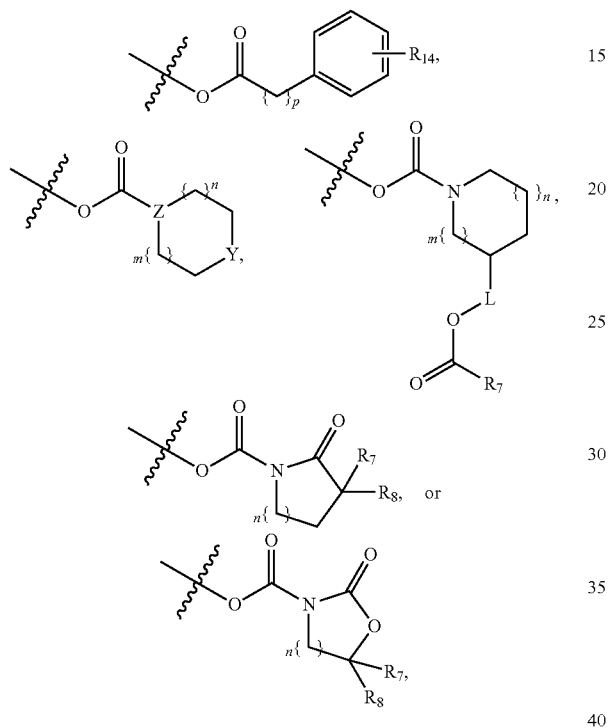

wherein Y is —CH$_2$—, —O—, —NR$_7$—, or —S—;
p is an integer from 1 to 3;
$R_{14}$ is hydrogen, halogen, C$_1$-C$_8$ alkyl, or C$_1$-C$_8$ alkoxyl; and
Z is

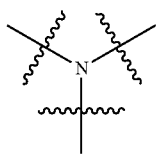 [SMILES: *N(*)*]

or

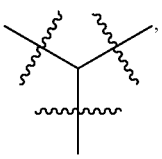 [SMILES: *C(*)*]

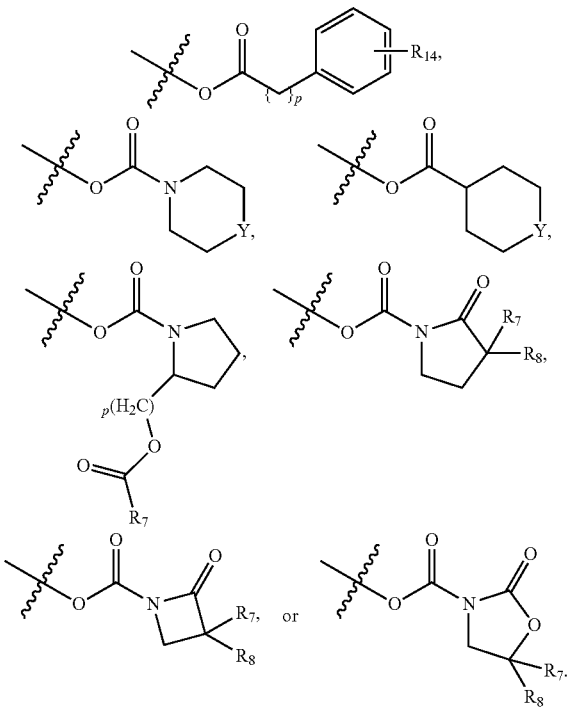

3. The method of claim 1, wherein one of $R_1$, $R_2$, $R_3$, $R_4$, and $R_5$ is —OR$_6$, —O-L-OC(O)R$_6$, —O-L—OC(O)OR$_6$, —OC(O)R$_6$, —OC(O)-L-OC(O)R$_6$, —OC(O)OR$_6$, —OC(O)O-L-C(O)R$_7$, —OC(O)NR$_6$R$_7$, —OC(O)N(R$_6$)-L-OC(O)R$_7$, —OC(O)N(-L-OC(O)R$_7$)(-L-OC(O)R$_8$),

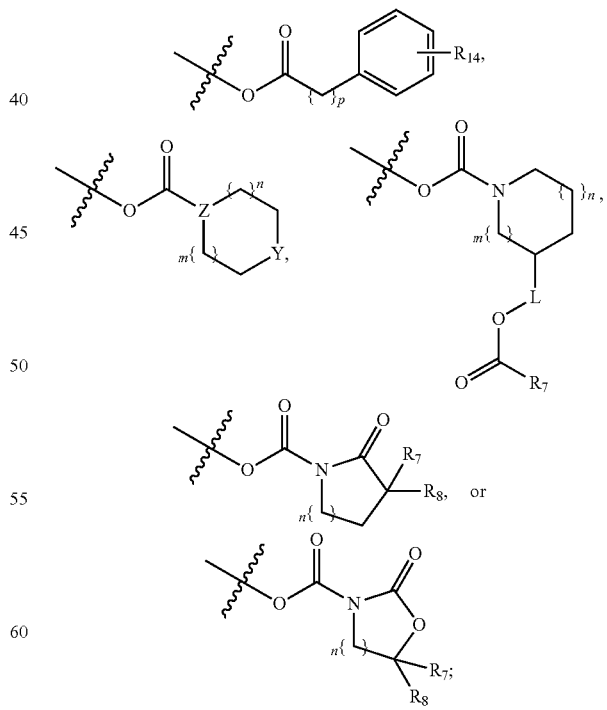

any two of the remaining $R_1$, $R_2$, $R_3$, $R_4$, and $R_5$ are halogen; and each of the remaining R-groups of $R_1$, $R_2$, $R_3$, $R_4$, and $R_5$ are hydrogen.

4. The method of claim 1, wherein one of $R_1$, $R_2$, $R_3$, $R_4$, and $R_5$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

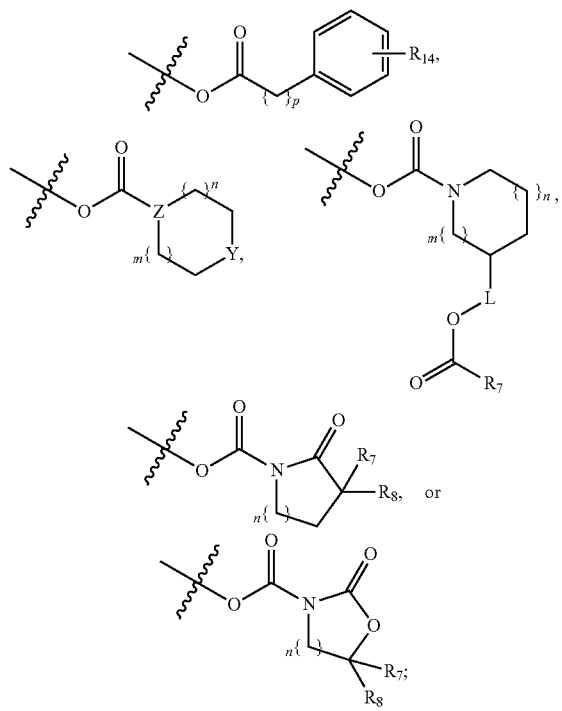

one of the remaining R-groups of $R_1$, $R_2$, $R_3$, $R_4$, and $R_5$ is halogen, —$CF_3$, $C_1$-$C_8$ alkyl, phenyl, —$OR_6$, or —C(O)$OR_6$; and each remaining R-group of $R_1$, $R_2$, $R_3$, $R_4$, and $R_5$ is hydrogen.

5. The method of claim 1, wherein one of $R_1$, $R_2$, $R_3$, $R_4$, and $R_5$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

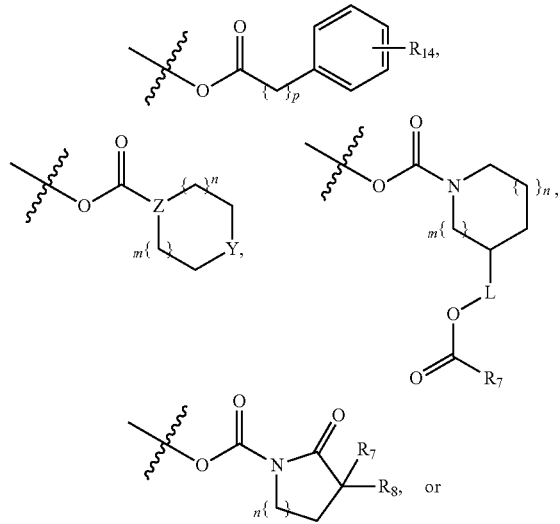

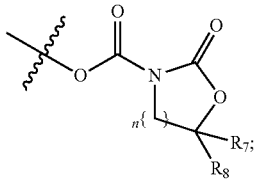

and the remaining R-groups of $R_1$, $R_2$, $R_3$, $R_4$, and $R_5$ are each hydrogen.

6. The method of claim 1, wherein $R_1$ and $R_5$ are each independently halogen; and $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)NR—OC(O)$R_7$)(-L-OC(O)$R_8$),

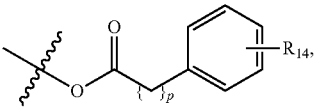

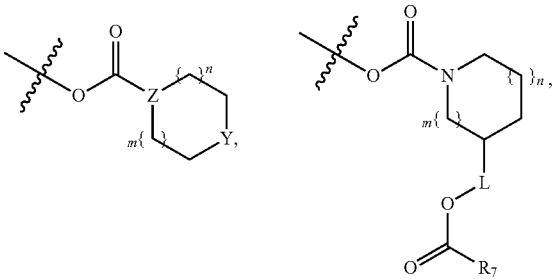

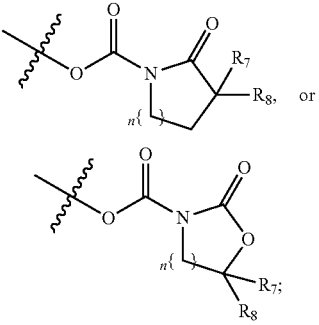

and the remaining R-groups of $R_1$, $R_2$, $R_3$, $R_4$, and $R_5$ are each hydrogen.

7. The method of claim 1, wherein $R_1$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)N$R_6R_7$, —OC(O)N($R_6$)-L-OC(O)$R_7$, —OC(O)N(-L-OC(O)$R_7$)(-L-OC(O)$R_8$),

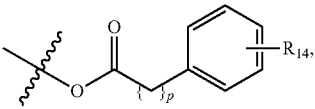

-continued

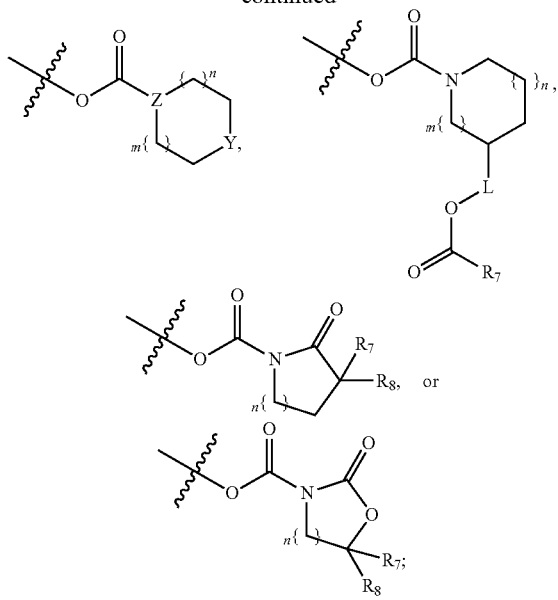

one of the remaining R-groups of $R_1$, $R_2$, $R_3$, $R_4$, and $R_5$ is halogen, —$CF_3$, $C_1$-$C_8$ alkyl, phenyl, —$OR_6$, or —$C(O)OR_6$; and each remaining R-group of $R_1$, $R_2$, $R_3$, $R_4$, and $R_5$ is hydrogen.

8. The method of claim 1, wherein $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)NR_6R_7$, —OC(O)N($R_6$)-L-OC(O)$R_7$, —OC(O)N(-L-OC(O)$R_7$)(-L-OC(O)$R_8$),

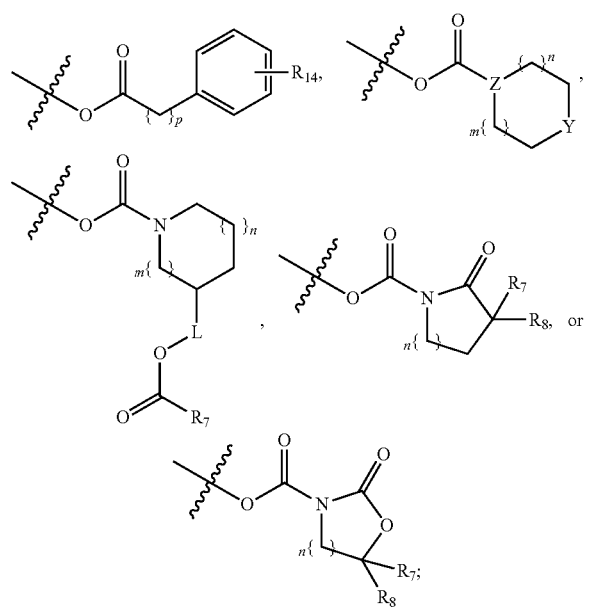

one of the remaining R-groups of $R_1$, $R_2$, $R_3$, $R_4$, and $R_5$ is halogen, —$CF_3$, $C_1$-$C_8$ alkyl, phenyl, —$OR_6$, or —$C(O)OR_6$; and each remaining R-group of $R_1$, $R_2$, $R_3$, $R_4$, and $R_5$ is hydrogen.

9. The method of claim 1, wherein $R_1$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)NR_6R_7$, —OC(O)N($R_6$)-L-OC(O)$R_7$, —OC(O)N(-L-OC(O)$R_7$)(-L-OC(O)$R_8$), and $R_2$, $R_3$, $R_4$, and $R_5$ are each hydrogen.

10. The method of claim 1, wherein $R_3$ is —$OR_6$, —O-L-OC(O)$R_6$, —O-L—OC(O)O$R_6$, —OC(O)$R_6$, —OC(O)-L-OC(O)$R_6$, —OC(O)O$R_6$, —OC(O)O-L-C(O)$R_7$, —OC(O)NR_6R_7$, —OC(O)N($R_6$)-L-OC(O)$R_7$, —OC(O)N(-L-OC(O)$R_7$)(-L-OC(O)$R_8$), and $R_1$, $R_2$, $R_4$, and $R_5$ are each hydrogen.

11. The method of claim 1, wherein the compound is:
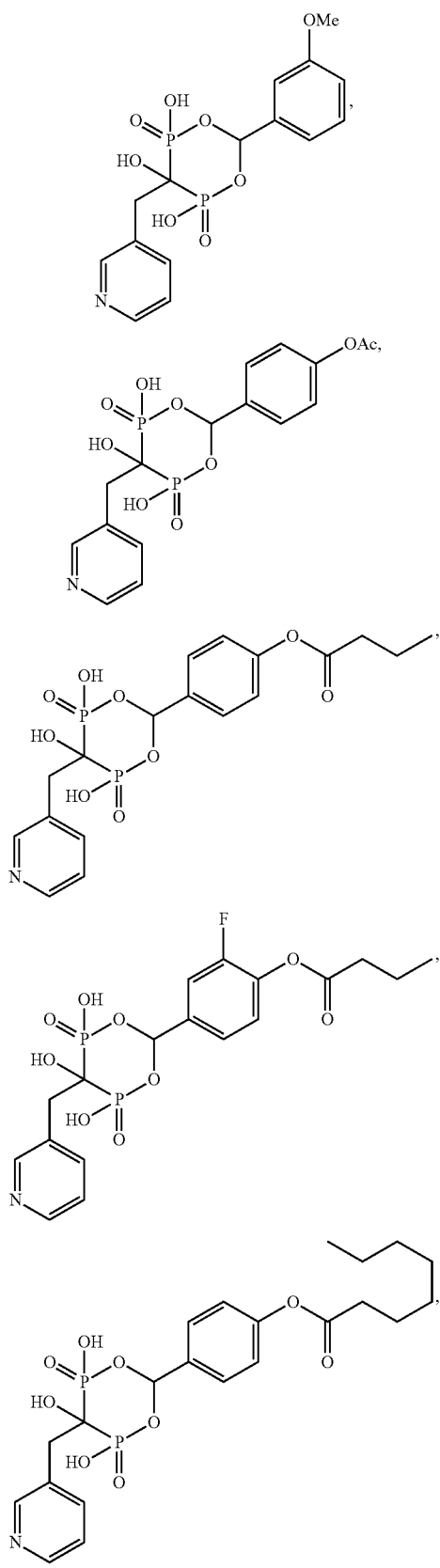
-continued
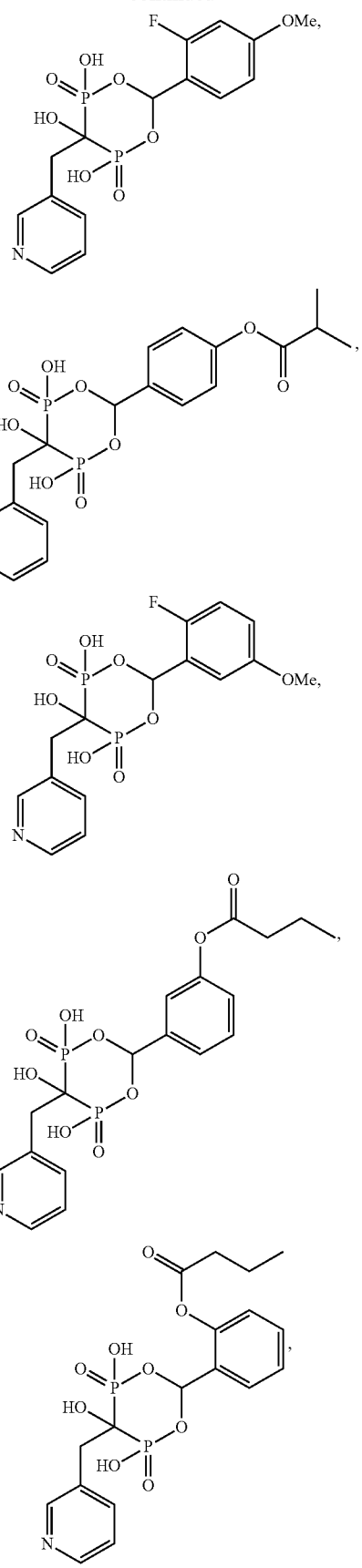

-continued
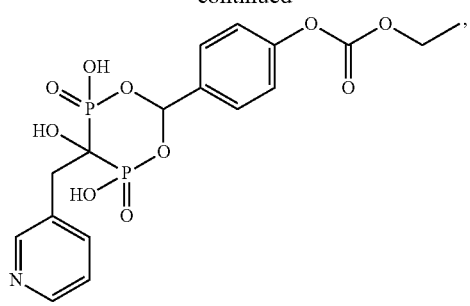
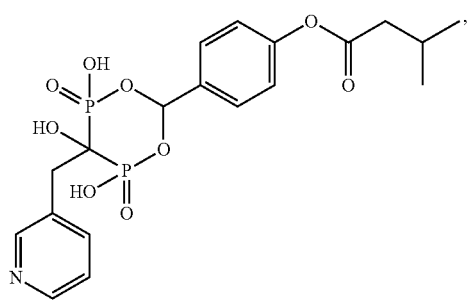
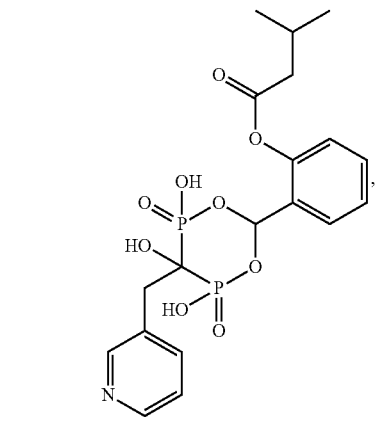
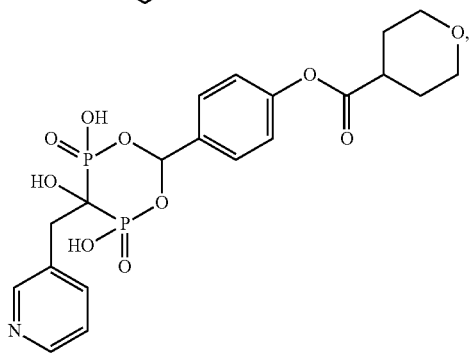
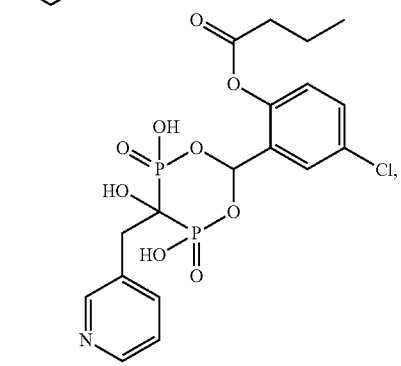
-continued
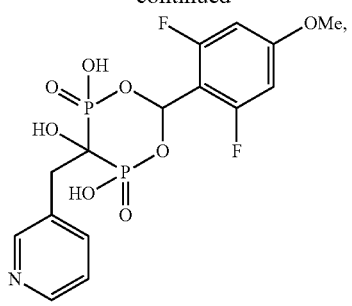
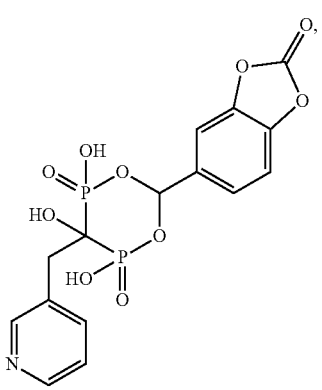
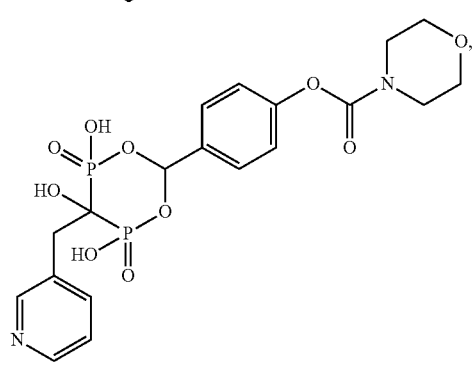
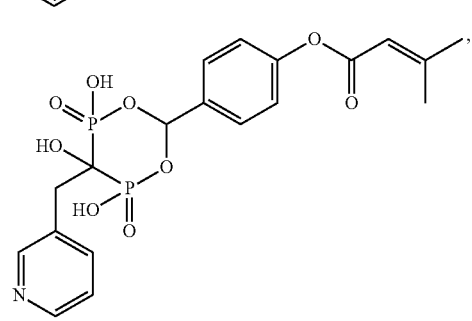
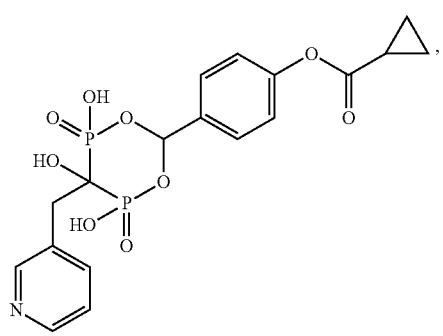

211
-continued
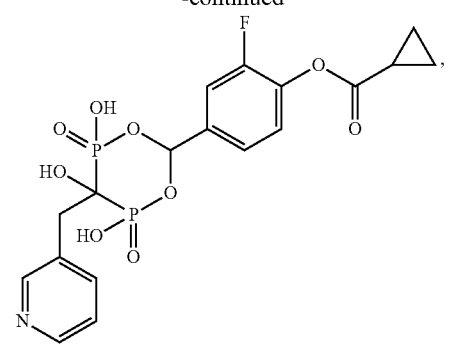
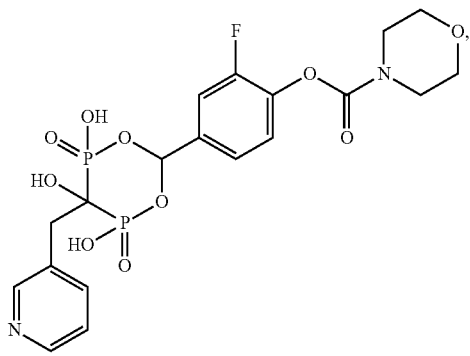
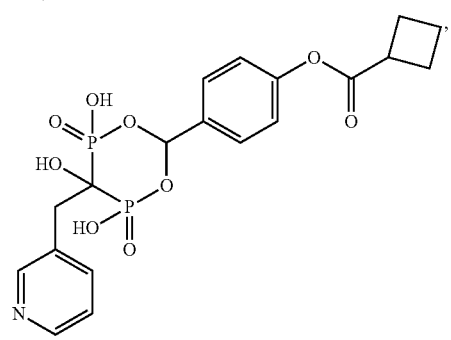
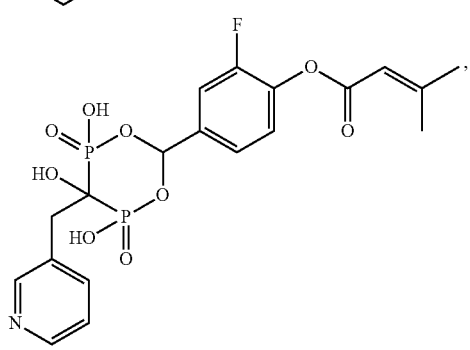
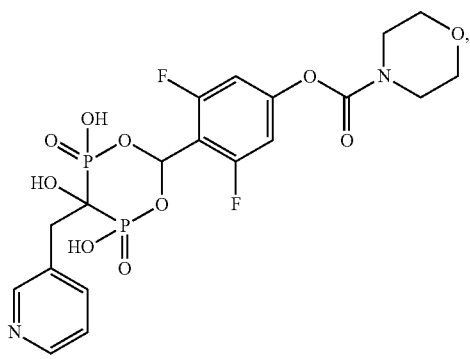
212
-continued
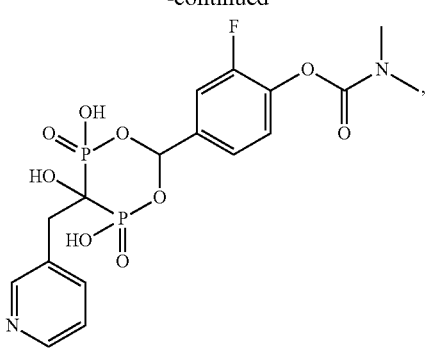
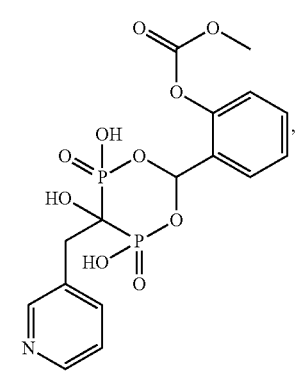
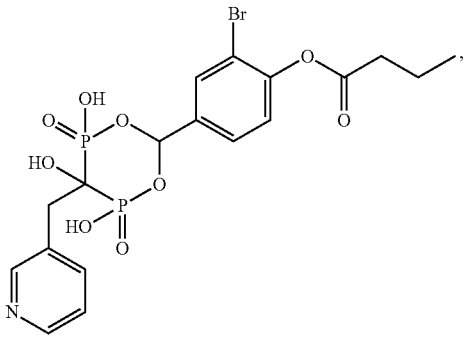
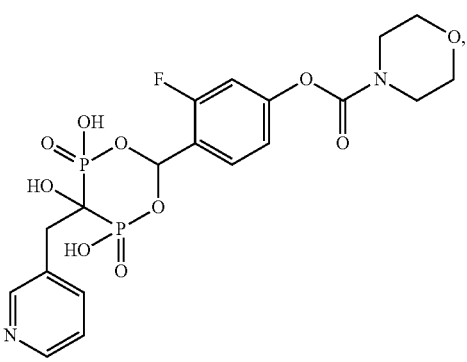

213
-continued
214
-continued
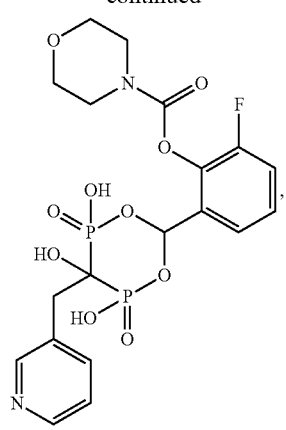
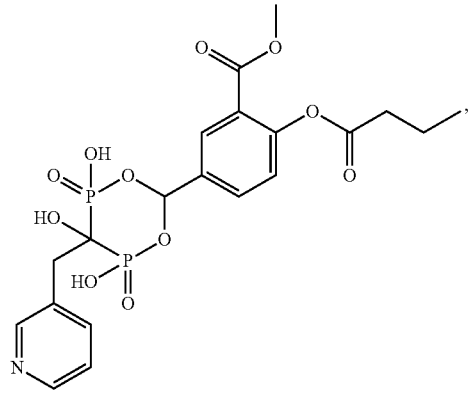
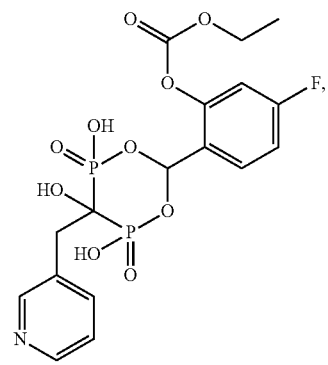
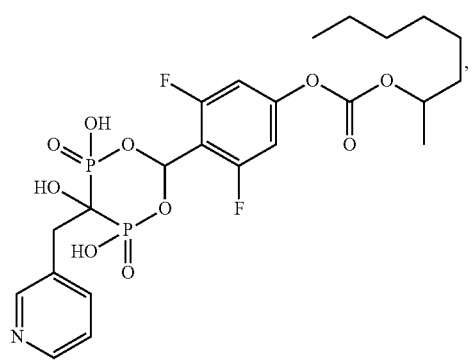
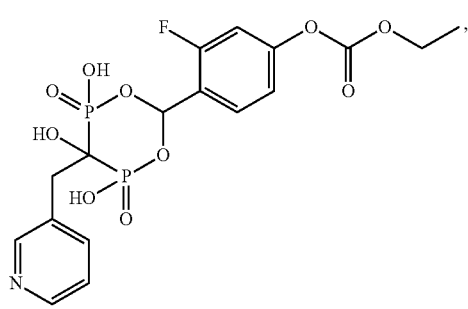
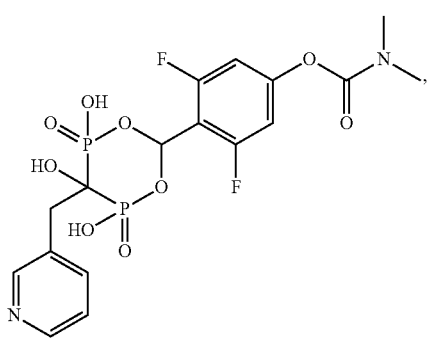
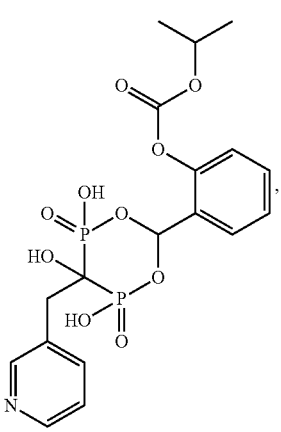

215
-continued
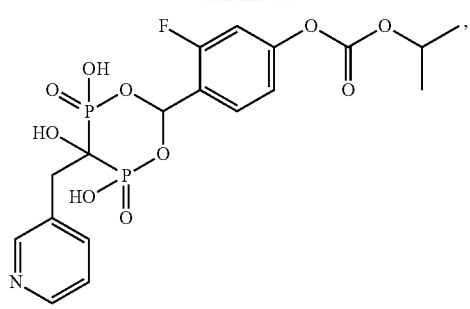
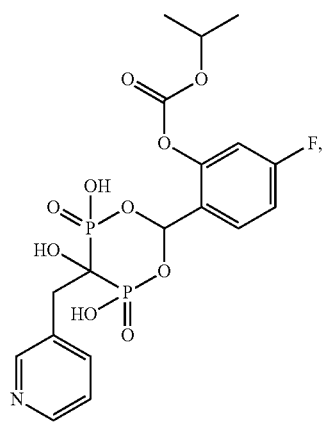
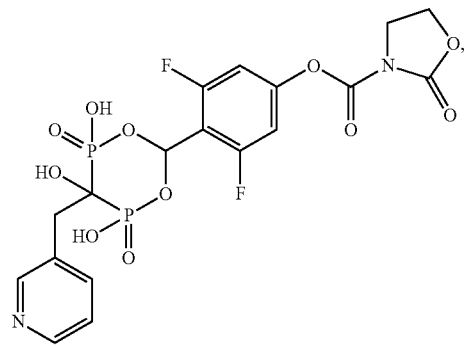
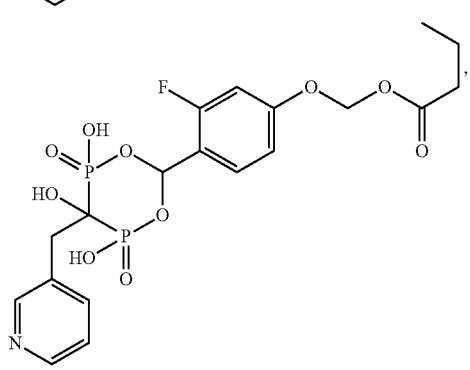
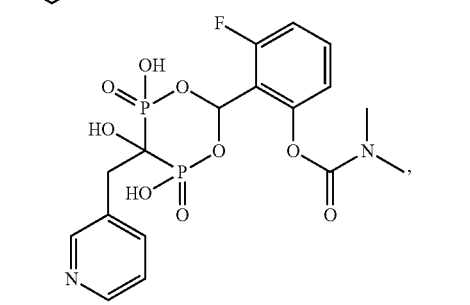
216
-continued
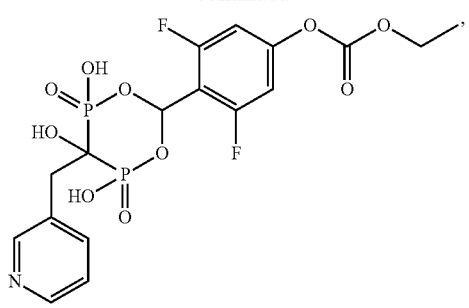
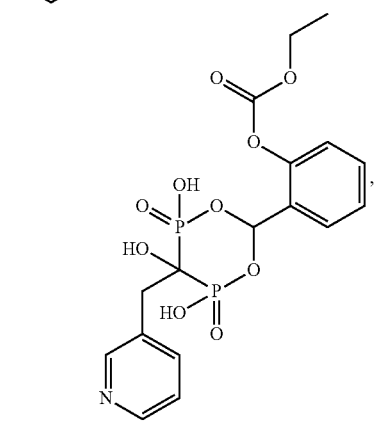
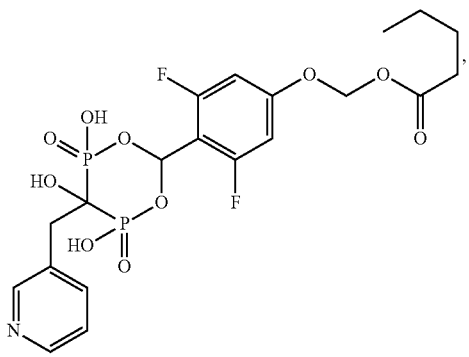
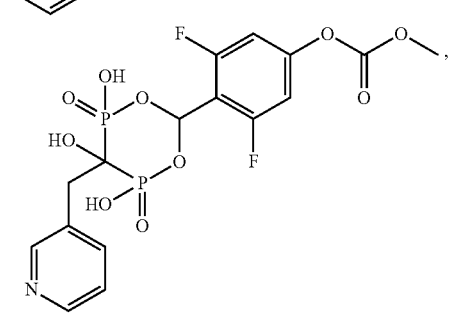
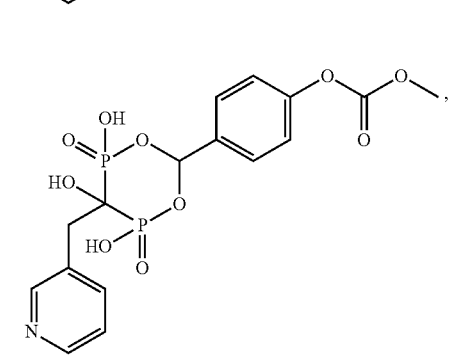

217
-continued
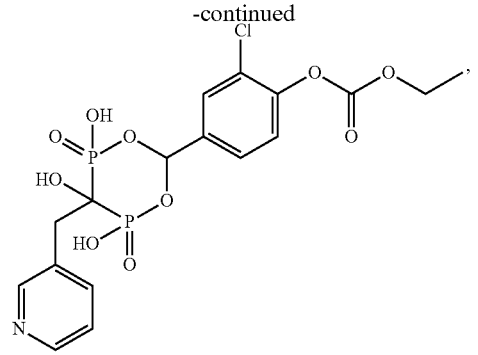
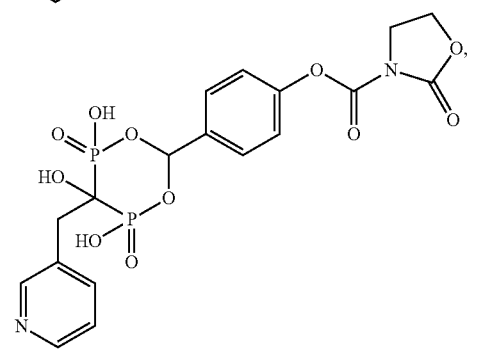
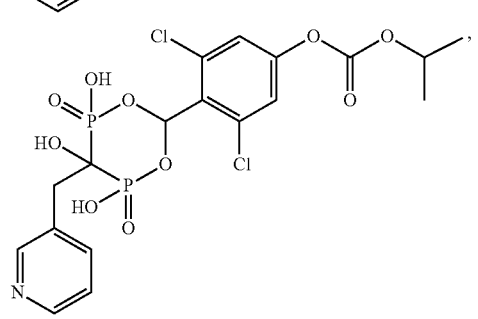
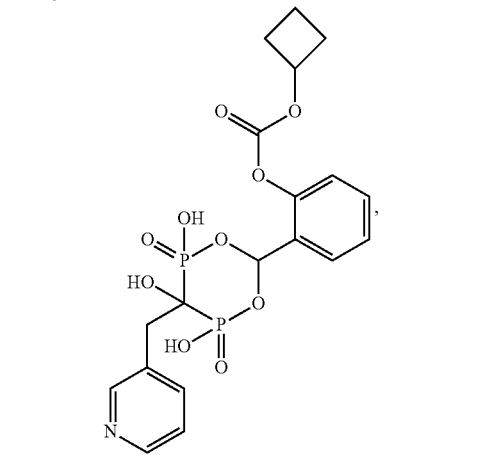
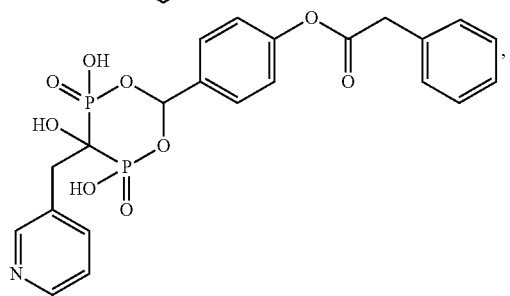
218
-continued
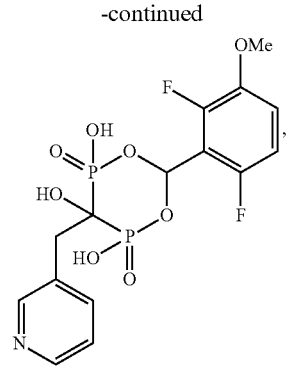
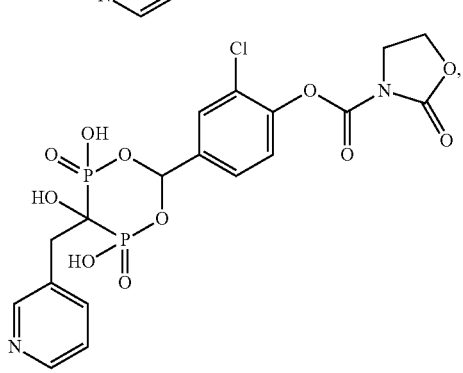
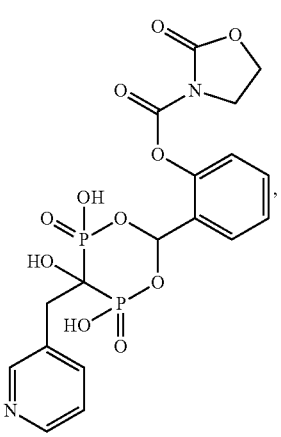
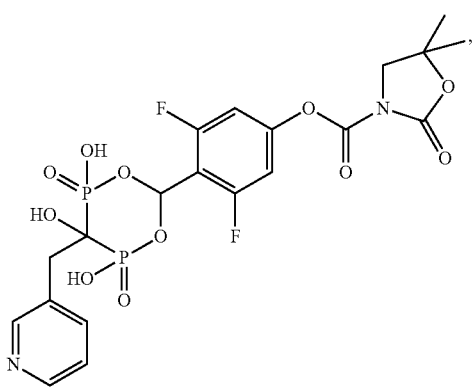

219
-continued
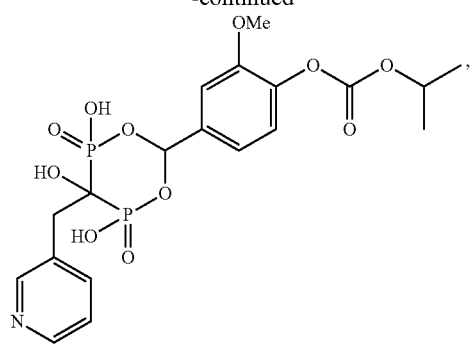
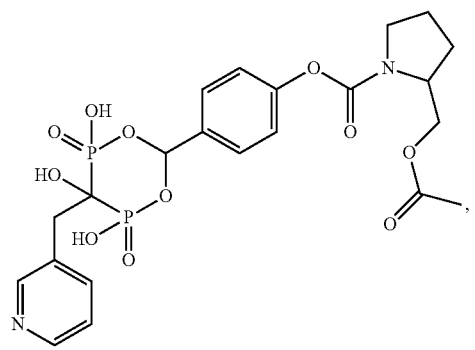
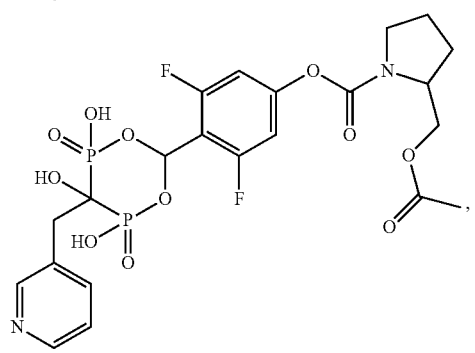
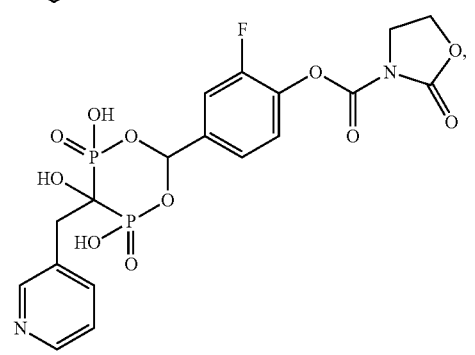
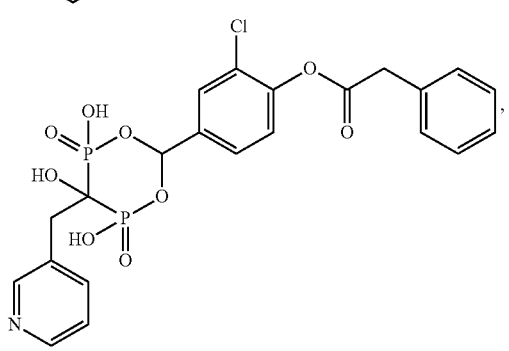
220
-continued
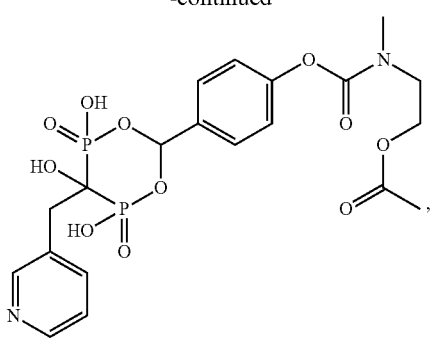
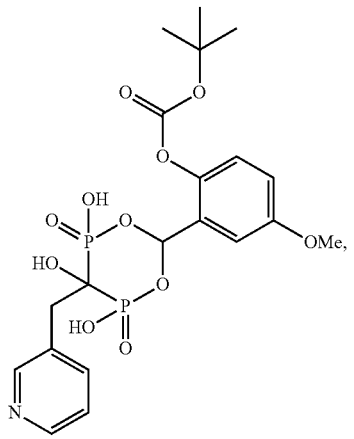
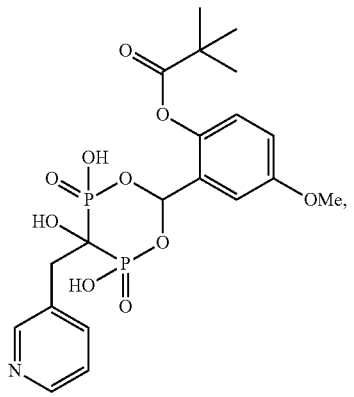
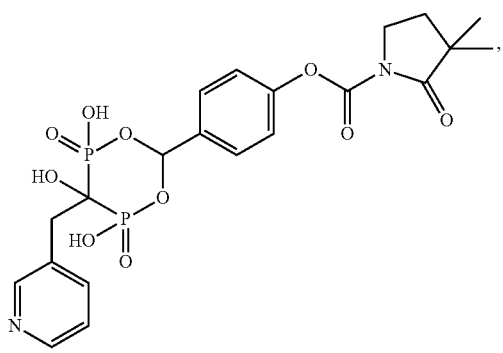

221
-continued
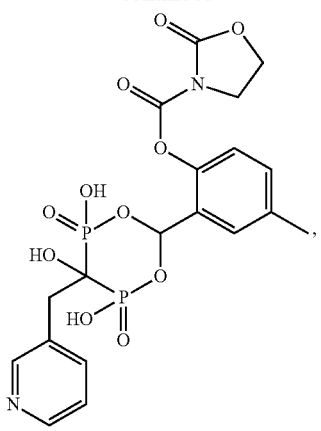
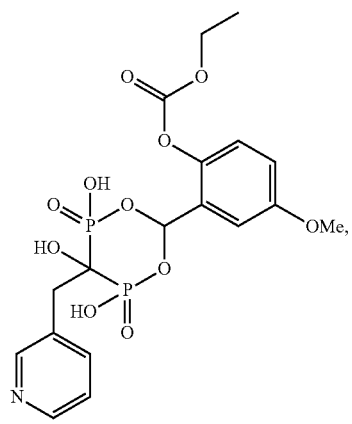
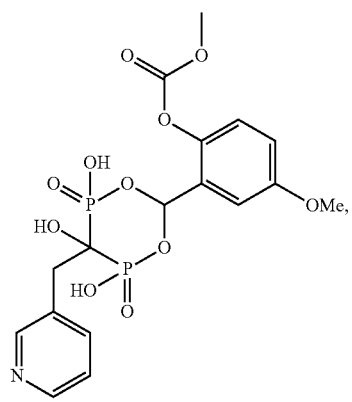
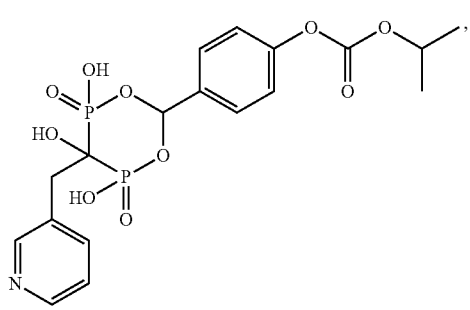
222
-continued
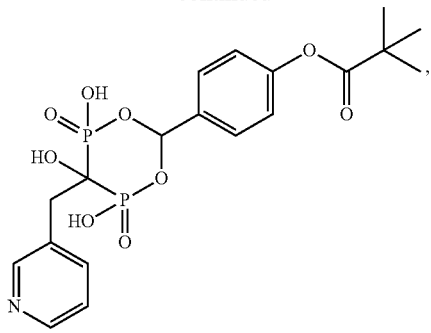
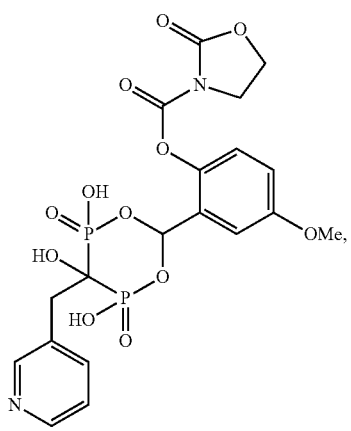
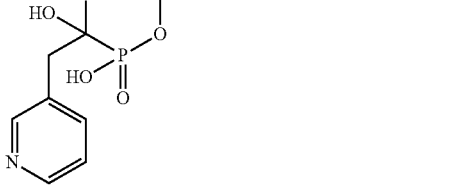
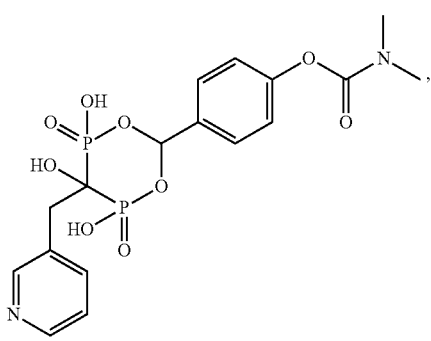

223
-continued
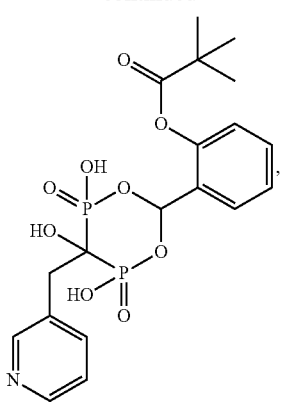
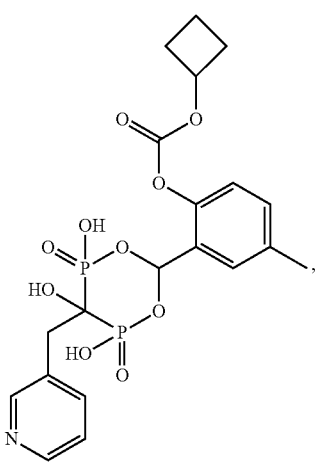
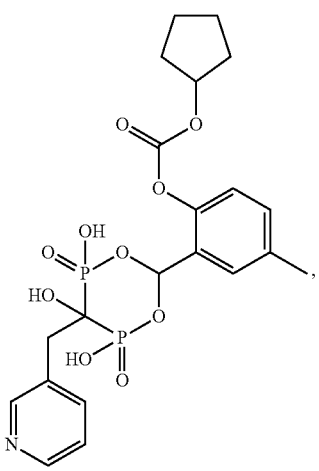
224
-continued
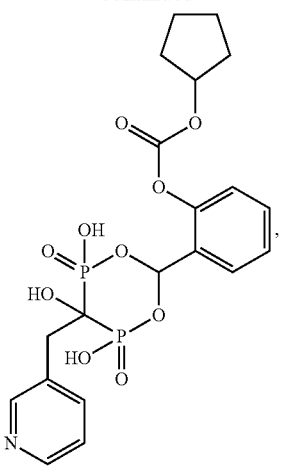
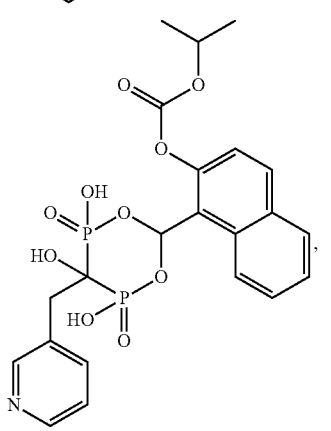
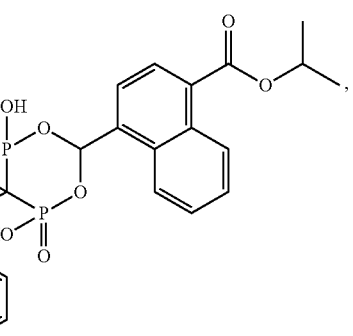
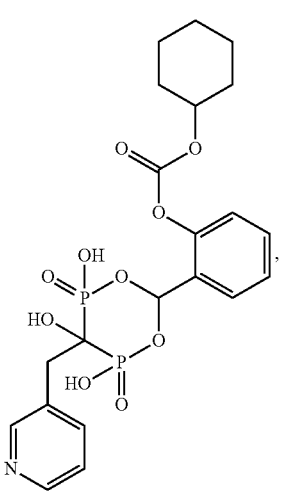

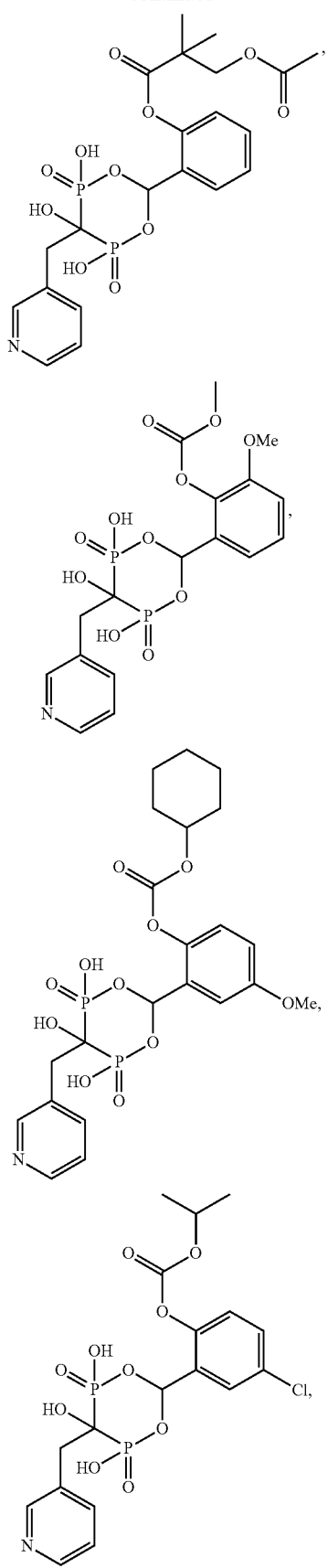
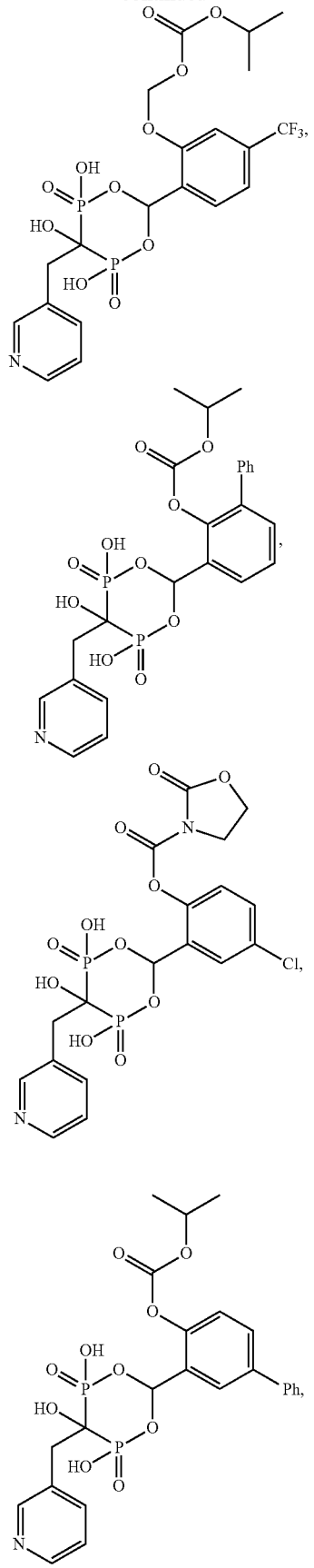

227
-continued
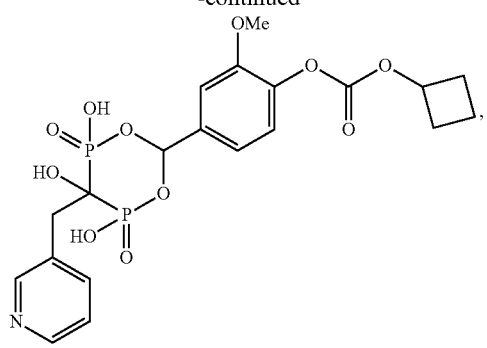
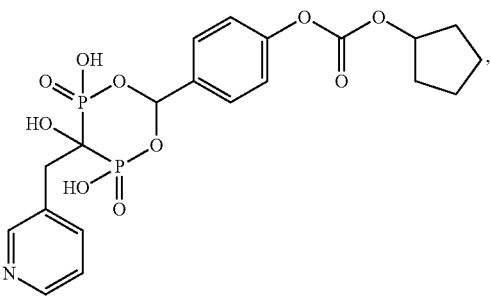
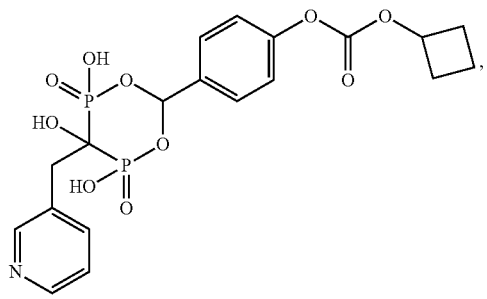
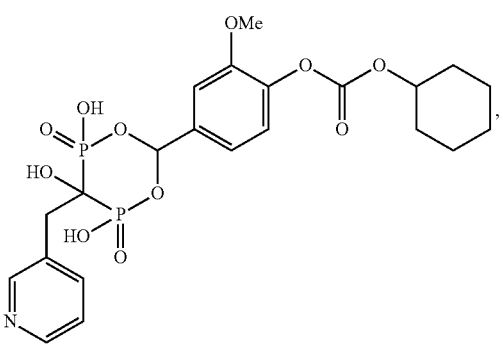
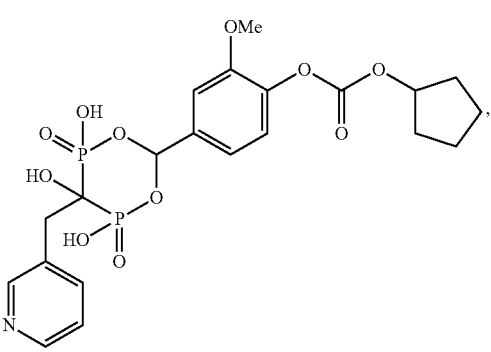
228
-continued
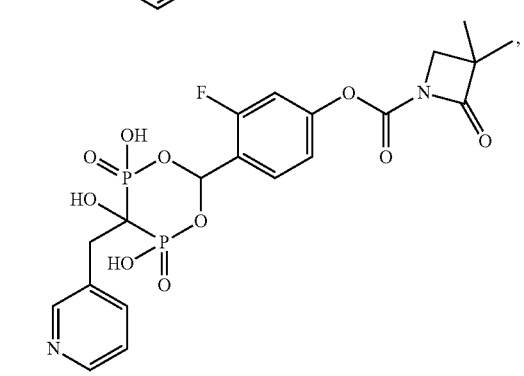
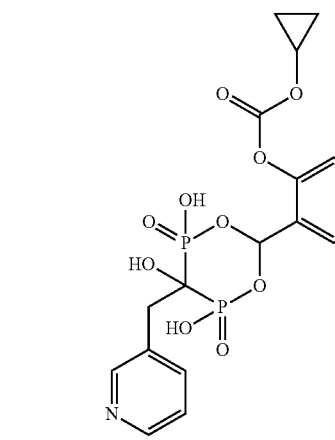
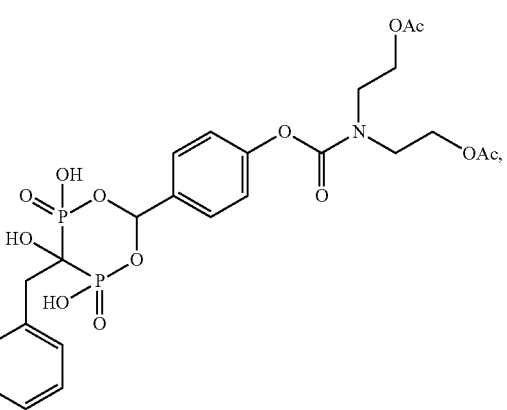

229
-continued

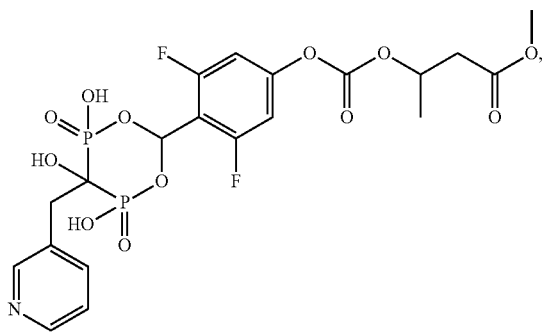

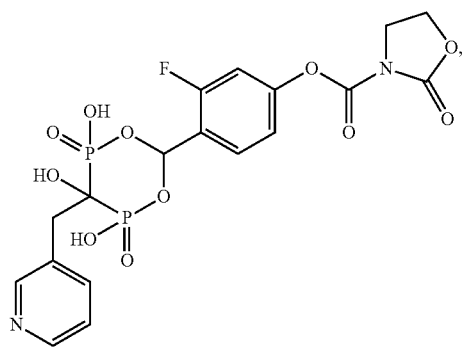

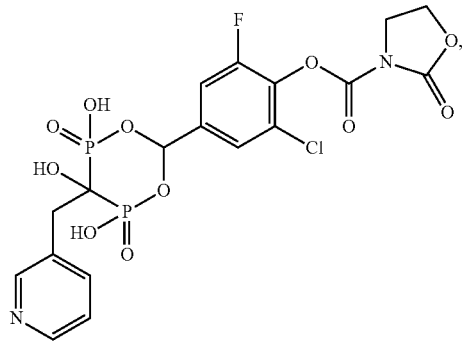

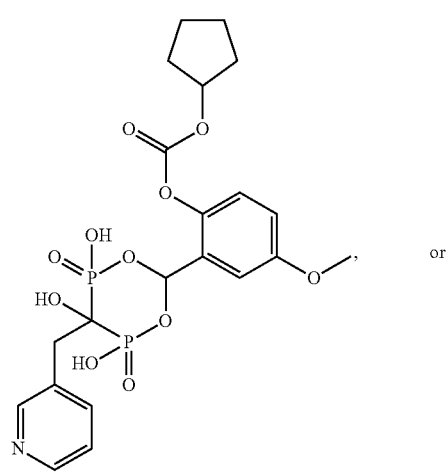

230
-continued

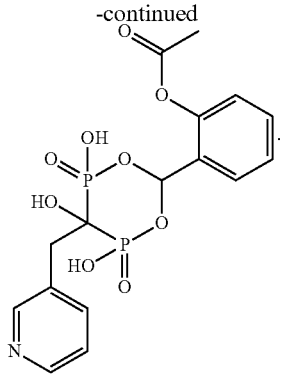

12. A method of treating osteoporosis, rheumatoid arthritis, osteoarthritis, Paget's disease, or alveolar bone loss comprising administering an effective amount of a compound of Formula II,

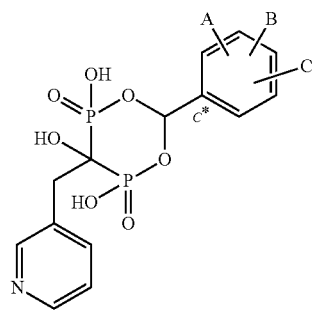

(II)

or a pharmaceutically acceptable salt thereof to a patient in need of such treatment, wherein A is —$OR_6$, —$CO_2R_6$, -L-OC(O)$R_6$, —O-L-OC(O)$R_6$, —O-L—OC(O)$OR_6$, —OC(O)$R_6$, —OC(O)-L-OC(O)$R_6$, —OC(O)$OR_6$, —OC(O)O-L-C(O)$R_7$, —OC(O)O-L-C(O)$OR_7$, —C(O)$NR_6R_7$, —$CNR_6R_7$, —OC(O)$NR_6R_7$, —OC(O)N($R_6$)-L-OC(O)$R_7$, —OC(O)N(-L-OC(O)$R_7$)(-L-OC(O)$R_8$),

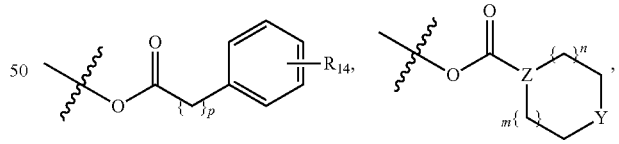

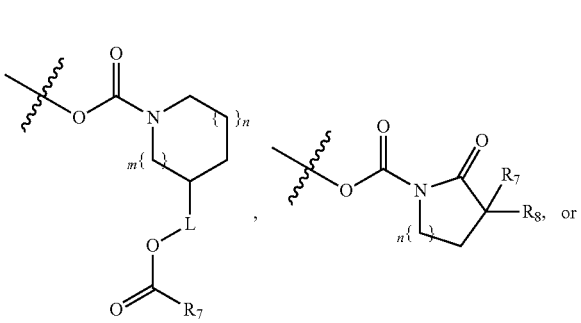

-continued

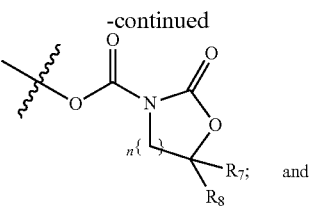

B and C are each independently hydrogen, halogen, —CF₃, —CN, C₁-C₈ alkyl, phenyl, —OR₆, or —C(O)OR₆, or B and C when taken together form an optionally substituted 4- to 8-membered carbocyclic or heterocyclic ring, wherein the ring is saturated, unsaturated or aromatic;

wherein m and n are each independently an integer from 0 to 2;

Y is —CH₂—, —O—, —NR₇—, or —S—;

p is an integer from 1 to 3;

Z is

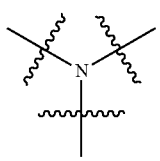 [SMILES: *N(*)*]

or

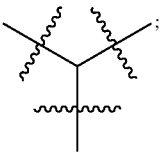 [SMILES: *C(*)*]

each R₆ is independently hydrogen, C₁-C₈ alkyl, C₁-C₈ haloalkyl, C₂-C₈ alkenyl, C₂-C₈ haloalkenyl, C₂-C₈ alkynyl, C₂-C₈ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

L is C₁-C₈ alkyl;

R₁₄ is hydrogen, halogen, C₁-C₈ alkyl, or C₁-C₈ alkoxyl;

R₇ and R₈ are each independently hydrogen or C₁-C₈ alkyl; or

R₆ and R₇ taken together form an optionally substituted 4- to 8-membered carbocyclic or heterocyclic ring, wherein the ring is saturated, unsaturated or aromatic.

13. A method of treating osteoporosis, rheumatoid arthritis, osteoarthritis, Paget's disease, or alveolar bone loss comprising administering an effective amount of a compound of Formula IV,

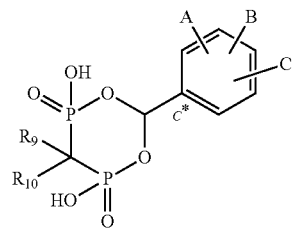

or a pharmaceutically acceptable salt thereof to a patient in need of such treatment, wherein A is —OR₆, —CO₂R₆, -L-OC(O)R₆, —O-L-OC(O)R₆, —O-L—OC(O)OR₆, —OC(O)R₆, —OC(O)-L-OC(O)R₆, —OC(O)OR₆, —OC(O)O-L-C(O)R₇, —OC(O)O-L-C(O)OR₇, —C(O)NR₆R₇, —CNR₆R₇, —OC(O)NR₆R₇, —OC(O)N(R₆)-L-OC(O)R₇, —OC(O)N(-L-OC(O)R₇)(-L-OC(O)R₈),

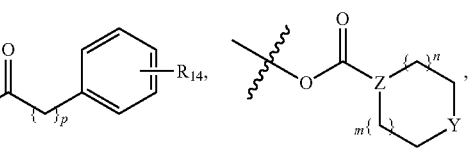

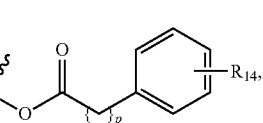

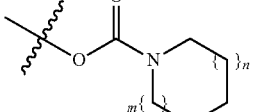

B and C are each independently hydrogen, halogen, —CF₃, —CN, C₁-C₈ alkyl, phenyl, —OR₆, or —C(O)OR₆, or B and C when taken together form an optionally substituted 4- to 8-membered carbocyclic or heterocyclic ring, wherein the ring is saturated, unsaturated or aromatic; and R₉ and R₁₀ are each independently hydrogen, halogen, oxygen, C₁-C₈ alkyl, C₁-C₈ haloalkyl, C₂-C₈ alkenyl, C₂-C₈ haloalkenyl, C₂-C₈ alkynyl, C₂-C₈ haloalkynyl, optionally substituted aryl, optionally substituted heteroaryl, —OR₆, —SR₆, —NR₆R₇, —(C₁-C₈ alkyl)-NR₆R₇, —(C₁-C₈ haloalkyl)-NR₆R₇, —(C₂-C₈ alkenyl)-NR₆R₇, —(C₂-C₈ haloalkenyl)-NR₆R₇, —(C₂-C₈ alkynyl)-NR₆R₇, —(C₂-C₈ haloalkyl)-NR₆R₇, -L-R₁₁; or R₉ and R₁₀ taken together form a monocyclic or bicyclic optionally substituted carbocyclic or heterocyclic ring, wherein the ring is saturated, unsaturated or aromatic;

wherein R₁₁ is optionally substituted aryl or optionally substituted heteroaryl;

m and n are each independently an integer from 0 to 2;

Y is —CH$_2$—, —O—, —NR$_7$—, or —S—;

p is an integer from 1 to 3;

Z is

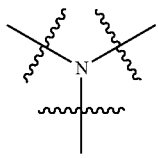 [SMILES: *N(*)*]

or

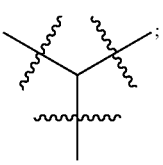 [SMILES: *C(*)*]

;

each R$_6$ is independently hydrogen, C$_1$-C$_8$ alkyl, C$_1$-C$_8$ haloalkyl, C$_2$-C$_8$ alkenyl, C$_2$-C$_8$ haloalkenyl, C$_2$-C$_8$ alkynyl, C$_2$-C$_8$ haloalkynyl, an optionally substituted 4-8 membered saturated carbocyclic or heterocyclic ring, optionally substituted aryl, optionally substituted heteroaryl, -L-optionally substituted aryl or -L-optionally substituted heteroaryl;

L is C$_1$-C$_8$ alkyl;

R$_{14}$ is hydrogen, halogen, C$_1$-C$_8$ alkyl, or C$_1$-C$_8$ alkoxyl;

R$_7$ and R$_8$ are each independently hydrogen or C$_1$-C$_8$ alkyl; or

R$_6$ and R$_7$ taken together form an optionally substituted 4- to 8-membered carbocyclic or heterocyclic ring, wherein the ring is saturated, unsaturated or aromatic.

14. The method of claim 13, wherein the compound is a compound or a pharmaceutically acceptable salt or hydrate of a compound of Formula IVa, IVb, IVc, IVd, or IVe:

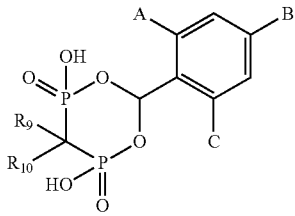
(IVa)

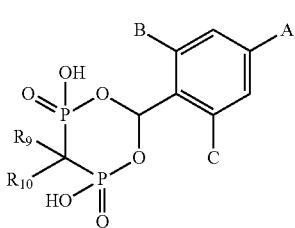
(IVb)

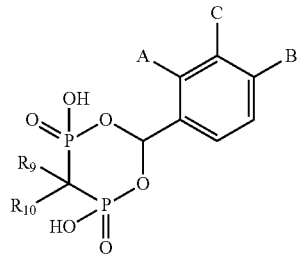
(IVc)

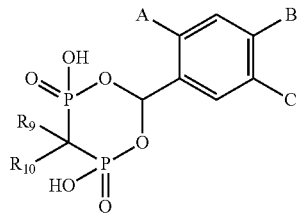
(IVd)

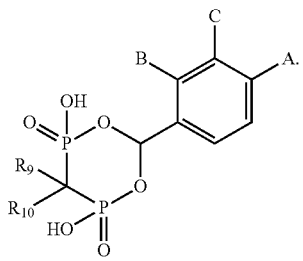
(IVe)

15. The method of claim 14, wherein the compound or a pharmaceutically acceptable salt or hydrate of a compound of Formula IVa is a compound or a pharmaceutically acceptable salt or hydrate of a compound of Formula IVf,

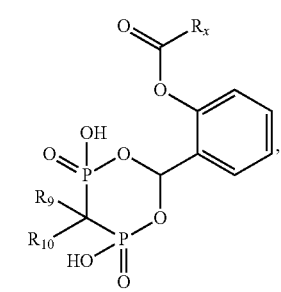
(IVf)

wherein R$_9$ is H, OH, or F; R$_{10}$ is

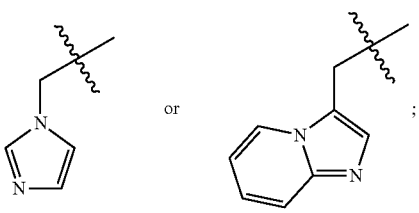 [SMILES: *Cn1ccnc1 ; *Cc1cnc2ccccn12]

and $R_x$ is $C_1$-$C_8$ alkyl, $C_1$-$C_8$ alkoxyl or
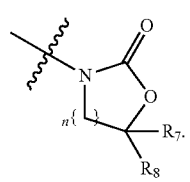
16. The method of claim 15, wherein the compound is
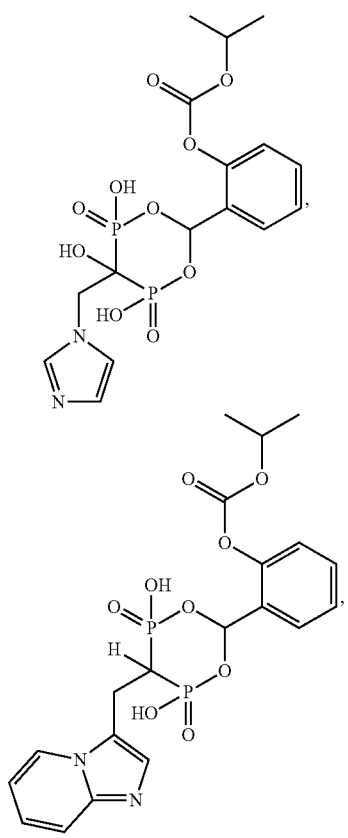
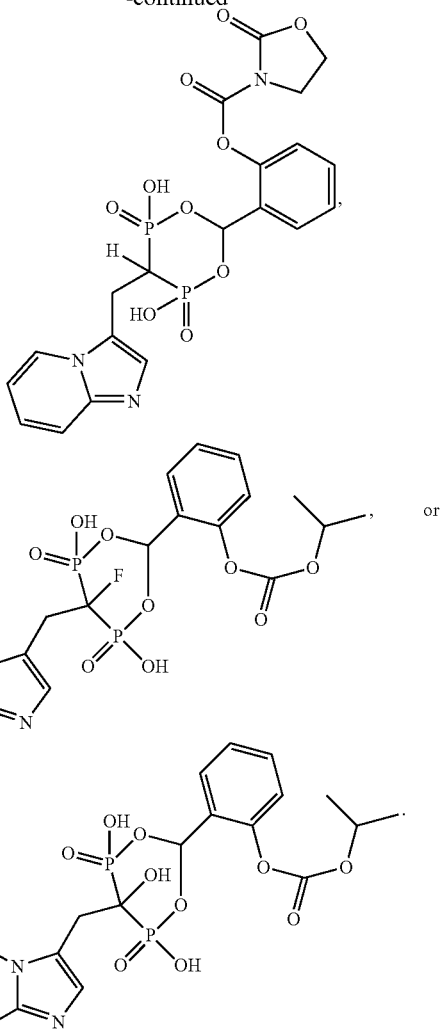
* * * * *